(12) United States Patent
Andersen et al.

(10) Patent No.: US 11,345,670 B2
(45) Date of Patent: May 31, 2022

(54) HETEROCYCLIC COMPOUNDS FOR CANCER IMAGING AND TREATMENT AND METHODS FOR THEIR USE

(71) Applicants: The University of British Columbia, Vancouver (CA); British Columbia Cancer Agency Branch, Vancouver (CA)

(72) Inventors: Raymond John Andersen, Vancouver (CA); Javier Garcia Fernandez, Asturias (ES); Kunzhong Jian, Surrey (CA); Marianne Dorothy Sadar, West Vancouver (CA); Nasrin R. Mawji, Burnaby (CA); Carmen Adriana Banuelos, Richmond (CA)

(73) Assignees: The University of British Columbia, Vancouver (CA); British Columbia Cancer Agency Branch, Vancouver (CA)

( * ) Notice: Subject to any disclaimer, the term of this patent is extended or adjusted under 35 U.S.C. 154(b) by 0 days.

(21) Appl. No.: 16/864,479

(22) Filed: May 1, 2020

(65) Prior Publication Data
US 2020/0325106 A1 Oct. 15, 2020

Related U.S. Application Data

(62) Division of application No. 15/543,389, filed as application No. PCT/CA2016/000008 on Jan. 13, 2016, now Pat. No. 10,654,811.

(60) Provisional application No. 62/102,719, filed on Jan. 13, 2015.

(51) Int. Cl.
| | | |
|---|---|---|
| C07D 249/04 | (2006.01) |
| A61K 45/06 | (2006.01) |
| C07D 233/60 | (2006.01) |
| A61K 31/4164 | (2006.01) |
| A61K 31/4192 | (2006.01) |
| A61K 31/5375 | (2006.01) |
| A61K 51/04 | (2006.01) |
| C07D 295/088 | (2006.01) |
| C07B 59/00 | (2006.01) |
| C07D 265/30 | (2006.01) |
| A61P 35/00 | (2006.01) |
| C07D 295/084 | (2006.01) |

(52) U.S. Cl.
CPC ........ *C07D 249/04* (2013.01); *A61K 31/4164* (2013.01); *A61K 31/4192* (2013.01); *A61K 31/5375* (2013.01); *A61K 45/06* (2013.01); *A61K 51/0453* (2013.01); *A61K 51/0459* (2013.01); *A61K 51/0463* (2013.01); *A61K 51/0465* (2013.01); *A61P 35/00* (2018.01); *C07B 59/002* (2013.01); *C07D 233/60* (2013.01); *C07D 265/30* (2013.01); *C07D 295/084* (2013.01); *C07D 295/088* (2013.01)

(58) Field of Classification Search
CPC . C07D 295/84; C07D 249/04; A61K 31/5375
See application file for complete search history.

(56) References Cited

U.S. PATENT DOCUMENTS

| | | |
|---|---|---|
| 2,571,217 A | 10/1951 | Davis et al. |
| 2,890,189 A | 6/1959 | Greenlee |
| 3,074,974 A | 1/1963 | Gebura |
| 3,162,615 A | 12/1964 | Bremmer |
| 4,284,574 A | 8/1981 | Bagga |
| 4,369,298 A | 1/1983 | Kida et al. |

(Continued)

FOREIGN PATENT DOCUMENTS

| | | |
|---|---|---|
| CA | 2206422 A1 | 6/1996 |
| CA | 2226469 A1 | 1/1997 |

(Continued)

OTHER PUBLICATIONS

Shode et al. CAS: 107: 8065, 1987.*
Levoin et al. CAS: 159, 207816, 2013.*
Zalinyan et al. CAS: 90: 105001, 1979.*
Alvarez, C. et al., "Conformational and Experimental Studies on the Dipole Moments of Models of Comblike Polymers", Macromolecules, 30(20): 6369-6375 (1997).
Anderson, R. et al., "Regression of Castrate-Recurrent Prostate Cancer by a Small-Molecule Inhibitor of the Amino-Terminus Domain of the Androgen Receptor", Cancer Cell, 17:535-546 (2010).
Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A diglycidyl ether, BADGE), REF. No. 13510 and 39700 (EFSA-Q-2003-178), The EFSA Journal, 86:1-40 (2004).

(Continued)

*Primary Examiner* — Rei Tsang Shiao
(74) *Attorney, Agent, or Firm* — Cooley LLP

(57) ABSTRACT

Compounds having a structure of Formula I:

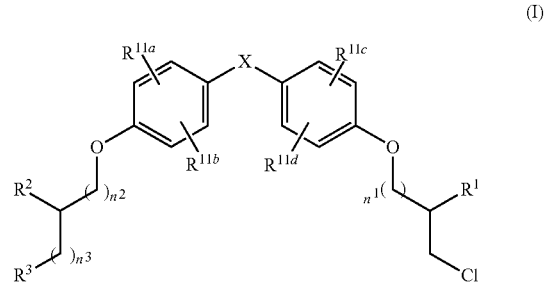

(I)

or a pharmaceutically acceptable salt, tautomer or stereoisomer thereof, wherein $R^1$, $R^2$, $R^3$, $R^{11a}$, $R^{11b}$, $R^{11c}$, $R^{11d}$, X, $n^1$, $n^2$, and $n^3$ are as defined herein, are provided. Uses of such compounds for modulating androgen receptor activity, imaging diagnostics in cancer and therapeutics, and methods for treatment of subjects in need thereof, including prostate cancer are also provided.

31 Claims, 17 Drawing Sheets

(56) References Cited

U.S. PATENT DOCUMENTS

| | | |
|---|---|---|
| 4,855,184 A | 8/1989 | Klun et al. |
| 4,904,760 A | 2/1990 | Gaku et al. |
| 5,043,375 A | 8/1991 | Henning et al. |
| 5,155,196 A | 10/1992 | Kolb et al. |
| 5,362,615 A | 11/1994 | Hagemann et al. |
| 5,403,697 A | 4/1995 | Doessel et al. |
| 5,753,730 A | 5/1998 | Nagata et al. |
| 5,807,899 A | 9/1998 | Rolf et al. |
| 5,998,674 A | 12/1999 | Taketani et al. |
| 6,218,430 B1 | 4/2001 | Allegretto et al. |
| 6,245,117 B1 | 6/2001 | Nishikawa et al. |
| 7,183,323 B2 | 2/2007 | Chinn et al. |
| 7,595,345 B2 | 9/2009 | Bunel et al. |
| 7,674,795 B2 | 3/2010 | Mailliet et al. |
| 8,048,888 B2 | 11/2011 | Wosikowski-Buters et al. |
| 8,455,477 B2 | 6/2013 | Katz |
| 8,686,050 B2 | 4/2014 | Sadar et al. |
| 9,173,939 B2 | 11/2015 | Andersen et al. |
| 9,365,510 B2 | 6/2016 | Andersen et al. |
| 9,375,496 B2 | 6/2016 | Andersen et al. |
| 9,388,112 B2 | 7/2016 | Sadar et al. |
| 9,862,667 B2 | 1/2018 | Sadar et al. |
| 10,654,811 B2 | 5/2020 | Andersen et al. |
| 2003/0092724 A1 | 5/2003 | Kao et al. |
| 2003/0105268 A1 | 6/2003 | Boriack et al. |
| 2004/0049004 A1 | 3/2004 | Boriack et al. |
| 2004/0243316 A1 | 12/2004 | Weinmann et al. |
| 2008/0153837 A1 | 6/2008 | Mailliet et al. |
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2009/0246158 A1 | 10/2009 | Rudolph et al. |
| 2011/0230556 A1 | 9/2011 | Sadar et al. |
| 2013/0045204 A1 | 2/2013 | Sadar et al. |
| 2013/0109758 A1 | 5/2013 | Sadar et al. |
| 2013/0131167 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |
| 2015/0010469 A1 | 1/2015 | Andersen et al. |
| 2015/0125389 A1 | 5/2015 | Andersen et al. |
| 2016/0068466 A1 | 3/2016 | Andersen et al. |
| 2016/0367707 A1 | 12/2016 | Andersen et al. |
| 2017/0056336 A1 | 3/2017 | Sadar et al. |
| 2017/0121261 A1 | 5/2017 | Sadar et al. |
| 2017/0298033 A1 | 10/2017 | Andersen et al. |
| 2018/0064657 A1 | 3/2018 | Andersen et al. |
| 2018/0235925 A1 | 8/2018 | Andersen et al. |
| 2018/0327368 A1 | 11/2018 | Andersen et al. |
| 2020/0123117 A1 | 4/2020 | Zhou et al. |
| 2020/0247763 A1 | 8/2020 | Zhou et al. |

FOREIGN PATENT DOCUMENTS

| | | |
|---|---|---|
| CA | 2339775 A1 | 3/2000 |
| CA | 2606262 A1 | 11/2006 |
| CA | 2728219 A1 | 1/2010 |
| CA | 2786319 A1 | 7/2011 |
| CN | 102083780 A | 6/2011 |
| CN | 103342892 A | 10/2013 |
| EP | 0056175 A1 | 7/1982 |
| EP | 0155238 A2 | 9/1985 |
| EP | 0293768 A1 | 12/1988 |
| EP | 0515128 A1 | 11/1992 |
| FR | 1389005 | 2/1965 |
| JP | B-S45-008432 | 3/1970 |
| JP | S56-5472 A | 1/1981 |
| JP | 63-196675 | 8/1988 |
| JP | S63-317539 A | 12/1988 |
| JP | H01-503541 | 11/1989 |
| JP | H02-4815 | 1/1990 |
| JP | 6-049473 A2 | 2/1994 |
| JP | 7-117349 A | 5/1995 |
| JP | 09-176240 A | 7/1997 |
| JP | H10133427 A | 5/1998 |
| JP | A-H10-316803 | 12/1998 |
| JP | 11-166087 A2 | 6/1999 |
| JP | 2000-072705 A2 | 3/2000 |
| JP | 2001-511170 A | 8/2001 |
| JP | 2005-325301 A | 11/2005 |
| JP | 2006-208607 A | 8/2006 |
| JP | 2006-265351 A2 | 10/2006 |
| JP | 2007-513089 A | 5/2007 |
| JP | 2007-290980 | 11/2007 |
| KR | 10-2011-0044216 A | 4/2011 |
| PL | 141793 B1 | 8/1987 |
| RU | 2454394 C2 | 6/2012 |
| SU | 638596 | 12/1978 |
| SU | 929630 | 5/1982 |
| WO | WO 1988/009782 A1 | 12/1988 |
| WO | WO 1996/16646 A1 | 6/1996 |
| WO | WO 1998/034930 A1 | 8/1998 |
| WO | WO 2000/001813 A2 | 1/2000 |
| WO | WO 2000/010958 A1 | 3/2000 |
| WO | WO 2001/088013 A2 | 11/2001 |
| WO | WO 2002/005813 A2 | 1/2002 |
| WO | WO 2003/004481 A1 | 1/2003 |
| WO | WO 2005/042464 A1 | 5/2005 |
| WO | WO 2005/077967 A1 | 8/2005 |
| WO | WO 2008/101806 A2 | 8/2008 |
| WO | WO 2010/000066 A1 | 1/2010 |
| WO | WO 2011/082487 A1 | 7/2011 |
| WO | WO 2011/082488 A1 | 7/2011 |
| WO | WO 2012/139039 A2 | 10/2012 |
| WO | WO 2012/145328 A1 | 10/2012 |
| WO | WO 2012/145330 A1 | 10/2012 |
| WO | WO 2013/028572 A1 | 2/2013 |
| WO | WO 2013/028791 A1 | 2/2013 |
| WO | WO 2014/179867 A1 | 11/2014 |
| WO | WO 2015/031984 A1 | 3/2015 |
| WO | WO 2016/058080 A1 | 4/2016 |
| WO | WO 2016/058082 A1 | 4/2016 |
| WO | WO 2016/112455 A1 | 7/2016 |
| WO | WO 2016/141458 A1 | 9/2016 |
| WO | WO 2017/177307 A1 | 10/2017 |
| WO | WO 2017/210771 A1 | 12/2017 |

OTHER PUBLICATIONS

Antonarakis et al., "Androgen receptor variant-driven prostate cancer: clinical implications and therapeutic targeting," Prostate Cancer and Prostatic Diseases (2016), 1-11.

Antonarakis et al., "Targeting the N-Terminal Domain of the Androgen Receptor: A New Approach for the Treatment of Advanced Prostate Cancer," The Oncologist 2016;21:1-9.

Auzou et al., European Journal of Medicinal Chemistry, 9(5):548-554 (1974) (with English Abstract).

Balbay, M.D. et al., "Highly Metastatic Human Prostate Cancer Growing within the Prostate of Athymic Mice Overexpresses Vascular Endothelial Growth Factor", Clinical Cancer Research, 5:783-789 (1999).

Banuelos et al., "Sintokamide A is a novel antagonist of androgen receptor that uniquely binds activation function-1 in its amino-terminal domain," The Journal of Biological Chemistry, vol. 291, No. 42, pp. 22231-22243, Oct. 14, 2016.

Bao, B. et al., "Androgen signaling is required for the vitamin D-mediated growth inhibition in human prostate cancer cells", Oncogene, 23:3350-3360 (2004).

Berge, S.M. et al., "Pharmaceutical Salts", Pharmaceutical Sciences, 66(1):1-19 (1977).

Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, Food Chemical Contaminants, 83(6): 1367-1376 (2000).

Biles, J.E. et al., "Determination of the Diglycidyl Ether of Bisphenol A and its Derivatives in Canned Foods", J. Agric. Food Chem., 47:1965-1969 (1999).

Bisson, W.H. et al., "Discovery of antiandrogen activity of nonsteroidal scaffolds of marketed drugs", PNAS, 104(29):11927-11932 (2007).

(56) References Cited

OTHER PUBLICATIONS

Blaszczyk, N. et al., "Osteoblast-Derived factors Induce Androgen-Independent Proliferation and Expression of Prostate-Specific Antigen in Human Prostate Cancer Cells", Clin. Cancer Res., 10:1860-1869 (2004).
Bodei, et al., "Radionuclide Therapy with Iodine-125 and Other Auger-Electron-Emitting Radionuclides: Experimental Models and Clinical Applications." Cancer Biother. & Radiopharm. (2003); 18(6): 861-877.
Bohler, Paul et al., "Identification of Migrants from Coatings of Food Cans and Tubes: Reaction Products of Bisphenol-A-Diglycidyl Ether (BADGE) with Phenols and Solvents", Mitt. Gebiete Lebensm. Hyg., 89:529-547 (1998).
Brand et al., "EPI-001 is a selective peroxisome proliferator-activated receptor-gamma modulator with inhibitory effects on androgen receptor expression and activity in prostate cancer." Oncotarget (2015); 6(6): 3811-3824.
Brzozowski, Z. et al., "Precursors for bisphenolic resins", CAPLUS Database Accession No. 1990:36690, Document No. 112:33690, (1987), 1 page (Abstract).
Bruckheimer, E.M et al., "Apoptosis in prostate carcinogenesis A growth regulator and a therapeutic target", Cell Tissue Res, 301:153-162 (2000).
Cascini, et al., "Iodine: A Longer-Life Positron Emitter Isotope—New Opportunities in Molecular Imaging." Hindawi Publishing Corp. Biomed. Res. Int. (2014); vol. 2014, Article ID 672094, 7 pages.
Chang, C. et al., "Development of Peptide Antagonists for the Androgen Receptor Using Combinatorial Peptide Phage Display", Molecular Endocrinology, 19(10):2478-2490 (2005).
Choi, K. M. et al., "New Families of Photocurable Oligomeric Fluoromonomers for Use in Dental Composites", Chemistry of Materials, 8(12):2704-2707 (1996).
Clinton, G.M. et al., "Estrogen action in human ovarian cancer", Critical Reviews in Oncology/Hematology, 25:1-9 (1997).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", Journal of Macromolecular Science, Pure and Applied Chemistry, A31(9):1105-1119 (1994).
Cook, W. D., "Fracture and Structure of Highly Crosslinked Polymer Composites", Journal of Applied Polymer Science, 42:1259-1269 (1991).
Culig, Zoran et al., "Androgen Receptor Activation in Prostatic Tumor Cell Lines by Insulin-like Growth Factor-I, Keratinocyte Growth Factor, and Epidermal Growth Factor", Cancer Research, 54:5474-5478 (1994).
Danquah, M. et al., "Micellar Delivery of Bicalutamide and Embelin for Treating Prostate Cancer", Pharmaceutical Research, 26:2081-2092 (2009).
Das, Debasish et al., "Sulfonic acid functionalized mesoporous MCM-41 silica as a convenient catalyst for Bisphenol-A synthesis", Chemical Communications, pp. 2178-2179 (2001).
De Mol et al., "EPI-001, a compound active against castration-resistant prostate cancer, targets transactivation unit 5 of the androgen receptor," ACS Chem. Biol., 2016, 11, 9, 2499-2505.
Dehm, S. et al., "Ligand-independent Androgen Receptor Activity is Activation Function-2-independent and Resistant to Antiandrogens in Androgen Refractory Prostate Cancer Cells", The Journal of Biological Chemistry, 281(38):27882-27893 (2006).
Dehm, S. et al., "Splicing of a Novel Androgen Receptor Exon Generates a Constitutively Active Androgen Receptor that Mediates Prostate Cancer Therapy Resistance", Cancer Research, 68:5469-5477 (2008).
Edmondson, R.J., et al., "The human ovarian surface epithelium is an androgen responsive tissue", British Journal of Cancer, 86:879-885 (2002).

Estebanez-Perpiñá, E. et al., "A surface on the androgen receptor that allosterically regulates coactivator binding," PNAS, 104(41):16074-16079 (2007).
Estebanez-Perpiñá, E. et al., "The Molecular Mechanisms of Coactivator Utilization in Liganddependent Transactivation by the Androgen Receptor," The Journal of Biological Chemistry, 280(9):8060-8068 (2005).
Fehlberg S. et al., "Bisphenol A diglycidyl ether induces apoptosis in tumor cells independently of peroxisome proliferator-activated receptor-y, in caspase-dependent and -independent manners," Biochem. J. 362:573-578 (2002).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", Thermo Fisher Scientific Inc., 4 pages (2011).
Garuti, L., et al., "Irreversible Protein Kinase Inhibitors", Current Medicinal Chemistry, 18:2981-2994 (2011).
Garcia et al., "Determination of compounds from epoxy resins in food simulants by HPLC-fluorescence." Chromatographia, 58(5-6): 337-342 (2003).
Gleave, Martin et al., "Acceleration of Human Prostate Cancer Growth in Vivo by Factors Produced by Prostate and Bone Fibroblasts", Cancer Research, 51:3753-3761 (1991).
Gregory, Christopher et al., "Epidermal Growth Factor Increases Coactivation of the Androgen Receptor in Recurrent Prostate Cancer", The Journal of Biological Chemistry, 279(8):7119-7130 (2004).
Guinan, P.D. et al., "Impotence Therapy and Cancer of the Prostate", The American Journal of Surgery, 131:599-600 (1976).
Guo, Zhiyong et al., "A Novel Androgen Receptor Splice Variant Is Up-regulated during Prostate Cancer Progression and Promotes Androgen Depletion—Resistant Growth", Cancer Research, 69:2305-13 (2009).
Haggstrom, Stina et al., "Testosterone Induces Vascular Endothelial Growth Factor Synthesis in the Ventral Prostate in Castrated Rats", The Journal of Urology, 161:1620-1625 (1999).
Harper et al., "Expression of Androgen Receptor and Growth Factors in Premalignant Lesions of the Prostate", Journal of Pathology, 186:169-177 (1998).
He, B. et al., "Activation Function 2 in the Human Androgen Receptor Ligand Binding Domain Mediates Interdomain Communication with the $NH_2$-terminal Domain", The Journal of Biological Chemistry, 274(52):37219-37225 (1999).
He, B. et al., "Structural Basis for Androgen Receptor Interdomain and Coactivator Interactions Suggests a Transition in Nuclear Receptor Activation Function Dominance", Molecular Cell, 16:425-438 (2004).
Henke, H., "Selektive praparative gelchromatographische Trennung niedermolekularer Verbindungen an Sephadex LH-20", Journal of Chromatography, 254: 296-308 (1983).
Heinlein, Cynthia A., et al., "Androgen Receptor in Prostate Cancer", Endocrine Reviews, 25(2):276-308 (2004).
Helzlsouer, Kathy J., et al., "Serum Gonadotropins and Steroid Hormones and the Development of Ovarian Cancer", JAMA, 274(24):1926-1930 (1995).
Horoszewicz, J.S. et al., "LNCaP Model of Human Prostatic Carcinoma", Cancer Research, 43:1809-1818 (1983).
Hu, R. et al., "Ligand-Independent Androgen Receptor Variants Derived from Splicing of Cryptic Exons Signify Hormone-Refractory Prostate Cancer", Cancer Research, 69:16-22 (2009).
Huber, P.R. et al., "Prostate Specific Antigen. Experimental and Clinical Observations", Scand. J. Urol Nephrol., 104:33-39 (1987).
Hur, E. et al., "Recognition and Accommodation at the Androgen Receptor Coactivator Binding Interface", PLoS Biology, 2(9)(e274):1303-1312 (2004).
Imamura et al., "An imaging agent to detect androgen receptor and its active splice variants in prostate cancer," JCI Insight. 2016;1(11):e87850 15 pages.
Imamura et al., "Androgen receptor targeted therapies in castration-resistant prostate cancer: Bench to clinic," International Journal of Urology (2016), 23(8):654-65.

(56) References Cited

OTHER PUBLICATIONS

Isaacs, J.T., et al., "New Biochemical Methods to Determine Androgen Sensitivity of Prostatic Cancer: The Relative Enzymatic Index (REI)", Prostate Cancer and Hormone Receptors, pp. 133-144 (1979).
Isaacs, J.T., "Antagonistic Effect of Androgen on Prostatic Cell Death", The Prostate, 5:545-557 (1984).
Jackson, J. A. et al., "Prostatic Complications of Testosterone Replacement Therapy", Arch Intern Med., 149:2365-2366 (1989).
Japanese Patent Application No. 2016-512175, Notice of Reasons for Rejection dated Jun. 21, 2016 (and English translation), 12 pages.
Jenster, G. et al., "Domains of the Human Androgen Receptor Involved in Steroid Binding, Transcriptional Activation, and Subcellular Localization", Molecular Endocrinology, 5:1396-1404 (1991).
Jenster, G., et al. "Identification of two transcription activation units in the N-terminal domain of the human androgen receptor." Journal of Biological Chemistry (1995); 270.13: 7341-7346.
Jia, L. et al., "Androgen Receptor Signaling: Mechanism of Interleukin-6 Inhibition", Cancer Research, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", Cancer Research, 65:8003-8008 (2005).
Kaighn, M.E. et al., "Prostate Carcinoma: Tissue Culture Cell Lines", National Cancer Institute Monograph No. 49, pp. 17-21 (1978).
Kemppainen, J. A. et al., "Distinguishing Androgen Receptor Agonists and Antagonists: Distinct Mechanisms of Activation by Medroxyprogesterone Acetate and Dihydrotestosterone", Mol. Endocrinol., 13:440-454(1999).
Kim, D. et al., "Androgen Receptor Expression and Cellular Proliferation During Transition from Androgen-Dependent to Recurrent Growth after Castration in the CWR22 Prostate Cancer Xenograft", American Journal of Pathology, 160(1):219-226 (2002).
Kolbel, M. et al., "Design of Liquid Crystalline Block Molecules with Nonconventional Mesophase Morphologies: Calamitic Bolaamphiphiles with Lateral Alkyl Chains", J. Am. Chem. Soc., 123:6809-6818 (2001).
Kumar, S. et al., "Synthesis of new crown analogs derived from bisphenol," Indian Journal Chemistry, 36B:656-661 (1997).
L'Heureux, A. et al., "Aminodifluorosulfinium Salts: Selective Fluorination Reagents with Enhanced Thermal Stability and Ease of Handling", J. Org. Chem, 75:3401-3411 (2010).
Langley, E. et al., "Evidence for an Anti-parallel Orientation of the Ligand-activated Human Androgen Receptor Dimer", The Journal of Biological Chemistry, 270(50):29983-29990 (1995).
Lannoye, G.S. et al.,"N-Fluoroalkylated and N-alkylated analogs of the dopaminergic D-2 receptor antagonist raclopride", J. Med. Chem., 33(9):2430-2437 (1990).
Leepipatpiboon, N. et al., "Simultaneous determination of bisphenol-A-diglycidyl ether, bisphenol-F-diglycidyl ether, and their derivatives in oil-in-water and aqueous-based canned foods by high-performance liquid chromatography with fluorescence detection." Journal of Chromatography A (2005); 1073.1: 331-339.
Levoin et al., "Determination of the binding mode and interacting amino-acids for dibasic H3 receptor antagonists", Bioorganic & Medicinal Chemistry, 21 (2013) 4526-4529 and Levoin et al., "Supporting Information—Determination of the binding mode and interacting amino-acids for dibasic H3 receptor agonists", Bioorganic & Medicinal Chemistry, vol. 21, Jan. 2013, pp. S1-S3.
Loren, J.C. et al., "Synthesis of achiral and racemic catenanes based on terpyridine and a directionalized terpyridine mimic, pyridyl-phenanthroline", Org. Biomol. Chem., 3(17):3105-3116 (2005).
Louie, M.C. et al., "Androgen-induced recruitment of RNA polymerase II to a nuclear receptor-p160 coactivator complex", PNAS, 100(5):2226-2230 (2003).
Makary, P., "Principles of salt formation." UK Journal of Pharmaceutical and Biosciences (2014); 2(4): 01-04.

Marriott et al., "Pharmaceutical Compounding and Dispensing," Second Edition, Pharmaceutical Press, 305 pages (2005).
Martin, S.J. et al., "A new precursor for the radiosynthesis of [$^{18}$F]FLT", Nuclear Medicine and Biology, 29:263-273 (2002).
Masiello, D. et al., "Bicalutamide Functions as an Androgen Receptor Antagonist by Assembly of a Transcriptionally Inactive Receptor", The Journal of Biological Chemistry, 277(29):26321-26326 (2002).
Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages (Abstract).
Melnyk, O. et al., "Neutralizing Anti-Vascular Endothelial Growth Factor Antibody Inhibits Further Growth of Established Prostate Cancer and Metastases in a Pre-Clinical Model", The Journal of Urology, 161:960-963 (1999).
Miller, J.I. et al., "The Clinical Usefulness of Serum Prostate Specific Antigen After Hormonal Therapy of Metastatic Prostate Cancer", The Journal of Urology, 147:956-961 (1992).
Mitsiades, C.S. et al., "Molecular biology and cellular physiology of refractoriness to androgen ablation therapy in advanced prostate cancer", Expert Opin. Investig. Drugs, 10(6): 1099-1115 (2001).
Lima, Lidia M., and Barreiro, Eliezer J. "Bioisosterism: a useful strategy for molecular modification and drug design." Current Medicinal Chemistry (2005); 12.1: 23-49.
Myung, J-K et al., "An androgen receptor N-terminal domain antagonist for treating prostate cancer", The Journal of Clinical Investigation, 123(7):2948-2960 (2013).
Nakazawa, H. et al., "In vitro assay of hydrolysis and chlorohydroxy derivatives of bisphenol A diglycidyl ether for estrogenic activity", Food and Chemical Toxicology, 40:1827-1832 (2002).
Nazareth, L.V. et al., "Activation of the Human Androgen Receptor through a Protein Kinase A Signaling Pathway", The Journal of Biological Chemistry, 271(33):19900-19907 (1996).
Nedolya, N. A. et al., Zhurnal Organicheskoi Khimii, 30(8):1 163-1166 (1994) (non English document).
Nishikawa et al., "Epichlorohydrin derivative-based modifier of cellulose fibers and modification method of cellulose fibers," Accession No. 2000:98153 CAPLUS (2009).
Noble, R. L., "The development of prostatic adenocarcinoma in Nb Rats following prolonged sex hormone administration", Cancer Research, 37:1929-1933 (1977).
Noble, R. L., "Sex steroids as a cause of adenocarcinoma of the dorsal prostate in Nb Rats, and their influence on the growth of transplants", Oncology, 34:138-141 (1977).
Ogawa, Y. et al., "Estrogenic activities of chemicals related to food contact plastics and rubbers tested by the yeast two-hybrid assay," Food Additives and Contaminants, 23:4, 422-430 (2006).
Paris, F. et al., "Phenylphenols, biphenols, bisphenol-A and 4-tert-octyphenol exhibit a and β estrogen activities and antiandrogen activity in reporter cell lines," Molecular and Cellular Endocrinology, 193:43-49 (2002).
Patani and LaVoie, "Bioisosterism: A Rational Approach in Drug Design", Chem. Rev., 96: 3147-3176 (1996).
Penczek, P. et al., "Synthesis and cyclotrimerization of dipropargyl derivatives of diepoxides," Database CAPLUS [Online] Chemical Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-277 (1995).
Petersen, H. et al., "Determination of bisphenol A diglycidyl ether (BADGE) and its derivatives in food: identification and quantification by internal Standard", Eur. Food Res. Technol., 216:355-364 (2003).
Poouthree, K. et al., "Comparison of resolution in microemulsion EKC and MEKC employing suppressed electroosmosis: Application to bisphenol-A-diglycidyl ether and its derivatives", Electrophoresis, 28(20):3705-3711 (2007).
Poustka, J. et al., "Determination and occurrence of bisphenol A, bisphenol A diglycidyl ether, and bisphenol F diglycidyl ether, including their derivatives, in canned foodstuffs' from the Czech retail market," Czech J. Food Sci., 25(4):221 -229 (2006).

(56) References Cited

OTHER PUBLICATIONS

Poustková et al., "Stability of bisphenol A diglycidyl ether and bisphenol F diglycidyl ether in water-based food simulants." European Food Research and Technology, 219(5): 534-539 (2004).
Quayle, S. et al., "Androgen receptor decoy molecules block the growth of prostate cancer", PNAS, 104(4):1331-1336 (2007).
Rao, B.R. et al., "Endocrine Factors in Common Epithelial Ovarian Cancer", Endocrine Reviews, 12(1):14-26 (1991).
Reader, C. E. L., "Epoxy Resin Derivatives for Stoving Systems", Surface Coatings Australia, 25(10):6-9 (1988).
Reid, J. et al., "Conformational Analysis of the Androgen Receptor Amino-terminal Domain Involved in Transactivation," The Journal of Biological Chemistry, 277:20079-20086 (2002).
Risch, H.A., "Hormonal Etiology of Epithelial Ovarian Cancer, With a Hypothesis Concerning the Role of Androgens and Progesterone", Journal of the National Cancer Institute, 90(23): 1774-1786 (1998).
Riu, A. et al., "Characterization of Novel Ligands of ERα, Erβ, and PPARγ: The Case of Halogenated Bisphenol A and Their Conjugated Metabolites", Toxicology Sciences, 122(2): 372-382 (2011).
Roberts, J. T. et al., "Adenocarcinoma of Prostate in 40-Year-Old Body-Builder", Lancet, 2:742 (1986).
Roberts et al., "Emerging drugs for hepatocellular carcinoma," Expert Opin Emerg Drugs, 11(3):469-487 (2006).
Rokicki, G. et al., "Reactions of 4-chloromethyl-1,3-dioxolan-2-one with phenols as a new route to polyols and cyclic carbonates", Journal f. prakt. Chemie., 327:718-722 (1985).
Ross, R.K. et al., "Androgen Metabolism and Prostate Cancer: Establishing a Model of Genetic Susceptibility", European Urology, 35:355-361 (1999).
Roulin et al., "Targeting renal cell carcinoma with NVP-BEZ235, a dual PI3K/mTOR inhibitor, in combination with sorafenib," Mol Cancer, 10:90 (2011).
Rusu, E. et al.: "Photosensitive compounds with chloromethyl groups", Revue Roumaine de Chimie, 45(5):451 -456 (2000).
Sadar, M., "Androgen-independent Induction of Prostate-specific Antigen Gene Expression via Cross-talk between the Androgen Receptor and Protein Kinase A signal Transduction Pathways," The Journal of Biological Chemistry, 274(12):7777-7783 (1999).
Sadar, M. et al., "Prostate cancer: molecular biology of early progression to androgen independence", Endocrine-Related Cancer, 6:487-502 (1999).
Sadar, M.D. et al., "Characterization of a New in Vivo Hollow Fiber Model for the Study of Progression of Prostate Cancer to Androgen Independence", Molecular Cancer Therapeutics, 1:629-637 (2002).
Sato, N. et al., "Intermittent Androgen Suppression Delays Progression to Androgen-independent Regulation of Prostate-specific Antigen Gene in the LNCaP Prostate Tumour Model", J. Steroid Biochem. Mol. Biol., 58:139-146 (1996).
Sato, N. et al., "A Metastatic and Androgen-sensitive Human Prostate Cancer Model Using Intraprostatic Inoculation of LNCaP Cells in SCID Mice", Cancer Research, 57:1584-1589 (1997).
Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", Food and Chemical Toxicology, 42:983-993 (2004).
Schaefer, A. et al., "Migration from can coatings: Part 3. Synthesis, identification and quantification of migrating epoxy-based substances below 1000 Da", Food Additives and Contaminants, 21(4):390-405 (2004).
Schellhammer, "An evaluation of bicalutamide in the treatment of prostate cancer." Expert Opinion on Pharmacotherapy, 3(9): 1313-1328 (2002).
Sharp et al., "Targeting Androgen Receptor Aberrations in Castration-Resistant Prostate Cancer," Clin Cancer Res., Sep. 1, 2016;22(17):4280-4282.
Silverman, R. B., The Organic Chemistry of Drug Design and Drug Action, Academic Press, Inc., Harcourt Brace Jovanovich, pp. 15-20, 9 pages (1992).

Snoek, R. et al., "Induction of Cell-free, In Vitro Transcription by Recombinant Androgen Receptor Peptides", J. Steroid Biochem. Mol. Biol., 59:243-250 (1996).
Stanciuc et al., "Reaction of Pyrylium Salts with Nucleophiles. 23: Triarylethene Derivatives Containing an Oxyalkyleneamino or Oxyalkylene-N-pyridinium Side Chain", Journal of Pharmaceutical Sciences, vol. 82, No. 9, Sep. 1993, pp. 927-933.
Still, W. C. et al., "Rapid Chromatographic Technique for Preparative Separations with Moderate Resolution", J. Org. Chem., 43(14):2923-2925 (1978).
STN Structure Search, dated Oct. 30, 2014 citing PL 135932, 3 pages.
STrub and McKim, "Dimethyl Sulfoxide USP, PhEur in Approved Pharmaceutical Products and Medical Devices", PharmaTech.com, 6 pages (2008). http://www. pharmtech.com/print/224268?page=full&rel=canonical.
Sun, S. et al., "Castration resistance in human prostate cancer is conferred by a frequently occurring androgen receptor splice variant", The Journal of Clinical Investigation, 120(8):2715-30 (2010).
Tanji, N. et al., "Growth Factors: Roles in Andrology", Archives of Andrology, 47:1-7 (2001).
Taplin, M.E. et al., "Selection for Androgen Receptor Mutations in Prostate cancers Treated with Androgen Antagonist", Cancer Research, 59:2511-2515 (1999).
Taskeen, A. et al., "Analysis of bisphenol A in canned food: A mini review", Asian Journal of Chemistry, 22(5):4133-4135 (2010).
Thomson, A.A., "Role of androgens and fibroblast growth factors in prostatic development", Reproduction, 121:187-195 (2001).
Ueda, T. et al., "Activation of the Androgen Receptor N-terminal Domain by lnterleukin-6 via MAPK and STAT3 Signal Transduction Pathways", The Journal of Biological Chemistry, 277(9):7076-7085 (2002).
Ueda, T. et al., "Ligand-independent Activation of the Androgen Receptor by lnterleukin-6 and the Role of Steroid Receptor Coactivator-1 in Prostate cancer Cells", The Journal of Biological Chemistry, 277(41): 38087-38094 (2002).
Uematsu, Y. et al., "Chlorohydrins of bisphenol A diglycidyl ether (BADGE) and bisphenol F diglycidyl ether (BFDGE) in canned foods and ready-to-drink coffees from the Japanese market", Food Additives and Contaminants, 18(2):177-185 (2001).
Van Der Kwast, T.H. et al., "Androgen Receptors in Endocrine-Therapy-Resistant Human Prostate Cancer", Inter. J. Cancer, 48:189-193 (1991).
Van Scherpenzeel, M. et al., "Nanomolar affinity, iminosugar-based chemical probes for specific labeling of lysosomal glucocerebrosidase", Bioorganic & Medicinal Chemistry, 18:267-273 (2010).
Venkatesh, Srini, and LIPPER, Robert A. "Role of the development scientist in compound lead selection and optimization." Journal of Pharmaceutical Sciences (2000); 89.2:145-154.
Walfried et al., "Bisphenol F-Diglycidylether (BFDGE) und Folgeprodukte in Konservenfullgutern: Synthese und Analytik," Deutsche Lebensmittel-Rundschau, vol. 96, No. 11, 2000, pp. 417-422 (with English abstract).
Wang, G. et al., "Identification of genes targeted by the androgen and PKA signaling pathways in prostate cancer cells", Oncogene, 25:7311-7323 (2006).
Wang, Q. et al., "Spatial and Temporal Recruitment of Androgen Receptor and Its Coactivators Involves Chromosomal Looping and Polymerase Tracking", Molecular Cell, 19:631-642 (2005).
Wetherill, Y. B. et al., "In vitro molecular mechanisms of bisphenol A action," Reproductive Toxicology, 24:178-198 (2007).
Wiedmann and Naqwi, "Pharmaceutical salts: Theory, use in solid dosage forms and in situ preparation in an aerosol." Asian Journal of Pharmaceutical Sciences (2016); 11(6): 722-734.
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
Wilding, G., "The Importance of Steroid Hormones in Prostate Cancer", Cancer Surveys, 14:113-130 (1992).

(56) References Cited

OTHER PUBLICATIONS

Wilson, J.D. et al., "Long-Term Consequences of Castration in Men: Lessons from the Skoptzy and the Eunuchs of the Chinese and Ottoman Courts", The Journal of Clinical Endocrinology & Metabolism, 84:4324-4331 (1999).
Wong, C. et al., "Steroid Requirement for Androgen Receptor Dimerization and DNA Binding", J. Bioi. Chem., 268(25):19004-19012 (1993).
Xu, X. et al., "Synthesis and Stability Study of Dental Monomers Containing Methacrylamidoethyl Phosphonic Acids", Journal of Polymer Science: Part A Polymer Chemistry, 45:99-110 (2007).
Yang et al., "Targeting Androgen Receptor Activation Function-1 with EPI to Overcome Resistance Mechanisms in Castration-Resistant Prostate Cancer," Clin Cancer Res; 22(17) Sep. 1, 2016, 4466-4477.
Ye, Deyong, "An Introduction to Computer-Aided Drug Design", 3 pages, Jan. 31, 2004 (non-English document).
Yong, Eu Leong, et al. "Molecular basis of androgen receptor diseases." Annals of Medicine (2000); 32.1:15-22.
Zuhayra, M. et al., "New approach for the synthesis of [$^{18}$F]fluoroethyltyrosine for cancer imaging: Simple, fast, and high yielding automated synthesis", Bioorganic & Medicinal Chemistry, 17:7441-7448 (2009).
Extended European Search Report in Application No. EP 12768410.8 dated Sep. 22, 2014, 10 pages.
Extended European Search Report in Application No. EP 14793978.9 dated Sep. 1, 2016, 8 pages.
Supplementary European Search Report in EP Application No. 09771876.1 dated Jun. 20, 2011, 5 pages.
Supplementary European Search Report in EP Application No. 11731645.5 dated Jun. 20, 2013, 11 pages.
Extended European Search Report in Application No. EP 14843037.4 dated Mar. 8, 2017, 5 pages.
Extended European Search Report in Application No. EP 17177010.0 dated Oct. 20, 2017, 10 pages.
Extended European Search Report in Application No. 16736999.0 dated May 24, 2018, 14 pages.
Extended European Search Report for European Application No. 17781660.0 dated Oct. 31, 2019, 8 pages.
Decision of Refusal for Japanese Application No. 2011-515039, dated Dec. 2, 2014, 18 pages (English translation).
International Search Report for International Application No. PCT/CA2009/000902 dated Sep. 1, 2009, 4 pages.
Written Opinion for International Application No. PCT/CA2009/000902 dated Sep. 1, 2009, 6 pages.
International Preliminary Report on Patentability for International Application No. PCT/CA2009/000902 dated Jan. 5, 2011, 7 pages.
International Search Report for International Application No. PCT/US2012/032584 dated Jul. 31, 2012, 3 pages.
Written Opinion for International Application No. PCT/US2012/032584 dated Jul. 31, 2012, 5 pages.
International Preliminary Report on Patentability for PCT/US2012/032584 dated Oct. 8, 2013, 6 pages.
International Search Report for International Application No. PCT/US2012/033959 dated Jul. 18, 2012, 3 pages.
Written Opinion for International Application No. PCT/US2012/033959 dated Jul. 18, 2012, 7 pages.
International Preliminary Report on Patentability for International Application No. PCT/US2012/033959 dated Oct. 22, 2013, 8 pages.
International Search Report for International Application No. PCT/US2012/033957 dated Jul. 18, 2012, 3 pages.
Written Opinion for International Application No. PCT/US2012/033957 dated Jul. 18, 2012, 5 pages.
International Preliminary Report on Patentability for International Application No. PCT/US2012/033957 dated Oct. 22, 2013, 6 pages.
International Search Report for International Application No. PCT/CA2011/000019 dated Mar. 21, 2011, 7 pages.
Written Opinion for International Application No. PCT/CA2011/000019 dated Mar. 21, 2011, 7 pages.
International Preliminary Report on Patentability for International Application No. PCT/CA2011/000019 dated Jul. 10, 2012, 8 pages.
International Search Report for International Application No. PCT/CA2011/000021 dated Apr. 18, 2011, 8 pages.
Written Opinion for International Application No. PCT/CA2011/000021 dated Apr. 18, 2011, 7 pages.
International Preliminary Report on Patentability for International Application No. PCT/CA2011/000021 dated Jul. 10, 2012, 8 pages.
International Search Report for International Application No. PCT/US2012/051481 dated Nov. 26, 2012, 4 pages.
Written Opinion for International Application No. PCT/US2012/051481 dated Nov. 26, 2012, 7 pages.
International Preliminary Report on Patentability for International Application No. PCT/US2012/051481 dated Feb. 25, 2014, 8 pages.
International Search Report for International Application No. PCT/US2012/051923 dated Jan. 28, 2013, 4 pages.
Written Opinion for International Application No. PCT/US2012/051923 dated Jan. 28, 2013, 8 pages.
International Preliminary Report on Patentability for International Application No. PCT/US2012/051923 dated Feb. 25, 2014, 9 pages.
International Search Report and Written Opinion for International Application No. PCT/CA2014/000414 dated Aug. 5, 2014, 6 pages.
International Preliminary Report on Patentability for International Application No. PCT/CA2014/000414 dated Nov. 10, 2015, 7 pages.
International Search Report and Written Opinion for International Application No. PCT/CA2014/000685 dated Dec. 4, 2014, 13 pages.
International Preliminary Report on Patentability for International Application No. PCT/CA2014/000685 dated Mar. 15, 2016, 7 pages.
International Search Report and Written Opinion for International Application No. PCT/CA2015/000533 dated Dec. 18, 2015, 11 pages.
International Preliminary Report on Patentability for International Application No. PCT/CA2015/000533 dated Apr. 18, 2017, 7 pages.
International Search Report and Written Opinion for International Application No. PCT/CA2015/000535 dated Dec. 23, 2015, 9 pages.
International Preliminary Report on Patentability for International Application No. PCT/CA2015/000535 dated Apr. 18, 2017, 6 pages.
International Search Report and Written Opinion for International Application No. PCT/CA2016/000008 dated Mar. 15, 2016, 13 pages.
International Preliminary Report on Patentability for International Application No. PCT/CA2016/000008 dated Jul. 18, 2017, 7 pages.
International Search Report and Written Opinion for International Application No. PCT/CA2016/000070 dated Jun. 2, 2016, 10 pages.
International Search Report and Written Opinion for International Application No. PCT/CA2017/000083 dated Aug. 3, 2017, 14 pages.
International Preliminary Report on Patentability for International Application No. PCT/CA2016/000070 dated Sep. 12, 2017, 6 pages.
International Search Report and Written Opinion for International Application No. PCT/CA2017/000141 dated Sep. 1, 2017, 11 pages.
International Search Report and Written Opinion for International Application No. PCT/CA2017/000201 dated Dec. 8, 2017, 9 pages.
International Search Report and Written Opinion for International Application No. PCT/US2019/057034 dated Feb. 6, 2020, 10 pages.
Alabi, A. et al., "Quick and simple sample treatment for multiresidue analysis of bisphenols, bisphenol diglycidyl ethers and their derivatives in canned food prior to liquid chromatography and fluorescence detection," J. of Chromatography A, 2014, 1336, 23-33.
Banker (ed.) et al., Modern Pharmaceutics, Third Edition, Revised and Expanded, Marcel Dekker, Inc., 1997, pp. 451 and 596.
Vippagunta et al., "Crystalline solids," Advanced Drug Delivery Reviews (2001) 48: 3-26.
Wolff (ed.) et al., Burger's Medicinal Chemistry and Drug Discovery, Fifth Edition, vol. I: Principles and Practice, 1995, pp. 975-977.

(56) References Cited

OTHER PUBLICATIONS

Yonekubo, J. et al., "Concentrations of Bisphenol A, Bisphenol A Diglycidyl Ether, and Their Derivatives in Canned Foods in Japanese Markets," J. Agric. Food Chem., 2008, 56, 2041-2047.

* cited by examiner

HETEROCYCLIC COMPOUNDS FOR CANCER IMAGING AND TREATMENT AND METHODS FOR THEIR USE

CROSS-REFERENCE TO RELATED APPLICATIONS

This application is a divisional application of U.S. application Ser. No. 15/543,389, filed on Jul. 13, 2017, which claims priority to U.S. Provisional Application No. 62/102,719, filed on Jan. 23, 2015, the disclosures of which are hereby incorporated by reference in their entirety for all purposes.

STATEMENT OF GOVERNMENT INTEREST

This invention was made in part with government support under Grant No. 2R01 CA105304 awarded by the National Cancer Institute. The United States Government has certain rights in this invention.

TECHNICAL FIELD

This invention generally relates to bisphenol-related compounds and their use for treatment of various indications. In particular the invention relates to bisphenol ether compounds having novel heterocyclic groups and their use for treatment of various cancers, for example all stages of prostate cancer, including androgen dependent, androgen sensitive and castration-resistant prostate cancers. This invention also relates to bisphenol-related compounds and their use for modulating androgen receptor (AR) activity.

This invention further relates to radiolabeled bisphenol-related compounds and their use in methods for imaging the prostate gland. For example, in certain embodiments the compounds are useful for imaging benign prostate diseases such as benign prostate hyperplasia. In other embodiments, the compounds are useful for imaging cancerous prostate diseases, such as prostate cancer tumors. In certain embodiments the invention relates to radioactive $^{123}$I compounds and their use as an imaging tool in prostate cancer and benign prostate diseases. The disclosed compounds find utility in any number of imaging applications, including imaging of androgen receptor (AR) splice variants in prostate cancers, including all stages and androgen dependent, androgen-sensitive and castration-resistant prostate cancers (also referred to as hormone refractory, androgen-independent, androgen deprivation resistant, androgen ablation resistant, androgen depletion-independent, castration-recurrent, anti-androgen-recurrent).

DESCRIPTION OF THE RELATED ART

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration (androgen ablation).

Androgens also play a role in female diseases such as polycystic ovary syndrome as well as cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate epithelial cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 *Scand J. Urol Nephrol.* 104, 33-39). Castration-resistant prostate cancer is biochemically characterized before the onset of symptoms by a rising titre of serum PSA (Miller et al 1992 *J. Urol.* 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains one or more transcriptional activation domains. Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR can be activated in the absence of testicular androgens by alternative signal transduction pathways in castration-resistant disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Available inhibitors of the AR include nonsteroidal antiandrogens such as bicalutamide (Casodex™), nilutamide, flutamide, enzulutamide and investigational drug ARN-509 and steroidal antiandrogens, such as cyproterone acetate. These antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.,* 59, 2511-2515 (1999)). These antiandrogens would also have no effect on the recently discovered AR splice variants that lack the ligand-binding domain (LBD) to result in a constitutively active receptor which promotes progression of castration recurrent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 *Cancer Res.* 69, 16-22; Sun et al 2010 *J Clin Invest.* 2010 120, 2715-30).

Conventional therapy has concentrated on androgen-dependent activation of the AR through its C-terminal domain. Studies developing antagonists to the AR have concentrated on the C-terminus and specifically: 1) the allosteric pocket and AF-2 activity (Estébanez-Perpiñá et al 2007, *PNAS* 104, 16074-16079); 2) in silico "drug repurposing" procedure for identification of nonsteroidal antagonists (Bisson et al 2007, *PNAS* 104, 11927-11932); and coactivator or corepressor interactions (Chang et al 2005, *Mol Endocrinology* 19, 2478-2490; Hur et al 2004, *PLoS Biol* 2, E274; Estébanez-Perpiñá et al 2005, *JBC* 280, 8060-8068; He et al 2004, *Mol Cell* 16, 425-438).

The AR-NTD is also a target for drug development (e.g. WO 2000/001813), since the NTD contains Activation-Function-1 (AF-1) which is the essential region required for AR transcriptional activity (Jenster et al 1991. *Mol Endocrinol.* 5, 1396-404). The AR-NTD importantly plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR C-terminus LBD, this has not been the case for the NTD due to its high flexibility and intrinsic disorder in solution (Reid et al 2002 *J. Biol. Chem.* 277, 20079-20086) thereby hampering virtual docking drug discovery approaches. Compounds that modulate AR include the bis-phenol compounds disclosed in published PCT Nos: WO 2010/000066, WO 2011/082487; WO 2011/082488; WO 2012/145330; WO 2012/139039; WO 2012/145328; WO 2013/028572; WO 2013/028791; and WO 2014/179867, which are hereby incorporated by reference in their entireties, to the British Columbia Cancer Agency Branch and The University of British Columbia.

In addition to compounds which modulate AR, compounds and methods for imaging the prostate are useful research, diagnostic and prognostic tools. Such compounds are useful in many applications, including imaging of benign and/or malignant prostate cells and tissue. In this regard, positron emission tomography (PET) is an often used imaging technique for non-invasive identification of pathological state and tumors. In PET imaging, the distribution of a radioisotope (e.g., $^{18}$F) in the body can be determined. Thus incorporating $^{18}$F into compounds which concentrate in tumor sites (see e.g., WO 2013/028791) offers potential for diagnosis, staging, and monitoring treatment of cancers. However, improved methods for imaging are needed, for example methods which employ $^{123}$I and single photon emission coupled tomography (SPECT) techniques have potential to improve methods for imaging AR-rich tissues such as the benign prostate, and in particular prostate cancers and AR splice variants in castrate recurrent prostate cancers.

While significant advances have been made in this field, there remains a need for improved imaging agents. In particular, methods and compounds suitable for imaging benign and malignant prostate tissues and cells are needed. The present invention fulfills these needs, and provides other related advantages.

BRIEF SUMMARY

Some embodiments of the compounds described herein can be used for diagnostic purposes to investigate diseases of the prostate, including cancer. In particular embodiments, the compounds are useful for imaging diagnostics in cancer. In some embodiments, such imaging allows for the detection and/or location of cancer sites (e.g., tumor sites). Furthermore, these compounds can be used individually or as part of a kit for such purposes.

The present disclosure is based in part on the surprising discovery that the compounds described herein, can be used to modulate AR activity either in vivo or in vitro for both research and therapeutic uses. Accordingly, embodiments of the compounds are useful for imaging the prostate. The imaging can be for any number of diagnostic purposes. For example, in certain embodiments the compounds are useful for imaging benign prostate cancer diseases. In other embodiments, the compounds find utility for imaging of certain cancers, including prostate cancer since certain embodiments of the compounds localize in prostate tumor sites. Other imaging agents are androgen mimics; however, in one embodiment, the compounds are useful for imaging AR splice variants or any AR species (i.e., those mutated in other domains or regions). The AR can be mammalian. For example, the AR can be human. The prostate cancer can be castration-resistant prostate cancer. The prostate cancer can be androgen-dependent prostate cancer.

In accordance with one embodiment, there is provided a compound having a structure of Formula I:

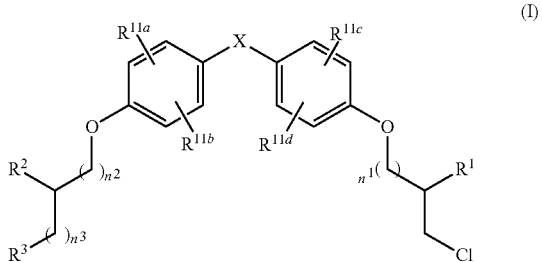

(I)

or a pharmaceutically acceptable salt, tautomer or stereoisomer thereof, wherein $R^1$, $R^2$, $R^3$, $R^{11a}$, $R^{11b}$, $R^{11c}$, $R^{11d}$, X, $n^1$, $n^2$ and $n^3$ are as defined herein. In one embodiment, the compound of Formula (I) comprising at least one F, Cl, Br, I, $^{18}F$ or $^{123}I$ moiety, are provided.

In other embodiments pharmaceutical compositions comprising a compound of Formula (I) are provided. Methods employing such pharmaceutical compositions for imaging cancer are also provided. Methods for modulating AR activity employing the present compounds and pharmaceutical compositions are also provided.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE FIGURES

FIG. 5 is a $^1H$ NMR spectrum of Compound 1a.
FIG. 6 is a $^{13}C$ NMR spectrum of Compound 1a.
FIG. 7 is a $^1H$ NMR spectrum of Compound 25a.
FIG. 8 is a $^{13}C$ NMR spectrum of Compound 25a.
FIG. 13 is a $^1H$ NMR spectrum of Compound 4a.
FIG. 14 is a $^{13}C$ NMR spectrum of Compound 5a.
FIG. 15 is a $^1H$ NMR spectrum of Compound 28a.
FIG. 16 is a $^{13}C$ NMR spectrum of Compound 28a.

DETAILED DESCRIPTION

I. Definitions

Figure 1:
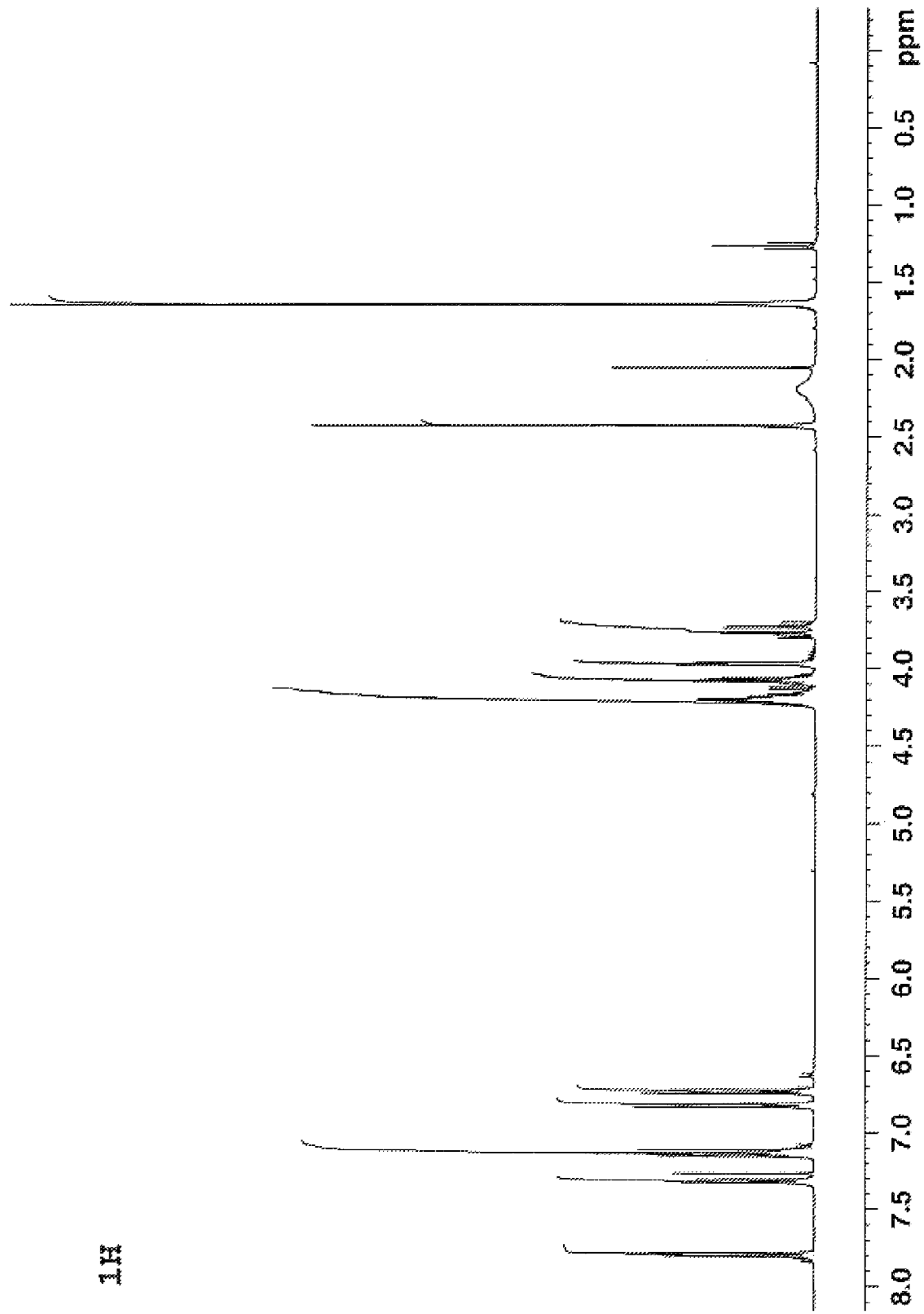
FIG. 1 is a $^1H$ NMR spectrum of Compound i-H.

In the following description, certain specific details are set forth in order to provide a thorough understanding of various embodiments. However, one skilled in the art will understand that the invention can be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.
"Cyano" refers to the —CN radical.
"Halo" or "halogen" refers to bromo, chloro, fluoro or iodo radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes C and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —$OR_a$ where $R_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —$NHR_a$ or —$NR_aR_a$ where each $R_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —$C(=O)R_a$ moiety, wherein $R_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in $R_a$, as defined above. For example, "$C_1$-$C_{10}$ acyl" refers to alkylcarbonyl group as defined above, where $R_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" refers to a radical of the formula —$R_b$—$R_c$ where $R_b$ is an alkylene, alkenylene or alkynylene group as defined above and $R_c$ is one or more aryl radicals as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclcl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heterocyclylalkyl" refers to a radical of the formula —$R_b$—$R_e$ where $R_b$ is an alkylene, alkenylene, or alkynylene chain as defined above and $R_c$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, bcnzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene, alkenylene, or alkynylene chain as defined above and $R_f$ is a heteroaryl radical as defined above. Unless stated otherwise specifically in the specification, a heteroarylalkyl group can be optionally substituted.

"$^{123}$I" refers to the radioactive isotope of iodine having atomic mass 123. The compounds of Formula I can comprise at least one $^{123}$I moiety. Throughout the present application, where structures depict a $^{123}$I moiety at a certain position it is meant that the I moiety at this position is enriched for $^{123}$I. In other words, the compounds contain more than the natural abundance of $^{123}$I at the indicated position(s). It is not required that the compounds comprise 100% $^{123}$I at the indicated positions, provided $^{123}$I is present in more than the natural abundance. Typically the $^{123}$I isotope is enriched to greater than 50%, greater than 60%, greater than 70%, greater than, 80% or greater than 90%, relative to $^{127}$I.

"$^{18}$F" refers to the radioactive isotope of fluorine having atomic mass 18. "F" or "$^{19}$F" refers to the abundant, non-radioactive fluorine isotope having atomic mass 19. The compounds of Formula I can comprise at least one $^{18}$F moiety. Throughout the present application, where structures depict a $^{18}$F moiety at a certain position it is meant that the F moiety at this position is enriched for $^{18}$F. In other words, the compounds contain more than the natural abundance of $^{18}$F at the indicated position(s). It is not required that the compounds comprise 100% $^{18}$F at the indicated positions, provided $^{18}$F is present in more than the natural abundance. Typically the $^{18}$F isotope is enriched to greater than 50%, greater than 60%, greater than 70%, greater than 80% or greater than 90%, relative to $^{19}$F.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

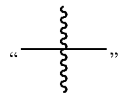

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

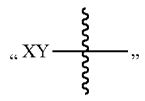

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

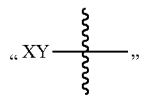

infers that when $R^3$ is "XY", the point of attachment bond is the same bond as the bond by which $R^3$ is depicted as being bonded to $CH_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

The invention disclosed herein is also meant to encompass the in vivo metabolic products of the disclosed compounds. Such products can result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

As used herein, a "subject" can be a human, non-human primate, mammal, rat, mouse, cow, horse, pig, sheep, goat, dog, cat and the like. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances can or can not occur, and that the description includes instances where said event or circumstance occurs and instances in which it does not. For example, "optionally substituted aryl" means that the aryl radical can or can not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent can be water, in which case the solvate can be a hydrate. Alternatively, the solvent can be an organic solvent. Thus, the compounds of the present invention can exist as a hydrate, including a monohydrate, dihydrate, hemihydrate, sesquihydrate, trihydrate, tetrahydrate and the like, as well as the corresponding solvated forms. The compound of the invention can be true solvates, while in other cases, the compound of the invention can merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound can vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to a castration-resistant form. Typically, a prophylactic dose is used in subjects prior to or at an earlier stage of disease, so that a prophylactically effective amount can be less than a therapeutically effective amount.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" can be used interchangeably or can be different in that the particular malady or condition can not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 software naming program (CambridgeSoft). For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

Throughout the present specification, the terms "about" and/or "approximately" can be used in conjunction with numerical values and/or ranges. The term "about" is understood to mean those values near to a recited value. For example, "about 40 [units]" can mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" can be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range can be an endpoint for the range encompassed thereby (e.g., the range 50-80 includes the ranges with endpoints such as 55-80, 50-75, etc.).

II. Compounds and Pharmaceutical Compositions

As noted above, certain embodiments of the present invention are directed to compounds useful for treatment of various cancers, including various types of prostate cancers. While not wishing to be bound by theory, it is believed that binding of the compounds to the androgen receptor (for example at the N-terminal domain) can contribute to the activity of the disclosed compounds. The compounds of the present invention include novel heteroaryl, aryl, heterocyclyl, or carbocyclyl groups (i.e., $R^3$ in Formula I) which impart improved properties to the compounds compared to compounds lacking the described $R^3$ moiety. For example, the improved properties include improved drug-like properties such as improved activity (e.g., androgen receptor (AR) modulation), longer half-life (e.g., in vivo); decreased toxicity; better solubility, improved formulation, better bioavailability, better pharmacokinetic profile; reduction in unwanted metabolites and the like.

In one embodiment the invention includes compounds which form covalent bonds with the androgen receptor (AR) (e.g., at the N-terminal domain), thus resulting in irreversible (or substantially irreversible) inhibition of the same. In this regard, the certain compounds of the present invention are designed to include functional groups capable of forming covalent bonds with a nucleophile under certain in vivo conditions. For example, in some embodiments the reactivity of compounds of the present invention is such that they will not substantially react with various nucleophiles (e.g., glutathione) when the compounds are free in solution. However, when the free mobility of the compounds is restricted, and an appropriate nucleophile is brought into close proximity to the compound, for example when the compounds associate with, or bind to, the androgen receptor, the compounds are capable of forming covalent bonds with certain nucleophiles (e.g., thiols).

The present invention includes all compounds which have the above described properties (i.e., binding to androgen receptor (AR)). In one embodiment, the present invention is directed to a compound having a structure of Formula I:

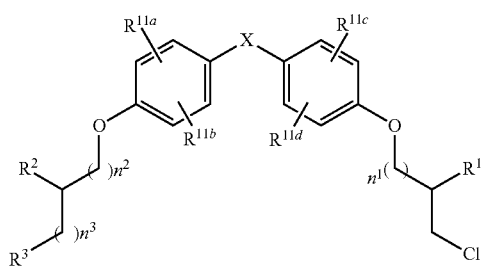

(I)

or a pharmaceutically acceptable salt, tautomer or stereoisomer thereof, wherein:

X is —O—, —S(O)$_{0-2}$—, —C(=O)—, —C(OR$^5$)$_2$—, —C(OR$^5$)(OC(=O)R$^{13}$)—, —C(R$^8$R$^9$)—, —C(=CR$^8$R$^9$)—, —N(R$^9$)—, —N(COR$^9$)—, —CHNR$^8$R$^9$—, —C(=NR$^5$)—, —C(=NOR$^5$)—, —C(=N—NHR$^5$)—;

R$^1$ and R$^2$ are each independently H, hydroxyl, —O-heterocyclyl, or —OC(=O)R$^3$;

R$^3$ is —N$_3$, aryl, carbocyclyl, heteroaryl or heterocyclyl which are optionally substituted with one or more R$^6$;

R$^5$ is each independently H, C$_1$-C$_6$ alkyl, C$_2$-C$_6$ alkenyl, or C$_2$-C$_6$ alkynyl;

R$^6$ is each independently selected from the group consisting of H, F, Cl, Br, I, $^{123}$I, hydroxyl, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;

R$^8$ and R$^9$ are each independently H, halogen, —S(O)$_{0-2}$R$^5$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^5$, or R$^8$ and R$^9$ can join to form a unsubstituted or substituted mono-, bi-, or tricyclic carbocycle or heterocycle containing from 3 to 20 carbon atoms;

R$^{11a}$, R$^{11b}$, R$^{11c}$ and R$^{11d}$ are each independently H, F, Cl, Br, I, $^{123}$I, hydroxyl, C$_1$-C$_6$ alkyl, C$_2$-C$_6$ alkenyl, or C$_2$-C$_6$ alkynyl; —OR$^5$, —OC(=O)R$^{13}$, C$_1$-C$_{10}$ acyl, —S(O)$_{0-2}$R$^5$, —NO$_2$, —CN, —NH$_2$, —NHR$^5$, or —N(R$^5$)$_2$;

R$^{13}$ is each independently C$_1$-C$_6$ alkyl, C$_2$-C$_6$ alkenyl, or C$_2$-C$_6$ alkynyl;

n$^1$ and n$^2$ are each independently 0, 1, or 2; and n$^3$ is 0, 1, 2, 3, 4, or 5.

Accordingly, certain embodiments of the present invention are directed to compounds that bind to the AR NTD and are useful for imaging of tumors with splice variants using SPECT and/or methods of modulating AR NTD activity.

Other embodiments are directed to compound and methods useful for imaging and/or treating benign prostate conditions or diseases. In one embodiment, the present disclosure provides a compound having a structure of Formula I:

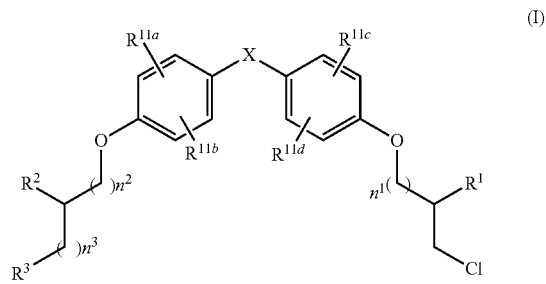

(I)

or a pharmaceutically acceptable salt, tautomer or stereoisomer thereof, wherein:

X is —O—, —S(O)$_{0-2}$—, —C(=O)—, —C(OR$^5$)$_2$—, —C(OR$^5$)(OC(=O)R$^{13}$)—, —C(R$^8$R$^9$)—, —C(=CR$^8$R$^9$)—, —N(R$^9$)—, —N(COR$^9$)—, —CHNR$^8$R$^9$—, —C(=NR$^9$)—, —C(=NOR$^5$)—, —C(=N—NHR$^5$)—;

R$^1$ and R$^2$ are each independently H, hydroxyl, —O-heterocyclyl, or —OC(=O)R$^{13}$;

R$^3$ is —N$_3$, aryl, carbocyclyl, heteroaryl or heterocyclyl which are optionally substituted with one or more R$^6$;

R$^5$ is each independently H, C$_1$-C$_6$ alkyl, C$_2$-C$_6$ alkenyl, or C$_2$-C$_6$ alkynyl;

R$^6$ is each independently selected from the group consisting of H, F, Cl, Br, I, $^{123}$I, hydroxyl, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;

R$^8$ and R$^9$ are each independently H, halogen, —S(O)$_{0-2}$R$^5$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^5$, or R$^8$ and R$^9$ can join to form a unsubstituted or substituted mono-, bi-, or tricyclic carbocycle or heterocycle containing from 3 to 20 carbon atoms;

R$^{11a}$, R$^{11b}$, R$^{11c}$ and R$^{11d}$ are each independently H, F, Cl, Br, I, $^{123}$I, hydroxyl, C$_1$-C$_6$ alkyl, C$_2$-C$_6$ alkenyl, or C$_2$-C$_6$ alkynyl; —OR$^5$, —OC(=O)R$^{13}$, C$_1$-C$_{10}$ acyl, —S(O)$_{0-2}$R$^5$, —NO$_2$, —CN, —NH$_2$, —NHR$^5$, or —N(R$^5$)$_2$;

R$^{13}$ is each independently C$_1$-C$_6$ alkyl, C$_2$-C$_6$ alkenyl, or C$_2$-C$_6$ alkynyl;

n$^1$ and n$^2$ are each independently 0, 1, or 2; and n$^3$ is 0, 1, 2, 3, 4, or 5.

In various embodiments, different stereoisomers of the compound of structure (I) are provided, for example in some embodiments the compound has one of the following structures (Ia), (Ib), (Ic) or (Id):

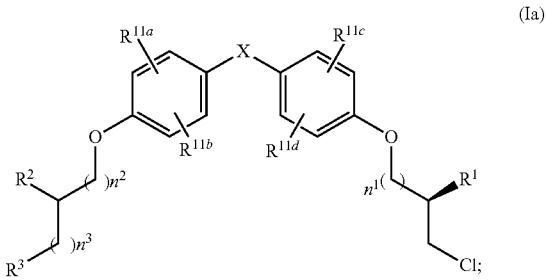

(Ia)

-continued

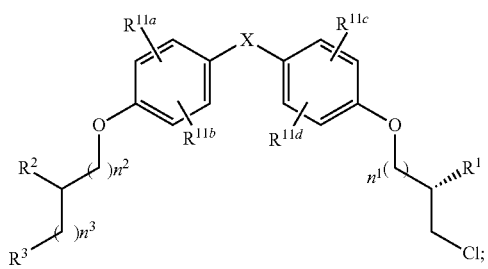
(Ib)

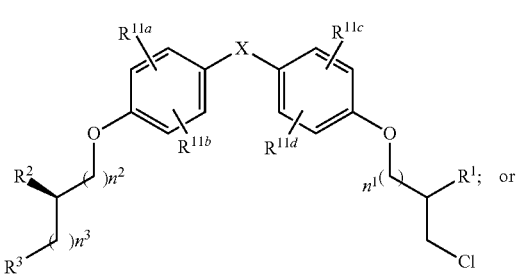
(Ic)

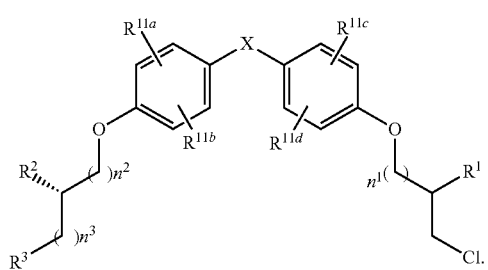
(Id)

In still other embodiments, the compound has one of the following structures (Ie), (If), (Ig) or (Ih):

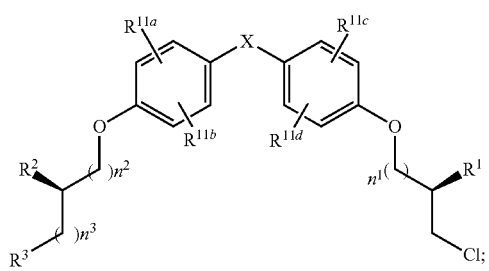
(Ie)

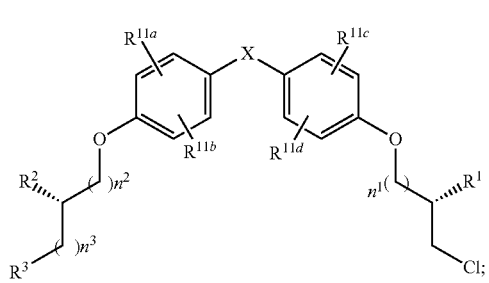
(If)

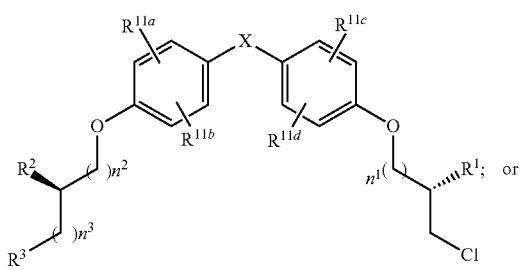
(Ig)

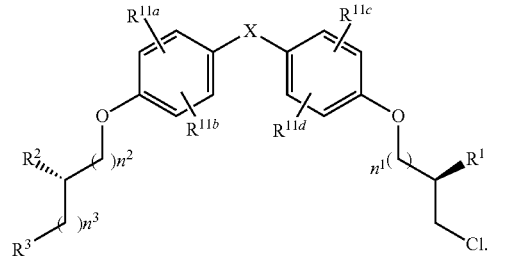
(Ih)

In some embodiments, X is —O—. In other embodiments, X is —S(O)$_{0-2}$—. In some embodiments, X is —C(=O)—. In one embodiment, X is —C(OR$^5$)$_2$—. In one embodiment, X is —C(OR$^5$)(OC(=O)R$^{13}$)—. In some embodiments, X is —C(R$^8$R$^9$)—. In some embodiments, X is —C(=CR$^8$R$^9$)—. In other embodiments, X is —N(R$^9$)—. In one embodiment, X is —N(COR$^9$)—. In one embodiment, X is —CHNR$^8$R$^9$—. In another embodiment, X is —C(=NR$^9$)—. In some embodiments, X is —C(=NOR$^5$)—. In other embodiments, X is —C(=N—NHR$^5$)—.

In some embodiments, X is —C(R$^8$R$^9$)— wherein R$^8$ and R$^9$ are each independently H, C$_1$-C$_{10}$ alkyl, C$_2$-C$_{10}$ alkenyl, or C$_2$-C$_{10}$ alkynyl. In some embodiments, X is —C(R$^8$R$^9$)— wherein R$^8$ and R$^9$ are each independently H or C$_1$-C$_{10}$ alkyl. In other embodiments, X is —C(R$^8$R$^9$)— wherein R$^8$ and R$^9$ are each independently C$_1$-C$_{10}$ alkyl. In some embodiments, X is —C(R$^8$R$^9$)— wherein R$^8$ and R$^9$ are each independently C$_1$-C$_5$ alkyl. In one embodiment, X is —C(R$^8$R$^9$)— wherein R$^8$ and R$^9$ are each independently C$_1$ alkyl. In another embodiment, X is —C(R$^8$R$^9$)— wherein R$^8$ and R$^9$ are each independently a methyl.

In certain of the foregoing embodiments, R$^3$ is 5-6 membered heteroaryl or 3-7 membered heterocylyl, wherein said heteroaryl or said heterocyclyl comprises at least one N atom in the ring.

In another embodiment, R$^3$ is selected from the group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine. In one embodiment R$^3$ is selected form the group consisting of triazole, morpholine, thiomorpholine, pyrazole, and imidazole.

In one embodiment, R$^3$ is substituted with at least one R$^6$. In some embodiments, R$^3$ is substituted with at least one $^{123}$I, I, Br, Cl, or F. In another embodiment, R$^3$ is substituted with at least one $^{123}$I or.

In one embodiment, R$^3$ is substituted with at least one R$^6$ which is further substituted with at least one $^{123}$I, I, or F. In another embodiment, $R^3$ is substituted with at least one $R^6$ which is $C_1$-$C_6$ alkyl, and said $C_1$-$C_6$ alkyl is further substituted with at least one $^{123}$I, I, or F. In some embodiments, $R^3$ is substituted with at least one $R^6$ which is $C_1$-$C_6$ alkyl, and said $C_1$-$C_6$ alkyl is further substituted with at least one [123]I. In other embodiments, $R^3$ is substituted with at least one $R^6$ which is $C_1$-$C_6$ alkyl, and said $C_1$-$C_6$ alkyl is further substituted with at least one [18]F.

In one embodiment, at least one of $R^5$, $R^{11a}$, $R^{11b}$, $R^{11c}$ and $R^{11d}$ is I. In another embodiment, at least one of $R^5$, $R^{11a}$, $R^{11b}$, $R^{11c}$ and $R^{11d}$ is [123]I. In some embodiments, at least one of $R_5$, $R^{11a}$, $R^{11b}$, $R^{11c}$ and $R^{11d}$ is I and at least one of $R^5$, $R^{11a}$, $R^{11b}$, $R^{11c}$ and $R^{11d}$ is [123]I.

In some embodiments, $R^{13}$ is $C_1$-$C_3$ alkyl. In other embodiments, $R^{13}$ is methyl, ethyl, or propyl. In one embodiment, $R^{13}$ is a methyl.

In one embodiment, $n^3$ is 0, 1, or 2.

The compounds for use in the imaging and treatment methods described herein. In some embodiments, the compounds comprise one F, Cl, Br, I, $^{18}$F or $^{123}$I substitution. For example in certain other embodiments, three of $R^{11a}$, $R^{11b}$, $R^{11c}$ and $R^{11d}$ are H, and the remaining $R^{11a}$, $R^{11b}$, $R^{11c}$ or $R^{11d}$ is F, Cl, Br, I or [123]I. In some embodiments, the compounds comprise two F, Cl, Br, I or $^{123}$I substitutions on the phenyl rings (i.e., two of $R^{11a}$, $R^{11b}$, $R^{11c}$ and $R^{11d}$ are H, and the other two of $R^{11a}$, $R^{11b}$, $R^{11c}$ or $R^{11d}$ are F, Cl, Br, I or $^{123}$I). In other embodiments, the compounds comprise three F, Cl, Br, I or $^{123}$I substitutions (i.e., one of $R^{11a}$, $R^{11b}$, $R^{11c}$ and $R^{11d}$ is H, and the remaining $R^{11a}$, $R^{11b}$, $R^{11c}$ or $R^{11d}$ is F, Cl, Br, I or $^{123}$I) and in other embodiments the compounds comprise four F, Cl, Br, I or $^{123}$I substitutions (i.e., each of $R^{11a}$, $R^{11b}$, $R^{11c}$ and $R^{11d}$ are F, Cl, Br, I or $^{123}$I).

In another embodiment, the compound comprise one or more F, Cl, Br, I or $^{123}$I substitutions for $R^3$. In one embodiment, the compound comprise one or more I or $^{123}$I substitutions for $R^3$.

In some embodiments, the compound comprises at least one $R^6$ substituent on $R^3$, wherein at least one $R^6$ is further substituted with at least one of $^{123}$I, I, or [18]F.

Favorable imaging and/or AR NTD modulating results can be obtained by substitution with F, Cl, Br, I or $^{123}$I at any of the "$R^{11}$" positions. In some of the foregoing embodiments, $R^{11a}$ is [123]I. In other embodiments, $R^{11c}$ is [123]I.

In some more specific embodiments of the compound of Formula I, the compound has one of the following structures from Table 1, or a pharmaceutically acceptable salt, tautomer, or stereoisomer thereof:

TABLE 1

| No. | Structure | Name |
|---|---|---|
| 1 | 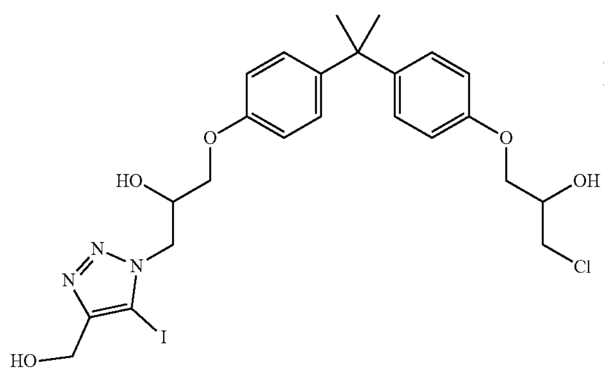 | 1-chloro-3-(4-(2-(4-(2-hydroxy-3-(4-(hydroxymethyl)-5-iodo-1H-1,2,3-triazol-1-yl)propoxy)phenyl)propan-2-yl)phenoxy)propan-2-ol |
| 1a | 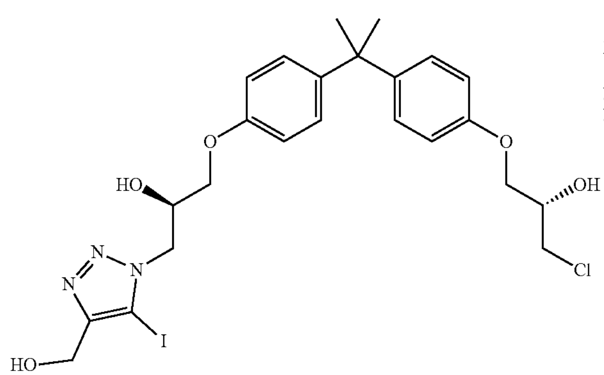 [SMILES: CC(C)(c1ccc(OC[C@H](O)CCl)cc1)c1ccc(OC[C@H](O)Cn2nnc(CO)c2I)cc1] | (S)-1-chloro-3-(4-(2-(4-((R)-2-hydroxy-3-(4-(hydroxymethyl)-5-iodo-1H-1,2,3-triazol-1-yl)propoxy)phenyl)propan-2-yl)phenoxy)propan-2-ol |

TABLE 1-continued

Compounds

| No. | Structure | Name |
|---|---|---|
| 1b | 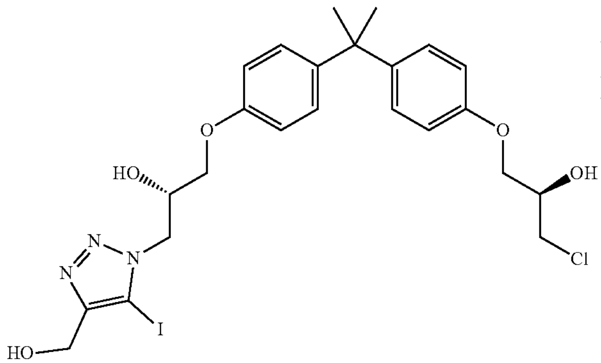 [SMILES: CC(C)(c1ccc(OC[C@@H](O)Cn2nnc(CO)c2I)cc1)c1ccc(OC[C@@H](O)CCl)cc1] | (R)-1-chloro-3-(4-(2-(4-(4-((S)-2-hydroxy-3-(4-(hydroxymethyl)-5-iodo-1H-1,2,3-triazol-1-yl)propoxy)phenyl)propan-2-yl)phenoxy)propan-2-ol |
| 1c | 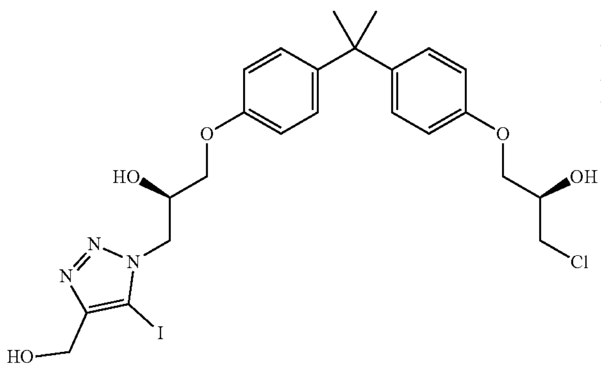 [SMILES: CC(C)(c1ccc(OC[C@@H](O)CCl)cc1)c1ccc(OC[C@H](O)Cn2nnc(CO)c2I)cc1] | (R)-1-chloro-3-(4-(2-(4-(4-((R)-2-hydroxy-3-(4-(hydroxymethyl)-5-iodo-1H-1,2,3-triazol-1-yl)propoxy)phenyl)propan-2-yl)phenoxy)propan-2-ol |
| 1d | 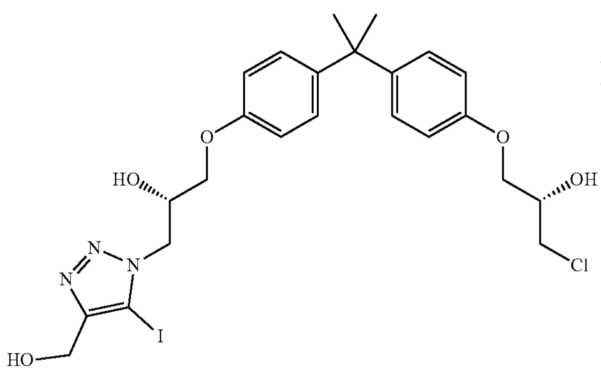 | (S)-1-chloro-3-(4-(2-(4-(4-((S)-2-hydroxy-3-(4-(hydroxymethyl)-5-iodo-1H-1,2,3-triazol-1-yl)propoxy)phenyl)propan-2-yl)phenoxy)propan-2-ol |
| 2 | 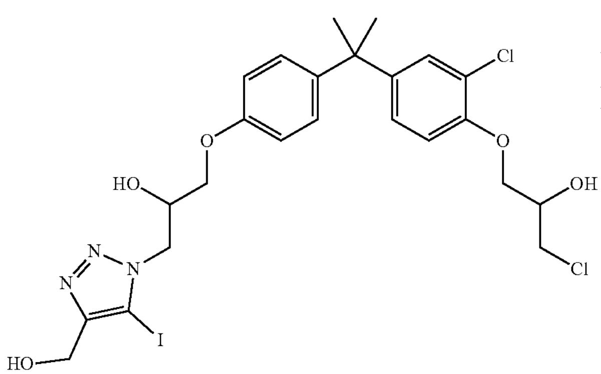 | 1-chloro-3-(2-chloro-4-(2-(4-(2-hydroxy-3-(4-(hydroxymethyl)-5-iodo-1H-1,2,3-triazol-1-yl)propoxy)phenyl)propan-2-yl)phenoxy)propan-2-ol |

TABLE 1-continued

| No. | Structure | Name |
|---|---|---|
| 2a | 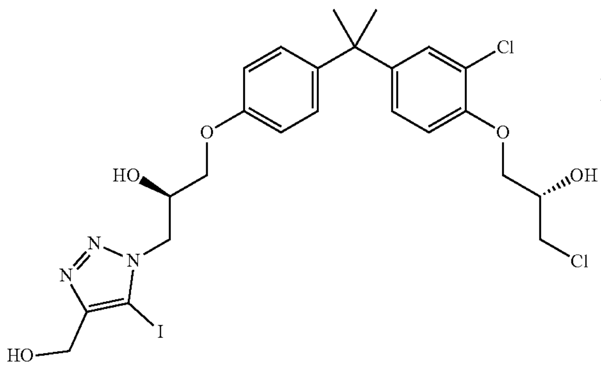 | (S)-1-chloro-3-(2-chloro-4-(2-(4-((R)-2-hydroxy-3-(4-(hydroxymethyl)-5-iodo-1H-1,2,3-triazol-1-yl)propoxy)phenyl)propan-2-yl)phenoxy)propan-2-ol |
| 2b | 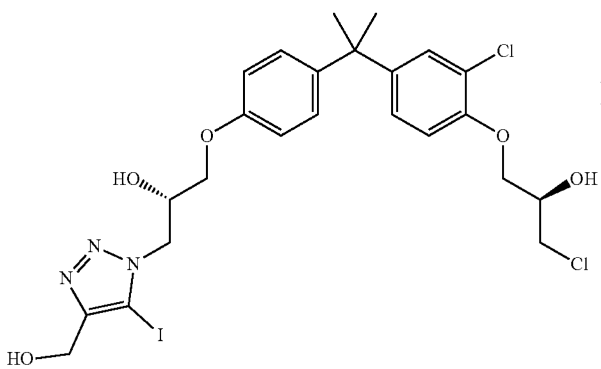 | (R)-1-chloro-3-(2-chloro-4-(2-(4-((S)-2-hydroxy-3-(4-(hydroxymethyl)-5-iodo-1H-1,2,3-triazol-1-yl)propoxy)phenyl)propan-2-yl)phenoxy)propan-2-ol |
| 2c | 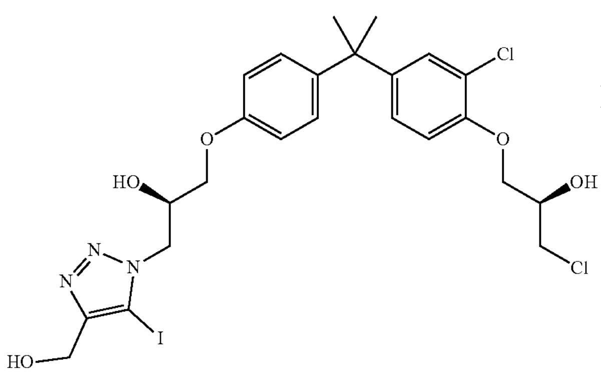 | (R)-1-chloro-3-(2-chloro-4-(2-(4-((R)-2-hydroxy-3-(4-(hydroxymethyl)-5-iodo-1H-1,2,3-triazol-1-yl)propoxy)phenyl)propan-2-yl)phenoxy)propan-2-ol |
| 2d | 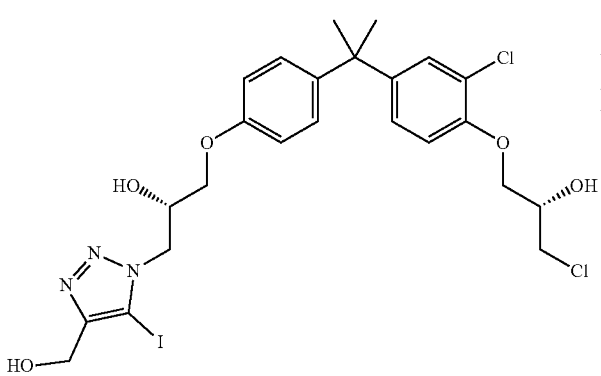 | (S)-1-chloro-3-(2-chloro-4-(2-(4-((S)-2-hydroxy-3-(4-(hydroxymethyl)-5-iodo-1H-1,2,3-triazol-1-yl)propoxy)phenyl)propan-2-yl)phenoxy)propan-2-ol |

TABLE 1-continued

| No. | Structure | Name |
|---|---|---|
| 3 | 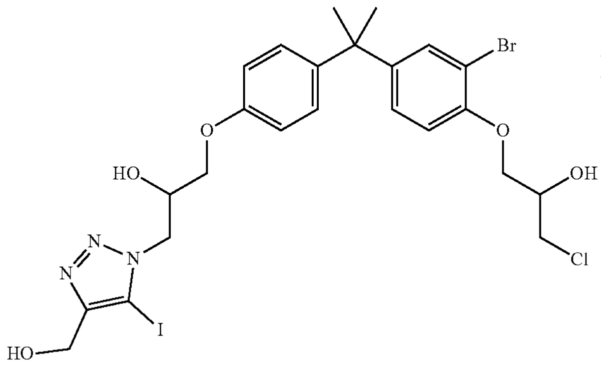 | 1-(2-bromo-4-(2-(4-(2-hydroxy-3-(4-(hydroxymethyl)-5-iodo-1H-1,2,3-triazol-1-yl)propoxy)phenyl)propan-2-yl)phenoxy)-3-chloropropan-2-ol |
| 3a | 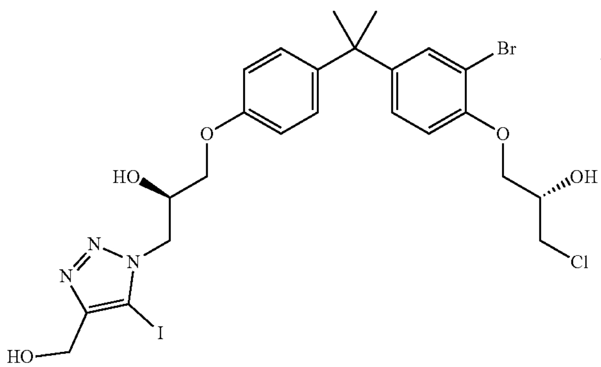 | (R)-1-(4-(2-(3-bromo-4-((S)-3-chloro-2-hydroxypropoxy)phenyl)propan-2-yl)phenoxy)-3-(4-(hydroxymethyl)-5-iodo-1H-1,2,3-triazol-1-yl)propan-2-ol |
| 3b | 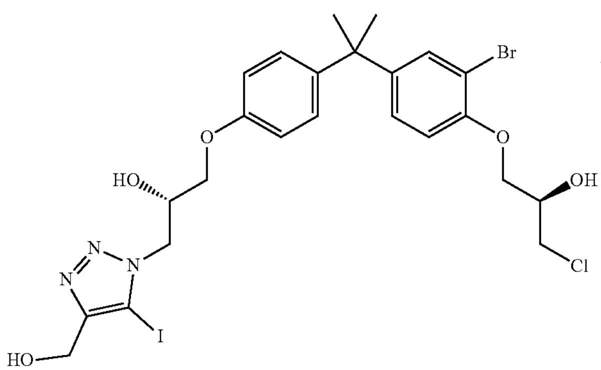 | (S)-1-(4-(2-(3-bromo-4-((R)-3-chloro-2-hydroxypropoxy)phenyl)propan-2-yl)phenoxy)-3-(4-(hydroxymethyl)-5-iodo-1H-1,2,3-triazol-1-yl)propan-2-ol |
| 3c | 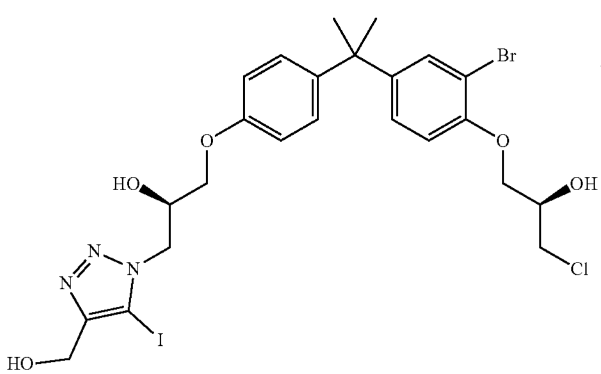 | (R)-1-(4-(2-(3-bromo-4-((R)-3-chloro-2-hydroxypropoxy)phenyl)propan-2-yl)phenoxy)-3-(4-(hydroxymethyl)-5-iodo-1H-1,2,3-triazol-1-yl)propan-2-ol |

TABLE 1-continued

| No. | Structure | Name |
|---|---|---|
| 3d | 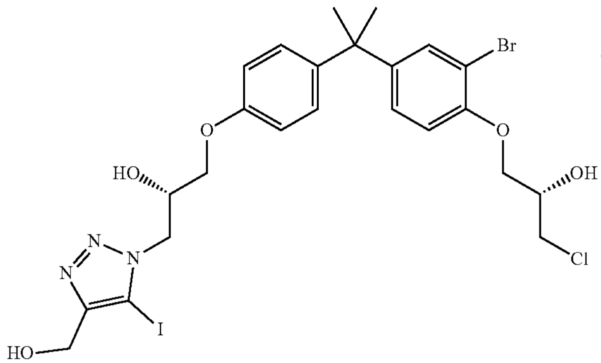 [SMILES: CC(C)(c1ccc(OC[C@@H](O)Cn2nnc(CO)c2I)cc1)c1ccc(OC[C@H](O)CCl)c(Br)c1] | (S)-1-(4-(2-(3-bromo-4-((S)-3-chloro-2-hydroxypropoxy)phenyl)propan-2-yl)phenoxy)-3-(4-(hydroxymethyl)-5-iodo-1H-1,2,3-triazol-1-yl)propan-2-ol |
| 4 | 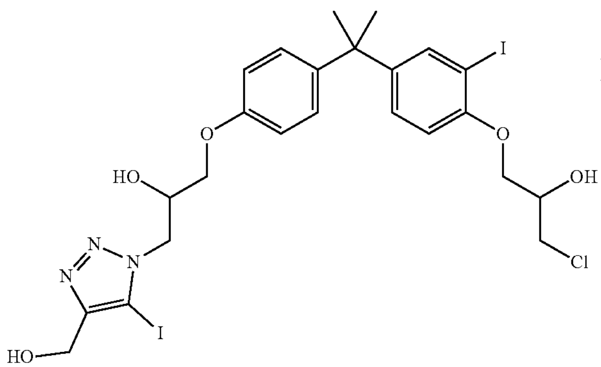 | 1-chloro-3-(4-(2-(4-(2-hydroxy-3-(4-(hydroxymethyl)-5-iodo-1H-1,2,3-triazol-1-yl)propoxy)phenyl)propan-2-yl)-2-iodophenoxy)propan-2-ol |
| 4a | 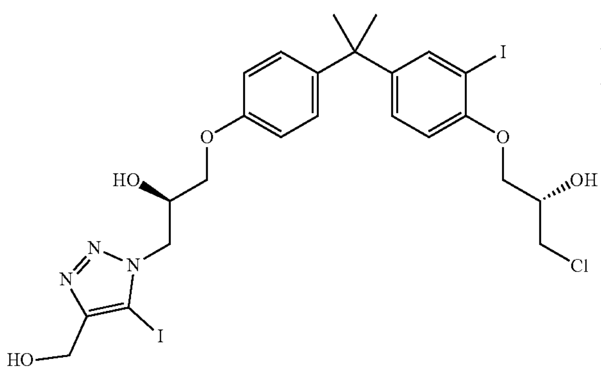 [SMILES: CC(C)(c1ccc(OC[C@H](O)Cn2nnc(CO)c2I)cc1)c1ccc(OC[C@H](O)CCl)c(I)c1] | (S)-1-chloro-3-(4-(2-(4-((R)-2-hydroxy-3-(4-(hydroxymethyl)-5-iodo-1H-1,2,3-triazol-1-yl)propoxy)phenyl)propan-2-yl)-2-iodophenoxy)propan-2-ol |
| 4b | 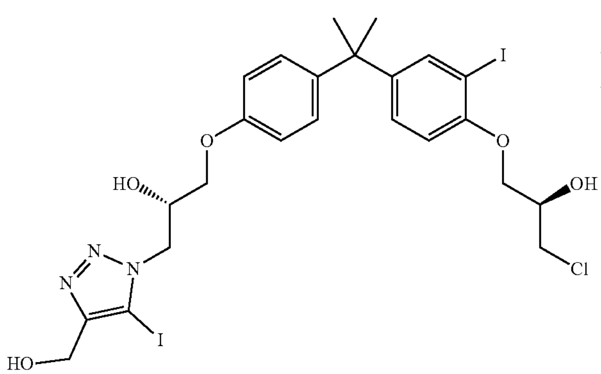 [SMILES: CC(C)(c1ccc(OC[C@@H](O)Cn2nnc(CO)c2I)cc1)c1ccc(OC[C@@H](O)CCl)c(I)c1] | (R)-1-chloro-3-(4-(2-(4-((S)-2-hydroxy-3-(4-(hydroxymethyl)-5-iodo-1H-1,2,3-triazol-1-yl)propoxy)phenyl)propan-2-yl)-2-iodophenoxy)propan-2-ol |

TABLE 1-continued

| No. | Structure | Name |
|---|---|---|
| 4c | 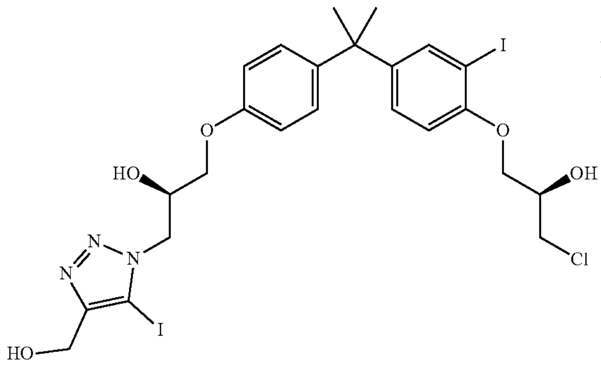 [SMILES: CC(C)(c1ccc(OC[C@H](O)Cn2nnc(CO)c2I)cc1)c1ccc(OC[C@@H](O)CCl)c(I)c1] | (R)-1-chloro-3-(4-(2-(4-((R)-2-hydroxy-3-(4-(hydroxymethyl)-5-iodo-1H-1,2,3-triazol-1-yl)propoxy)phenyl)propan-2-yl)-2-iodophenoxy)propan-2-ol |
| 4d | 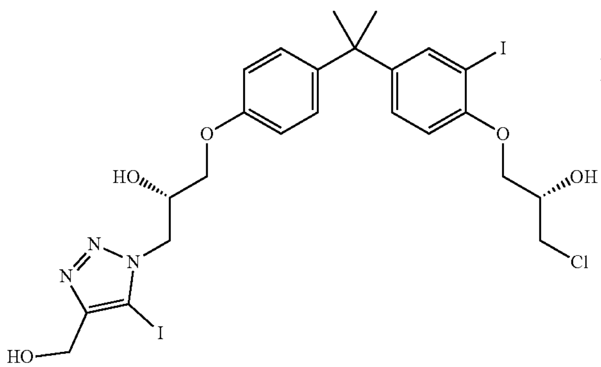 | (S)-1-chloro-3-(4-(2-(4-((S)-2-hydroxy-3-(4-(hydroxymethyl)-5-iodo-1H-1,2,3-triazol-1-yl)propoxy)phenyl)propan-2-yl)-2-iodophenoxy)propan-2-ol |
| 5 | 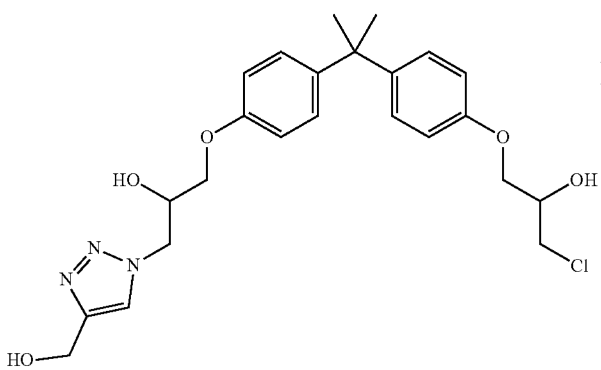 | 1-chloro-3-(4-(2-(4-(2-hydroxy-3-(4-(hydroxymethyl)-1H-1,2,3-triazol-1-yl)propoxy)phenyl)propan-2-yl)phenoxy)propan-2-ol |
| 5a | 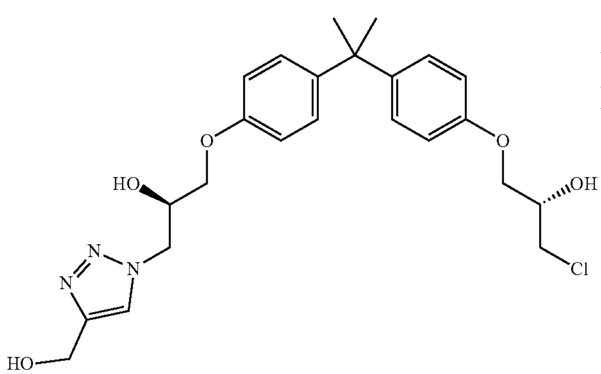 [SMILES: CC(C)(c1ccc(OC[C@H](O)CCl)cc1)c1ccc(OC[C@H](O)Cn2cc(CO)nn2)cc1] | (S)-1-chloro-3-(4-(2-(4-((R)-2-hydroxy-3-(4-(hydroxymethyl)-1H-1,2,3-triazol-1-yl)propoxy)phenyl)propan-2-yl)phenoxy)propan-2-ol |

TABLE 1-continued

| No. | Structure | Name |
|---|---|---|
| 5b | 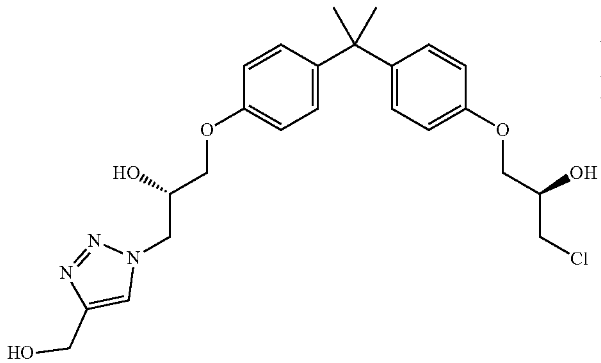 | (R)-1-chloro-3-(4-(2-(4-((S)-2-hydroxy-3-(4-(hydroxymethyl)-1H-1,2,3-triazol-1-yl)propoxy)phenyl)propan-2-yl)phenoxy)propan-2-ol |
| 5c | 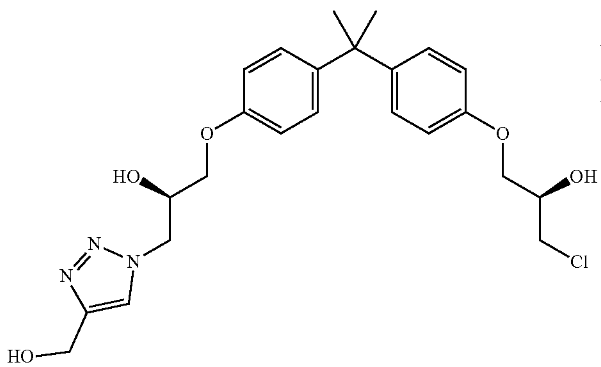 [SMILES: CC(C)(c1ccc(OC[C@@H](O)CCl)cc1)c1ccc(OC[C@H](O)Cn2cc(CO)nn2)cc1] | (R)-1-chloro-3-(4-(2-(4-((R)-2-hydroxy-3-(4-(hydroxymethyl)-1H-1,2,3-triazol-1-yl)propoxy)phenyl)propan-2-yl)phenoxy)propan-2-ol |
| 5d | 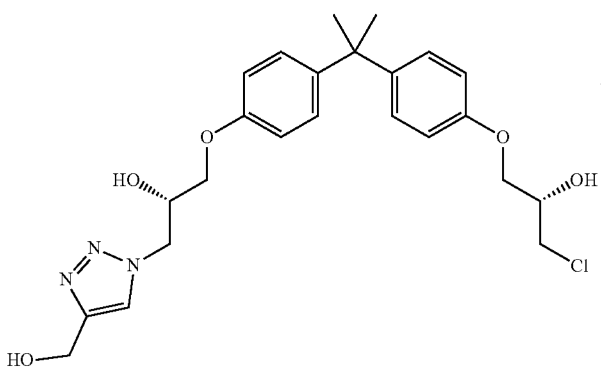 [SMILES: CC(C)(c1ccc(OC[C@H](O)CCl)cc1)c1ccc(OC[C@@H](O)Cn2cc(CO)nn2)cc1] | (S)-1-chloro-3-(4-(2-(4-((S)-2-hydroxy-3-(4-(hydroxymethyl)-1H-1,2,3-triazol-1-yl)propoxy)phenyl)propan-2-yl)phenoxy)propan-2-ol |
| 6 | 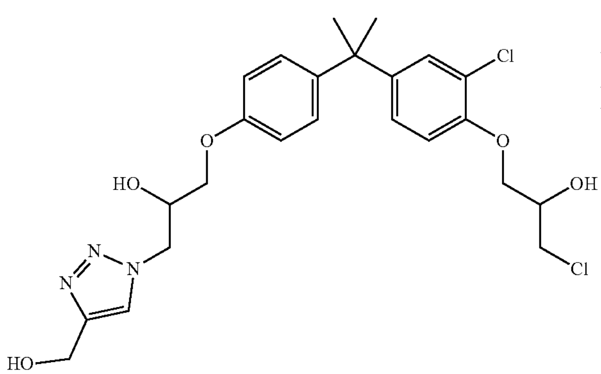 | 1-chloro-3-(2-chloro-4-(2-(4-(2-hydroxy-3-(4-(hydroxymethyl)-1H-1,2,3-triazol-1-yl)propoxy)phenyl)propan-2-yl)phenoxy)propan-2-ol |

TABLE 1-continued

| No. | Structure | Name |
|---|---|---|
| 6a | 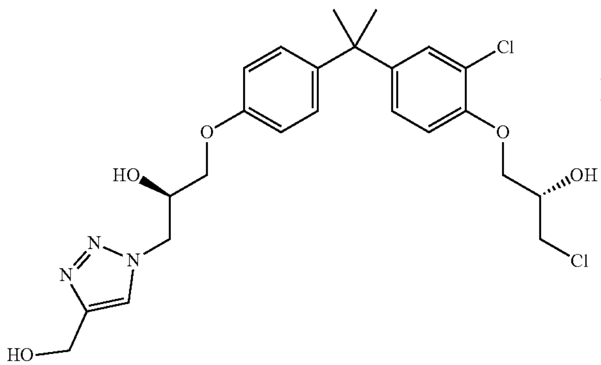 | (S)-1-chloro-3-(2-chloro-4-(2-(4-((R)-2-hydroxy-3-(4-(hydroxymethyl)-1H-1,2,3-triazol-1-yl)propoxy)phenyl)propan-2-yl)phenoxy)propan-2-ol |
| 6b | 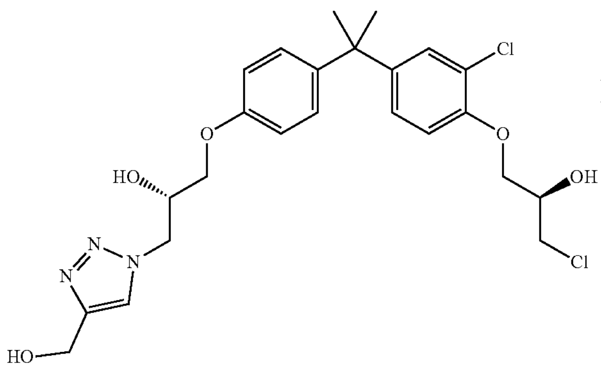 | (R)-1-chloro-3-(2-chloro-4-(2-(4-((S)-2-hydroxy-3-(4-(hydroxymethyl)-1H-1,2,3-triazol-1-yl)propoxy)phenyl)propan-2-yl)phenoxy)propan-2-ol |
| 6c | 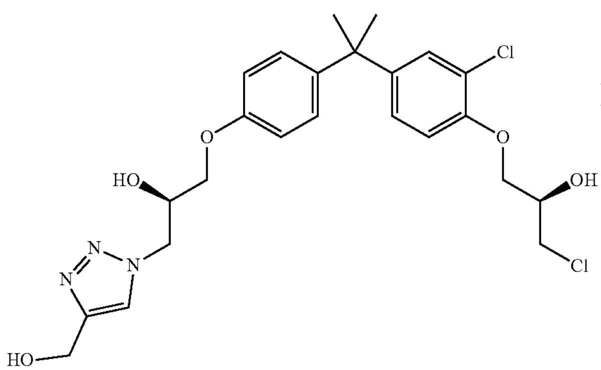 | (R)-1-chloro-3-(2-chloro-4-(2-(4-((R)-2-hydroxy-3-(4-(hydroxymethyl)-1H-1,2,3-triazol-1-yl)propoxy)phenyl)propan-2-yl)phenoxy)propan-2-ol |
| 6d | 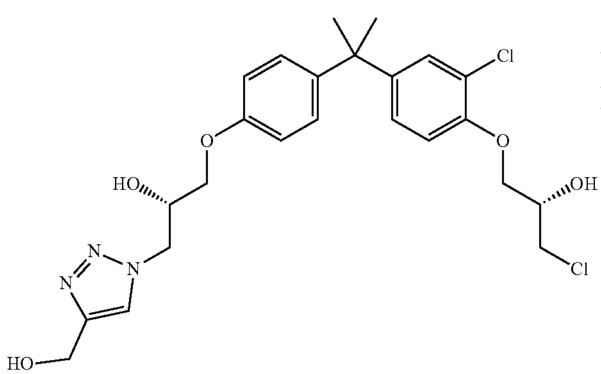 | (S)-1-chloro-3-(2-chloro-4-(2-(4-((S)-2-hydroxy-3-(4-(hydroxymethyl)-1H-1,2,3-triazol-1-yl)propoxy)phenyl)propan-2-yl)phenoxy)propan-2-ol |

TABLE 1-continued

| No. | Structure | Name |
|---|---|---|
| 7 | 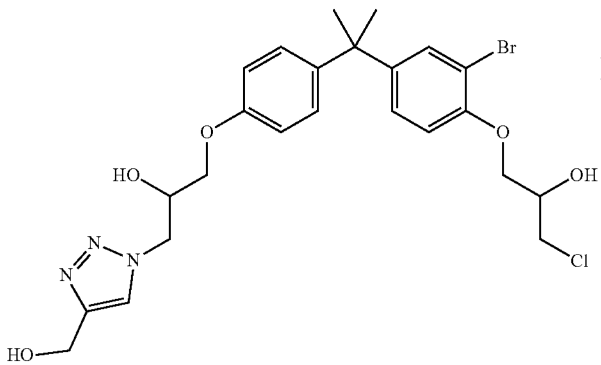 | 1-(2-bromo-4-(2-(4-(2-hydroxy-3-(4-(hydroxymethyl)-1H-1,2,3-triazol-1-yl)propoxy)phenyl)propan-2-yl)phenoxy)-3-chloropropan-2-ol |
| 7a | 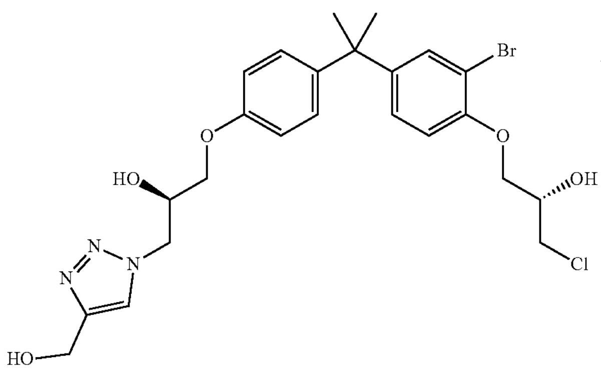 | (R)-1-(4-(2-(3-bromo-4-((S)-3-chloro-2-hydroxypropoxy)phenyl)propan-2-yl)phenoxy)-3-(4-(hydroxymethyl)-1H-1,2,3-triazol-1-yl)propan-2-ol |
| 7b | 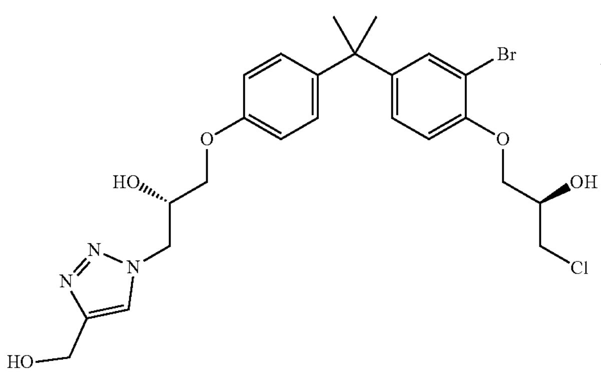 | (S)-1-(4-(2-(3-bromo-4-((R)-3-chloro-2-hydroxypropoxy)phenyl)propan-2-yl)phenoxy)-3-(4-(hydroxymethyl)-1H-1,2,3-triazol-1-yl)propan-2-ol |
| 7c | 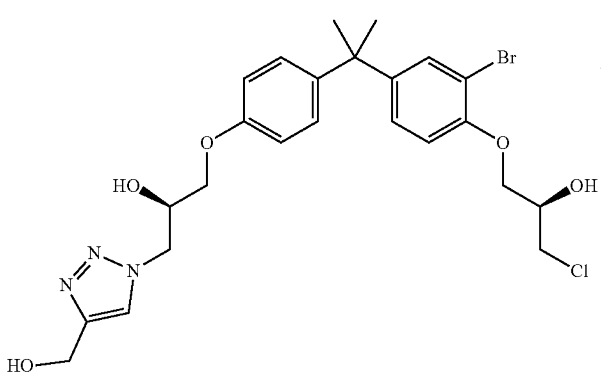 | (R)-1-(4-(2-(3-bromo-4-((R)-3-chloro-2-hydroxypropoxy)phenyl)propan-2-yl)phenoxy)-3-(4-(hydroxymethyl)-1H-1,2,3-triazol-1-yl)propan-2-ol |

TABLE 1-continued

Compounds

| No. | Structure | Name |
|---|---|---|
| 7d | 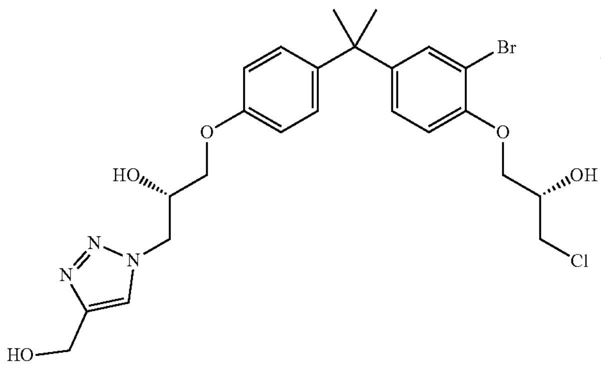 [SMILES: CC(C)(c1ccc(OC[C@@H](O)Cn2cc(CO)nn2)cc1)c1ccc(OC[C@H](O)CCl)c(Br)c1] | (S)-1-(4-(2-(3-bromo-4-((S)-3-chloro-2-hydroxypropoxy)phenyl)propan-2-yl)phenoxy)-3-(4-(hydroxymethyl)-1H-1,2,3-triazol-1-yl)propan-2-ol |
| 8 | 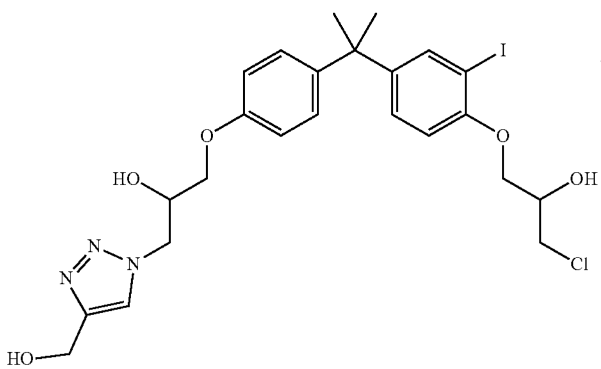 | 1-chloro-3-(4-(2-(4-(2-hydroxy-3-(4-(hydroxymethyl)-1H-1,2,3-triazol-1-yl)propoxy)phenyl)propan-2-yl)-2-iodophenoxy)propan-2-ol |
| 8a | 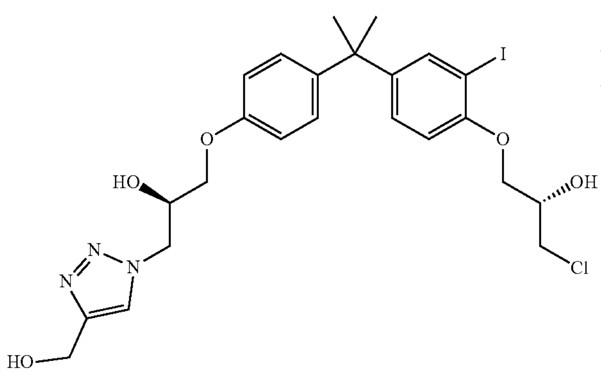 | (S)-1-chloro-3-(4-(2-(4-((R)-2-hydroxy-3-(4-(hydroxymethyl)-1H-1,2,3-triazol-1-yl)propoxy)phenyl)propan-2-yl)-2-iodophenoxy)propan-2-ol |
| 8b | 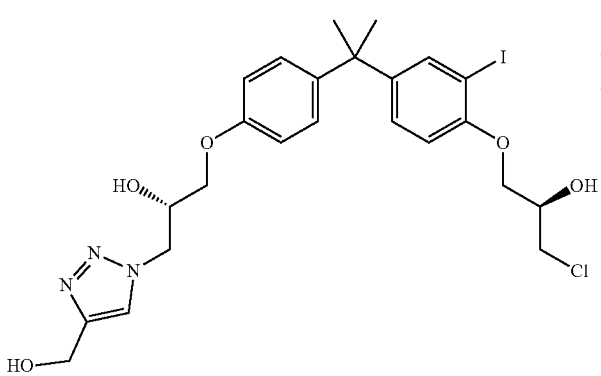 | (R)-1-chloro-3-(4-(2-(4-((SR)-2-hydroxy-3-(4-(hydroxymethyl)-1H-1,2,3-triazol-1-yl)propoxy)phenyl)propan-2-yl)-2-iodophenoxy)propan-2-ol |

TABLE 1-continued

| No. | Structure | Name |
|---|---|---|
| 8c | 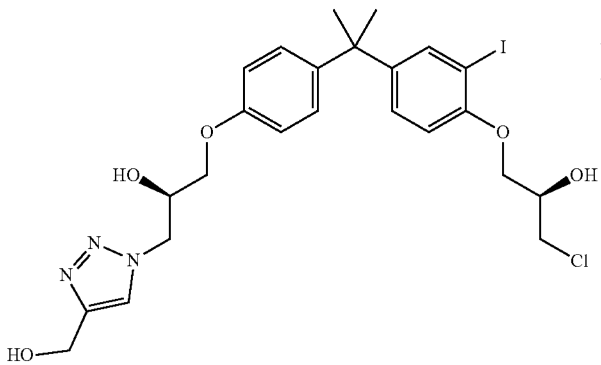 [SMILES: CC(C)(c1ccc(OC[C@H](O)Cn2cc(CO)nn2)cc1)c1ccc(OC[C@@H](O)CCl)c(I)c1] | (R)-1-chloro-3-(4-(2-(4-((R)-2-hydroxy-3-(4-(hydroxymethyl)-1H-1,2,3-triazol-1-yl)propoxy)phenyl)propan-2-yl)-2-iodophenoxy)propan-2-ol |
| 8d | 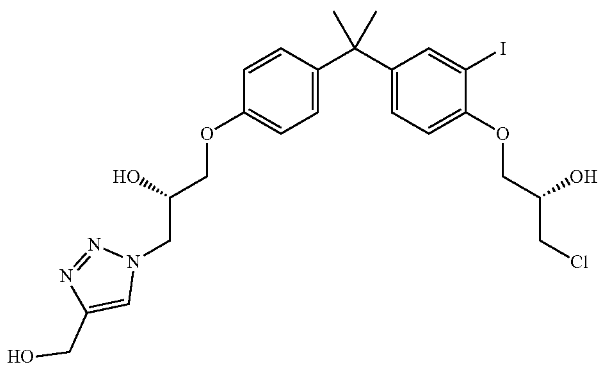 [SMILES: CC(C)(c1ccc(OC[C@@H](O)Cn2cc(CO)nn2)cc1)c1ccc(OC[C@H](O)CCl)c(I)c1] | (S)-1-chloro-3-(4-(2-(4-((S)-2-hydroxy-3-(4-(hydroxymethyl)-1H-1,2,3-triazol-1-yl)propoxy)phenyl)propan-2-yl)-2-iodophenoxy)propan-2-ol |
| 9 | 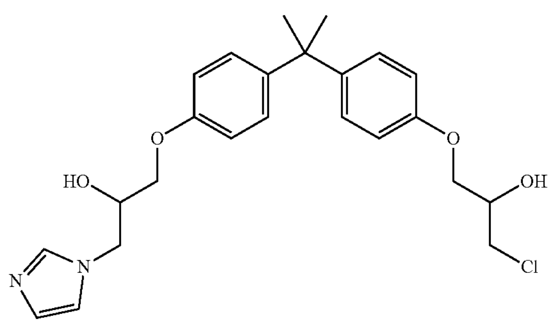 [SMILES: CC(C)(c1ccc(OCC(O)CCl)cc1)c1ccc(OCC(O)Cn2ccnc2)cc1] | 1-chloro-3-(4-(2-(4-(2-hydroxy-3-(1H-imidazol-1-yl)propoxy)phenyl)propan-2-yl)phenoxy)propan-2-ol |
| 9a | 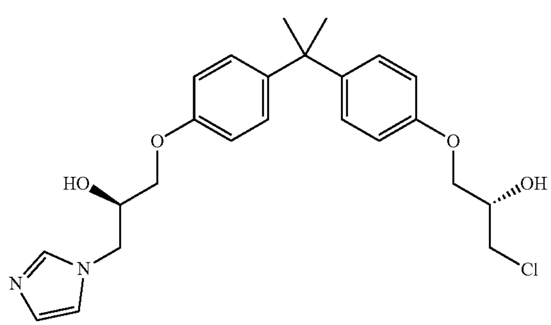 [SMILES: CC(C)(c1ccc(OC[C@H](O)CCl)cc1)c1ccc(OC[C@H](O)Cn2ccnc2)cc1] | (S)-1-chloro-3-(4-(2-(4-((R)-2-hydroxy-3-(1H-imidazol-1-yl)propoxy)phenyl)propan-2-yl)phenoxy)propan-2-ol |

TABLE 1-continued

| No. | Structure | Name |
|---|---|---|
| 9b | 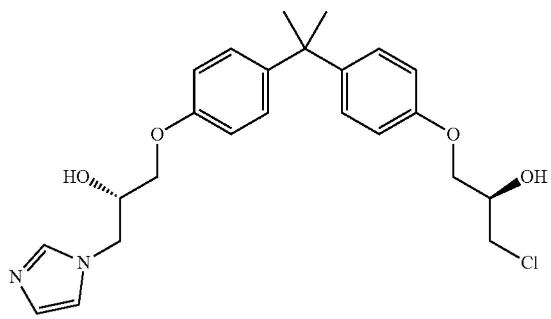 [SMILES: CC(C)(c1ccc(OC[C@@H](O)Cn2ccnc2)cc1)c1ccc(OC[C@@H](O)CCl)cc1] | (R)-1-chloro-3-(4-(2-(4-((S)-2-hydroxy-3-(1H-imidazol-1-yl)propoxy)phenyl)propan-2-yl)phenoxy)propan-2-ol |
| 9c | 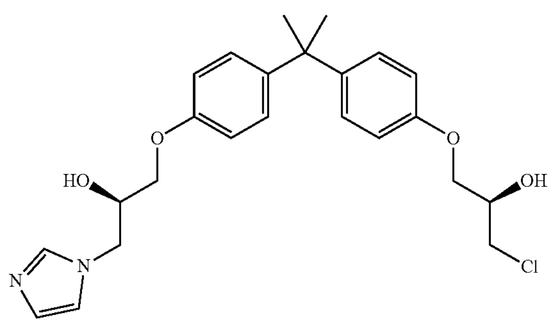 [SMILES: CC(C)(c1ccc(OC[C@@H](O)CCl)cc1)c1ccc(OC[C@H](O)Cn2ccnc2)cc1] | (R)-1-chloro-3-(4-(2-(4-((R)-2-hydroxy-3-(1H-imidazol-1-yl)propoxy)phenyl)propan-2-yl)phenoxy)propan-2-ol |
| 9d | 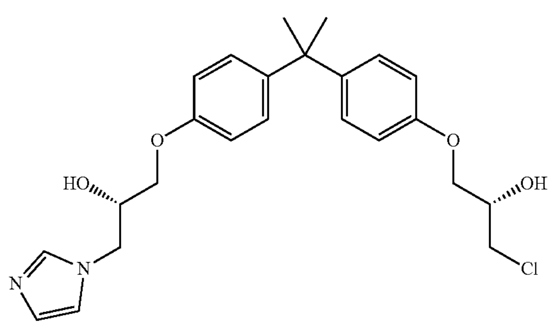 [SMILES: CC(C)(c1ccc(OC[C@H](O)CCl)cc1)c1ccc(OC[C@@H](O)Cn2ccnc2)cc1] | (S)-1-chloro-3-(4-(2-(4-((S)-2-hydroxy-3-(1H-imidazol-1-yl)propoxy)phenyl)propan-2-yl)phenoxy)propan-2-ol |
| 10 | 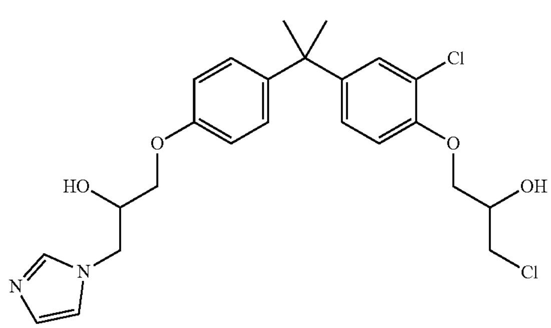 [SMILES: CC(C)(c1ccc(OCC(O)Cn2ccnc2)cc1)c1ccc(OCC(O)CCl)c(Cl)c1] | 1-chloro-3-(2-chloro-4-(2-(4-(2-hydroxy-3-(1H-imidazol-1-yl)propoxy)phenyl)propan-2-yl)phenoxy)propan-2-ol |

TABLE 1-continued

| No. | Structure | Name |
|---|---|---|
| 10a | 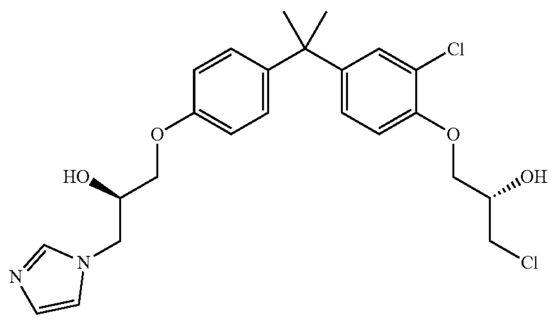 [SMILES: CC(C)(c1ccc(OC[C@H](O)Cn2ccnc2)cc1)c1ccc(OC[C@H](O)CCl)c(Cl)c1] | (S)-1-chloro-3-(2-chloro-4-(2-(4-((R)-2-hydroxy-3-(1H-imidazol-1-yl)propoxy)phenyl)propan-2-yl)phenoxy)propan-2-ol |
| 10b | 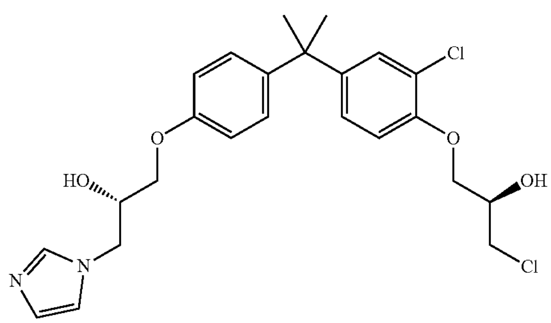 [SMILES: CC(C)(c1ccc(OC[C@@H](O)Cn2ccnc2)cc1)c1ccc(OC[C@@H](O)CCl)c(Cl)c1] | (R)-1-chloro-3-(2-chloro-4-(2-(4-((S)-2-hydroxy-3-(1H-imidazol-1-yl)propoxy)phenyl)propan-2-yl)phenoxy)propan-2-ol |
| 10c | 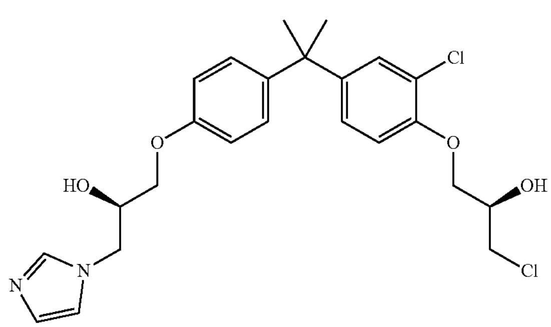 [SMILES: CC(C)(c1ccc(OC[C@H](O)Cn2ccnc2)cc1)c1ccc(OC[C@@H](O)CCl)c(Cl)c1] | (R)-1-chloro-3-(2-chloro-4-(2-(4-((R)-2-hydroxy-3-(1H-imidazol-1-yl)propoxy)phenyl)propan-2-yl)phenoxy)propan-2-ol |
| 10d | 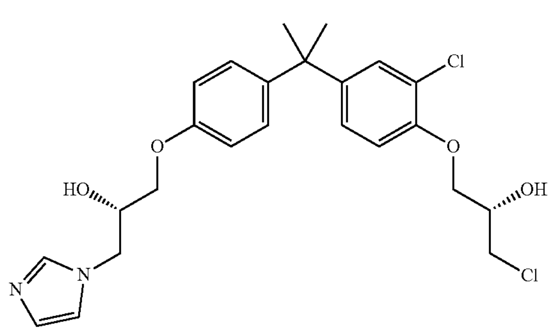 [SMILES: CC(C)(c1ccc(OC[C@@H](O)Cn2ccnc2)cc1)c1ccc(OC[C@H](O)CCl)c(Cl)c1] | (S)-1-chloro-3-(2-chloro-4-(2-(4-((S)-2-hydroxy-3-(1H-imidazol-1-yl)propoxy)phenyl)propan-2-yl)phenoxy)propan-2-ol |

TABLE 1-continued

| No. | Structure | Name |
|---|---|---|
| 11 | 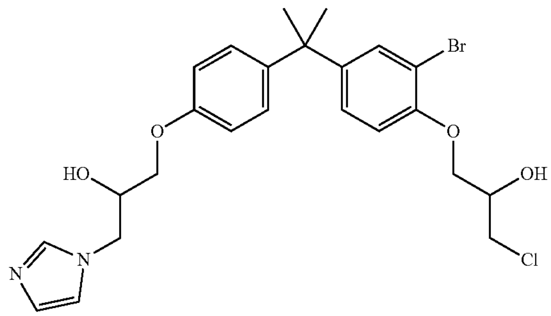 [SMILES: CC(C)(c1ccc(OCC(O)Cn2ccnc2)cc1)c1ccc(OCC(O)CCl)c(Br)c1] | 1-(2-bromo-4-(2-(4-(2-hydroxy-3-(1H-imidazol-1-yl)propoxy)phenyl)propan-2-yl)phenoxy)-3-chloropropan-2-ol |
| 11a | 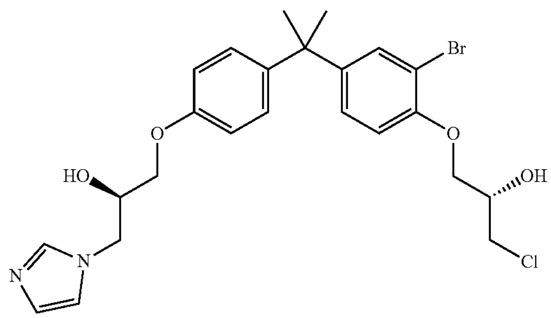 [SMILES: CC(C)(c1ccc(OC[C@H](O)Cn2ccnc2)cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-(1H-imidazol-1-yl)propan-2-ol |
| 11b | 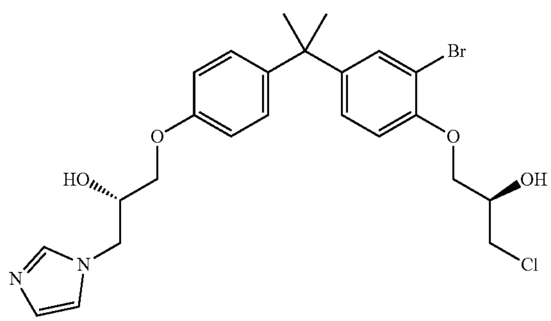 [SMILES: CC(C)(c1ccc(OC[C@@H](O)Cn2ccnc2)cc1)c1ccc(OC[C@@H](O)CCl)c(Br)c1] | (S)-1-(4-(2-(3-bromo-4-((R)-3-chloro-2-hydroxypropoxy)phenyl)propan-2-yl)phenoxy)-3-(1H-imidazol-1-yl)propan-2-ol |
| 11c | 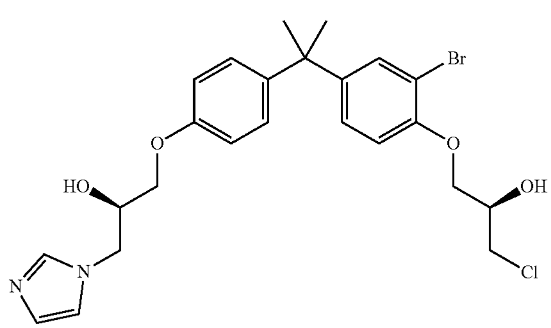 [SMILES: CC(C)(c1ccc(OC[C@H](O)Cn2ccnc2)cc1)c1ccc(OC[C@@H](O)CCl)c(Br)c1] | (R)-1-(4-(2-(3-bromo-4-((R)-3-chloro-2-hydroxypropoxy)phenyl)propan-2-yl)phenoxy)-3-(1H-imidazol-1-yl)propan-2-ol |

TABLE 1-continued

| No. | Structure | Name |
|---|---|---|
| 11d | 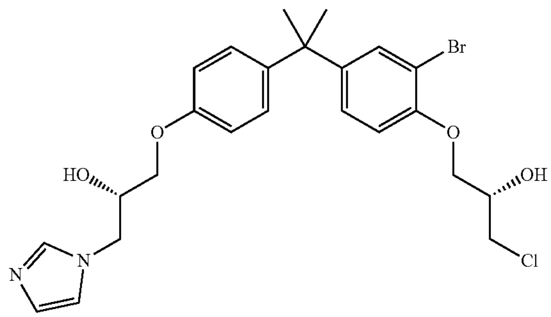 | (S)-1-(4-(2-(3-bromo-4-((S)-3-chloro-2-hydroxypropoxy)phenyl)propan-2-yl)phenoxy)-3-(1H-imidazol-1-yl)propan-2-ol |
| 12 | 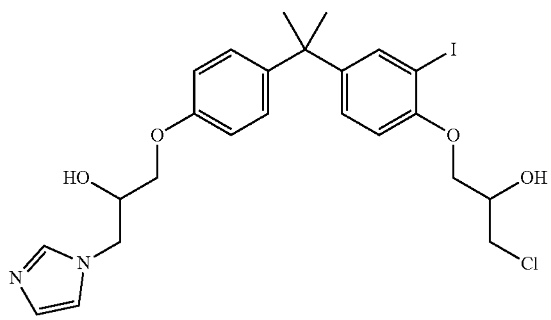 [SMILES: CC(C)(c1ccc(OCC(O)Cn2ccnc2)cc1)c1ccc(OCC(O)CCl)c(I)c1] | 1-chloro-3-(4-(2-(4-(2-hydroxy-3-(1H-imidazol-1-yl)propoxy)phenyl)propan-2-yl)-2-iodophenoxy)propan-2-ol |
| 12a | 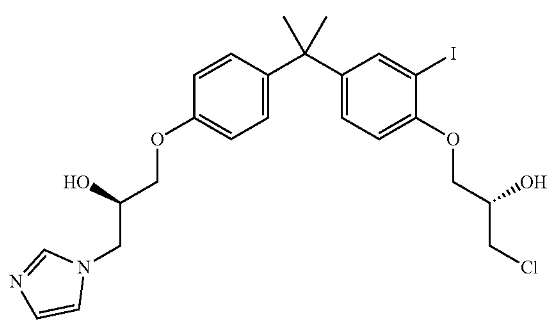 [SMILES: CC(C)(c1ccc(OC[C@H](O)Cn2ccnc2)cc1)c1ccc(OC[C@H](O)CCl)c(I)c1] | (S)-1-chloro-3-(4-(2-(4-((R)-2-hydroxy-3-(1H-imidazol-1-yl)propoxy)phenyl)propan-2-yl)-2-iodophenoxy)propan-2-ol |
| 12b | 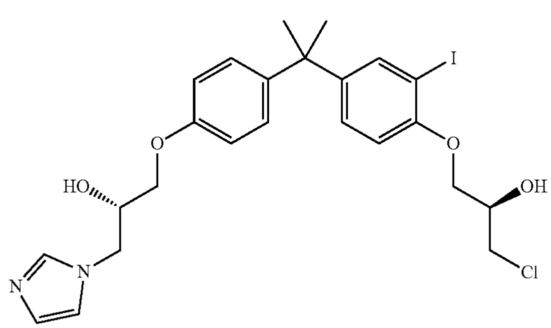 [SMILES: CC(C)(c1ccc(OC[C@@H](O)Cn2ccnc2)cc1)c1ccc(OC[C@@H](O)CCl)c(I)c1] | (R)-1-chloro-3-(4-(2-(4-((S)-2-hydroxy-3-(1H-imidazol-1-yl)propoxy)phenyl)propan-2-yl)-2-iodophenoxy)propan-2-ol |

TABLE 1-continued

| No. | Structure | Name |
|---|---|---|
| 12c | 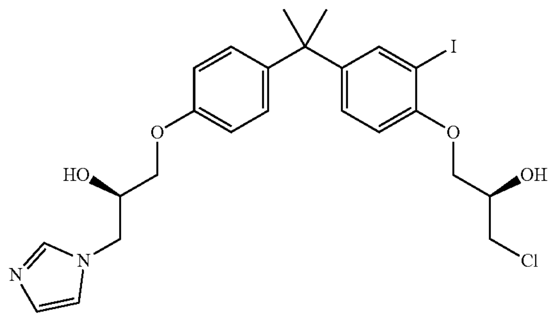 [SMILES: CC(C)(c1ccc(OC[C@H](O)Cn2ccnc2)cc1)c1ccc(OC[C@@H](O)CCl)c(I)c1] | (R)-1-chloro-3-(4-(2-(4-((R)-2-hydroxy-3-(1H-imidazol-1-yl)propoxy)phenyl)propan-2-yl)-2-iodophenoxy)propan-2-ol |
| 12d | 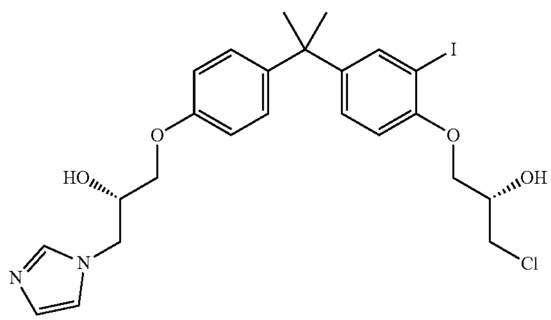 [SMILES: CC(C)(c1ccc(OC[C@@H](O)Cn2ccnc2)cc1)c1ccc(OC[C@H](O)CCl)c(I)c1] | (S)-1-chloro-3-(4-(2-(4-((S)-2-hydroxy-3-(1H-imidazol-1-yl)propoxy)phenyl)propan-2-yl)-2-iodophenoxy)propan-2-ol |
| 13 | 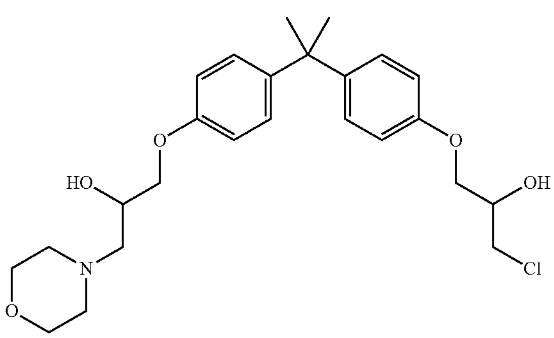 [SMILES: CC(C)(c1ccc(OCC(O)CCl)cc1)c1ccc(OCC(O)CN2CCOCC2)cc1] | 1-chloro-3-(4-(2-(4-(2-hydroxy-3-morpholinopropoxy)phenyl)propan-2-yl)phenoxy)propan-2-ol |
| 13a | 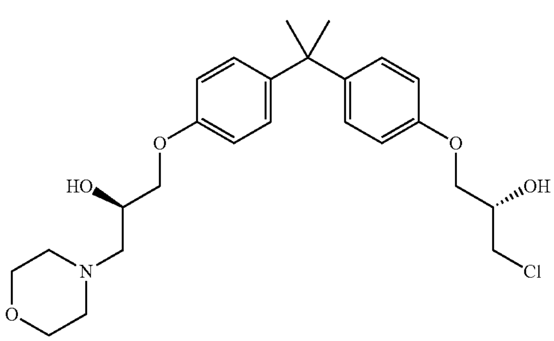 [SMILES: CC(C)(c1ccc(OC[C@H](O)CCl)cc1)c1ccc(OC[C@H](O)CN2CCOCC2)cc1] | (S)-1-chloro-3-(4-(2-(4-((R)-2-hydroxy-3-morpholinopropoxy)phenyl)propan-2-yl)phenoxy)propan-2-ol |

TABLE 1-continued

| No. | Structure | Name |
|---|---|---|
| 13b | 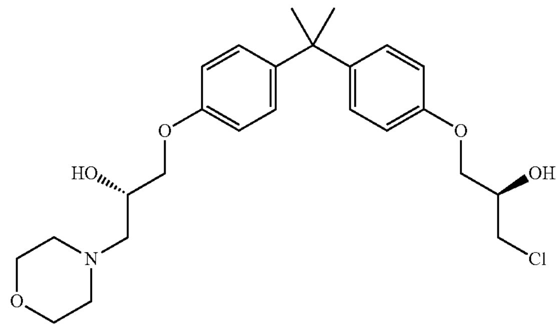 [SMILES: CC(C)(c1ccc(OC[C@@H](O)CN2CCOCC2)cc1)c1ccc(OC[C@@H](O)CCl)cc1] | (R)-1-chloro-3-(4-(2-(4-((S)-2-hydroxy-3-morpholinopropoxy)phenyl)propan-2-yl)phenoxy)propan-2-ol |
| 13c | 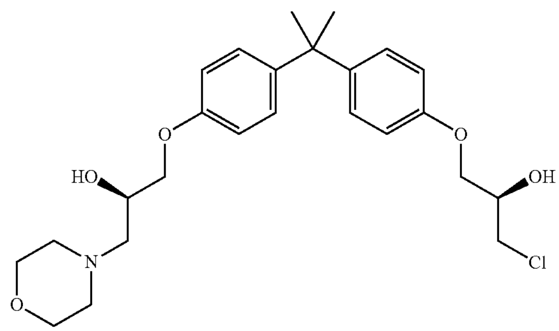 [SMILES: CC(C)(c1ccc(OC[C@@H](O)CCl)cc1)c1ccc(OC[C@H](O)CN2CCOCC2)cc1] | (R)-1-chloro-3-(4-(2-(4-((R)-2-hydroxy-3-morpholinopropoxy)phenyl)propan-2-yl)phenoxy)propan-2-ol |
| 13d | 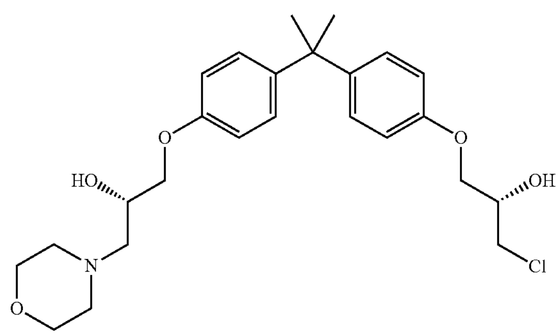 [SMILES: CC(C)(c1ccc(OC[C@H](O)CCl)cc1)c1ccc(OC[C@@H](O)CN2CCOCC2)cc1] | (S)-1-chloro-3-(4-(2-(4-((S)-2-hydroxy-3-morpholinopropoxy)phenyl)propan-2-yl)phenoxy)propan-2-ol |
| 14 | 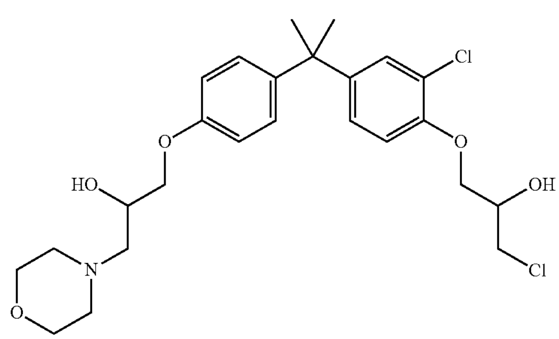 [SMILES: CC(C)(c1ccc(OCC(O)CN2CCOCC2)cc1)c1ccc(OCC(O)CCl)c(Cl)c1] | 1-chloro-3-(2-chloro-4-(2-(4-(2-hydroxy-3-morpholinopropoxy)phenyl)propan-2-yl)phenoxy)propan-2-ol |

TABLE 1-continued

| No. | Structure | Name |
|---|---|---|
| 14a | 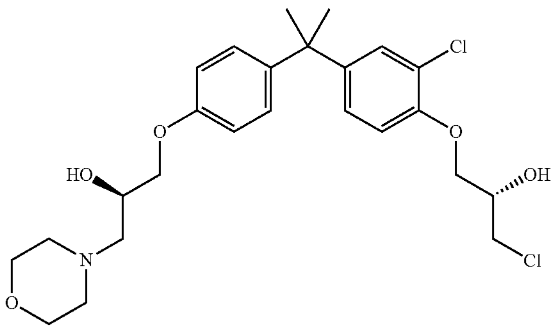 [SMILES: CC(C)(c1ccc(OC[C@H](O)CN2CCOCC2)cc1)c1ccc(OC[C@H](O)CCl)c(Cl)c1] | (S)-1-chloro-3-(2-chloro-4-(2-(4-((R)-2-hydroxy-3-morpholinopropoxy)phenyl)propan-2-yl)phenoxy)propan-2-ol |
| 14b | 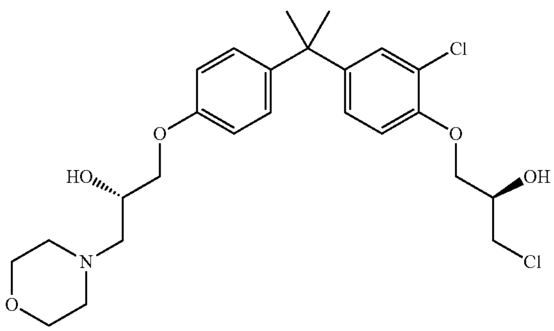 [SMILES: CC(C)(c1ccc(OC[C@@H](O)CN2CCOCC2)cc1)c1ccc(OC[C@@H](O)CCl)c(Cl)c1] | (R)-1-chloro-3-(2-chloro-4-(2-(4-((S)-2-hydroxy-3-morpholinopropoxy)phenyl)propan-2-yl)phenoxy)propan-2-ol |
| 14c | 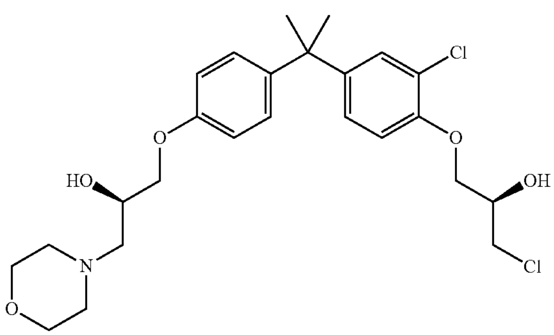 [SMILES: CC(C)(c1ccc(OC[C@H](O)CN2CCOCC2)cc1)c1ccc(OC[C@@H](O)CCl)c(Cl)c1] | (R)-1-chloro-3-(2-chloro-4-(2-(4-((R)-2-hydroxy-3-morpholinopropoxy)phenyl)propan-2-yl)phenoxy)propan-2-ol |
| 14d | 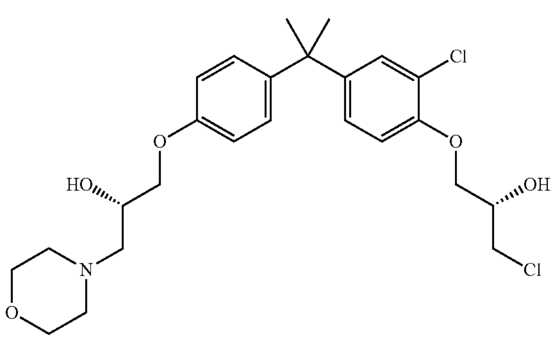 [SMILES: CC(C)(c1ccc(OC[C@@H](O)CN2CCOCC2)cc1)c1ccc(OC[C@H](O)CCl)c(Cl)c1] | (S)-1-chloro-3-(2-chloro-4-(2-(4-((S)-2-hydroxy-3-morpholinopropoxy)phenyl)propan-2-yl)phenoxy)propan-2-ol |

TABLE 1-continued

Compounds

| No. | Structure | Name |
|---|---|---|
| 15 | 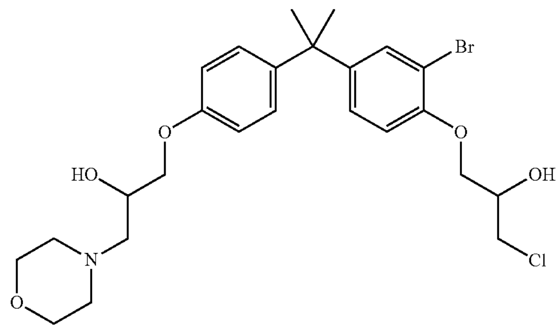 [SMILES: CC(C)(c1ccc(OCC(O)CN2CCOCC2)cc1)c1ccc(OCC(O)CCl)c(Br)c1] | 1-(2-bromo-4-(2-(4-(2-hydroxy-3-morpholinopropoxy)phenyl)propan-2-yl)phenoxy)-3-chloropropan-2-ol |
| 15a | 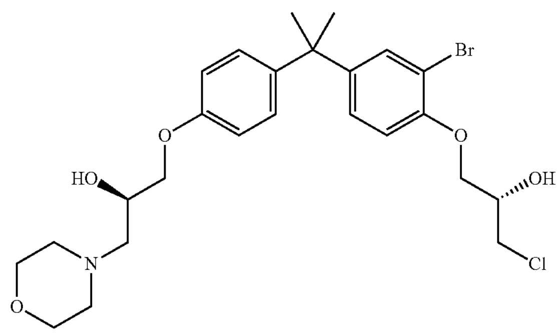 [SMILES: CC(C)(c1ccc(OC[C@H](O)CN2CCOCC2)cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-morpholinopropan-2-ol |
| 15b | 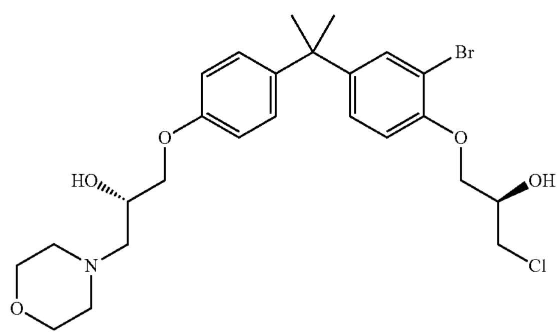 [SMILES: CC(C)(c1ccc(OC[C@@H](O)CN2CCOCC2)cc1)c1ccc(OC[C@@H](O)CCl)c(Br)c1] | (S)-1-(4-(2-(3-bromo-4-((R)-3-chloro-2-hydroxypropoxy)phenyl)propan-2-yl)phenoxy)-3-morpholinopropan-2-ol |
| 15c | 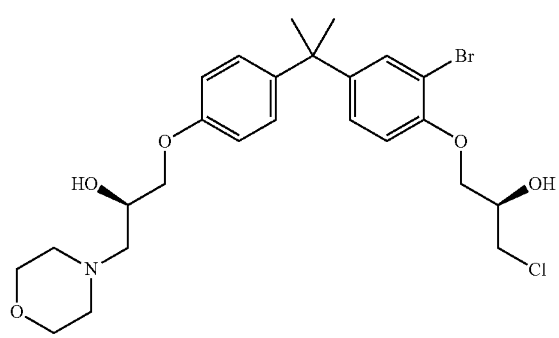 [SMILES: CC(C)(c1ccc(OC[C@H](O)CN2CCOCC2)cc1)c1ccc(OC[C@@H](O)CCl)c(Br)c1] | (R)-1-(4-(2-(3-bromo-4-((R)-3-chloro-2-hydroxypropoxy)phenyl)propan-2-yl)phenoxy)-3-morpholinopropan-2-ol |

TABLE 1-continued

| No. | Structure | Name |
|---|---|---|
| 15d | 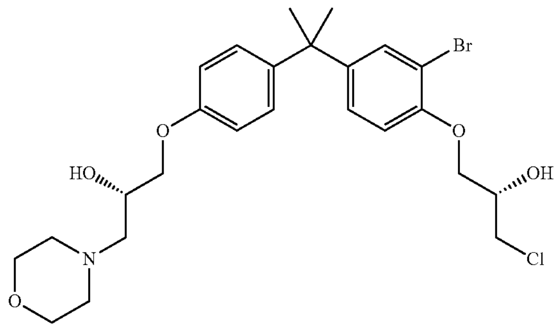 [SMILES: CC(C)(c1ccc(OC[C@@H](O)CN2CCOCC2)cc1)c1ccc(OC[C@H](O)CCl)c(Br)c1] | (S)-1-(4-(2-(3-bromo-4-((S)-3-chloro-2-hydroxypropoxy)phenyl)propan-2-yl)phenoxy)-3-morpholinopropan-2-ol |
| 16 | 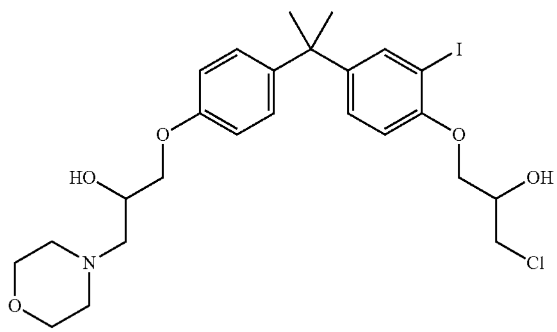 [SMILES: CC(C)(c1ccc(OCC(O)CN2CCOCC2)cc1)c1ccc(OCC(O)CCl)c(I)c1] | 1-chloro-3-(4-(2-(4-(2-hydroxy-3-morpholinopropoxy)phenyl)propan-2-yl)-2-iodophenoxy)propan-2-ol |
| 16a | 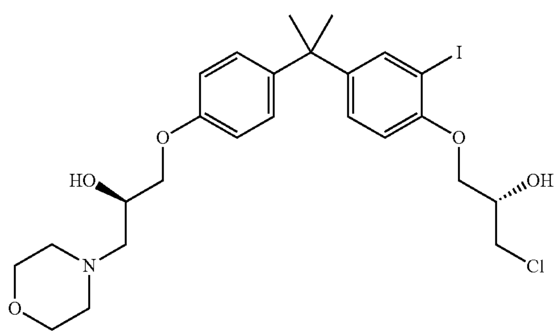 [SMILES: CC(C)(c1ccc(OC[C@H](O)CN2CCOCC2)cc1)c1ccc(OC[C@H](O)CCl)c(I)c1] | (S)-1-chloro-3-(4-(2-(4-((R)-2-hydroxy-3-morpholinopropoxy)phenyl)propan-2-yl)-2-iodophenoxy)propan-2-ol |
| 16b | 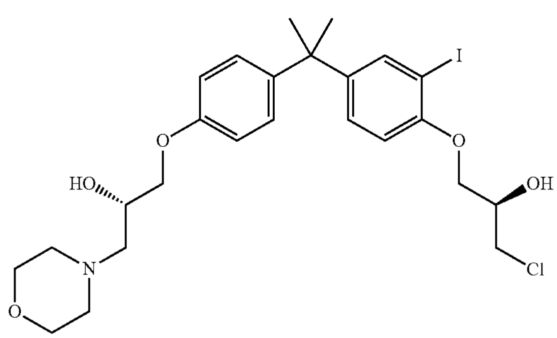 [SMILES: CC(C)(c1ccc(OC[C@@H](O)CN2CCOCC2)cc1)c1ccc(OC[C@@H](O)CCl)c(I)c1] | (R)-1-chloro-3-(4-(2-(4-((S)-2-hydroxy-3-morpholinopropoxy)phenyl)propan-2-yl)-2-iodophenoxy)propan-2-ol |

TABLE 1-continued

| No. | Structure | Name |
|---|---|---|
| 16c | 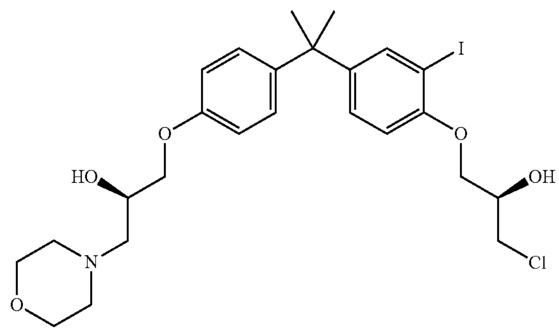 [SMILES: CC(C)(c1ccc(OC[C@H](O)CN2CCOCC2)cc1)c1ccc(OC[C@@H](O)CCl)c(I)c1] | (R)-1-chloro-3-(4-(2-(4-((R)-2-hydroxy-3-morpholinopropoxy)phenyl)propan-2-yl)-2-iodophenoxy)propan-2-ol |
| 16d | 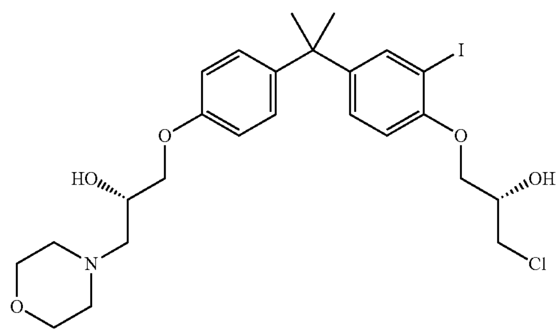 [SMILES: CC(C)(c1ccc(OC[C@@H](O)CN2CCOCC2)cc1)c1ccc(OC[C@H](O)CCl)c(I)c1] | (S)-1-chloro-3-(4-(2-(4-((S)-2-hydroxy-3-mopholinopropoxy)phenyl)propan-2-yl)-2-iodophenoxy)propan-2-ol |
| 17 | 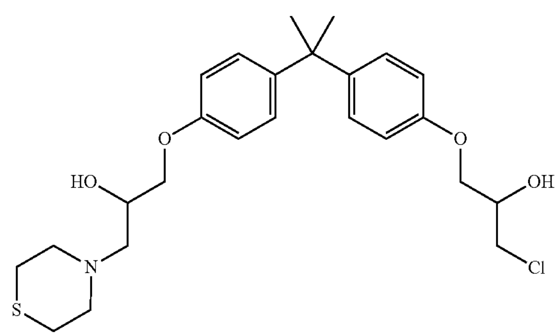 [SMILES: CC(C)(c1ccc(OCC(O)CCl)cc1)c1ccc(OCC(O)CN2CCSCC2)cc1] | 1-chloro-3-(4-(2-(4-(2-hydroxy-3-thiomorpholinopropoxy)phenyl)propan-2-yl)phenoxy)propan-2-ol |
| 17a | 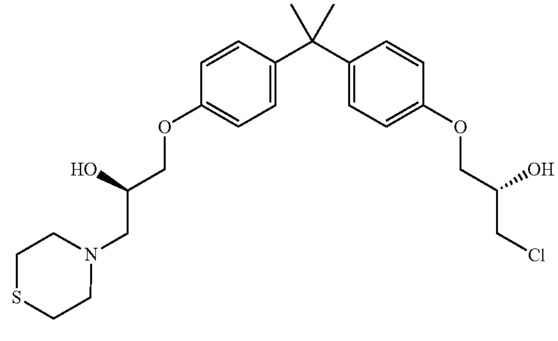 [SMILES: CC(C)(c1ccc(OC[C@H](O)CCl)cc1)c1ccc(OC[C@H](O)CN2CCSCC2)cc1] | (S)-1-chloro-3-(4-(2-(4-((R)-2-hydroxy-3-thiomorpholinopropoxy)phenyl)propan-2-yl)phenoxy)propan-2-ol |

TABLE 1-continued

| No. | Structure | Name |
|---|---|---|
| 17b | 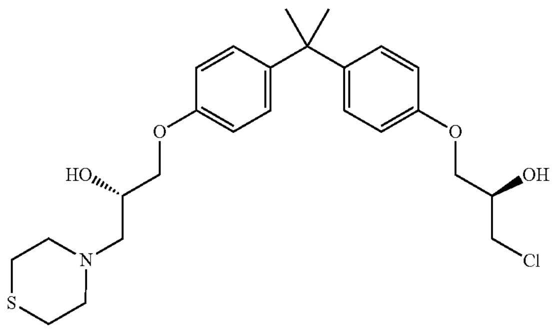 [SMILES: CC(C)(c1ccc(OC[C@@H](O)CN2CCSCC2)cc1)c1ccc(OC[C@@H](O)CCl)cc1] | (R)-1-chloro-3-(4-(2-(4-((S)-2-hydroxy-3-thiomorpholinopropoxy)phenyl)propan-2-yl)phenoxy)propan-2-ol |
| 17c | 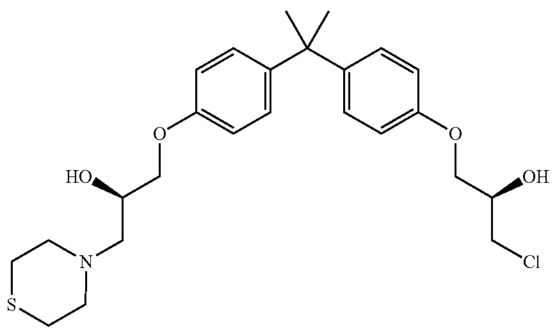 [SMILES: CC(C)(c1ccc(OC[C@@H](O)CCl)cc1)c1ccc(OC[C@H](O)CN2CCSCC2)cc1] | (R)-1-chloro-3-(4-(2-(4-((R)-2-hydroxy-3-thiomorpholinopropoxy)phenyl)propan-2-yl)phenoxy)propan-2-ol |
| 17d | 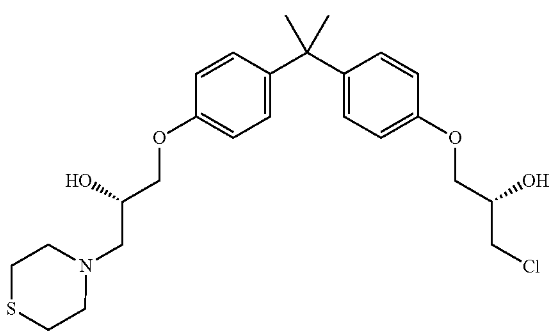 [SMILES: CC(C)(c1ccc(OC[C@H](O)CCl)cc1)c1ccc(OC[C@@H](O)CN2CCSCC2)cc1] | (S)-1-chloro-3-(4-(2-(4-((S)-2-hydroxy-3-thiomorpholinopropoxy)phenyl)propan-2-yl)phenoxy)propan-2-ol |
| 18 | 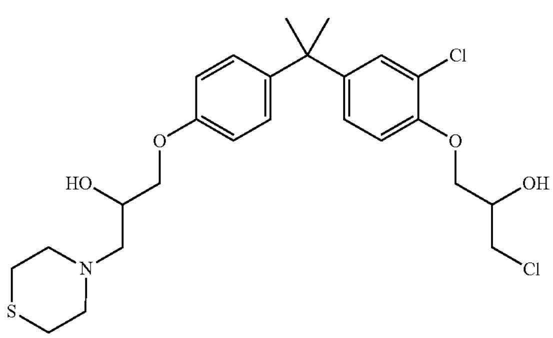 [SMILES: CC(C)(c1ccc(OCC(O)CN2CCSCC2)cc1)c1ccc(OCC(O)CCl)c(Cl)c1] | 1-chloro-3-(2-chloro-4-(2-(4-(2-hydroxy-3-thiomorpholinopropoxy)phenyl)propan-2-yl)phenoxy)propan-2-ol |

TABLE 1-continued

| No. | Structure | Name |
|---|---|---|
| 18a | 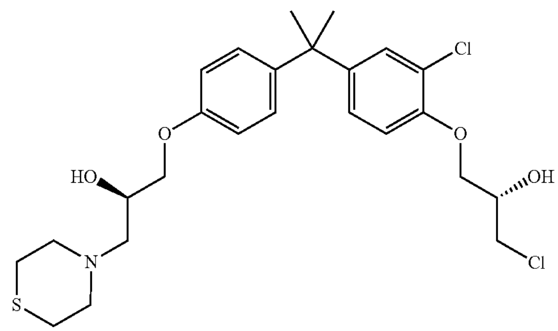 [SMILES: CC(C)(c1ccc(OC[C@H](O)CN2CCSCC2)cc1)c1ccc(OC[C@H](O)CCl)c(Cl)c1] | (S)-1-chloro-3-(2-chloro-4-(2-(4-((R)-2-hydroxy-3-thiomorpholinopropoxy)phenyl)propan-2-yl)phenoxy)propan-2-ol |
| 18b | 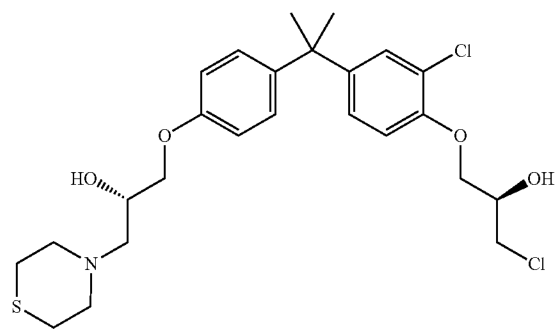 [SMILES: CC(C)(c1ccc(OC[C@@H](O)CN2CCSCC2)cc1)c1ccc(OC[C@@H](O)CCl)c(Cl)c1] | (R)-1-chloro-3-(2-chloro-4-(2-(4-((S)-2-hydroxy-3-thiomorpholinopropoxy)phenyl)propan-2-yl)phenoxy)propan-2-ol |
| 18c | 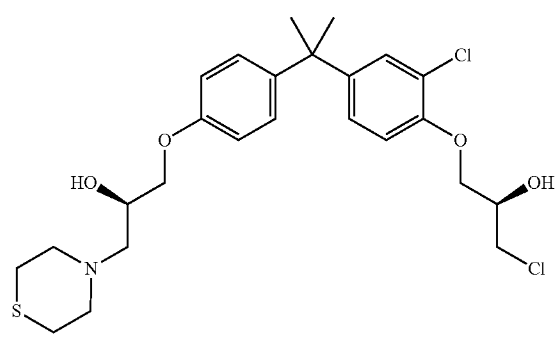 [SMILES: CC(C)(c1ccc(OC[C@H](O)CN2CCSCC2)cc1)c1ccc(OC[C@@H](O)CCl)c(Cl)c1] | (R)-1-chloro-3-(2-chloro-4-(2-(4-((R)-2-hydroxy-3-thiomorpholinopropoxy)phenyl)propan-2-yl)phenoxy)propan-2-ol |
| 18d | 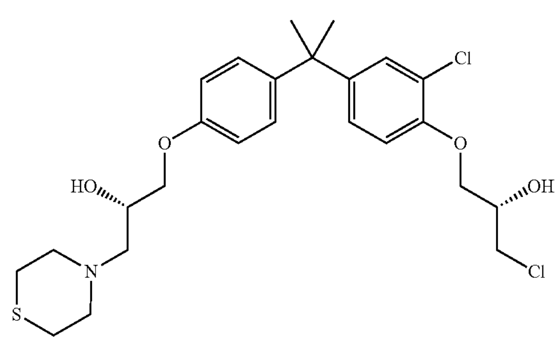 [SMILES: CC(C)(c1ccc(OC[C@@H](O)CN2CCSCC2)cc1)c1ccc(OC[C@H](O)CCl)c(Cl)c1] | (S)-1-chloro-3-(2-chloro-4-(2-(4-((S)-2-hydroxy-3-thiomorpholinopropoxy)phenyl)propan-2-yl)phenoxy)propan-2-ol |

TABLE 1-continued

| No. | Structure | Name |
|---|---|---|
| 19 | 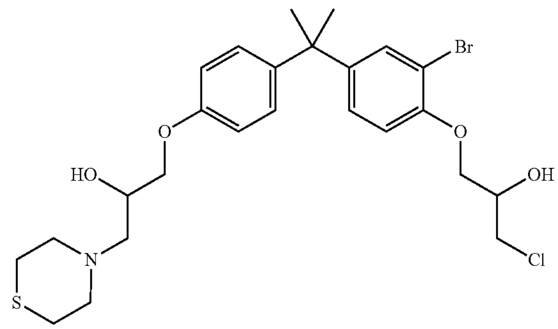 [SMILES: CC(C)(c1ccc(OCC(O)CN2CCSCC2)cc1)c1ccc(OCC(O)CCl)c(Br)c1] | 1-(2-bromo-4-(2-(4-(2-hydroxy-3-thiomorpholinopropoxy)phenyl)propan-2-yl)phenoxy)-3-chloropropan-2-ol |
| 19a | 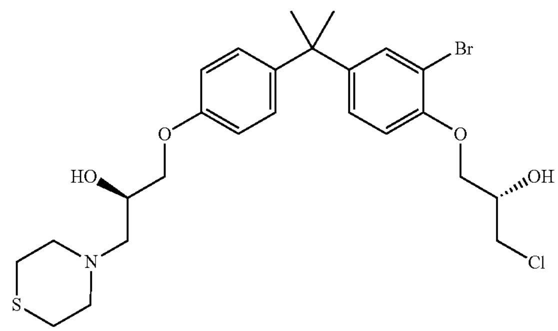 [SMILES: CC(C)(c1ccc(OC[C@H](O)CN2CCSCC2)cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-thiomorpholinopropan-2-ol |
| 19b | 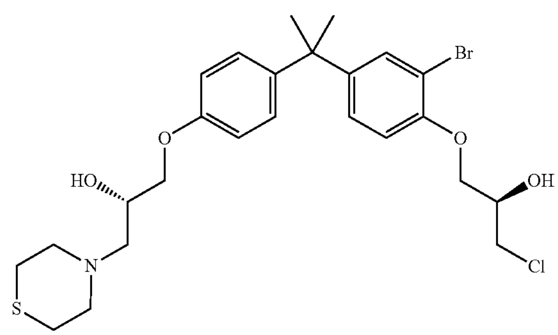 [SMILES: CC(C)(c1ccc(OC[C@@H](O)CN2CCSCC2)cc1)c1ccc(OC[C@@H](O)CCl)c(Br)c1] | (S)-1-(4-(2-(3-bromo-4-((R)-3-chloro-2-hydroxypropoxy)phenyl)propan-2-yl)phenoxy)-3-thiomorphohnopropan-2-ol |
| 19c | 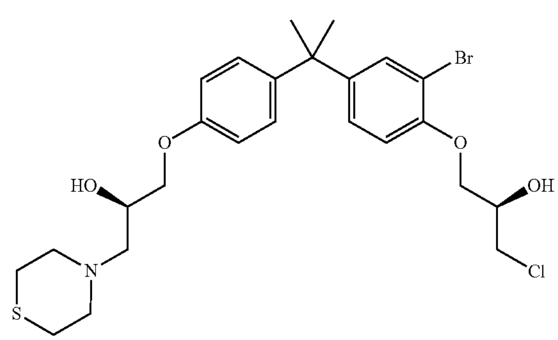 [SMILES: CC(C)(c1ccc(OC[C@H](O)CN2CCSCC2)cc1)c1ccc(OC[C@@H](O)CCl)c(Br)c1] | (R)-1-(4-(2-(3-bromo-4-((R)-3-chloro-2-hydroxypropoxy)phenyl)propan-2-yl)phenoxy)-3-thiomorpholinopropan-2-ol |

TABLE 1-continued

| No. | Structure | Name |
|---|---|---|
| 19d | 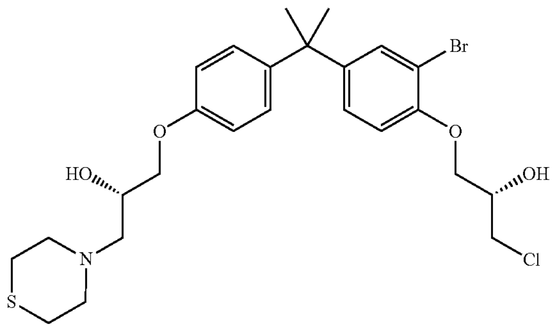 [SMILES: CC(C)(c1ccc(OC[C@@H](O)CN2CCSCC2)cc1)c1ccc(OC[C@H](O)CCl)c(Br)c1] | (S)-1-(4-(2-(3-bromo-4-((S)-3-chloro-2-hydroxypropoxy)phenyl)propan-2-yl)phenoxy)-3-thiomorpholinopropan-2-ol |
| 20 | 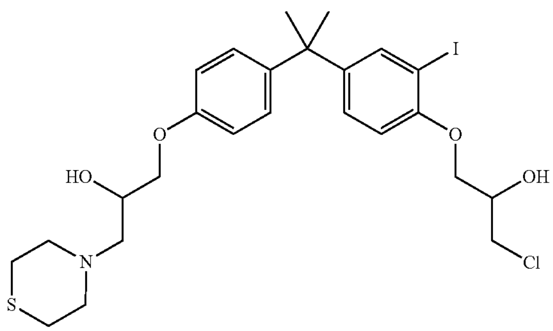 [SMILES: CC(C)(c1ccc(OCC(O)CN2CCSCC2)cc1)c1ccc(OCC(O)CCl)c(I)c1] | 1-chloro-3-(4-(2-(4-(2-hydroxy-3-thiomorpholinopropoxy)phenyl)propan-2-yl)-2-iodophenoxy)propan-2-ol |
| 20a | 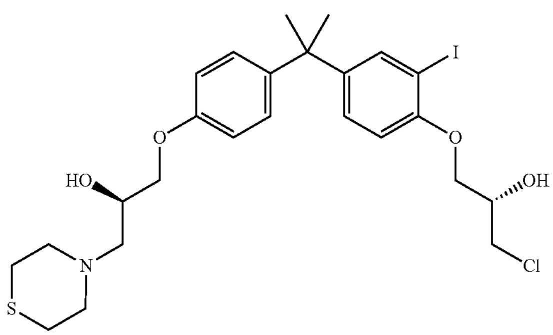 | (S)-1-chloro-3-(4-(2-(4-((R)-2-hydroxy-3-thiomorpholinopropoxy)phenyl)propan-2-yl)-2-iodophenoxy)propan-2-ol |
| 20b | 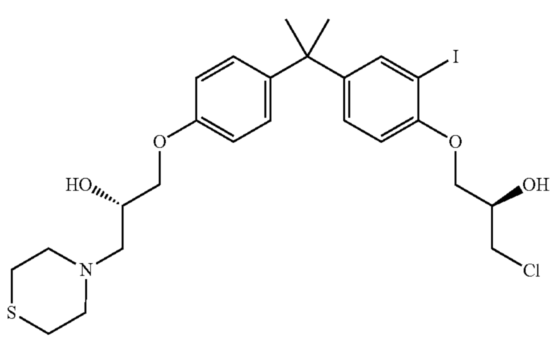 [SMILES: CC(C)(c1ccc(OC[C@@H](O)CN2CCSCC2)cc1)c1ccc(OC[C@@H](O)CCl)c(I)c1] | (R)-1-chloro-3-(4-(2-(4-((RS)-2-hydroxy-3-thiomorpholinopropoxy)phenyl)propan-2-yl)-2-iodophenoxy)propan-2-ol |

TABLE 1-continued

| No. | Structure | Name |
|---|---|---|
| 20c | 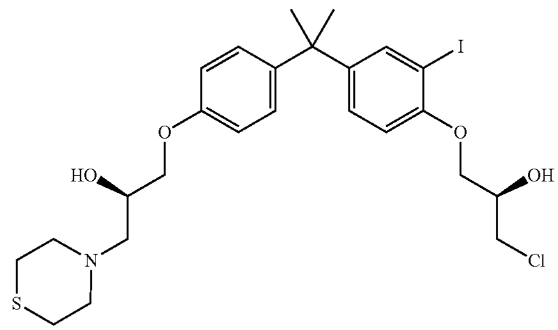 [SMILES: CC(C)(c1ccc(OC[C@H](O)CN2CCSCC2)cc1)c1ccc(OC[C@@H](O)CCl)c(I)c1] | (R)-1-chloro-3-(4-(2-(4-((R)-2-hydroxy-3-thiomorpholinopropoxy)phenyl)propan-2-yl)-2-iodophenoxy)propan-2-ol |
| 20d | 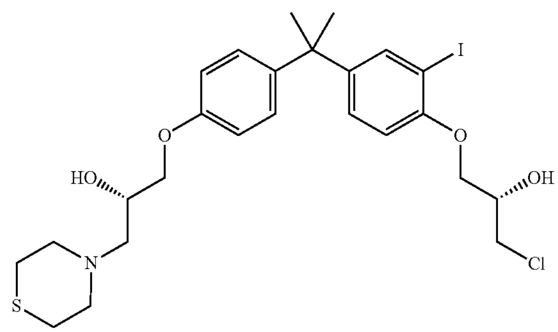 [SMILES: CC(C)(c1ccc(OC[C@@H](O)CN2CCSCC2)cc1)c1ccc(OC[C@H](O)CCl)c(I)c1] | (S)-1-chloro-3-(4-(2-(4-((S)-2-hydroxy-3-thiomorpholinopropoxy)phenyl)propan-2-yl)-2-iodophenoxy)propan-2-ol |
| 21 | 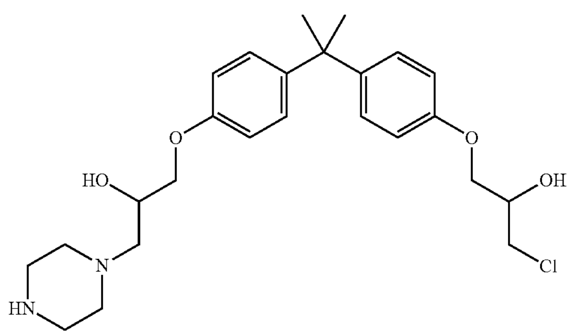 [SMILES: CC(C)(c1ccc(OCC(O)CCl)cc1)c1ccc(OCC(O)CN2CCNCC2)cc1] | 1-chloro-3-(4-(2-(4-(2-hydroxy-3-(piperazin-1-yl)propoxy)phenyl)propan-2-yl)phenoxy)propan-2-ol |
| 21a | 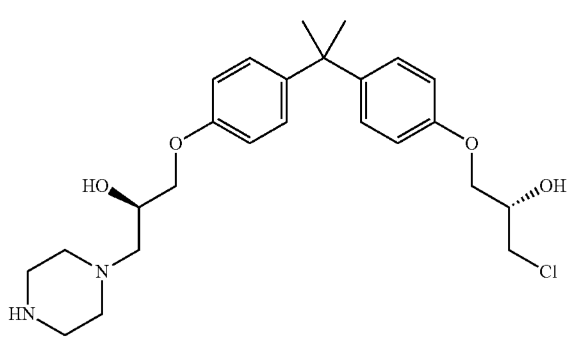 [SMILES: CC(C)(c1ccc(OC[C@H](O)CCl)cc1)c1ccc(OC[C@H](O)CN2CCNCC2)cc1] | (S)-1-chloro-3-(4-(2-(4-((R)-2-hydroxy-3-(piperazin-1-yl)propoxy)phenyl)propan-2-yl)phenoxy)propan-2-ol |

TABLE 1-continued

| No. | Structure | Name |
|---|---|---|
| 21b | 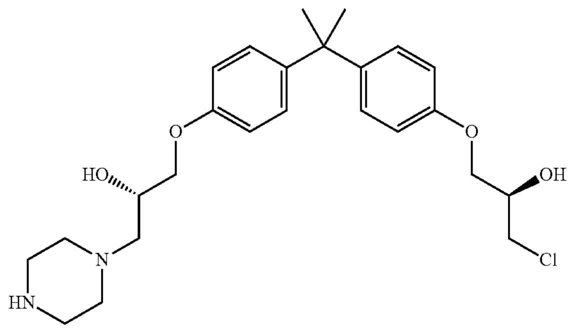 [SMILES: CC(C)(c1ccc(OC[C@@H](O)CN2CCNCC2)cc1)c1ccc(OC[C@@H](O)CCl)cc1] | (R)-1-chloro-3-(4-(2-(4-((S)-2-hydroxy-3-(piperazin-1-yl)propoxy)phenyl)propan-2-yl)phenoxy)propan-2-ol |
| 21c | 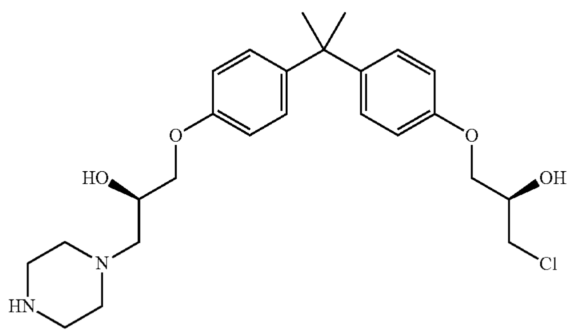 [SMILES: CC(C)(c1ccc(OC[C@@H](O)CCl)cc1)c1ccc(OC[C@H](O)CN2CCNCC2)cc1] | (R)-1-chloro-3-(4-(2-(4-((R)-2-hydroxy-3-(piperazin-1-yl)propoxy)phenyl)propan-2-yl)phenoxy)propan-2-ol |
| 21d | 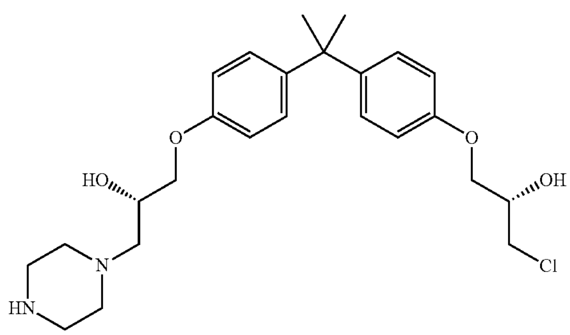 [SMILES: CC(C)(c1ccc(OC[C@H](O)CCl)cc1)c1ccc(OC[C@@H](O)CN2CCNCC2)cc1] | (S)-1-chloro-3-(4-(2-(4-((S)-2-hydroxy-3-(piperazin-1-yl)propoxy)phenyl)propan-2-yl)phenoxy)propan-2-ol |
| 22 | 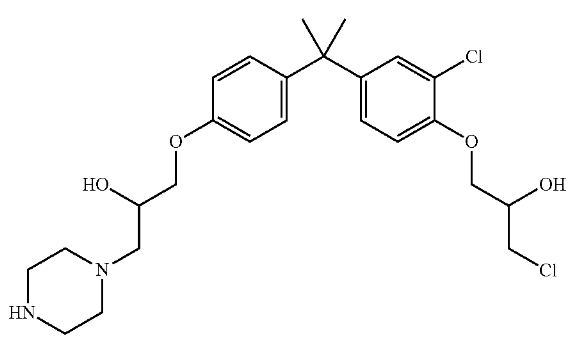 | 1-chloro-3-(2-chloro-4-(2-(4-(2-hydroxy-3-(piperazin-1-yl)propoxy)phenyl)propan-2-yl)phenoxy)propan-2-ol |

TABLE 1-continued

| No. | Structure | Name |
|---|---|---|
| 22a | 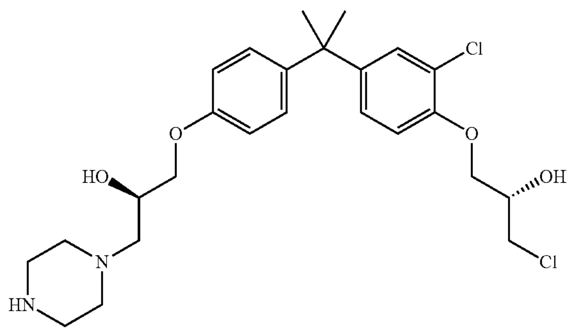 | (S)-1-chloro-3-(2-chloro-4-(2-(4-((R)-2-hydroxy-3-(piperazin-1-yl)propoxy)phenyl)propan-2-yl)phenoxy)propan-2-ol |
| 22b | 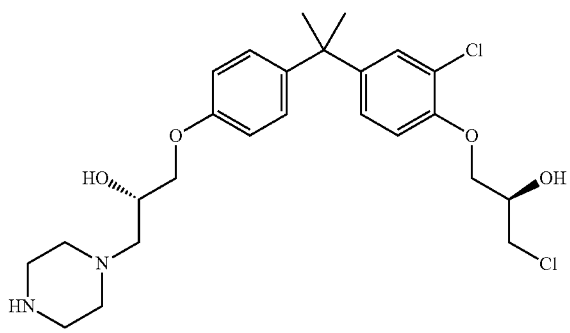 | (R)-1-chloro-3-(2-chloro-4-(2-(4-((S)-2-hydroxy-3-(piperazin-1-yl)propoxy)phenyl)propan-2-yl)phenoxy)propan-2-ol |
| 22c | 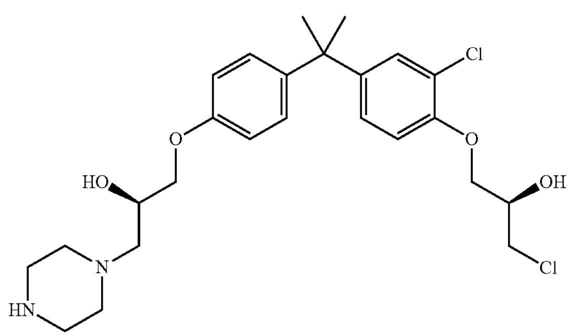 | (R)-1-chloro-3-(2-chloro-4-(2-(4-((R)-2-hydroxy-3-(piperazin-1-yl)propoxy)phenyl)propan-2-yl)phenoxy)propan-2-ol |
| 22d | 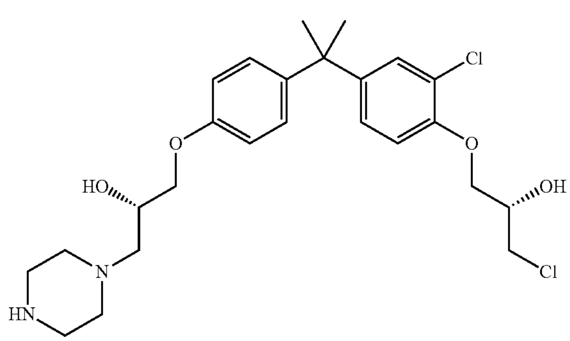 | (S)-1-chloro-3-(2-chloro-4-(2-(4-((S)-2-hydroxy-3-(piperazin-1-yl)propoxy)phenyl)propan-2-yl)phenoxy)propan-2-ol |

TABLE 1-continued

| No. | Structure | Name |
|---|---|---|
| 23 | 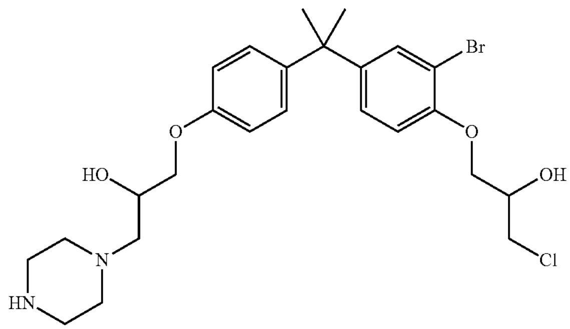 | 1-(2-bromo-4-(2-(4-(2-hydroxy-3-(piperazin-1-yl)propoxy)phenyl)propan-2-yl)phenoxy)-3-chloropropan-2-ol |
| 23a | 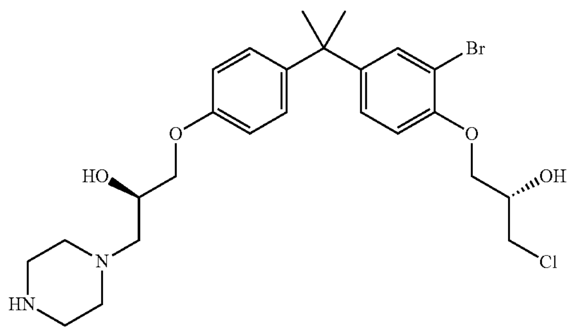 [SMILES: CC(C)(c1ccc(OC[C@H](O)CN2CCNCC2)cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-(piperazin-1-yl)propan-2-ol |
| 23b | 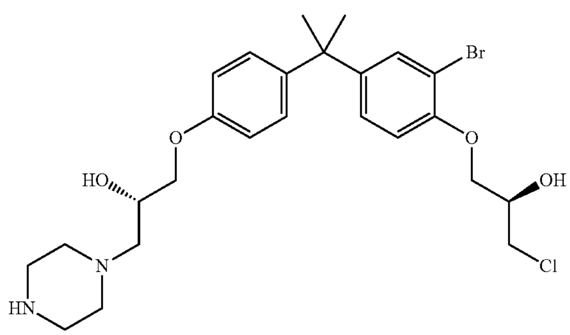 [SMILES: CC(C)(c1ccc(OC[C@@H](O)CN2CCNCC2)cc1)c1ccc(OC[C@@H](O)CCl)c(Br)c1] | (S)-1-(4-(2-(3-bromo-4-((R)-3-chloro-2-hydroxypropoxy)phenyl)propan-2-yl)phenoxy)-3-(piperazin-1-yl)propan-2-ol |
| 23c | 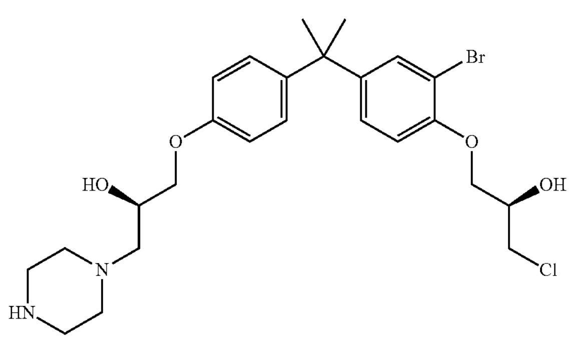 | (R)-1-(4-(2-(3-bromo-4-((R)-3-chloro-2-hydroxypropoxy)phenyl)propan-2-yl)phenoxy)-3-(piperazin-1-yl)propan-2-ol |

TABLE 1-continued

| No. | Structure | Name |
|---|---|---|
| 23d | 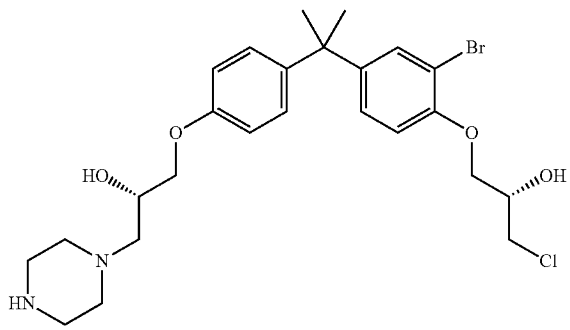 [SMILES: CC(C)(c1ccc(OC[C@@H](O)CN2CCNCC2)cc1)c1ccc(OC[C@H](O)CCl)c(Br)c1] | (S)-1-(4-(2-(3-bromo-4-((S)-3-chloro-2-hydroxypropoxy)phenyl)propan-2-yl)phenoxy)-3-(piperazin-1-yl)propan-2-ol |
| 24 | 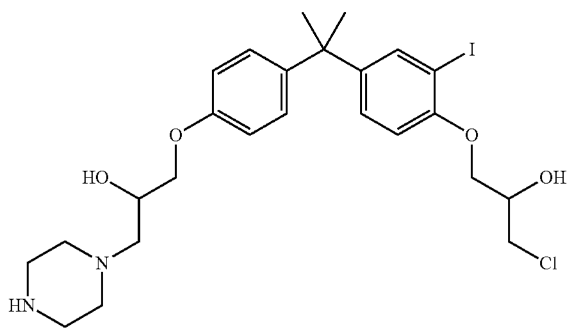 [SMILES: CC(C)(c1ccc(OCC(O)CN2CCNCC2)cc1)c1ccc(OCC(O)CCl)c(I)c1] | 1-chloro-3-(4-(2-(4-(2-hydroxy-3-(piperazin-1-yl)propoxy)phenyl)propan-2-yl)-2-iodophenoxy)propan-2-ol |
| 24a | 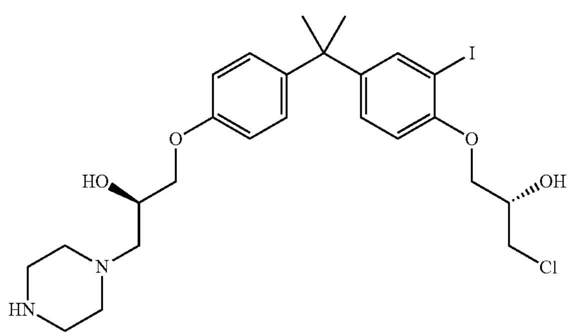 [SMILES: CC(C)(c1ccc(OC[C@H](O)CN2CCNCC2)cc1)c1ccc(OC[C@H](O)CCl)c(I)c1] | (S)-1-chloro-3-(4-(2-(4-((R)-2-hydroxy-3-(piperazin-1-yl)propoxy)phenyl)propan-2-yl)-2-iodophenoxy)propan-2-ol |
| 24b | 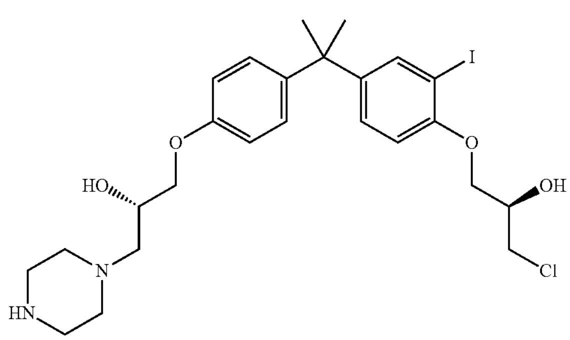 [SMILES: CC(C)(c1ccc(OC[C@@H](O)CN2CCNCC2)cc1)c1ccc(OC[C@@H](O)CCl)c(I)c1] | (R)-1-chloro-3-(4-(2-(4-((S)-2-hydroxy-3-(piperazin-1-yl)propoxy)phenyl)propan-2-yl)-2-iodophenoxy)propan-2-ol |

TABLE 1-continued

| No. | Structure | Name |
|---|---|---|
| 24c | 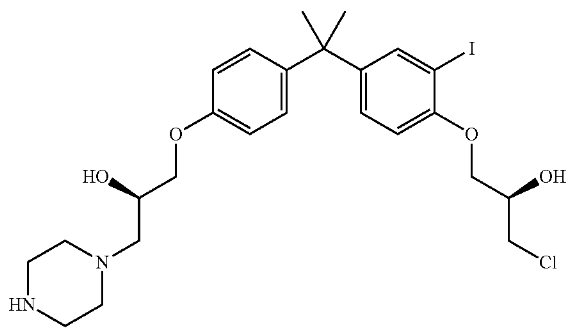 [SMILES: CC(C)(c1ccc(OC[C@H](O)CN2CCNCC2)cc1)c1ccc(OC[C@@H](O)CCl)c(I)c1] | (R)-1-chloro-3-(4-(2-(4-((R)-2-hydroxy-3-(piperazin-1-yl)propoxy)phenyl)propan-2-yl)-2-iodophenoxy)propan-2-ol |
| 24d | 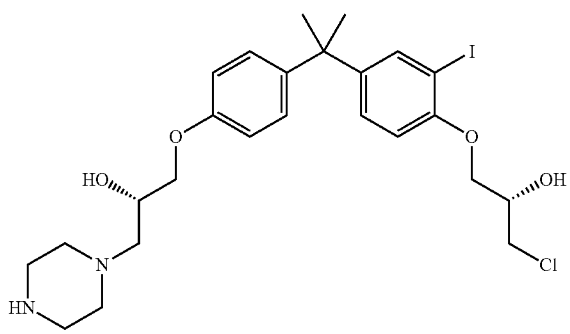 [SMILES: CC(C)(c1ccc(OC[C@@H](O)CN2CCNCC2)cc1)c1ccc(OC[C@H](O)CCl)c(I)c1] | (S)-1-chloro-3-(4-(2-(4-((S)-2-hydroxy-3-(piperazin-1-yl)propoxy)phenyl)propan-2-yl)-2-iodophenoxy)propan-2-ol |
| 25 | 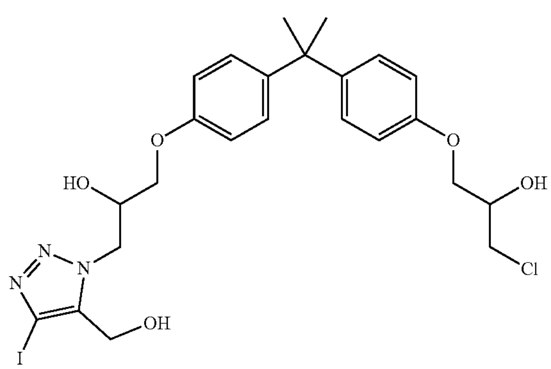 [SMILES: CC(C)(c1ccc(OCC(O)CCl)cc1)c1ccc(OCC(O)Cn2nnc(I)c2CO)cc1] | 1-chloro-3-(4-(2-(4-(2-hydroxy-3-(5-(hydroxymethyl)-4-iodo-1H-1,2,3-triazol-1-yl)propoxy)phenyl)propan-2-yl)phenoxy)propan-2-ol |
| 25a | 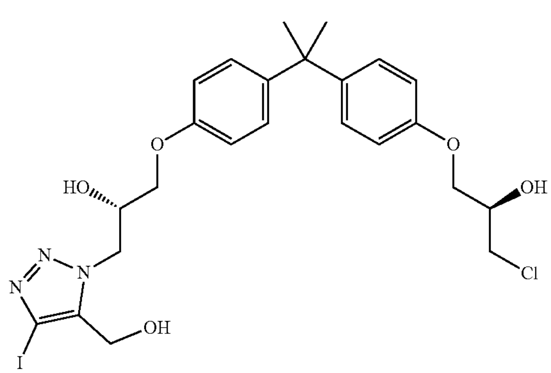 [SMILES: CC(C)(c1ccc(OC[C@@H](O)Cn2nnc(I)c2CO)cc1)c1ccc(OC[C@@H](O)CCl)cc1] | (S)-1-chloro-3-(4-(2-(4-((R)-2-hydroxy-3-(5-(hydroxymethyl)-4-iodo-1H-1,2,3-triazol-1-yl)propoxy)phenyl)propan-2-yl)phenoxy)propan-2-ol |

TABLE 1-continued

| No. | Structure | Name |
|---|---|---|
| 25b | 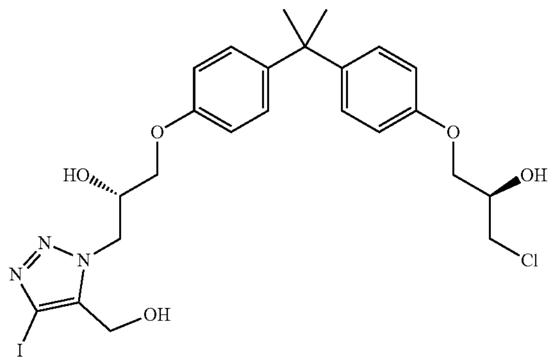 [SMILES: CC(C)(c1ccc(OC[C@@H](O)Cn2nnc(I)c2CO)cc1)c1ccc(OC[C@@H](O)CCl)cc1] | (R)-1-chloro-3-(4-(2-(4-((S)-2-hydroxy-3-(5-(hydroxymethyl)-4-iodo-1H-1,2,3-triazol-1-yl)propoxy)phenyl)propan-2-yl)phenoxy)propan-2-ol |
| 25c | 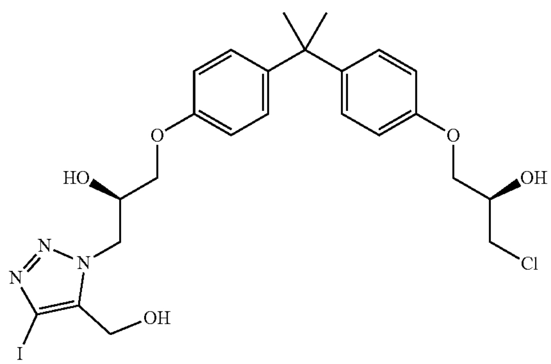 [SMILES: CC(C)(c1ccc(OC[C@@H](O)CCl)cc1)c1ccc(OC[C@H](O)Cn2nnc(I)c2CO)cc1] | (R)-1-chloro-3-(4-(2-(4-((R)-2-hydroxy-3-(5-(hydroxymethyl)-4-iodo-1H-1,2,3-triazol-1-yl)propoxy)phenyl)propan-2-yl)phenoxy)propan-2-ol |
| 25d | 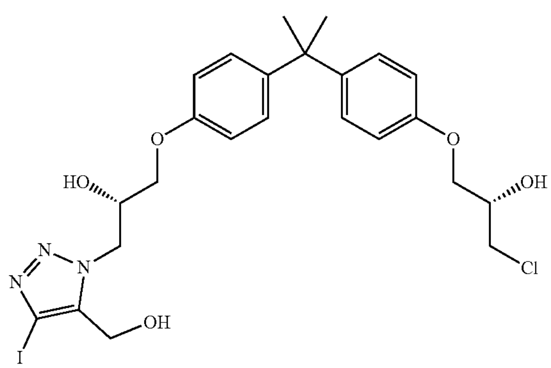 [SMILES: CC(C)(c1ccc(OC[C@H](O)CCl)cc1)c1ccc(OC[C@@H](O)Cn2nnc(I)c2CO)cc1] | (S)-1-chloro-3-(4-(2-(4-((S)-2-hydroxy-3-(5-(hydroxymethyl)-4-iodo-1H-1,2,3-triazol-1-yl)propoxy)phenyl)propan-2-yl)phenoxy)propan-2-ol |
| 26 | 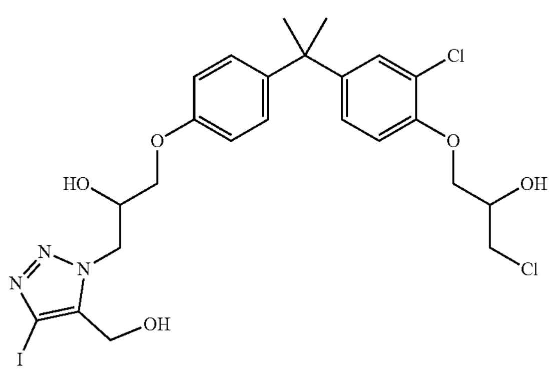 [SMILES: CC(C)(c1ccc(OCC(O)Cn2nnc(I)c2CO)cc1)c1ccc(OCC(O)CCl)c(Cl)c1] | 1-chloro-3-(2-chloro-4-(2-(4-(2-hydroxy-3-(5-(hydroxymethyl)-4-iodo-1H-1,2,3-triazol-1-yl)propoxy)phenyl)propan-2-yl)phenoxy)propan-2-ol |

TABLE 1-continued

Compounds

| No. | Structure | Name |
|---|---|---|
| 26a | 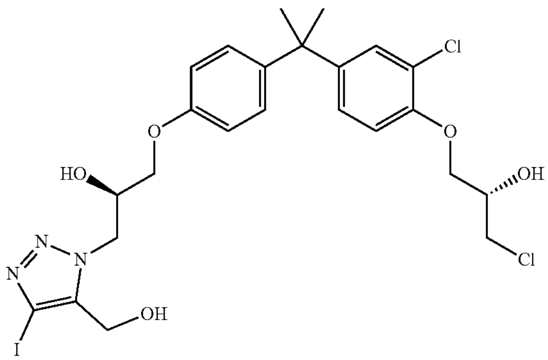 [SMILES: CC(C)(c1ccc(OC[C@H](O)Cn2nnc(I)c2CO)cc1)c1ccc(OC[C@H](O)CCl)c(Cl)c1] | (S)-1-chloro-3-(2-chloro-4-(2-(4-((R)-2-hydroxy-3-(5-(hydroxymethyl)-4-iodo-1H-1,2,3-triazol-1-yl)propoxy)phenyl)propan-2-yl)phenoxy)propan-2-ol |
| 26b | 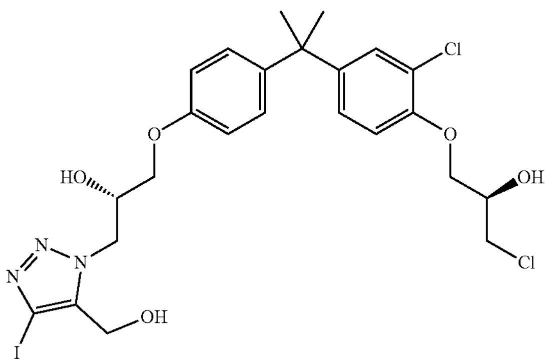 [SMILES: CC(C)(c1ccc(OC[C@@H](O)Cn2nnc(I)c2CO)cc1)c1ccc(OC[C@@H](O)CCl)c(Cl)c1] | (R)-1-chloro-3-(2-chloro-4-(2-(4-((S)-2-hydroxy-3-(5-(hydroxymethyl)-4-iodo-1H-1,2,3-triazol-1-yl)propoxy)phenyl)propan-2-yl)phenoxy)propan-2-ol |
| 26c | 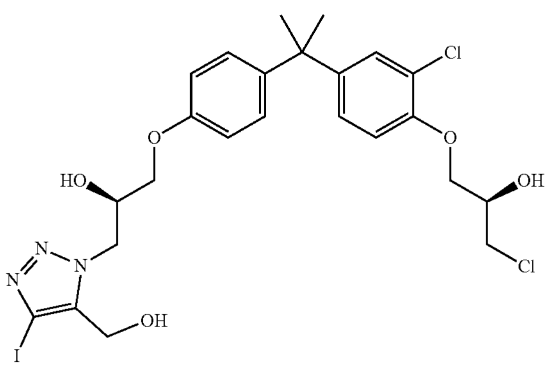 [SMILES: CC(C)(c1ccc(OC[C@H](O)Cn2nnc(I)c2CO)cc1)c1ccc(OC[C@@H](O)CCl)c(Cl)c1] | (R)-1-chloro-3-(2-chloro-4-(2-(4-((R)-2-hydroxy-3-(5-(hydroxymethyl)-4-iodo-1H-1,2,3-triazol-1-yl)propoxy)phenyl)propan-2-yl)phenoxy)propan-2-ol |
| 26d | 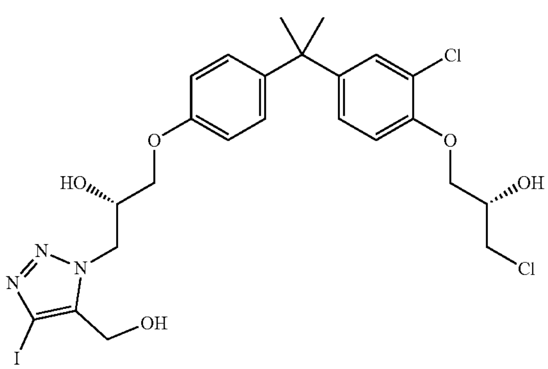 [SMILES: CC(C)(c1ccc(OC[C@@H](O)Cn2nnc(I)c2CO)cc1)c1ccc(OC[C@H](O)CCl)c(Cl)c1] | (S)-1-chloro-3-(2-chloro-4-(2-(4-((S)-2-hydroxy-3-(5-(hydroxymethyl)-4-iodo-1H-1,2,3-triazol-1-yl)propoxy)phenyl)propan-2-yl)phenoxy)propan-2-ol |

TABLE 1-continued

| No. | Structure | Name |
|---|---|---|
| 27 | 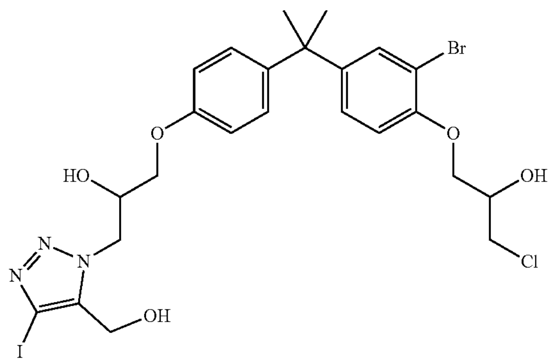 [SMILES: CC(C)(c1ccc(OCC(O)Cn2nnc(I)c2CO)cc1)c1ccc(OCC(O)CCl)c(Br)c1] | 1-(2-bromo-4-(2-(4-(2-hydroxy-3-(5-(hydroxymethyl)-4-iodo-1H-1,2,3-triazol-1-yl)propoxy)phenyl)propan-2-yl)phenoxy)-3-chloropropan-2-ol |
| 27a | 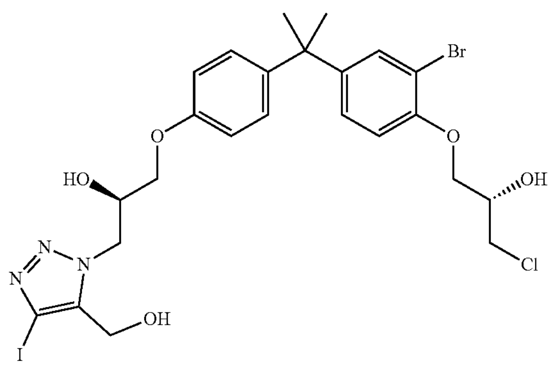 [SMILES: CC(C)(c1ccc(OC[C@H](O)Cn2nnc(I)c2CO)cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-(5-(hydroxymethyl)-4-iodo-1H-1,2,3-triazol-1-yl)propan-2-ol |
| 27b | 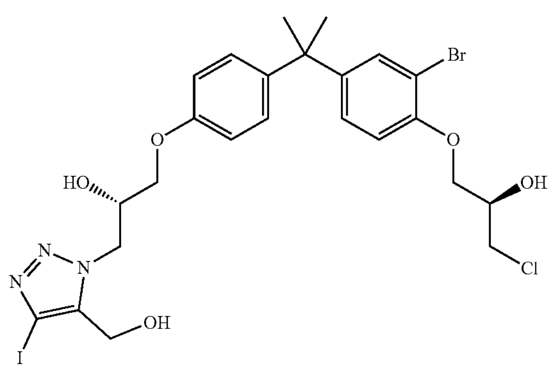 [SMILES: CC(C)(c1ccc(OC[C@@H](O)Cn2nnc(I)c2CO)cc1)c1ccc(OC[C@@H](O)CCl)c(Br)c1] | (S)-1-(4-(2-(3-bromo-4-((R)-3-chloro-2-hydroxypropoxy)phenyl)propan-2-yl)phenoxy)-3-(5-(hydroxymethyl)-4-iodo-1H-1,2,3-triazol-1-yl)propan-2-ol |
| 27c | 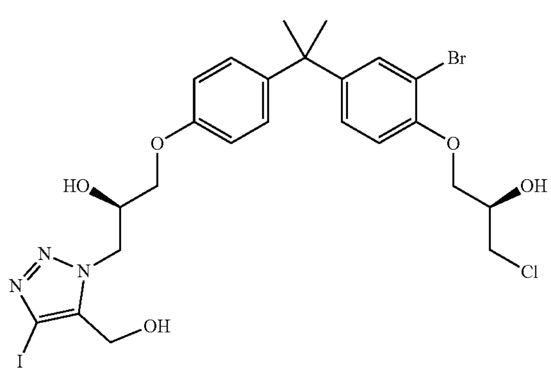 [SMILES: CC(C)(c1ccc(OC[C@H](O)Cn2nnc(I)c2CO)cc1)c1ccc(OC[C@@H](O)CCl)c(Br)c1] | (R)-1-(4-(2-(3-bromo-4-((R)-3-chloro-2-hydroxypropoxy)phenyl)propan-2-yl)phenoxy)-3-(5-(hydroxymethyl)-4-iodo-1H-1,2,3-triazol-1-yl)propan-2-ol |

TABLE 1-continued

| No. | Structure | Name |
|---|---|---|
| 27d | 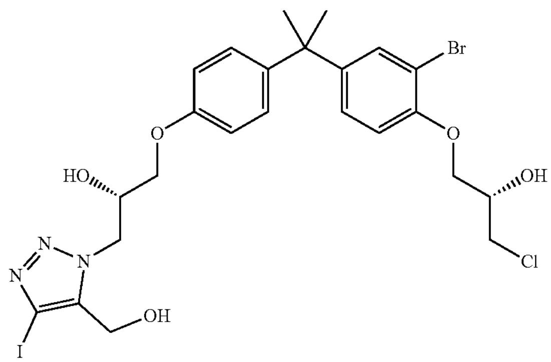 | (S)-1-(4-(2-(3-bromo-4-((S)-3-chloro-2-hydroxypropoxy)phenyl)propan-2-yl)phenoxy)-3-(5-(hydroxymethyl)-4-iodo-1H-1,2,3-triazol-1-yl)propan-2-ol |
| 28 | 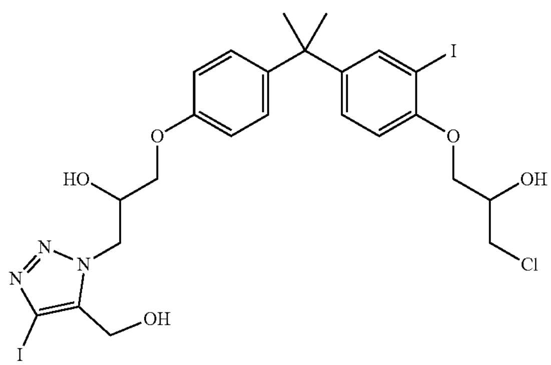 [SMILES: CC(C)(c1ccc(OCC(O)Cn2nnc(I)c2CO)cc1)c1ccc(OCC(O)CCl)c(I)c1] | 1-chloro-3-(4-(2-(4-(2-hydroxy-3-(5-(hydroxymethyl)-4-iodo-1H-1,2,3-triazol-1-yl)propoxy)phenyl)propan-2-yl)-2-iodophenoxy)propan-2-ol |
| 28a | 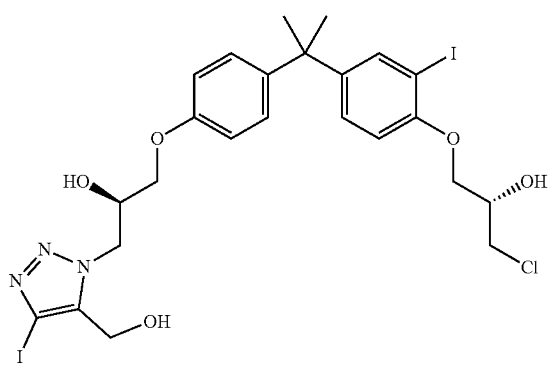 [SMILES: CC(C)(c1ccc(OC[C@H](O)Cn2nnc(I)c2CO)cc1)c1ccc(OC[C@H](O)CCl)c(I)c1] | (S)-1-chloro-3-(4-(2-(4-((R)-2-hydroxy-3-(5-(hydroxymethyl)-4-iodo-1H-1,2,3-triazol-1-yl)propoxy)phenyl)propan-2-yl)-2-iodophenoxy)propan-2-ol |
| 28b | 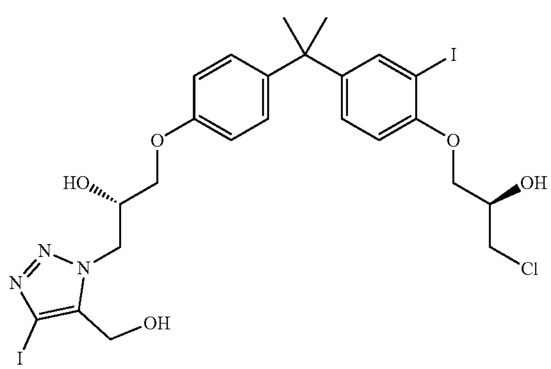 [SMILES: CC(C)(c1ccc(OC[C@@H](O)Cn2nnc(I)c2CO)cc1)c1ccc(OC[C@@H](O)CCl)c(I)c1] | (R)-1-chloro-3-(4-(2-(4-((S)-2-hydroxy-3-(5-(hydroxymethyl)-4-iodo-1H-1,2,3-triazol-1-yl)propoxy)phenyl)propan-2-yl)-2-iodophenoxy)propan-2-ol |

TABLE 1-continued

| No. | Structure | Name |
|---|---|---|
| 28c | 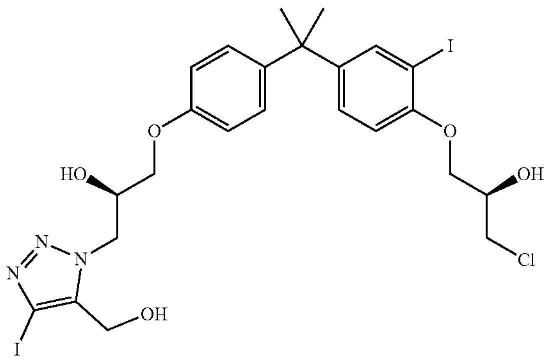 [SMILES: CC(C)(c1ccc(OC[C@H](O)Cn2nnc(I)c2CO)cc1)c1ccc(OC[C@@H](O)CCl)c(I)c1] | (R)-1-chloro-3-(4-(2-(4-((R)-2-hydroxy-3-(5-(hydroxymethyl)-4-iodo-1H-1,2,3-triazol-1-yl)propoxy)phenyl)propan-2-yl)-2-iodophenoxy)propan-2-ol |
| 28d | 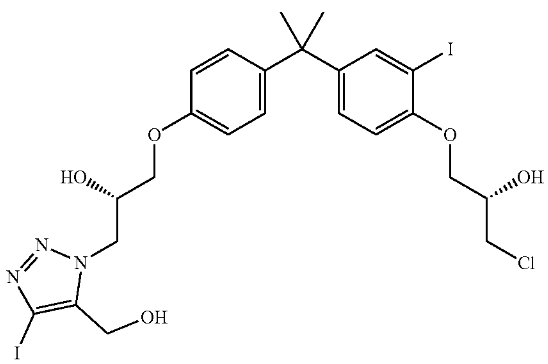 [SMILES: CC(C)(c1ccc(OC[C@@H](O)Cn2nnc(I)c2CO)cc1)c1ccc(OC[C@H](O)CCl)c(I)c1] | (S)-1-chloro-3-(4-(2-(4-((S)-2-hydroxy-3-(5-(hydroxymethyl)-4-iodo-1H-1,2,3-triazol-1-yl)propoxy)phenyl)propan-2-yl)-2-iodophenoxy)propan-2-ol |
| 29 | 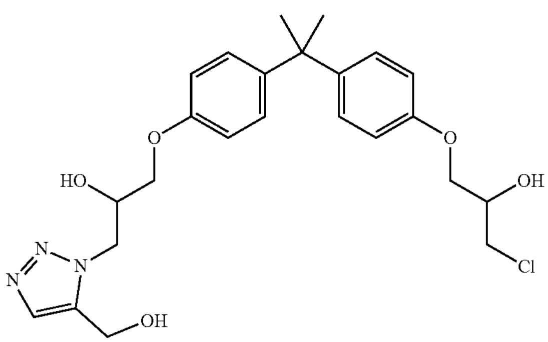 [SMILES: CC(C)(c1ccc(OCC(O)CCl)cc1)c1ccc(OCC(O)Cn2nncc2CO)cc1] | 1-chloro-3-(4-(2-(4-(2-hydroxy-3-(5-(hydroxymethyl)-1H-1,2,3-triazol-1-yl)propoxy)phenyl)propan-2-yl)phenoxy)propan-2-ol |
| 29a | 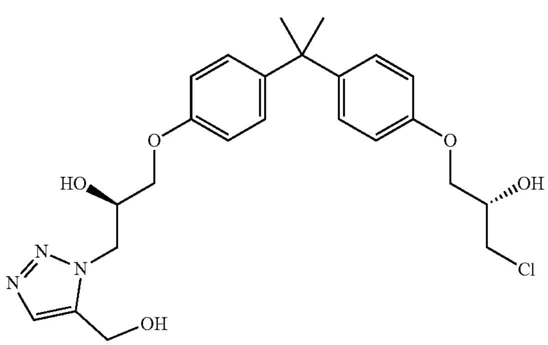 [SMILES: CC(C)(c1ccc(OC[C@H](O)CCl)cc1)c1ccc(OC[C@H](O)Cn2nncc2CO)cc1] | (S)-1-chloro-3-(4-(2-(4-((R)-2-hydroxy-3-(5-(hydroxymethyl)-1H-1,2,3-triazol-1-yl)propoxy)phenyl)propan-2-yl)phenoxy)propan-2-ol |

TABLE 1-continued

| No. | Structure | Name |
|---|---|---|
| 29b | 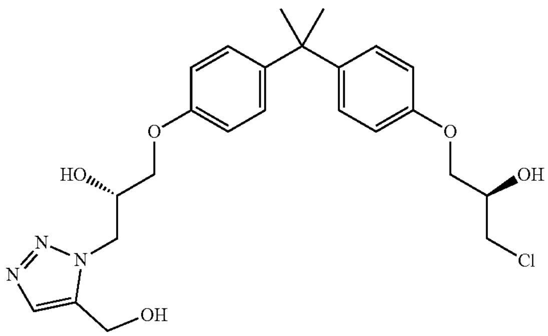 [SMILES: CC(C)(c1ccc(OC[C@@H](O)Cn2nncc2CO)cc1)c1ccc(OC[C@@H](O)CCl)cc1] | (R)-1-chloro-3-(4-(2-(4-((S)-2-hydroxy-3-(5-(hydroxymethyl)-1H-1,2,3-triazol-1-yl)propoxy)phenyl)propan-2-yl)phenoxy)propan-2-ol |
| 29c | 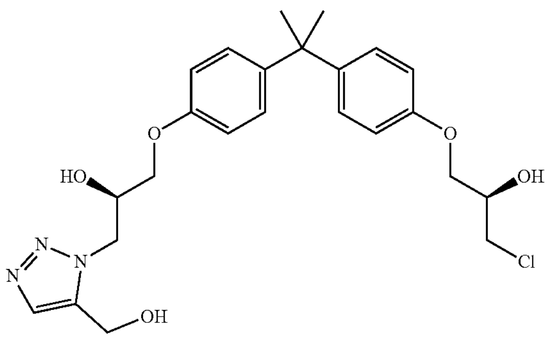 [SMILES: CC(C)(c1ccc(OC[C@@H](O)CCl)cc1)c1ccc(OC[C@H](O)Cn2nncc2CO)cc1] | (R)-1-chloro-3-(4-(2-(4-((R)-2-hydroxy-3-(5-(hydroxymethyl)-1H-1,2,3-triazol-1-yl)propoxy)phenyl)propan-2-yl)phenoxy)propan-2-ol |
| 29d | 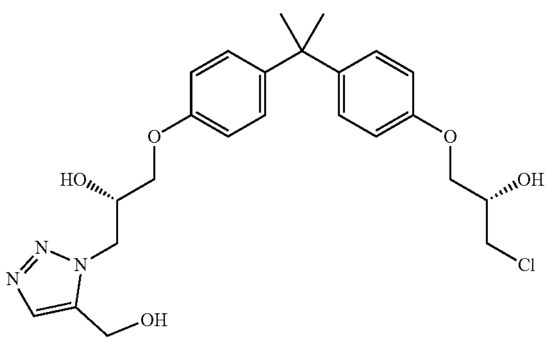 [SMILES: CC(C)(c1ccc(OC[C@H](O)CCl)cc1)c1ccc(OC[C@@H](O)Cn2nncc2CO)cc1] | (S)-1-chloro-3-(4-(2-(4-((S)-2-hydroxy-3-(5-(hydroxymethyl)-1H-1,2,3-triazol-1-yl)propoxy)phenyl)propan-2-yl)phenoxy)propan-2-ol |
| 30 | 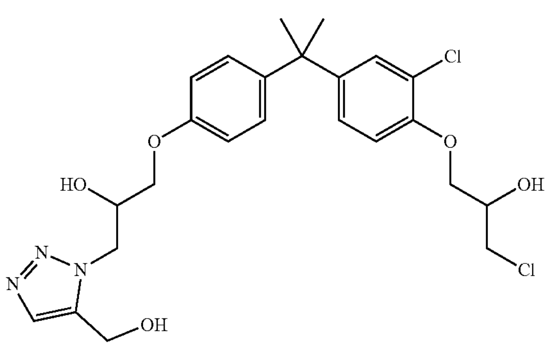 [SMILES: CC(C)(c1ccc(OCC(O)Cn2nncc2CO)cc1)c1ccc(OCC(O)CCl)c(Cl)c1] | 1-chloro-3-(2-chloro-4-(2-(4-(2-hydroxy-3-(5-(hydroxymethyl)-1H-1,2,3-triazol-1-yl)propoxy)phenyl)propan-2-yl)phenoxy)propan-2-ol |

TABLE 1-continued

| No. | Structure | Name |
|---|---|---|
| 30a | 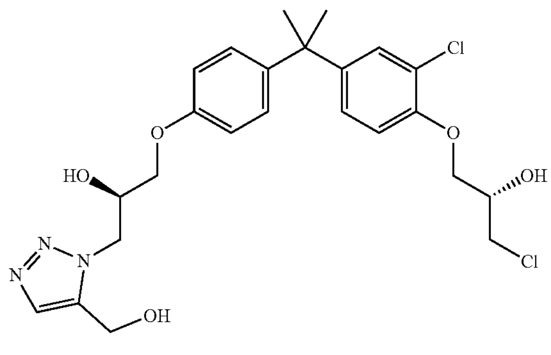 [SMILES: CC(C)(c1ccc(OC[C@H](O)Cn2nncc2CO)cc1)c1ccc(OC[C@H](O)CCl)c(Cl)c1] | (S)-1-chloro-3-(2-chloro-4-(2-(4-((R)-2-hydroxy-3-(5-(hydroxymethyl)-1H-1,2,3-triazol-1-yl)propoxy)phenyl)propan-2-yl)phenoxy)propan-2-ol |
| 30b | 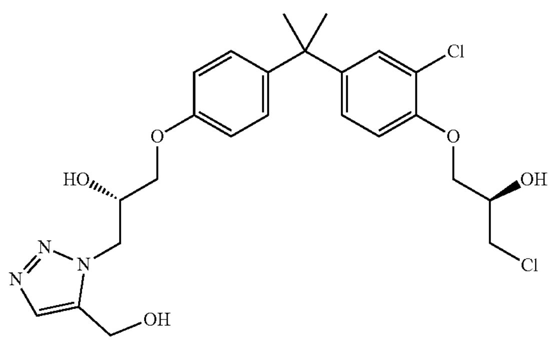 [SMILES: CC(C)(c1ccc(OC[C@@H](O)Cn2nncc2CO)cc1)c1ccc(OC[C@@H](O)CCl)c(Cl)c1] | (R)-1-chloro-3-(2-chloro-4-(2-(4-((S)-2-hydroxy-3-(5-(hydroxymethyl)-1H-1,2,3-triazol-1-yl)propoxy)phenyl)propan-2-yl)phenoxy)propan-2-ol |
| 30c | 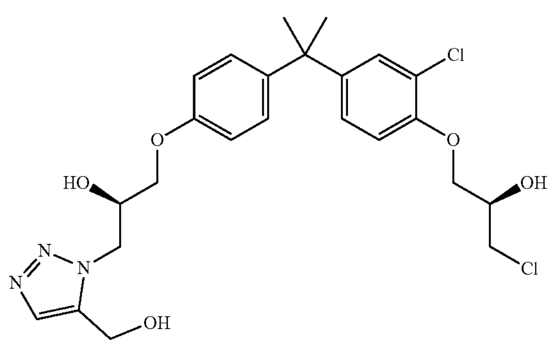 [SMILES: CC(C)(c1ccc(OC[C@H](O)Cn2nncc2CO)cc1)c1ccc(OC[C@@H](O)CCl)c(Cl)c1] | (R)-1-chloro-3-(2-chloro-4-(2-(4-((R)-2-hydroxy-3-(5-(hydroxymethyl)-1H-1,2,3-triazol-1-yl)propoxy)phenyl)propan-2-yl)phenoxy)propan-2-ol |
| 30d | 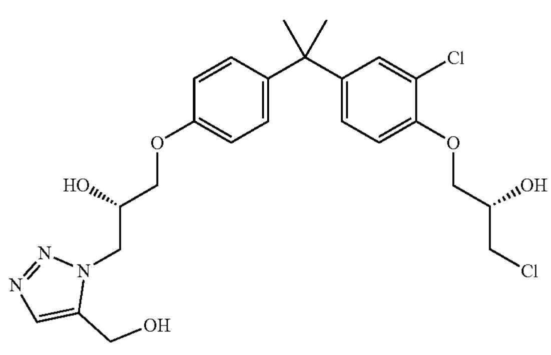 [SMILES: CC(C)(c1ccc(OC[C@@H](O)Cn2nncc2CO)cc1)c1ccc(OC[C@H](O)CCl)c(Cl)c1] | (S)-1-chloro-3-(2-chloro-4-(2-(4-((S)-2-hydroxy-3-(5-(hydroxymethyl)-1H-1,2,3-triazol-1-yl)propoxy)phenyl)propan-2-yl)phenoxy)propan-2-ol |

TABLE 1-continued

| No. | Structure | Name |
|---|---|---|
| 31 | 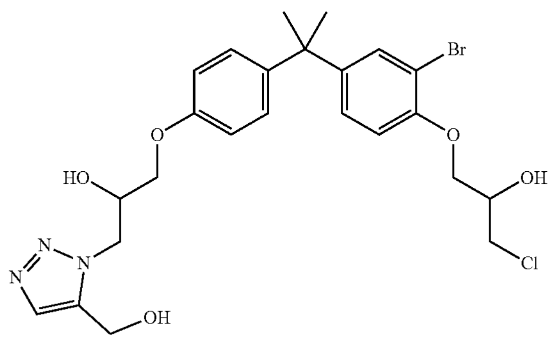 | 1-(2-bromo-4-(2-(4-(2-hydroxy-3-(5-(hydroxymethyl)-1H-1,2,3-triazol-1-yl)propoxy)phenyl)propan-2-yl)phenoxy)-3-chloropropan-2-ol |
| 31a | 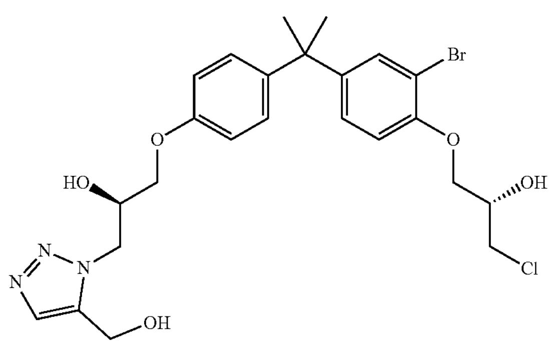 [SMILES: CC(C)(c1ccc(OC[C@H](O)Cn2nncc2CO)cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-(5-(hydroxymethyl)-1H-1,2,3-triazol-1-yl)propan-2-ol |
| 31b | 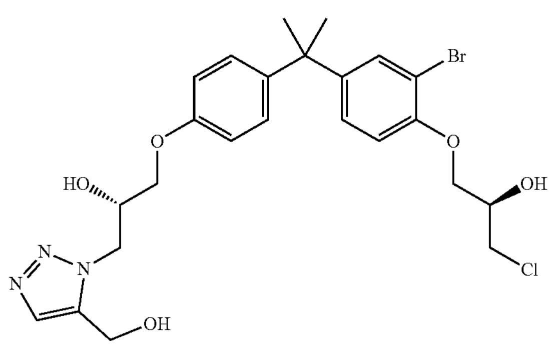 | (S)-1-(4-(2-(3-bromo-4-((R)-3-chloro-2-hydroxypropoxy)phenyl)propan-2-yl)phenoxy)-3-(5-(hydroxymethyl)-1H-1,2,3-triazol-1-yl)propan-2-ol |
| 31c | 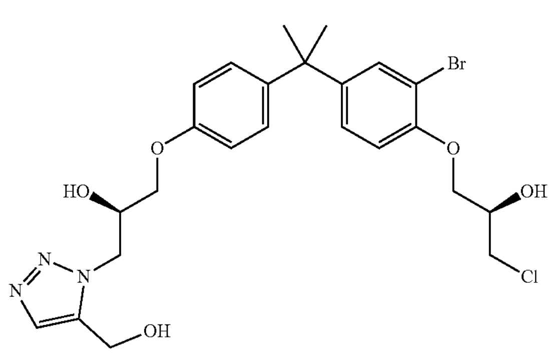 [SMILES: CC(C)(c1ccc(OC[C@H](O)Cn2nncc2CO)cc1)c1ccc(OC[C@@H](O)CCl)c(Br)c1] | (R)-1-(4-(2-(3-bromo-4-((R)-3-chloro-2-hydroxypropoxy)phenyl)propan-2-yl)phenoxy)-3-(5-(hydroxymethyl)-1H-1,2,3-triazol-1-yl)propan-2-ol |

TABLE 1-continued

| No. | Structure | Name |
|---|---|---|
| 31d | 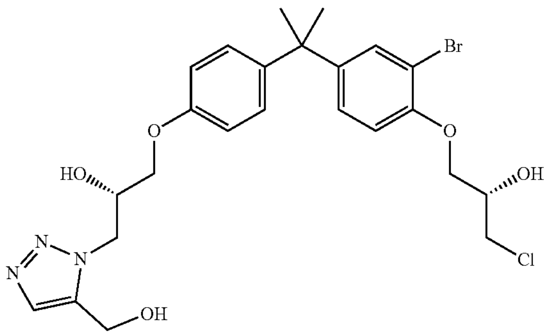 | (S)-1-(4-(2-(3-bromo-4-((S)-3-chloro-2-hydroxypropoxy)phenyl)propan-2-yl)phenoxy)-3-(5-(hydroxymethyl)-1H-1,2,3-triazol-1-yl)propan-2-ol |
| 32 | 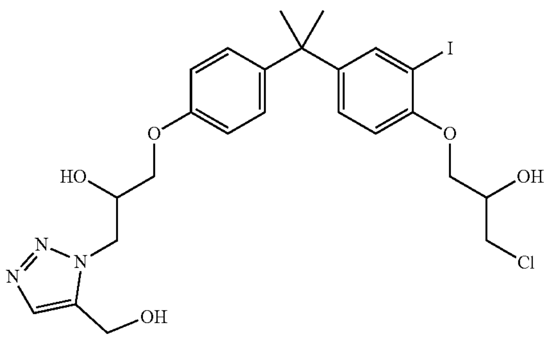 [SMILES: CC(C)(c1ccc(OCC(O)Cn2nncc2CO)cc1)c1ccc(OCC(O)CCl)c(I)c1] | 1-chloro-3-(4-(2-(4-(2-hydroxy-3-(5-(hydroxymethyl)-1H-1,2,3-triazol-1-yl)propoxy)phenyl)propan-2-yl)-2-iodophenoxy)propan-2-ol |
| 32a | 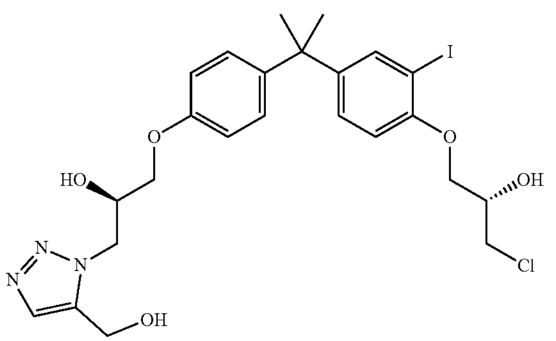 [SMILES: CC(C)(c1ccc(OC[C@H](O)Cn2nncc2CO)cc1)c1ccc(OC[C@H](O)CCl)c(I)c1] | (S)-1-chloro-3-(4-(2-(4-((R)-2-hydroxy-3-(5-(hydroxymethyl)-1H-1,2,3-triazol-1-yl)propoxy)phenyl)propan-2-yl)-2-iodophenoxy)propan-2-ol |
| 32b | 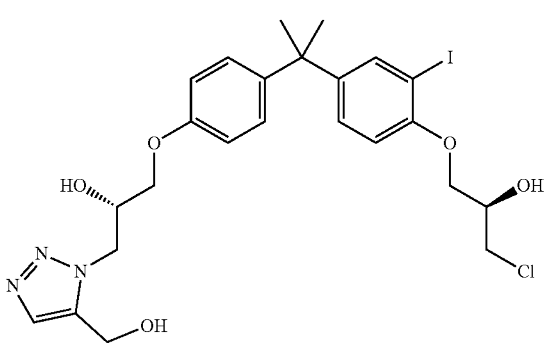 [SMILES: CC(C)(c1ccc(OC[C@@H](O)Cn2nncc2CO)cc1)c1ccc(OC[C@@H](O)CCl)c(I)c1] | (R)-1-chloro-3-(4-(2-(4-((S)-2-hydroxy-3-(5-(hydroxymethyl)-1H-1,2,3-triazol-1-yl)propoxy)phenyl)propan-2-yl)-2-iodophenoxy)propan-2-ol |

TABLE 1-continued

Compounds

| No. | Structure | Name |
|---|---|---|
| 32c | 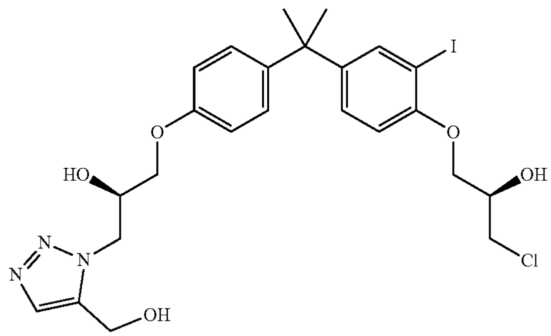 [SMILES: CC(C)(c1ccc(OC[C@H](O)Cn2nncc2CO)cc1)c1ccc(OC[C@@H](O)CCl)c(I)c1] | (R)-1-chloro-3-(4-(2-(4-((R)-2-hydroxy-3-(5-(hydroxymethyl)-1H-1,2,3-triazol-1-yl)propoxy)phenyl)propan-2-yl)-2-iodophenoxy)propan-2-ol |
| 32d | 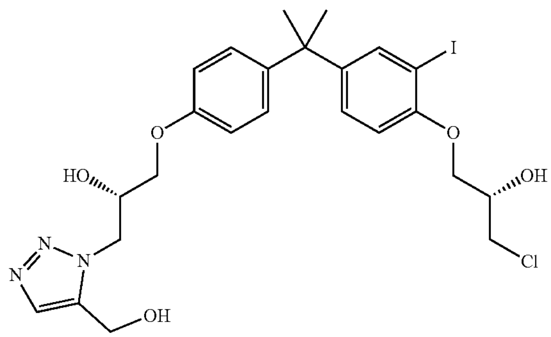 [SMILES: CC(C)(c1ccc(OC[C@@H](O)Cn2nncc2CO)cc1)c1ccc(OC[C@H](O)CCl)c(I)c1] | (S)-1-chloro-3-(4-(2-(4-((S)-2-hydroxy-3-(5-(hydroxymethyl)-1H-1,2,3-triazol-1-yl)propoxy)phenyl)propan-2-yl)-2-iodophenoxy)propan-2-ol |

In some more specific embodiments of the compound of Formula I, the compound has one of the following structures, or a pharmaceutically acceptable salt, tautomer, or stereoisomer thereof including all 4 distinct stereoisomers e.g., (S,R), (R,S), (R,R), and (S,S):

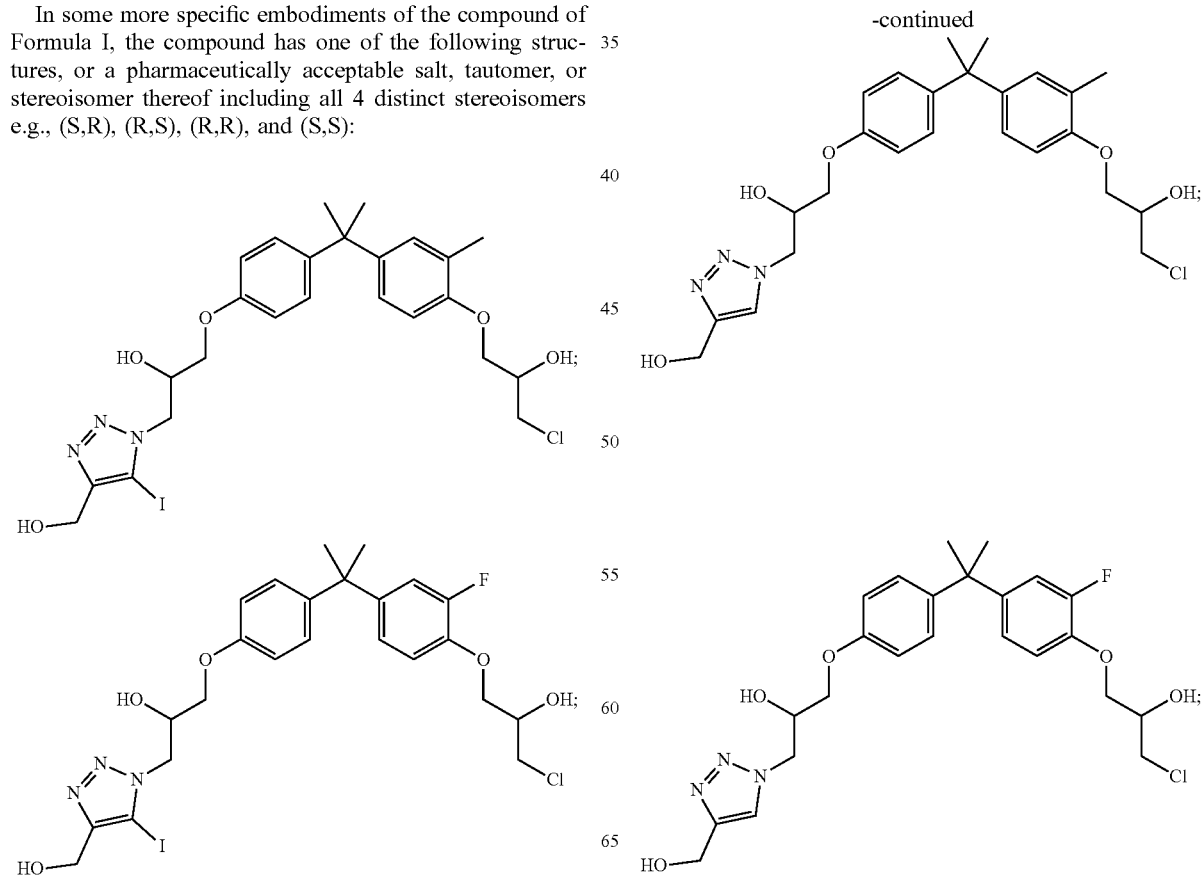

103
-continued
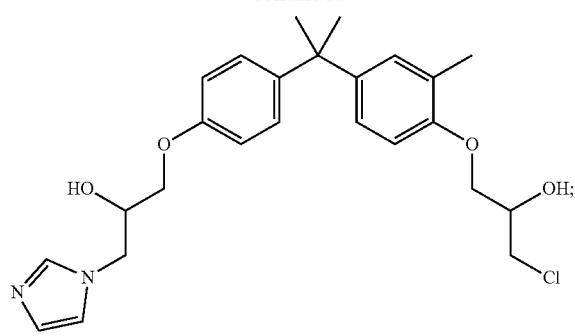
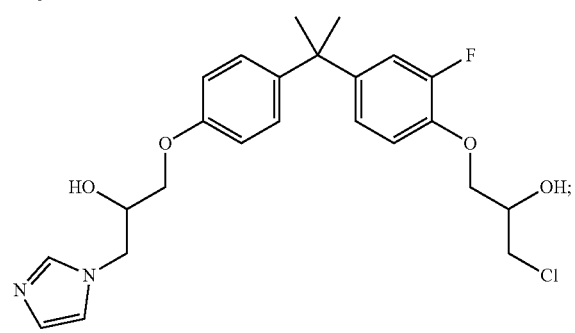
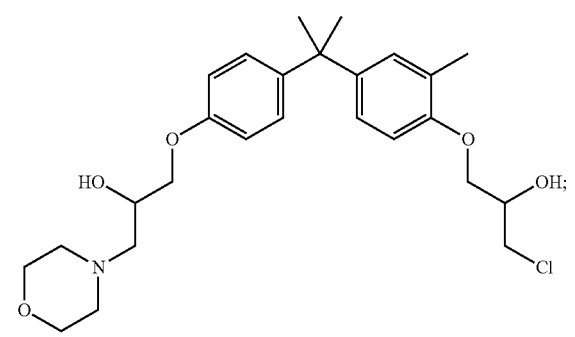
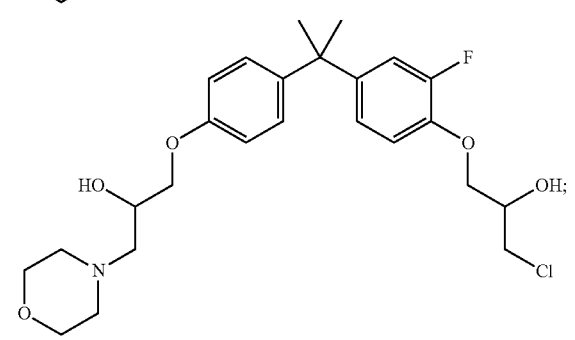
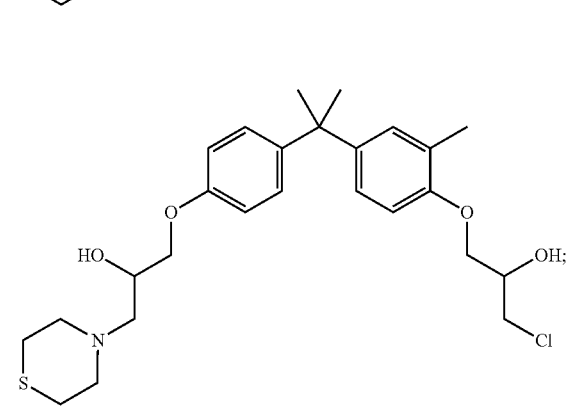
104
-continued
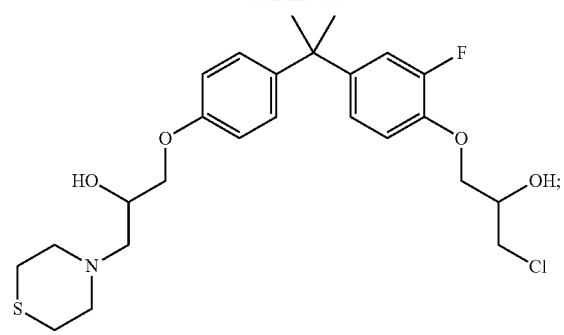
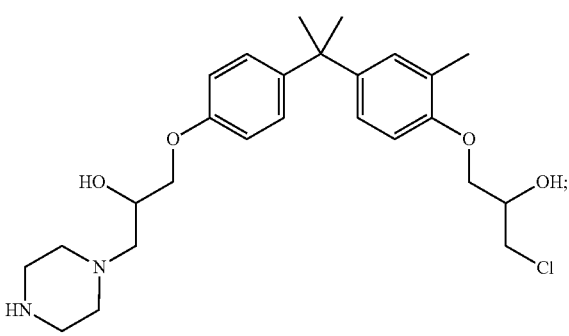
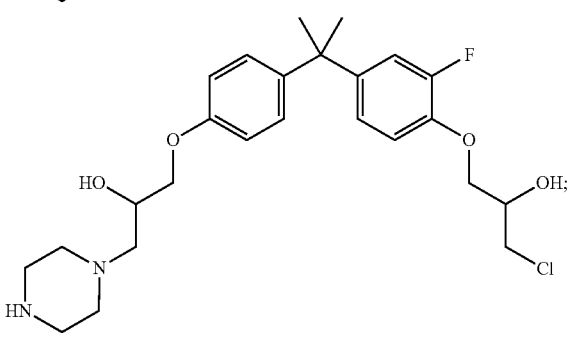
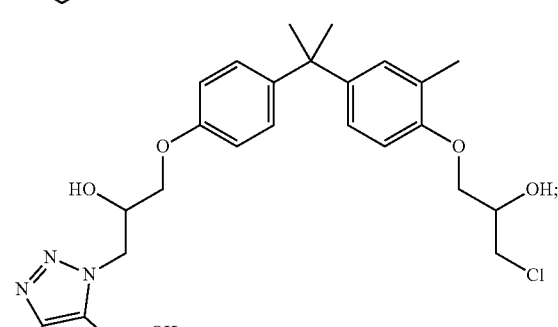
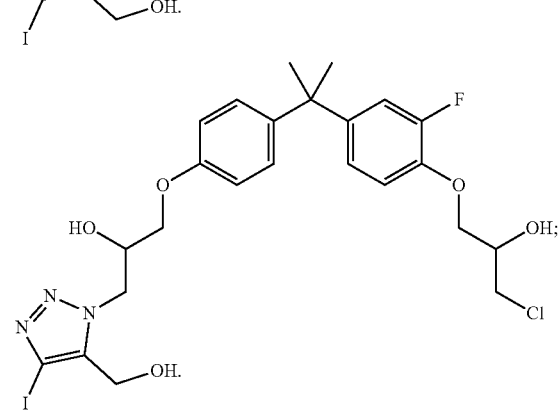

105
-continued

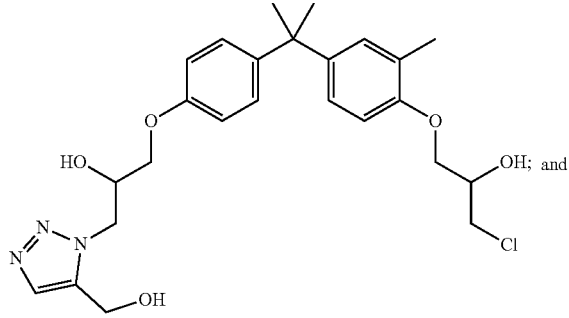

OH; and

106
-continued

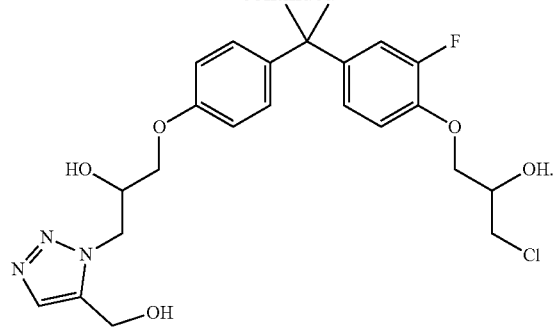

In some more specific embodiments of the compound of Formula I, the compound has one of the following structures from Table 2, or a pharmaceutically acceptable salt, tautomer, or stereoisomer thereof:

TABLE 2

| | $^{123}$I Compounds | |
|---|---|---|
| No. | Structure | Name |
| 33 | | 1-chloro-3-(4-(2-(4-(2-hydroxy-3-(4-(hydroxymethyl)-5-iodo-1H-1,2,3-triazol-1-yl)propoxy)phenyl)propan-2-yl)-2-(iodo-$^{123}$I)phenoxy)propan-2-ol |
| 33a | | (S)-1-chloro-3-(4-(2-(4-((R)-2-hydroxy-3-(4-(hydroxymethyl)-5-iodo-1H-1,2,3-triazol-1-yl)propoxy)phenyl)propan-2-yl)-2-(iodo-$^{123}$I)phenoxy)propan-2-ol |
| 33b | | (R)-1-chloro-3-(4-(2-(4-((S)-2-hydroxy-3-(4-(hydroxymethyl)-5-iodo-1H-1,2,3-triazol-1-yl)propoxy)phenyl)propan-2-yl)-2-(iodo-$^{123}$I)phenoxy)propan-2-ol |

TABLE 2-continued

¹²³I Compounds

| No. | Structure | Name |
|---|---|---|
| 33c | 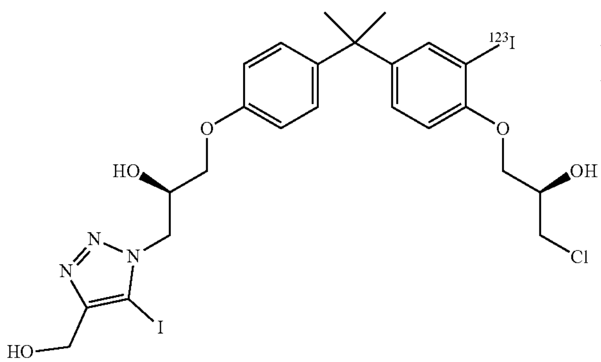 | (R)-1-chloro-3-(4-(2-(4-((R)-2-hydroxy-3-(4-(hydroxymethyl)-5-iodo-1H-1,2,3-triazol-1-yl)propoxy)phenyl)propan-2-yl)-2-(iodo-¹²³I)phenoxy)propan-2-ol |
| 33d | 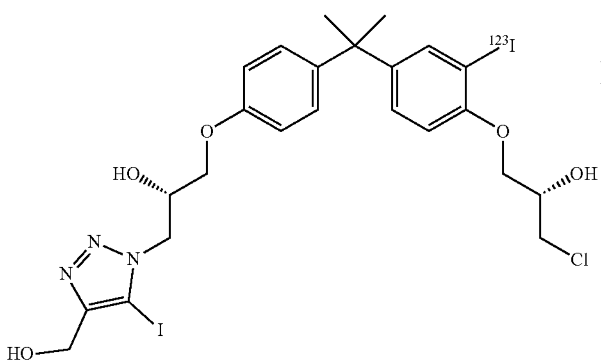 | (S)-1-chloro-3-(4-(2-(4-((S)-2-hydroxy-3-(4-(hydroxymethyl)-5-iodo-1H-1,2,3-triazol-1-yl)propoxy)phenyl)propan-2-yl)-2-(iodo-¹²³I)phenoxy)propan-2-ol |
| 34 | 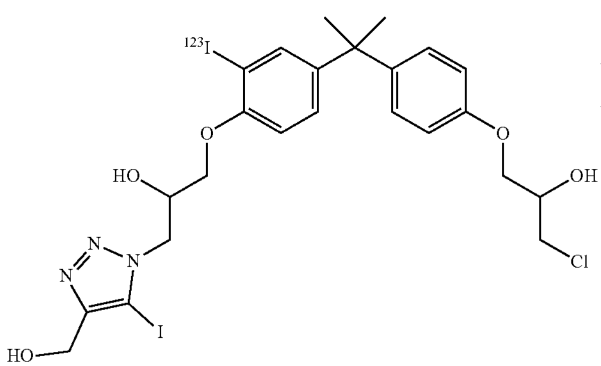 [SMILES: CC(C)(c1ccc(OCC(O)CCl)cc1)c1ccc(OCC(O)Cn2nnc(CO)c2I)c([123I])c1] | 1-chloro-3-(4-(2-(4-(2-hydroxy-3-(4-(hydroxymethyl)-5-iodo-1H-1,2,3-triazol-1-yl)propoxy)-3-(iodo-¹²³I)phenyl)propan-2-yl)phenoxy)propan-2-ol |
| 34a | 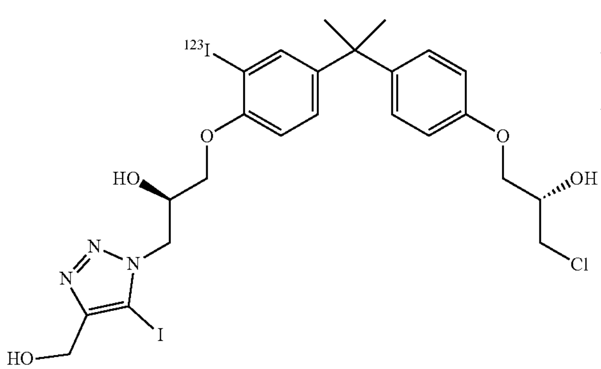 [SMILES: CC(C)(c1ccc(OC[C@H](O)CCl)cc1)c1ccc(OC[C@H](O)Cn2nnc(CO)c2I)c([123I])c1] | (S)-1-chloro-3-(4-(2-(4-((R)-2-hydroxy-3-(4-(hydroxymethyl)-5-iodo-1H-1,2,3-triazol-1-yl)propoxy)-3-(iodo-¹²³I)phenyl)propan-2-yl)phenoxy)propan-2-ol |

TABLE 2-continued $^{123}$I Compounds

| No. | Structure | Name |
|---|---|---|
| 34b | 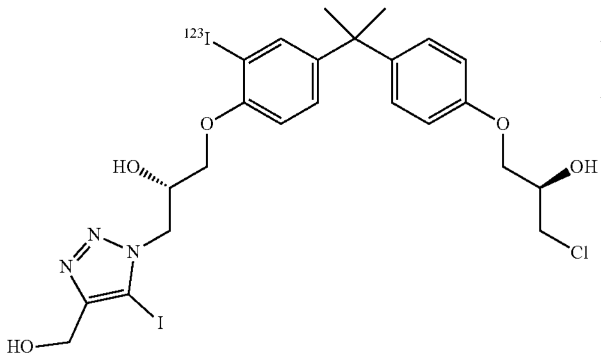 [SMILES: CC(C)(c1ccc(OC[C@@H](O)CCl)cc1)c1ccc(OC[C@@H](O)Cn2nnc(CO)c2I)c([123I])c1] | (R)-1-chloro-3-(4-(2-(4-((S)-2-hydroxy-3-(4-(hydroxymethyl)-5-iodo-1H-1,2,3-triazol-1-yl)propoxy)-3-(iodo-$^{123}$I)phenyl)propan-2-yl)phenoxy)propan-2-ol |
| 34c | 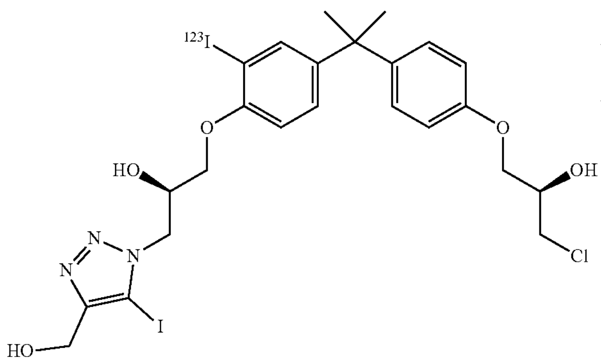 [SMILES: CC(C)(c1ccc(OC[C@@H](O)CCl)cc1)c1ccc(OC[C@H](O)Cn2nnc(CO)c2I)c([123I])c1] | (R)-1-chloro-3-(4-(2-(4-((R)-2-hydroxy-3-(4-(hydroxymethyl)-5-iodo-1H-1,2,3-triazol-1-yl)propoxy)-3-(iodo-$^{123}$I)phenyl)propan-2-yl)phenoxy)propan-2-ol |
| 34d | 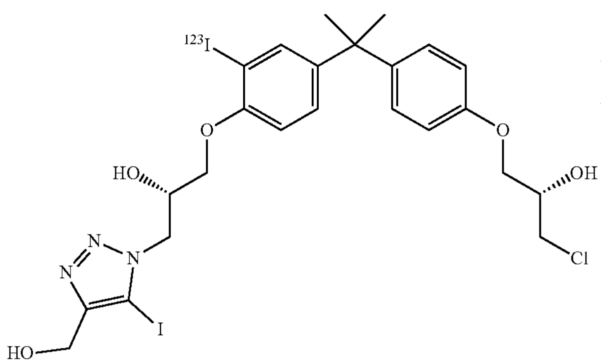 [SMILES: CC(C)(c1ccc(OC[C@H](O)CCl)cc1)c1ccc(OC[C@@H](O)Cn2nnc(CO)c2I)c([123I])c1] | (S)-1-chloro-3-(4-(2-(4-((S)-2-hydroxy-3-(4-(hydroxymethyl)-5-iodo-1H-1,2,3-triazol-1-yl)propoxy)-3-(iodo-$^{123}$I)phenyl)propan-2-yl)phenoxy)propan-2-ol |
| 35 | 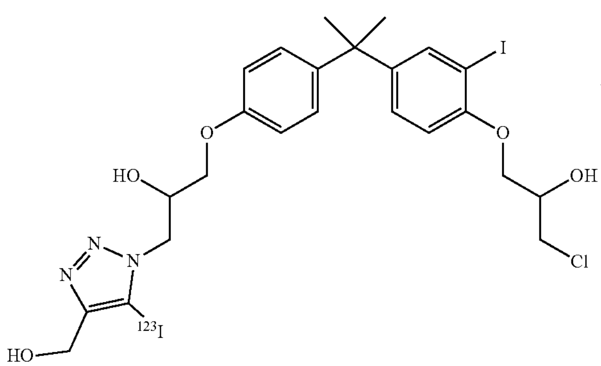 | 1-chloro-3-(4-(2-(4-(2-hydroxy-3-(4-(hydroxymethyl)-5-(iodo-$^{123}$I)-1H-1,2,3-triazol-1-yl)propoxy)phenyl)propan-2-yl)-2-iodophenoxy)propan-2-ol |

TABLE 2-continued

| | $^{123}$I Compounds | |
|---|---|---|
| No. | Structure | Name |
| 35a | | (S)-1-chloro-3-(4-(2-(4-((R)-2-hydroxy-3-(4-(hydroxymethyl)-5-(iodo-$^{123}$I)-1H-1,2,3-triazol-1-yl)propoxy)phenyl)propan-2-yl)-2-iodophenoxy)propan-2-ol |
| 35b | | (R)-1-chloro-3-(4-(2-(4-((S)-2-hydroxy-3-(4-(hydroxymethyl)-5-(iodo-$^{123}$I)-1H-1,2,3-triazol-1-yl)propoxy)phenyl)propan-2-yl)-2-iodophenoxy)propan-2-ol |
| 35c | | (R)-1-chloro-3-(4-(2-(4-((R)-2-hydroxy-3-(4-(hydroxymethyl)-5-(iodo-$^{123}$I)-1H-1,2,3-triazol-1-yl)propoxy)phenyl)propan-2-yl)-2-iodophenoxy)propan-2-ol |
| 35d | | (S)-1-chloro-3-(4-(2-(4-((S)-2-hydroxy-3-(4-(hydroxymethyl)-5-(iodo-$^{123}$I)-1H-1,2,3-triazol-1-yl)propoxy)phenyl)propan-2-yl)-2-iodophenoxy)propan-2-ol |

TABLE 2-continued

¹²³I Compounds

| No. | Structure | Name |
|---|---|---|
| 36 | 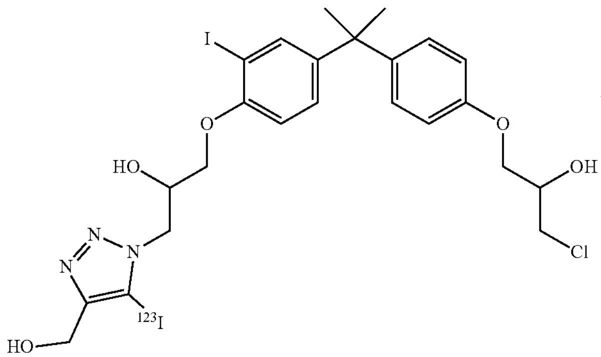 [SMILES: CC(C)(c1ccc(OCC(O)CCl)cc1)c1ccc(OCC(O)Cn2nnc(CO)c2[123I])c(I)c1] | 1-chloro-3-(4-(2-(4-(2-hydroxy-3-(4-(hydroxymethyl)-5-(iodo-¹²³I)-1H-1,2,3-triazol-1-yl)propoxy)-3-iodophenyl)propan-2-yl)phenoxy)propan-2-ol |
| 36a | 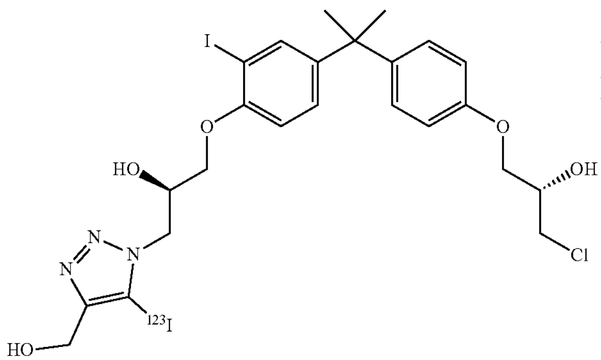 [SMILES: CC(C)(c1ccc(OC[C@H](O)CCl)cc1)c1ccc(OC[C@H](O)Cn2nnc(CO)c2[123I])c(I)c1] | (S)-1-chloro-3-(4-(2-(4-((R)-2-hydroxy-3-(4-(hydroxymethyl)-5-(iodo-¹²³I)-1H-1,2,3-triazol-1-yl)propoxy)-3-iodophenyl)propan-2-yl)phenoxy)propan-2-ol |
| 36b | 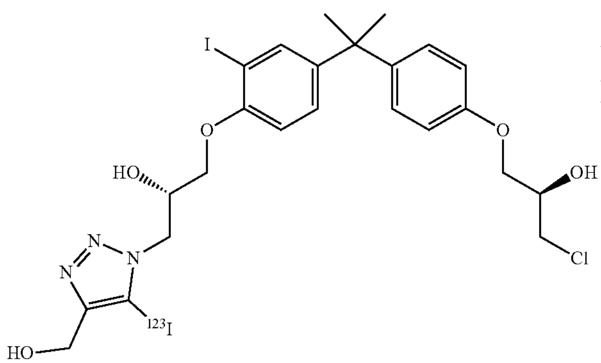 [SMILES: CC(C)(c1ccc(OC[C@@H](O)CCl)cc1)c1ccc(OC[C@@H](O)Cn2nnc(CO)c2[123I])c(I)c1] | (R)-1-chloro-3-(4-(2-(4-((S)-2-hydroxy-3-(4-(hydroxymethyl)-5-(iodo-¹²³I)-1H-1,2,3-triazol-1-yl)propoxy)-3-iodophenyl)propan-2-yl)phenoxy)propan-2-ol |
| 36c | 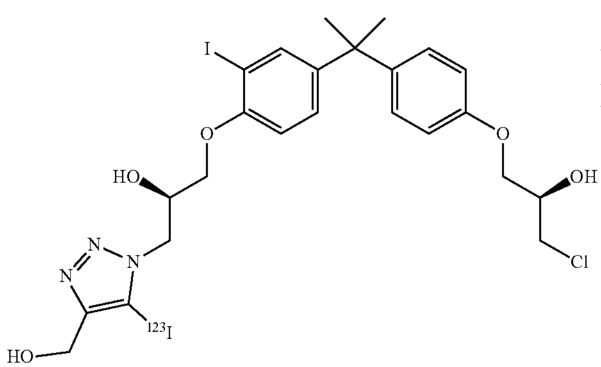 [SMILES: CC(C)(c1ccc(OC[C@@H](O)CCl)cc1)c1ccc(OC[C@H](O)Cn2nnc(CO)c2[123I])c(I)c1] | (R)-1-chloro-3-(4-(2-(4-((R)-2-hydroxy-3-(4-(hydroxymethyl)-5-(iodo-¹²³I)-1H-1,2,3-triazol-1-yl)propoxy)-3-iodophenyl)propan-2-yl)phenoxy)propan-2-ol |

TABLE 2-continued $^{123}$I Compounds

| No. | Structure | Name |
|---|---|---|
| 36d | 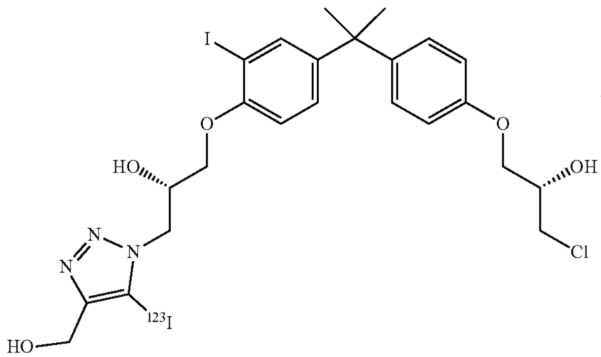 [SMILES: CC(C)(c1ccc(OC[C@H](O)CCl)cc1)c1ccc(OC[C@@H](O)Cn2nnc(CO)c2[123I])c(I)c1] | (S)-1-chloro-3-(4-(2-(4-((S)-2-hydroxy-3-(4-(hydroxymethyl)-5-(iodo-$^{123}$I)-1H-1,2,3-triazol-1-yl)propoxy)-3-iodophenyl)propan-2-yl)phenoxy)propan-2-ol |
| 37 | 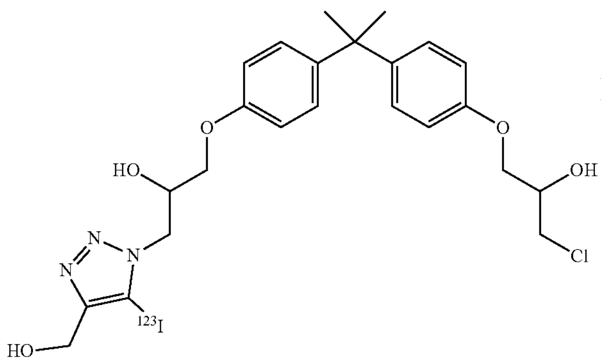 [SMILES: CC(C)(c1ccc(OCC(O)CCl)cc1)c1ccc(OCC(O)Cn2nnc(CO)c2[123I])cc1] | 1-chloro-3-(4-(2-(4-(2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 37a | 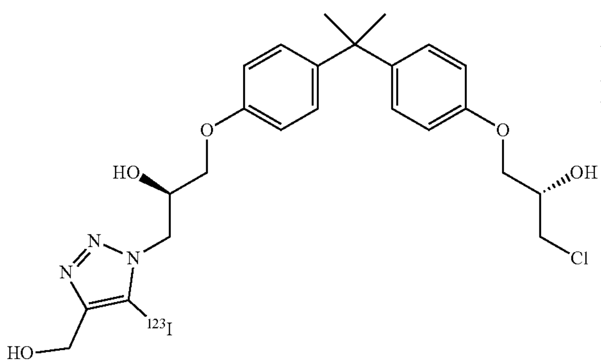 [SMILES: CC(C)(c1ccc(OC[C@H](O)CCl)cc1)c1ccc(OC[C@H](O)Cn2nnc(CO)c2[123I])cc1] | (S)-1-chloro-3-(4-(2-(4-((R)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 37b | 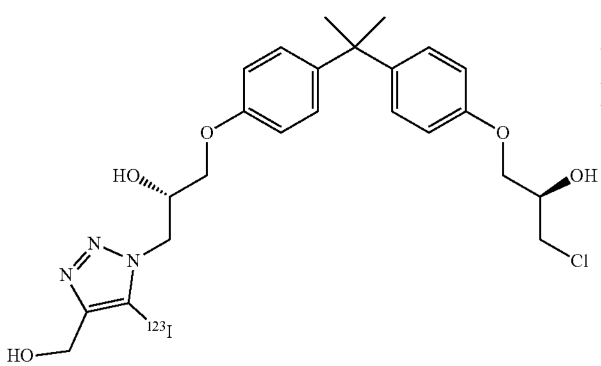 [SMILES: CC(C)(c1ccc(OC[C@@H](O)Cn2nnc(CO)c2[123I])cc1)c1ccc(OC[C@@H](O)CCl)cc1] | (R)-1-chloro-3-(4-(2-(4-((S)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |

TABLE 2-continued

| | $^{123}$I Compounds | |
|---|---|---|
| No. | Structure | Name |
| 37c | | (R)-1-ohloro-3-(4-(2-(4-((R)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 37d | | (S)-1-chloro-3-(4-(2-(4-((S)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 38 | | 1-chloro-3-(2-chloro-4-(2-(4-(2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 38a | | (S)-1-chloro-3-(2-chloro-4-(2-(4-((R)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |

TABLE 2-continued

$^{123}$I Compounds

| No. | Structure | Name |
|---|---|---|
| 38b | 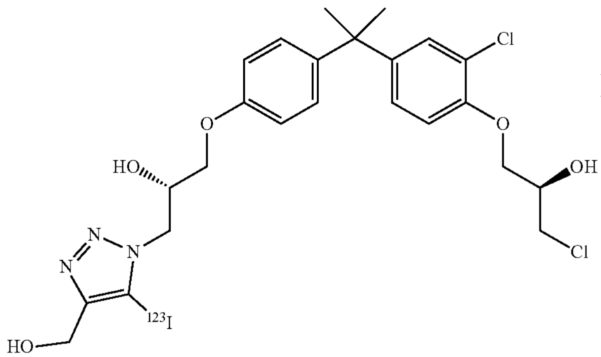 [SMILES: CC(C)(c1ccc(OC[C@@H](O)Cn2nnc(CO)c2[123I])cc1)c1ccc(OC[C@@H](O)CCl)c(Cl)c1] | (R)-1-chloro-3-(2-chloro-4-(2-(4-((S)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 38c | 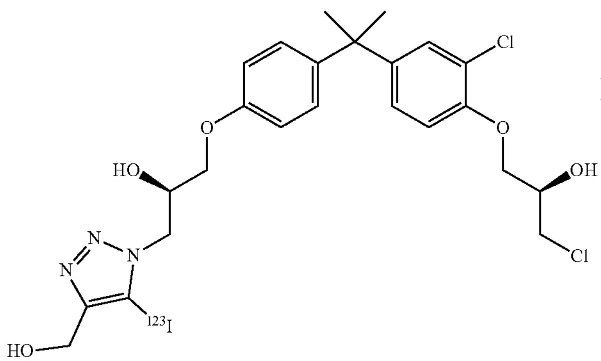 | (R)-1-chloro-3-(2-chloro-4-(2-(4-((R)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 38d | 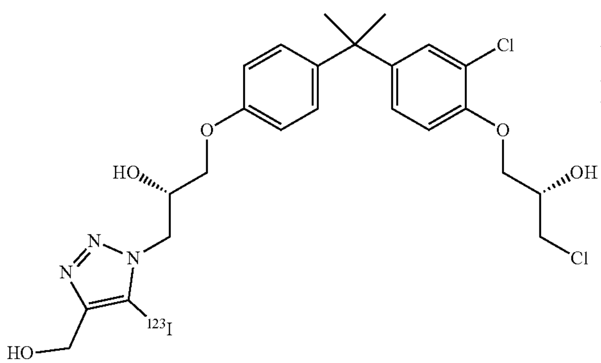 | (S)-1-chloro-3-(2-chloro-4-(2-(4-((S)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol |
| 39 | 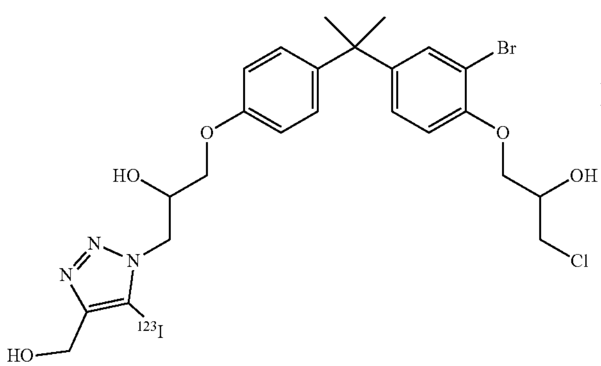 | 1-(2-bromo-4-(2-(4-(2-hydroxy-3-(4-(hydroxymethyl)-5-(iodo-$^{123}$I)-1H-1,2,3-triazol-1-yl)propoxy)phenyl)propan-2-yl)phenoxy)-3-chloropropan-2-ol |

TABLE 2-continued

123I Compounds

| No. | Structure | Name |
|---|---|---|
| 39a | 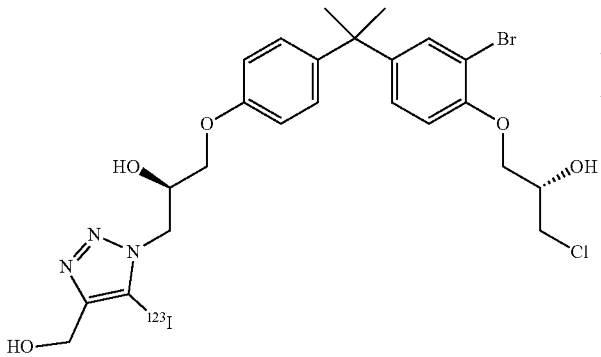 [SMILES: CC(C)(c1ccc(OC[C@H](O)Cn2nnc(CO)c2[123I])cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-(4-(hydroxymethyl)-5-(iodo-$^{123}$I)-1H-1,2,3-triazol-1-yl)propan-2-ol |
| 39b | 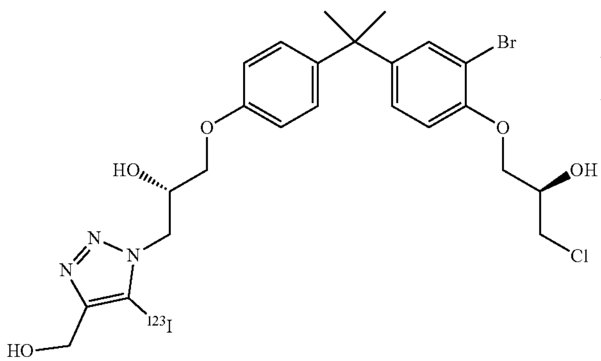 [SMILES: CC(C)(c1ccc(OC[C@@H](O)Cn2nnc(CO)c2[123I])cc1)c1ccc(OC[C@@H](O)CCl)c(Br)c1] | (S)-1-(4-(2-(3-bromo-4-((R)-3-chloro-2-hydroxypropoxy)phenyl)propan-2-yl)phenoxy)-3-(4-(hydroxymethyl)-5-(iodo-$^{123}$I)-1H-1,2,3-triazol-1-yl)propan-2-ol |
| 39c | 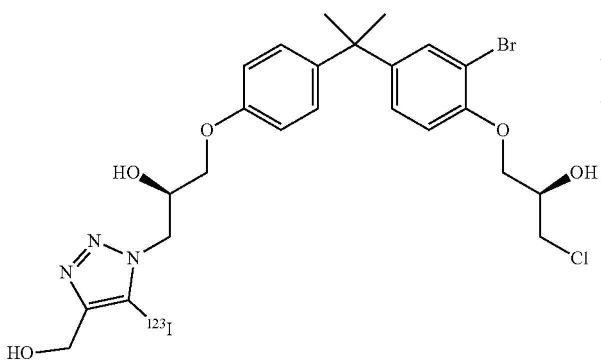 | (R)-1-(4-(2-(3-bromo-4-((R)-3-chloro-2-hydroxypropoxy)phenyl)propan-2-yl)phenoxy)-3-(4-(hydroxymethyl)-5-(iodo-$^{123}$I)-1H-1,2,3-triazol-1-yl)propan-2-ol |
| 39d | 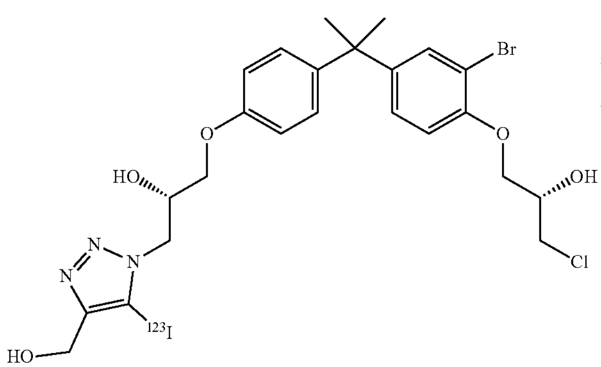 | (S)-1-(4-(2-(3-bromo-4-((S)-3-chloro-2-hydroxypropoxy)phenyl)propan-2-yl)phenoxy)-3-(4-(hydroxymethyl)-5-(iodo-$^{123}$I)-1H-1,2,3-triazol-1-yl)propan-2-ol |

TABLE 2-continued

¹²³I Compounds

| No. | Structure | Name |
|---|---|---|
| 40 | 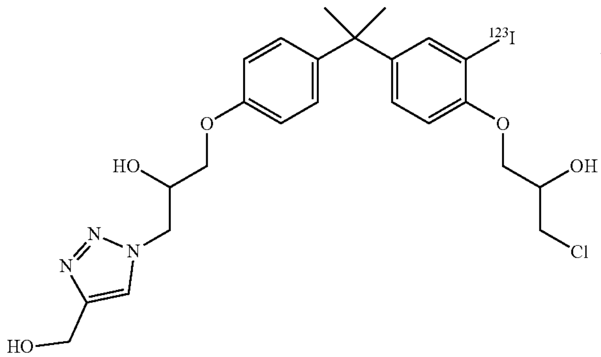 [SMILES: CC(C)(c1ccc(OCC(O)Cn2cc(CO)nn2)cc1)c1ccc(OCC(O)CCl)c([123I])c1] | 1-chloro-3-(4-(2-(4-(2-hydroxy-3-(4-(hydroxymethyl)-1H-1,2,3-triazol-1-yl)propoxy)phenyl)propan-2-yl)-2-(iodo-¹²³I)phenoxy)propan-2-ol |
| 40a | 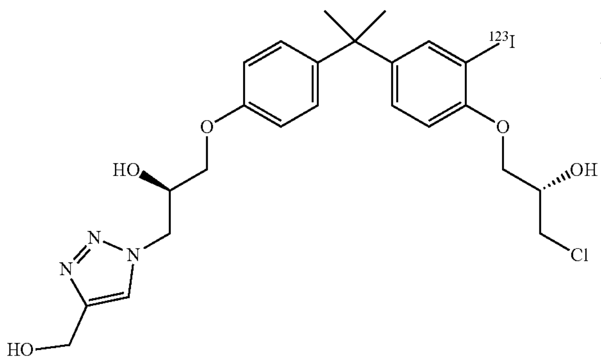 [SMILES: CC(C)(c1ccc(OC[C@H](O)Cn2cc(CO)nn2)cc1)c1ccc(OC[C@H](O)CCl)c([123I])c1] | (S)-1-chloro-3-(4-(2-(4-((R)-2-hydroxy-3-(4-(hydroxymethyl)-1H-1,2,3-triazol-1-yl)propoxy)phenyl)propan-2-yl)-2-(iodo-¹²³I)phenoxy)propan-2-ol |
| 40b | 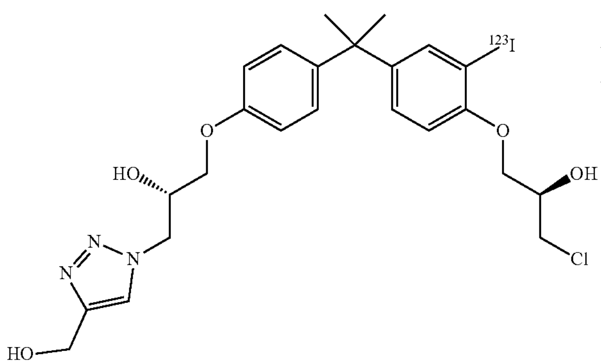 | (R)-1-chloro-3-(4-(2-(4-((S)-2-hydroxy-3-(4-(hydroxymethyl)-1H-1,2,3-triazol-1-yl)propoxy)phenyl)propan-2-yl)-2-(iodo-¹²³I)phenoxy)propan-2-ol |
| 40c | 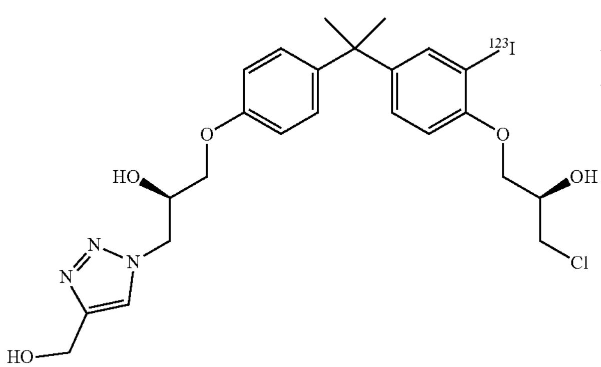 [SMILES: CC(C)(c1ccc(OC[C@H](O)Cn2cc(CO)nn2)cc1)c1ccc(OC[C@@H](O)CCl)c([123I])c1] | (R)-1-chloro-3-(4-(2-(4-((R)-2-hydroxy-3-(4-(hydroxymethyl)-1H-1,2,3-triazol-1-yl)propoxy)phenyl)propan-2-yl)-2-(iodo-¹²³I)phenoxy)propan-2-ol |

TABLE 2-continued $^{123}$I Compounds

| No. | Name |
|---|---|
| 40d | (S)-1-chloro-3-(4-(2-(4-((S)-2-hydroxy-3-(4-(hydroxymethyl)-1H-1,2,3-triazol-1-yl)propoxy)phenyl)propan-2-yl)-2-(iodo-$^{123}$I)phenoxy)propan-2-ol |
| 41 | 1-chloro-3-(4-(2-(4-(2-hydroxy-3-(1H-imidazol-1-yl)propoxy)phenyl)propan-2-yl)-2-(iodo-$^{123}$I)phenoxy)propan-2-ol |
| 41a | (S)-1-chloro-3-(4-(2-(4-((R)-2-hydroxy-3-(1H-imidazol-1-yl)propoxy)phenyl)propan-2-yl)-2-(iodo-$^{123}$I)phenoxy)propan-2-ol |
| 41b | (R)-1-chloro-3-(4-(2-(4-((S)-2-hydroxy-3-(1H-imidazol-1-yl)propoxy)phenyl)propan-2-yl)-2-(iodo-$^{123}$I)phenoxy)propan-2-ol |

TABLE 2-continued

| | $^{123}$I Compounds | |
|---|---|---|
| No. | Structure | Name |
| 41c | | (R)-1-chloro-3-(4-(2-(4-((R)-2-hydroxy-3-(1H-imidazol-1-yl)propoxy)phenyl)propan-2-yl)-2-(iodo-$^{123}$I)phenoxy)propan-2-ol |
| 41d | | (S)-1-chloro-3-(4-(2-(4-((S)-2-hydroxy-3-(1H-imidazol-1-yl)propoxy)phenyl)propan-2-yl)-2-(iodo-$^{123}$I)phenoxy)propan-2-ol |
| 42 | | 1-chloro-3-(4-(2-(4-(2-hydroxy-3-morpholinopropoxy)phenyl)propan-2-yl)-2-(iodo-$^{123}$I)phenoxy)propan-2-ol |
| 42a | | (S)-1-chloro-3-(4-(2-(4-((R)-2-hydroxy-3-morpholinopropoxy)phenyl)propan-2-yl)-2-(iodo-$^{123}$I)phenoxy)propan-2-ol |

TABLE 2-continued

| | $^{123}$I Compounds | | |
|---|---|---|---|
| No. | Structure | | Name |
| 42b | | | (R)-1-chloro-3-(4-(2-(4-((S)-2-hydroxy-3-morpholinopropoxy)phenyl)propan-2-yl)-2-(iodo-$^{123}$I)phenoxy)propan-2-ol |
| 42c | | | (R)-1-chloro-3-(4-(2-(4-((R)-2-hydroxy-3-morpholinopropoxy)phenyl)propan-2-yl)-2-(iodo-$^{123}$I)phenoxy)propan-2-ol |
| 42d | | | (S)-1-chloro-3-(4-(2-(4-((S)-2-hydroxy-3-morpholinopropoxy)phenyl)propan-2-yl)-2-(iodo-$^{123}$I)phenoxy)propan-2-ol |
| 43 | | | 1-chloro-3-(4-(2-(4-(2-hydroxy-3-thiomorpholinopropoxy)phenyl)propan-2-yl)-2-(iodo-$^{123}$I)phenoxy)propan-2-ol |

TABLE 2-continued

| | $^{123}$I Compounds | |
|---|---|---|
| No. | Structure | Name |
| 43a | | (S)-1-chloro-3-(4-(2-(4-((R)-2-hydroxy-3-thiomorpholinopropoxy)phenyl)propan-2-yl)-2-(iodo-$^{123}$I)phenoxy)propan-2-ol |
| 43b | | (R)-1-chloro-3-(4-(2-(4-((S)-2-hydroxy-3-thiomorpholinopropoxy)phenyl)propan-2-yl)-2-(iodo-$^{123}$I)phenoxy)propan-2-ol |
| 43c | | (R)-1-chloro-3-(4-(2-(4-((R)-2-hydroxy-3-thiomorpholinopropoxy)phenyl)propan-2-yl)-2-(iodo-$^{123}$I)phenoxy)propan-2-ol |
| 43d | | (S)-1-chloro-3-(4-(2-(4-((S)-2-hydroxy-3-thiomorpholinopropoxy)phenyl)propan-2-yl)-2-(iodo-$^{123}$I)phenoxy)propan-2-ol |

TABLE 2-continued

| | $^{123}$I Compounds | |
|---|---|---|
| No. | Structure | Name |
| 44 | | 1-chloro-3-(4-(2-(4-(2-hydroxy-3-(piperazin-1-yl)propoxy)phenyl)propan-2-yl)-2-(iodo-$^{123}$I)phenoxy)propan-2-ol |
| 44a | | (S)-1-chloro-3-(4-(2-(4-((R)-2-hydroxy-3-(piperazin-1-yl)propoxy)phenyl)propan-2-yl)-2-(iodo-$^{123}$I)phenoxy)propan-2-ol |
| 44b | | (R)-1-chloro-3-(4-(2-(4-((S)-2-hydroxy-3-(piperazin-1-yl)propoxy)phenyl)propan-2-yl)-2-(iodo-$^{123}$I)phenoxy)propan-2-ol |
| 44c | | (R)-1-chloro-3-(4-(2-(4-((R)-2-hydroxy-3-(piperazin-1-yl)propoxy)phenyl)propan-2-yl)-2-(iodo-$^{123}$I)phenoxy)propan-2-ol |

TABLE 2-continued $^{123}$I Compounds

| No. | Structure | Name |
|---|---|---|
| 44d | 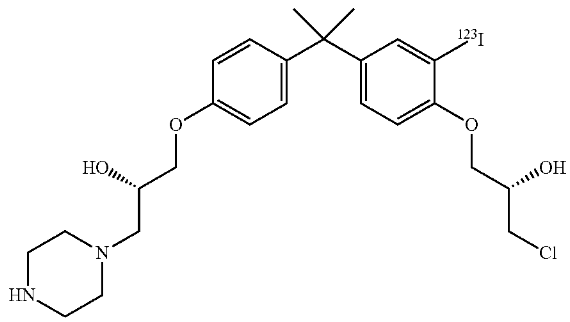 [SMILES: CC(C)(c1ccc(OC[C@@H](O)CN2CCNCC2)cc1)c1ccc(OC[C@H](O)CCl)c([123I])c1] | (S)-1-chloro-3-(4-(2-(4-(($^{123}$I)-2-hydroxy-3-(piperazin-1-yl)propoxy)phenyl)propan-2-yl)-2-(iodo-$^{123}$I)phenoxy)propan-2-ol |
| 45 | 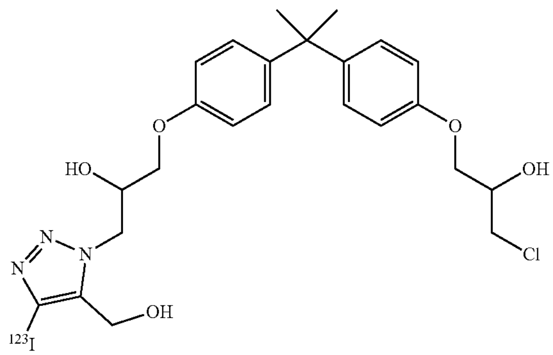 [SMILES: CC(C)(c1ccc(OCC(O)CCl)cc1)c1ccc(OCC(O)Cn2nnc([123I])c2CO)cc1] | 1-chloro-3-(4-(2-(4-(2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 45a | 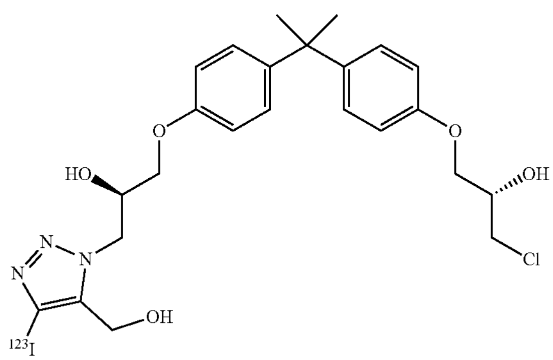 [SMILES: CC(C)(c1ccc(OC[C@H](O)CCl)cc1)c1ccc(OC[C@H](O)Cn2nnc([123I])c2CO)cc1] | (S)-1-chloro-3-(4-(2-(4-((R)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 45b | 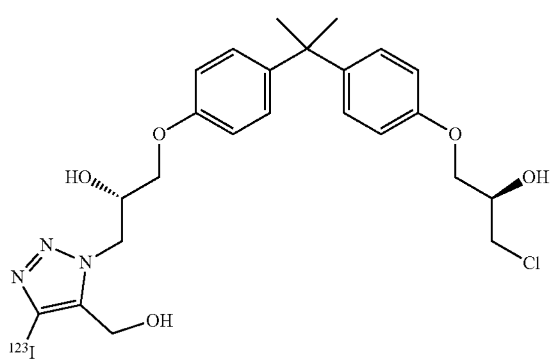 [SMILES: CC(C)(c1ccc(OC[C@@H](O)Cn2nnc([123I])c2CO)cc1)c1ccc(OC[C@@H](O)CCl)cc1] | (R)-1-chloro-3-(4-(2-(4-((S)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |

TABLE 2-continued $^{123}$I Compounds

| No. | Structure | Name |
|---|---|---|
| 45c | 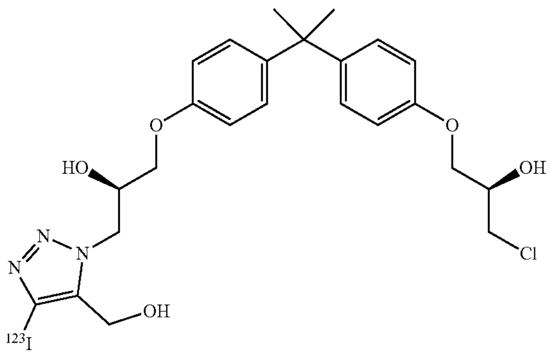 [SMILES: CC(C)(c1ccc(OC[C@@H](O)CCl)cc1)c1ccc(OC[C@H](O)Cn2nnc([123I])c2CO)cc1] | (R)-1-chloro-3-(4-(2-(4-((R)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 45d | 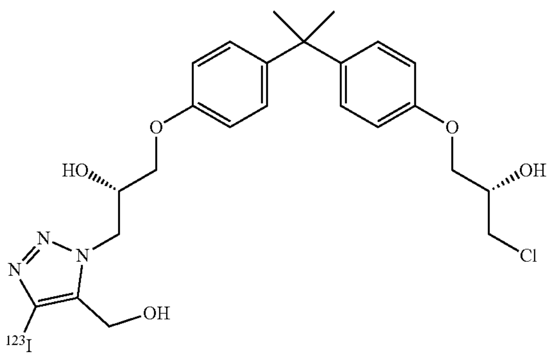 | (S)-1-chloro-3-(4-(2-(4-((S)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 46 | 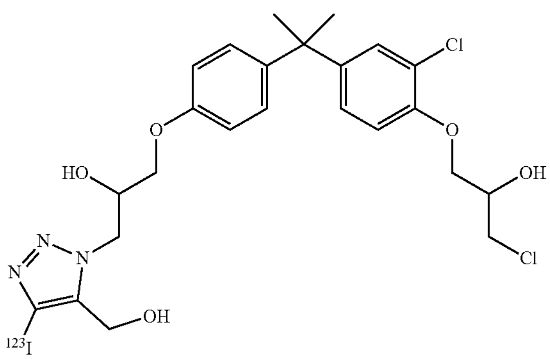 | 1-chloro-3-(2-chloro-4-(2-(4-(2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 46a | 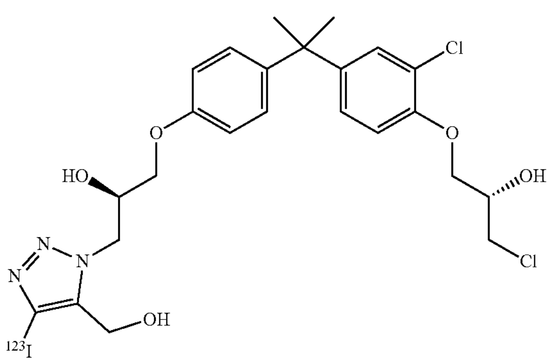 [SMILES: CC(C)(c1ccc(OC[C@H](O)Cn2nnc([123I])c2CO)cc1)c1ccc(OC[C@H](O)CCl)c(Cl)c1] | (S)-1-chloro-3-(2-chloro-4-(2-(4-((R)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |

TABLE 2-continued

| | $^{123}$I Compounds | |
|---|---|---|
| No. | Structure | Name |
| 46b | | (R)-1-chloro-3-(2-chloro-4-(2-(4-((S)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 46c | | (R)-1-chloro-3-(2-chloro-4-(2-(4-((R)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 46d | | (S)-1-chloro-3-(2-chloro-4-(2-(4-((S)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol |
| 47 | | 1-(2-bromo-4-(2-(4-(2-hydroxy-3-(5-(hydroxymethyl)-4-(iodo-$^{123}$I)-1H-1,2,3-triazol-1-yl)propoxy)phenyl)propan-2-yl)phenoxy)-3-chloropropan-2-ol |

TABLE 2-continued $^{123}$I Compounds

| No. | Structure | Name |
|---|---|---|
| 47a | 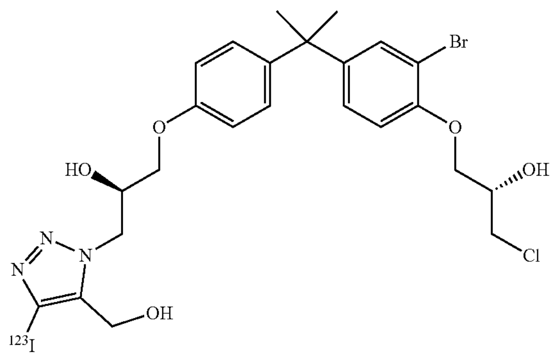 [SMILES: CC(C)(c1ccc(OC[C@H](O)Cn2nnc([123I])c2CO)cc1)c1ccc(OC[C@H](O)CCl)c(Br)c1] | (R)-1-(4-(2-(3-bromo-4-((S)-3-chloro-2-hydroxypropoxy)phenyl)propan-2-yl)phenoxy)-3-(5-(hydroxymethyl)-4-(iodo-$^{123}$I)-1H-1,2,3-triazol-1-yl)propan-2-ol |
| 47b | 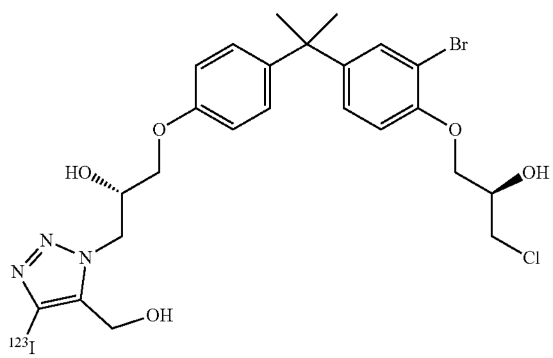 [SMILES: CC(C)(c1ccc(OC[C@@H](O)Cn2nnc([123I])c2CO)cc1)c1ccc(OC[C@@H](O)CCl)c(Br)c1] | (S)-1-(4-(2-(3-bromo-4-((R)-3-chloro-2-hydroxypropoxy)phenyl)propan-2-yl)phenoxy)-3-(5-(hydroxymethyl)-4-(iodo-$^{123}$I)-1H-1,2,3-triazol-1-yl)propan-2-ol |
| 47c | 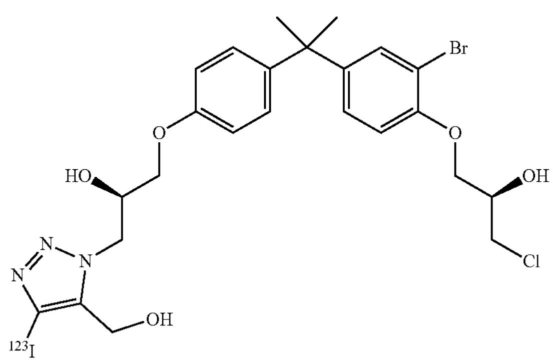 [SMILES: CC(C)(c1ccc(OC[C@H](O)Cn2nnc([123I])c2CO)cc1)c1ccc(OC[C@@H](O)CCl)c(Br)c1] | (R)-1-(4-(2-(3-bromo-4-((R)-3-chloro-2-hydroxypropoxy)phenyl)propan-2-yl)phenoxy)-3-(5-(hydroxymethyl)-4-(iodo-$^{123}$I)-1H-1,2,3-triazol-1-yl)propan-2-ol |
| 47d | 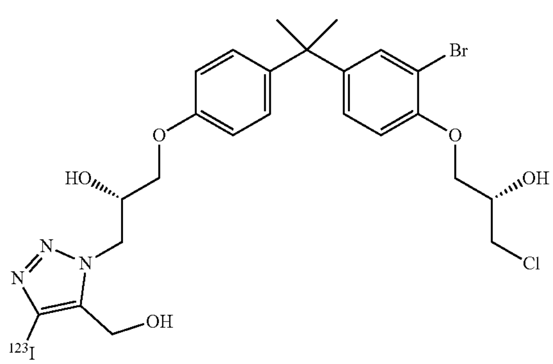 [SMILES: CC(C)(c1ccc(OC[C@@H](O)Cn2nnc([123I])c2CO)cc1)c1ccc(OC[C@H](O)CCl)c(Br)c1] | (S)-1-(4-(2-(3-bromo-4-((S)-3-chloro-2-hydroxypropoxy)phenyl)propan-2-yl)phenoxy)-3-(5-(hydroxymethyl)-4-(iodo-$^{123}$I)1,2,3-triazol-1-yl)propan-2-ol |

TABLE 2-continued $^{123}$I Compounds

| No. | Structure | Name |
|---|---|---|
| 48 | 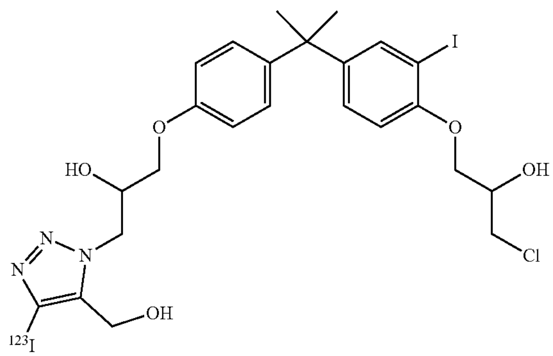 [SMILES: CC(C)(c1ccc(OCC(O)Cn2nnc([123I])c2CO)cc1)c1ccc(OCC(O)CCl)c(I)c1] | 1-chloro-3-(4-(2-(4-(2-hydroxy-3-(5 (hydroxymethyl)-4-(iodo-$^{123}$I)-1H-1,2,3-triazol-1-yl)propoxy)phenyl)propan-2-yl)-2-iodophenoxy)propan-2-ol |
| 48a | 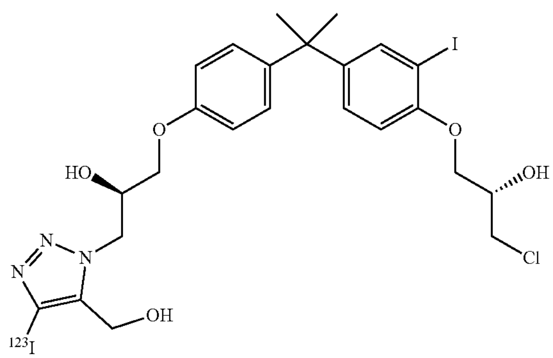 [SMILES: CC(C)(c1ccc(OC[C@H](O)Cn2nnc([123I])c2CO)cc1)c1ccc(OC[C@H](O)CCl)c(I)c1] | (S)-1-chloro-3-(4-(2-(4-((R)-2-hydroxy-3-(5-(hydroxymethyl)-4-(iodo-$^{123}$I)-1H-1,2,3-triazol-1-yl)propoxy)phenyl)propan-2-yl)-2-iodophenoxy)propan-2-ol |
| 48b | 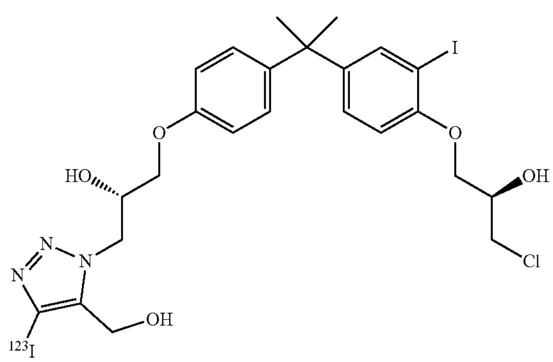 [SMILES: CC(C)(c1ccc(OC[C@@H](O)Cn2nnc([123I])c2CO)cc1)c1ccc(OC[C@@H](O)CCl)c(I)c1] | (R)-1-chloro-3-(4-(2-(4-((S)-2-hydroxy-3-(5-(hydroxymethyl)-4-(iodo-$^{123}$I)-1,2,3-triazol-1-yl)propoxy)phenyl)propan-2-yl)-2-iodophenoxy)propan-2-ol |
| 48c | 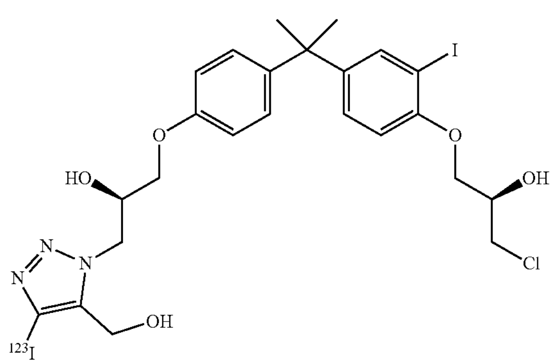 [SMILES: CC(C)(c1ccc(OC[C@H](O)Cn2nnc([123I])c2CO)cc1)c1ccc(OC[C@@H](O)CCl)c(I)c1] | (R)-1-chloro-3-(4-(2-(4-((R)-2-hydroxy-3-(5-(hydroxymethyl)-4-(iodo-$^{123}$I)-1H-1,2,3-triazol-1-yl)propoxy)phenyl)propan-2-yl)-2-iodophenoxy)propan-2-ol |

TABLE 2-continued $^{123}$I Compounds

| No. | Structure | Name |
|---|---|---|
| 48d | 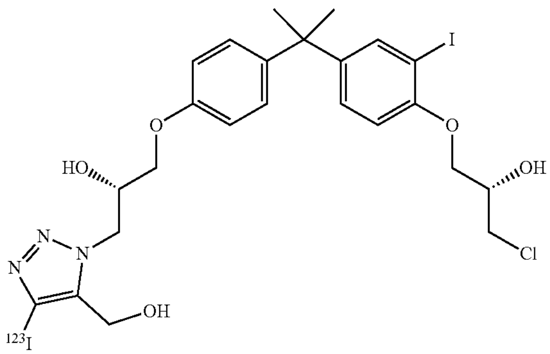 [SMILES: CC(C)(c1ccc(OC[C@@H](O)Cn2nnc([123I])c2CO)cc1)c1ccc(OC[C@H](O)CCl)c(I)c1] | (S)-1-chloro-3-(4-(2-(4-((S)-2-hydroxy-3-(5-(hydroxymethyl)-4-(iodo-$^{123}$I)-1H-1,2,3-triazol-1-yl)propoxy)phenyl)propan-2-yl)-2-iodophenoxy)propan-2-ol |
| 49 | 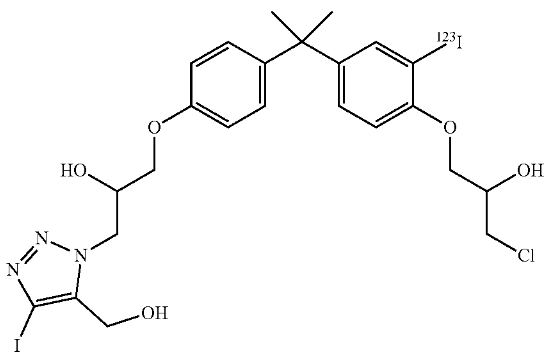 [SMILES: CC(C)(c1ccc(OCC(O)Cn2nnc(I)c2CO)cc1)c1ccc(OCC(O)CCl)c([123I])c1] | 1-chloro-3-(4-(2-(4-(2-hydroxy-3-(5-(hydroxymethyl)-4-iodo-1H-1,2,3-triazol-1-yl)propoxy)phenyl)propan-2-yl)-2-(iodo-$^{123}$I)phenoxy)propan-2-ol |
| 49a | 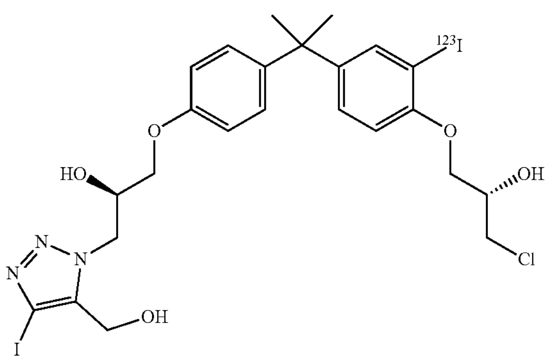 [SMILES: CC(C)(c1ccc(OC[C@H](O)Cn2nnc(I)c2CO)cc1)c1ccc(OC[C@H](O)CCl)c([123I])c1] | (S)-1-chloro-3-(4-(2-(4-((R)-2-hydroxy-3-(5-(hydroxymethyl)-4-iodo-1H-1,2,3-triazol-1-yl)propoxy)phenyl)propan-2-yl)-2-(iodo-$^{123}$I)phenoxy)propan-2-ol |
| 49b | 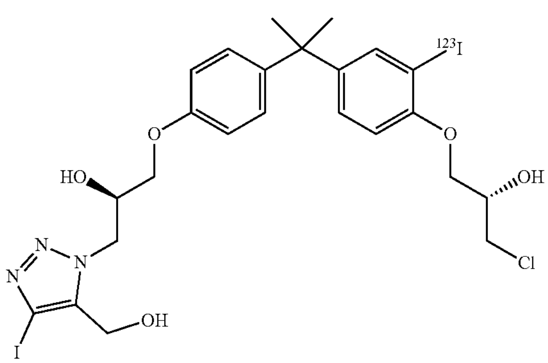 [SMILES: CC(C)(c1ccc(OC[C@H](O)Cn2nnc(I)c2CO)cc1)c1ccc(OC[C@H](O)CCl)c([123I])c1] | (R)-1-chloro-3-(4-(2-(4-((S)-2-hydroxy-3-(5-(hydroxymethyl)-4-iodo-1H-1,2,3-triazol-1-yl)propoxy)phenyl)propan-2-yl)-2-(iodo-$^{123}$I)phenoxy)propan-2-ol |

TABLE 2-continued

| | $^{123}$I Compounds | |
|---|---|---|
| No. | Structure | Name |
| 49c | | (R)-1-chloro-3-(4-(2-(4-((R)-2-hydroxy-3-(5-(hydroxymethyl)-4-iodo-1H-1,2,3-triazol-1-yl)propoxy)phenyl)propan-2-yl)-2-(iodo-$^{123}$I)phenoxy)propan-2-ol |
| 49d | | (S)-1-chloro-3-(4-(2-(4-((S)-2-hydroxy-3-(5-(hydroxymethyl)-4-iodo-1H-1,2,3-triazol-1-yl)propoxy)phenyl)propan-2-yl)-2-(iodo-$^{123}$I)phenoxy)propan-2-ol |
| 50 | | 1-chloro-3-(4-(2-(4-(2-hydroxy-3-(5-(hydroxymethyl)-1H-1,2,3-triazol-1-yl)propoxy)phenyl)propan-2-yl)-2-(iodo-$^{123}$I)phenoxy)propan-2-ol |
| 50a | | (S)-1-chloro-3-(4-(2-(4-((R)-2-hydroxy-3-(5-(hydroxymethyl)-1H-1,2,3-triazol-1-yl)propoxy)phenyl)propan-2-yl)-2-(iodo-$^{123}$I)phenoxy)propan-2-ol |

TABLE 2-continued

$^{123}$I Compounds

| No. | Structure | Name |
|---|---|---|
| 50b | 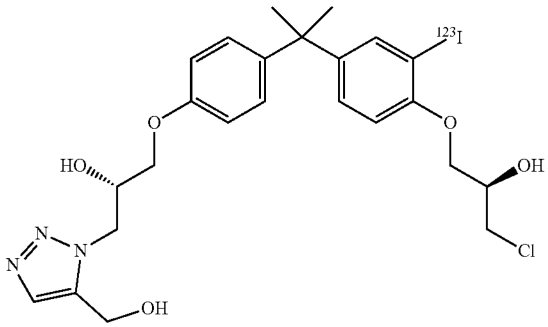 [SMILES: CC(C)(c1ccc(OC[C@@H](O)Cn2nncc2CO)cc1)c1ccc(OC[C@@H](O)CCl)c([123I])c1] | (R)-1-chloro-3-(4-(2-(4-((S)-2-hydroxy-3-(5-(hydroxymethyl)-1H-1,2,3-triazol-1-yl)propoxy)phenyl)propan-2-yl)-2-(iodo-$^{123}$I)phenoxy)propan-2-ol |
| 50c | 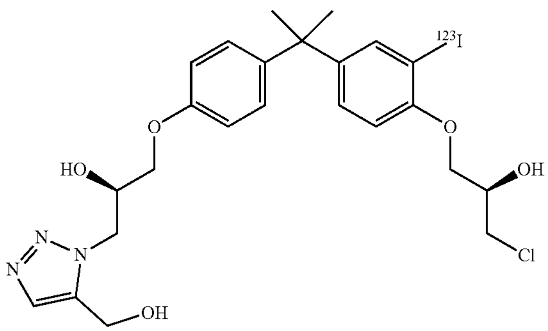 [SMILES: CC(C)(c1ccc(OC[C@H](O)Cn2nncc2CO)cc1)c1ccc(OC[C@@H](O)CCl)c([123I])c1] | (R)-1-chloro-3-(4-(2-(4-((R)-2-hydroxy-3-(5-(hydroxymethyl)-1H-1,2,3-triazol-1-yl)propoxy)phenyl)propan-2-yl)-2-(iodo-$^{123}$I)phenoxy)propan-2-ol |
| 50d | 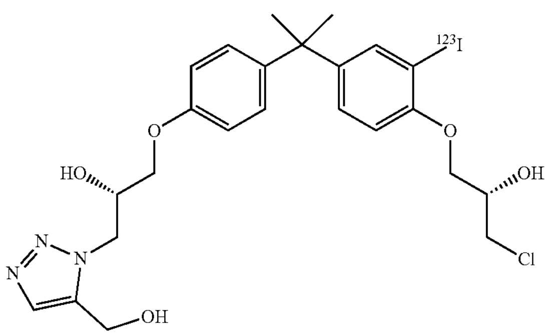 [SMILES: CC(C)(c1ccc(OC[C@@H](O)Cn2nncc2CO)cc1)c1ccc(OC[C@H](O)CCl)c([123I])c1] | (S)-1-chloro-3-(4-(2-(4-((S)-2-hydroxy-3-(5-(hydroxymethyl)-1H-1,2,3-triazol-1-yl)propoxy)phenyl)propan-2-yl)-2-(iodo-$^{123}$I)phenoxy)propan-2-ol |

In some embodiments of the compound of Formula I, or a pharmaceutically acceptable salt, tautomer, or stereoisomer thereof including all 4 distinct stereoisomers e.g., (S,R), (R,S), (R,R), and (S,S), has one of the following structures:

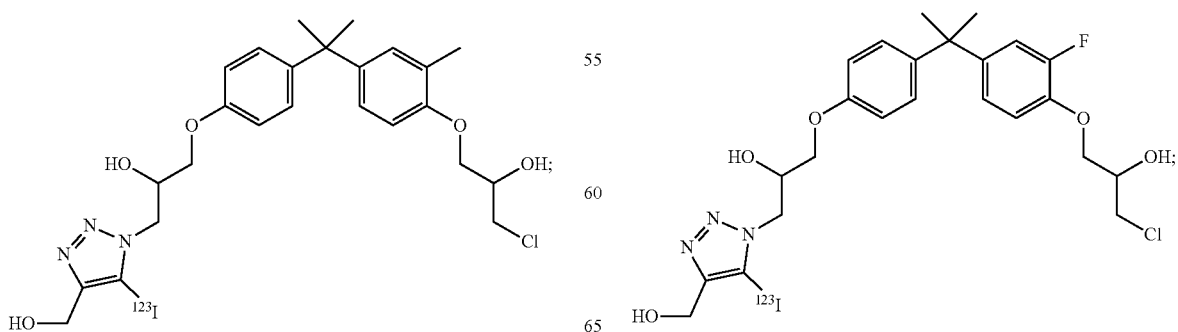

151

-continued

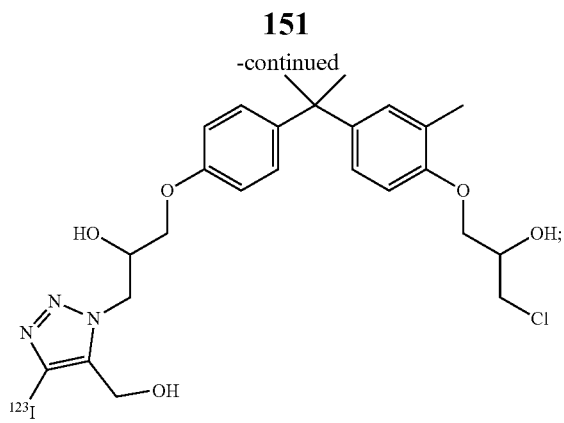

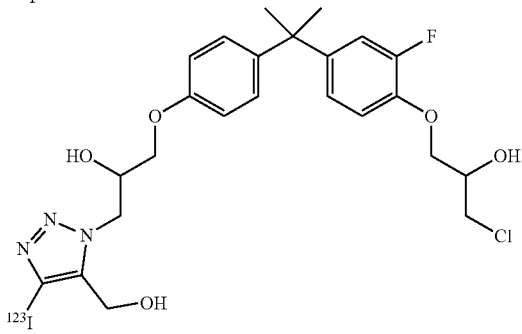

152

-continued

In some embodiments of the compound of Formula I, the compound has one of the following structures from Table 3, or a pharmaceutically acceptable salt, tautomer, or stereoisomer thereof:

TABLE 3

$^{18}F$ Compounds

| No. | Structure | Name |
|---|---|---|
| 51 | 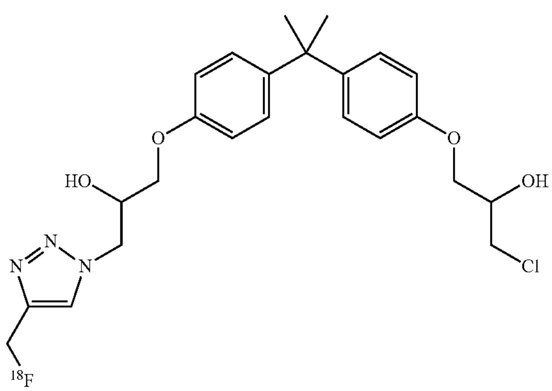 [SMILES: CC(C)(c1ccc(OCC(O)CCl)cc1)c1ccc(OCC(O)Cn2cc(C[18F])nn2)cc1] | 1-chloro-3-(4-(2-(4-(3-(4-((fluoro-$^{18}F$)methyl)-1H-1,2,3-triazol-1-yl)-2-hydroxypropoxy)phenyl)propan-2-yl)phenoxy)propan-2-ol |
| 51a | 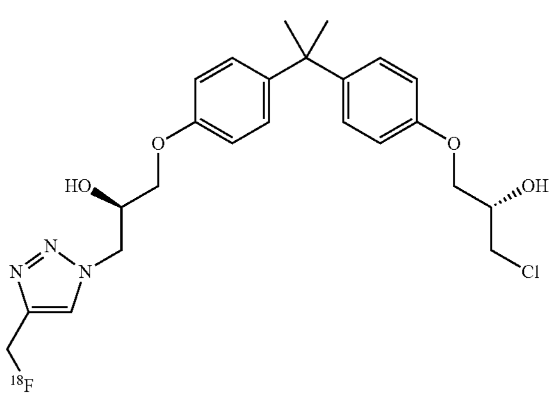 [SMILES: CC(C)(c1ccc(OC[C@H](O)CCl)cc1)c1ccc(OC[C@H](O)Cn2cc(C[18F])nn2)cc1] | (S)-1-chloro-3-(4-(2-(4-((R)-3-(4-((fluoro-$^{18}F$)methyl)-1H-1,2,3-triazol-1-yl)-2-hydroxypropoxy)phenyl)propan-2-yl)phenoxy)propan-2-ol |

TABLE 3-continued

| | $^{18}$F Compounds | |
|---|---|---|
| No. | Structure | Name |
| 51b | | (R)-1-chloro-3-(4-(2-(4-((S)-3-(4-((fluoro-$^{18}$F)methyl)-1H-1,2,3-triazol-1-yl)-2-hydroxypropoxy)phenyl)propan-2-yl)phenoxy)propan-2-ol |
| 51c | | (R)-1-chloro-3-(4-(2-(4-((R)-3-(4-((fluoro-$^{18}$F)methyl)-1H-1,2,3-triazol-1-yl)-2-hydroxypropoxy)phenyl)propan-2-yl)phenoxy)propan-2-ol |
| 51d | | (S)-1-chloro-3-(4-(2-(4-((S)-3-(4-((fluoro-$^{18}$F)methyl)-1H-1,2,3-triazol-1-yl)-2-hydroxypropoxy)phenyl)propan-2-yl)phenoxy)propan-2-ol |
| 52 | | 1-chloro-3-(2-chloro-4-(2-(4-(3-(4-((fluoro-$^{18}$F)methyl)-1H-1,2,3-triazol-1-yl)-2-hydroxypropoxy)phenyl)propan-2-yl)phenoxy)propan-2-ol |

TABLE 3-continued

| | $^{18}$F Compounds | |
|---|---|---|
| No. | Structure | Name |
| 52a | | (S)-1-chloro-3-(2-chloro-4-(2-(4-((R)-3-(4-((fluoro-$^{18}$F)methyl)-1H-1,2,3-triazol-1-yl)-2-hydroxypropoxy)phenyl)propan-2-yl)phenoxy)propan-2-ol |
| 52b | | (R)-1-chloro-3-(2-chloro-4-(2-(4-((S)-3-(4-((fluoro-$^{18}$F)methyl)-1H-1,2,3-triazol-1-yl)-2-hydroxypropoxy)phenyl)propan-2-yl)phenoxy)propan-2-ol |
| 52c | | (R)-1-chloro-3-(2-chloro-4-(2-(4-((R)-3-(4-((fluoro-$^{18}$F)methyl)-1H-1,2,3-triazol-1-yl)-2-hydroxypropoxy)phenyl)propan-2-yl)phenoxy)propan-2-ol |
| 52d | | (S)-1-chloro-3-(2-chloro-4-(2-(4-((S)-3-(4-((fluoro-$^{18}$F)methyl)-1H-1,2,3-triazol-1-yl)-2-hydroxypropoxy)phenyl)propan-2-yl)phenoxy)propan-2-ol |

TABLE 3-continued

| | ¹⁸F Compounds | |
|---|---|---|
| No. | Structure | Name |
| 53 | | 1-(2-bromo-4-(2-(4-(3-(4-((fluoro-¹⁸F)methyl)-1H-1,2,3-triazol-1-yl)-2-hydroxypropoxy)phenyl)propan-2-yl)phenoxy)-3-chloropropan-2-ol |
| 53a | | (R)-1-(4-(2-(3-bromo-4-((S)-3-chloro-2-hydroxypropoxy)phenyl)propan-2-yl)phenoxy)-3-(4-((fluoro-¹⁸F)methyl)-1H-1,2,3-triazol-1-yl)propan-2-ol |
| 53b | | (S)-1-(4-(2-(3-bromo-4-((R)-3-chloro-2-hydroxypropoxy)phenyl)propan-2-yl)phenoxy)-3-(4-((fluoro-¹⁸F)methyl)-1H-1,2,3-triazol-1-yl)propan-2-ol |
| 53c | | (R)-1-(4-(2-(3-bromo-4-((R)-3-chloro-2-hydroxypropoxy)phenyl)propan-2-yl)phenoxy)-3-(4-((fluoro-¹⁸F)methyl)-1H-1,2,3-triazol-1-yl)propan-2-ol |

TABLE 3-continued

¹⁸F Compounds

| No. | Structure | Name |
|---|---|---|
| 53d | 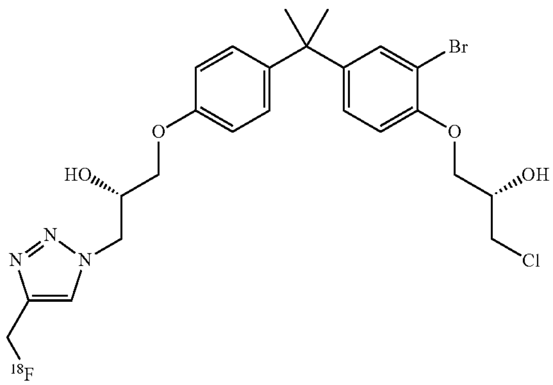 | (S)-1-(4-(2-(3-bromo-4-((S)-3-chloro-2-hydroxypropoxy)phenyl)propan-2-yl)phenoxy)-3-(4-((fluoro-¹⁸F)methyl)-1H-1,2,3-triazol-1-yl)propan-2-ol |
| 54 | 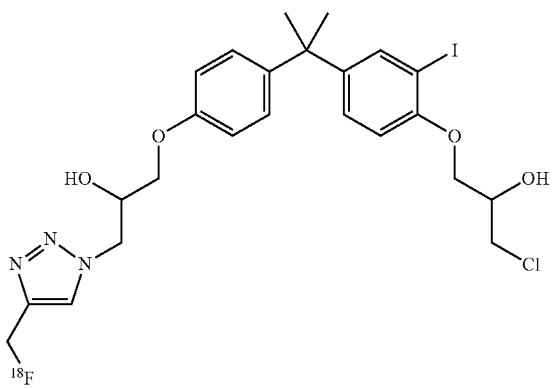 | 1-chloro-3-(4-(2-(4-(3-(4-((fluoro-18F)methyl)-1H-1,2,3-triazol-1-yl)-2-hydroxypropoxy)phenyl)propan-2-yl)-2-iodophenoxy)propan-2-ol |
| 54a | 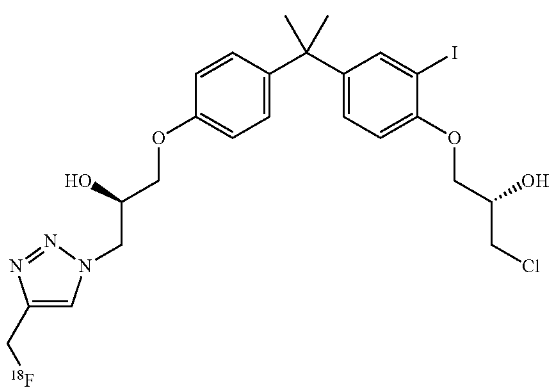 [SMILES: CC(C)(c1ccc(OC[C@H](O)Cn2cc(C[18F])nn2)cc1)c1ccc(OC[C@H](O)CCl)c(I)c1] | (S)-1-chloro-3-(4-(2-(4-((R)-3-(4-((fluoro-¹⁸F)methyl)-1H-1,2,3-triazol-1-yl)-2-hydroxypropoxy)phenyl)propan-2-yl)-2-iodophenoxy)propan-2-ol |
| 54b | 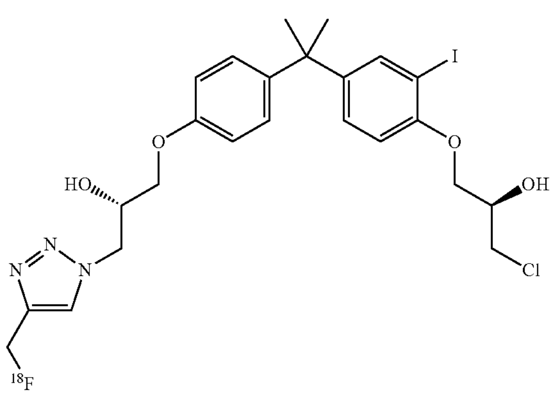 | (R)-1-chloro-3-(4-(2-(4-((S)-3-(4-((fluoro-¹⁸F)methyl)-1H-1,2,3-triazol-1-yl)-2-hydroxypropoxy)phenyl)propan-2-yl)-2-iodophenoxy)propan-2-ol |

TABLE 3-continued

<sup>18</sup>F Compounds

| No. | Structure | Name |
|---|---|---|
| 54c | 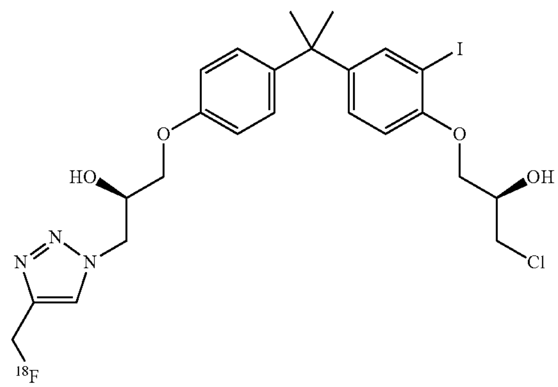 | (R)-1-chloro-3-(4-(2-(4-((R)-3-(4-((fluoro-<sup>18</sup>F)methyl)-1H-1,2,3-triazol-1-yl)-2-hydroxypropoxy)phenyl)propan-2-yl)-2-iodophenoxy)propan-2-ol |
| 54d | 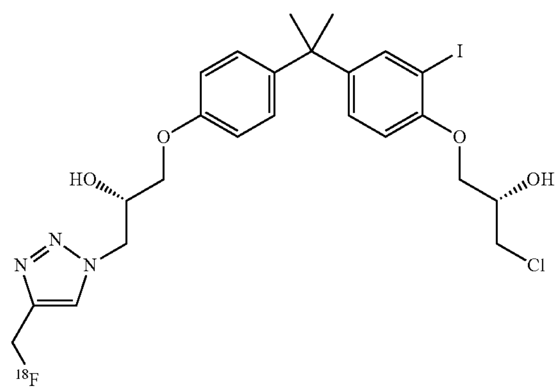 | (S)-1-chloro-3-(4-(2-(4-((S)-3-(4-((fluoro-<sup>18</sup>F)methyl)-1H-1,2,3-triazol-1-yl)-2-hydroxypropoxy)phenyl)propan-2-yl)-2-iodophenoxy)propan-2-ol |
| 55 | 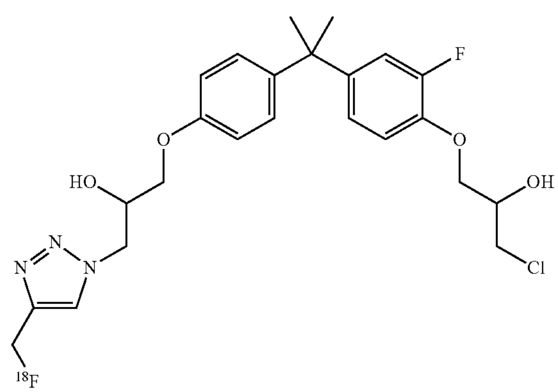 | 1-chloro-3-(2-fluoro-4-(2-(4-(3-(4-((fluoro-<sup>18</sup>F)methyl)-1H-1,2,3-triazol-1-yl)-2-hydroxypropoxy)phenyl)propan-2-yl)phenoxy)propan-2-ol |
| 55a | 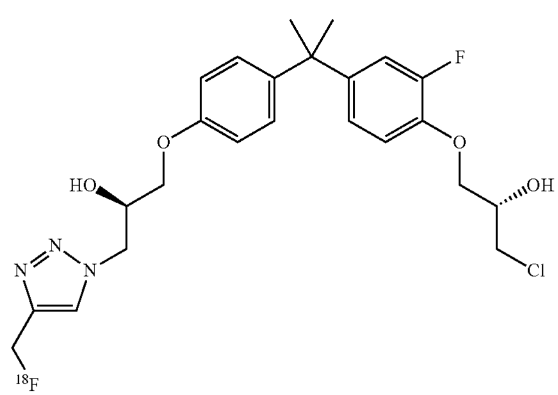 [SMILES: CC(C)(c1ccc(OC[C@H](O)Cn2cc(C[18F])nn2)cc1)c1ccc(OC[C@H](O)CCl)c(F)c1] | (S)-1-chloro-3-(2-fluoro-4-(2-(4-((R)-3-(4-((fluoro-<sup>18</sup>F)methyl)-1H-1,2,3-triazol-1-yl)-2-hydroxypropoxy)phenyl)propan-2-yl)phenoxy)propan-2-ol |

TABLE 3-continued

| | $^{18}$F Compounds | |
|---|---|---|
| No. | Structure | Name |
| 55b | | (R)-1-chloro-3-(2-fluoro-4-(2-(4-((S)-3-(4-(fluoro-$^{18}$F)methyl)-1H-1,2,3-triazol-1-yl)-2-hydroxypropoxy)phenyl)propan-2-yl)phenoxy)propan-2-ol |
| 55c | | (R)-1-chloro-3-(2-fluoro-4-(2-(4-((R)-3-(4-((fluoro-$^{18}$F)methyl)-1H-1,2,3-triazol-1-yl)-2-hydroxypropoxy)phenyl)propan-2-yl)phenoxy)propan-2-ol |
| 55d | | (S)-1-chloro-3-(2-fluoro-4-(2-(4-((S)-3-(4-((fluoro-$^{18}$F)methyl)-1H-1,2,3-triazol-1-yl)-2-hydroxypropoxy)phenyl)propan-2-yl)phenoxy)propan-2-ol |
| 56 | | 1-chloro-3-(4-(2-(4-(3-(4-((fluoro-$^{18}$F)methyl)-1H-1,2,3-triazol-1-yl)-2-hydroxypropoxy)phenyl)propan-2-yl)-2-methylphenoxy)propan-2-ol |

TABLE 3-continued

| No. | Structure | Name |
|---|---|---|
| 56a | 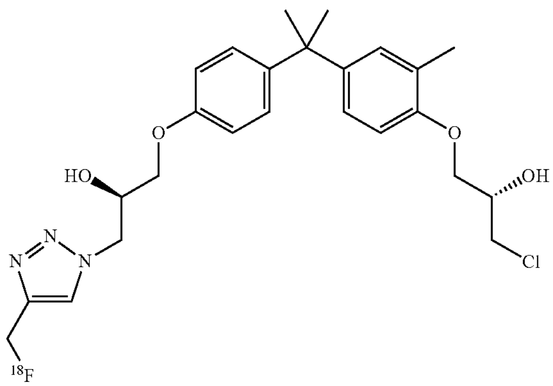 [SMILES: Cc1cc(C(C)(C)c2ccc(OC[C@H](O)Cn3cc(C[18F])nn3)cc2)ccc1OC[C@H](O)CCl] | (S)-1-chloro-3-(4-(2-(4-((R)-3-(4-((fluoro-$^{18}$F)methyl)-1H-1,2,3-triazol-1-yl)-2-hydroxypropoxy)phenyl)propan-2-yl)-2-methylphenoxy)propan-2-ol |
| 56b | 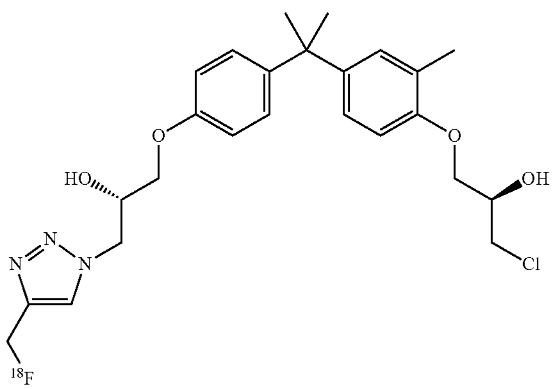 [SMILES: Cc1cc(C(C)(C)c2ccc(OC[C@@H](O)Cn3cc(C[18F])nn3)cc2)ccc1OC[C@@H](O)CCl] | (R)-1-chloro-3-(4-(2-(4-((S)-3-(4-((fluoro-$^{18}$F)methyl)-1H-1,2,3-triazol-1-yl)-2-hydroxypropoxy)phenyl)propan-2-yl)-2-methylphenoxy)propan-2-ol |
| 56c | 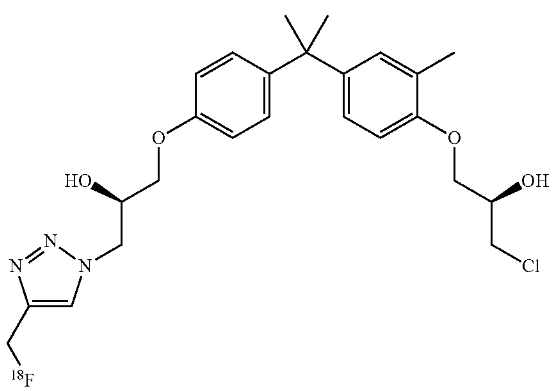 [SMILES: Cc1cc(C(C)(C)c2ccc(OC[C@H](O)Cn3cc(C[18F])nn3)cc2)ccc1OC[C@@H](O)CCl] | (R)-1-chloro-3-(4-(2-(4-((R)-3-(4-((fluoro-$^{18}$F)methyl)-1H-1,2,3-triazol-1-yl)-2-hydroxypropoxy)phenyl)propan-2-yl)-2-methylphenoxy)propan-2-ol |
| 56d | 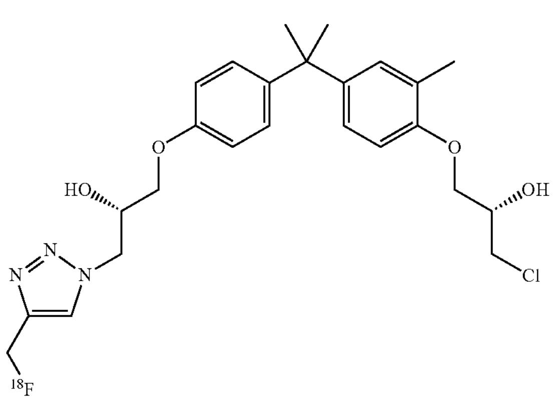 [SMILES: Cc1cc(C(C)(C)c2ccc(OC[C@@H](O)Cn3cc(C[18F])nn3)cc2)ccc1OC[C@H](O)CCl] | (S)-1-chloro-3-(4-(2-(4-((S)-3-(4-((fluoro-$^{18}$F)methyl)-1H-1,2,3-triazol-1-yl)-2-hydroxypropoxy)phenyl)propan-2-yl)-2-methylphenoxy)propan-2-ol |

In some embodiments of the compound of Formula I, the compound has one of the following structures, or a pharmaceutically acceptable salt, tautomer, or stereoisomer thereof including all 4 distinct stereoisomers e.g., (S,R), (R,S), (R,R), and (S,S):

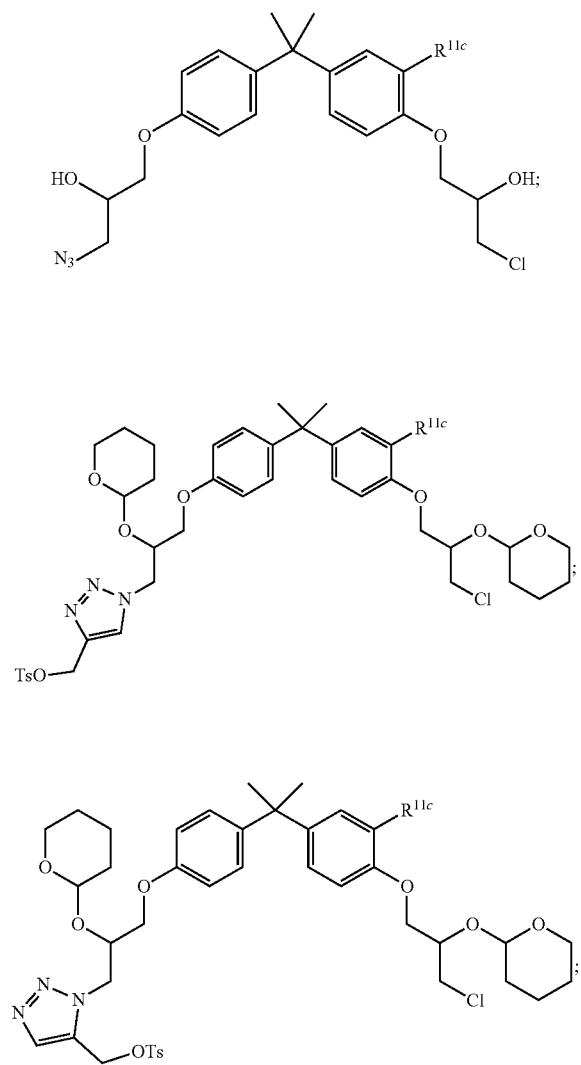

wherein $R^{11c}$ is H, Cl, Br, I, F, or $C_1$-$C_6$ alkyl.

In some embodiments of the compound of Formula I, the compound has one of the following structures, or a pharmaceutically acceptable salt thereof:

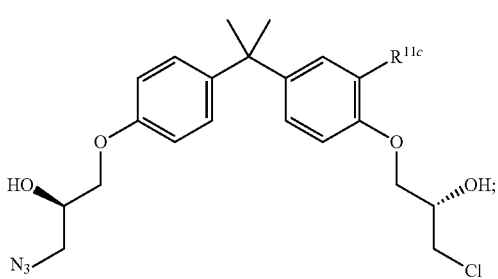

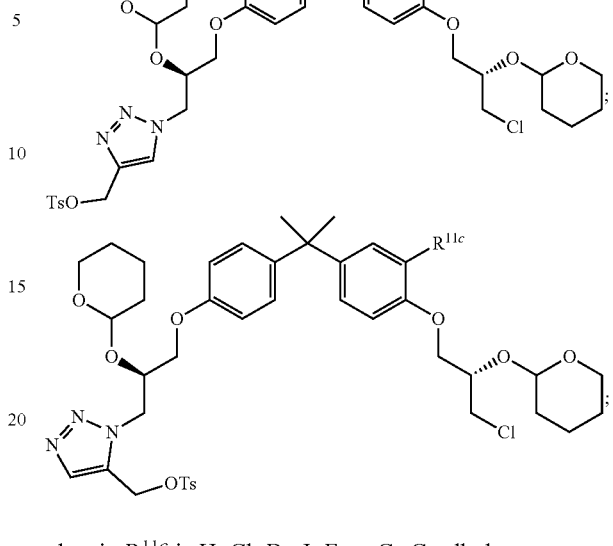

wherein $R^{11c}$ is H, Cl, Br, I, F, or $C_1$-$C_6$ alkyl.

In one embodiment, the present invention is directed to a pharmaceutical composition, comprising a compound having a structure of Formula I:

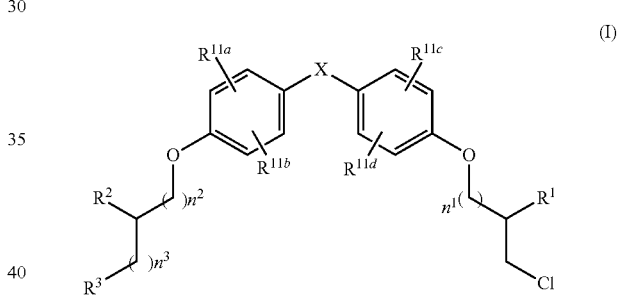

or a pharmaceutically acceptable salt, tautomer or stereoisomer thereof, wherein:

X is —O—, —S(O)$_{0-2}$—, —C(═O)—, —C(OR$^5$)$_2$—, —C(OR$^5$)(OC(═O)R$^{13}$)—, —C(R$^8$R$^9$)—, —C(═CR$^8$R$^9$)—, —N(R$^9$)—, —N(COR$^9$)—, —CHNR$^8$R$^9$—, —C(═NR$^9$)—, —C(═NOR$^5$)—, —C(═N—NHR$^5$)—;

$R^1$ and $R^2$ are each independently H, hydroxyl, —O-heterocyclyl, or —OC(═O)R$^{13}$;

$R^3$ is —N$_3$, aryl, carbocyclyl, heteroaryl or heterocyclyl which are optionally substituted with one or more $R^6$;

$R^5$ is each independently H, $C_1$-$C_6$ alkyl, $C_2$-$C_6$ alkenyl, or $C_2$-$C_6$ alkynyl;

$R^6$ is each independently selected from the group consisting of H, F, Cl, Br, I, $^{123}$I, hydroxyl, oxo, $C_1$-$C_6$ alkyl, $C_2$-$C_6$ alkenyl, $C_2$-$C_6$ alkynyl, $C_1$-$C_6$ alkoxy, $C_6$-$C_{12}$ aryl, wherein each $R^6$ is optionally substituted with one or more of halogen, $^{123}$I, $^{18}$F, hydroxyl, —OS(O)$_2$-aryl, $C_1$-$C_6$ alkyl, $C_2$-$C_6$ alkenyl, or $C_2$-$C_6$ alkynyl;

$R^8$ and $R^9$ are each independently H, halogen, —S(O)$_{0-2}$R$^5$, $C_1$-$C_{10}$ alkyl, $C_2$-$C_{10}$ alkenyl, $C_2$-$C_{10}$ alkynyl, aryl, aralkyl, $C_1$-$C_{10}$ acyl, or —NR$^5$R$^5$, or $R^8$ and $R^9$ can join to form a unsubstituted or substituted mono-, bi-, or tri-cyclic carbocycle or heterocycle containing from 3 to 20 carbon atoms;

$R^{11a}$, $R^{11b}$, $R^{11c}$ and $R^{11d}$ are each independently H, F, Cl, Br, I, $^{123}$I, hydroxyl, $C_1$-$C_6$ alkyl, $C_2$-$C_6$ alkenyl, or $C_2$-$C_6$ alkynyl; —$OR^5$, —OC(=O)$R^{13}$, $C_1$-$C_{10}$ acyl, —S(O)$_{0-2}R^5$, —$NO_2$, —CN, —$NH_2$, —$NHR^5$, or —N($R^5$)$_2$;

$R^{13}$ is each independently $C_1$-$C_6$ alkyl, $C_2$-$C_6$ alkenyl, or $C_2$-$C_6$ alkynyl;

$n^1$ and $n^2$ are each independently 0, 1, or 2; and $n^3$ is 0, 1, 2, 3, 4, or 5.

In some embodiment, the pharmaceutical composition comprising a compound having a structure of Formula I further comprises a pharmaceutically acceptable carrier. In another embodiment, the pharmaceutical composition comprising a compound having a structure of Formula I further comprises an additional therapeutic agent. In one embodiment, the pharmaceutical composition comprising a compound having a structure of Formula I further comprises a pharmaceutically acceptable carrier and an additional therapeutic agent.

In another embodiment, the pharmaceutical composition comprising a compound having a structure of Formula I further comprises an additional therapeutic agent which is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

Accordingly, one embodiment comprises the use of the disclosed compounds in combination therapy with one or more currently-used or experimental pharmacological therapies which are utilized for treating the above disease states irrespective of the biological mechanism of action of such pharmacological therapies, including without limitation pharmacological therapies which directly or indirectly inhibit the androgen receptor, pharmacological therapies which are cyto-toxic in nature, and pharmacological therapies which interfere with the biological production or function of androgen (hereinafter, an "additional therapeutic agent"). By "combination therapy" is meant the administration of any one or more of a compound of Formula I with one or more of another therapeutic agent to the same patient such that their pharmacological effects are contemporaneous with one another, or if not contemporaneous, that their effects are synergistic with one another even though dosed sequentially rather than contemporaneously.

Such administration includes without limitation dosing of one or more of a compound of Formula I and one or more of the additional therapeutic agent(s) as separate agents without any comingling prior to dosing, as well as formulations which include one or more other androgen-blocking therapeutic agents mixed with one or more compound of Formula I as a pre-mixed formulation. Administration of the compound(s) of Formula I in combination with the additional therapeutic agents for treatment of the above disease states also includes dosing by any dosing method including without limitation, intravenous delivery, oral delivery, intra-peritoneal delivery, intra-muscular delivery, or intra-tumoral delivery.

In another aspect of the present disclosure, the one or more of the additional therapeutic agents can be administered to the patient before administration of the compound(s) of Formula I. In another embodiment, the compound(s) of Formula I can be co-administered with one or more of the additional therapeutic agents. In yet another aspect, the one or more additional therapeutic agents can be administered to the patient after administration of the compound(s) of Formula I.

The ratio of the doses of compound(s) of Formula I to that of the one or more additional therapeutic agents can be about 1:1 or can vary, e.g., about 2:1, about 3:1, about 4:1, about 5:1, about 6:1, about 7:1, about 8:1, about 9:1, about 10:1, about 1:2, about 1:3, about 1:4, about 1:5, about 1:6, about 1:7, about 1:8, about 1:9, about 1:10, and can be varied accordingly to achieve the optimal therapeutic benefit.

The compound(s) of Formula I that are combined with the one or more additional therapeutic agents for improved treatment of the above disease states can comprise, but are not limited to any compound having a structure of Formula I, including those compounds shown in Tables 1, 2, or 3.

The additional therapeutic agents include without limitation any pharmacological agent which is currently approved by the FDA in the U.S. (or elsewhere by any other regulatory body) for use as pharmacological treatment of any of the above disease states, or which is currently being used experimentally as part of a clinical trial program that relates to the above disease states. Non-limiting examples of the Other Pharmacological Agents comprise, without limitation: the chemical entity known as ODM-201 (also known as BAY1841788) and related compounds; which appears to bind to the AR and blocks its cellular function, and is currently in clinical development as a treatment for prostate cancer); the chemical entity known as enzalutamide (4-(3-(4-cyano-3-(trifluoromethyl)phenyl)-5,5-dimethyl-4-oxo-2-thioxoimidazolidin-1-yl)-2-fluoro-N-methylbenzamide) and related compounds, which appears to be a blocker of the androgen receptor (AR) LBD and a FDA-approved treatment for prostate cancer; the chemical entity known as Galeterone and related compounds which appears to be a blocker of the androgen receptor (AR) LBD, and a CYP17 lyase inhibitor, and also appears to decrease overall androgen receptor levels in prostate cancer cells. Galeterone is currently in development as a treatment for prostate cancer; the chemical entity known as ARN-509 (4-[7-[6-cyano-5-(trifluoromethyl)pyridin-3-yl]-8-oxo-6-sulfanylidene-5,7-diazaspiro[3.4]octan-5-yl]-2-fluoro-N-methylbenzamide) and related compounds which appears to be a blocker of the androgen receptor (AR) LBD and is currently in development as a treatment for prostate cancer; the chemical entity known as abiraterone (or CB-7630; (3S,8R,9S,10R,13S, 14S)-10,13-dimethyl-17-(pyridin-3-yl) 2,3,4,7,8,9,10,11,12, 13,14,15-dodecahydro-1H-cyclopenta[a]phenanthren-3-ol), and related molecules, which appears to block the production of androgen and FDA-approved treatment for prostate cancer; the chemical entity known as bicalutamide (N-[4-cyano-3-(trifluoromethyl)phenyl]-3-[(4-fluorophenyl)sulfonyl]-2-hydroxy-2-methylpropanamide) and related compounds, which appears to be a blocker of the androgen receptor (AR) LBD and which is currently used to treat prostate cancer, the chemical entity known as nilutamide (5,5-dimethyl-3-[4-nitro-3-(trifluoromethyl)phenyl]imidazolidine-2,4-dione) and related compounds, which appears to be a blocker of the AR LBD and which is currently used to treat prostate cancer, the chemical entity known as flutamide (2-methyl-N-[4-nitro-3-(trifluoromethyl)phenyl]-propanamide) and related compounds, which appears to be a blocker of the androgen receptor (AR) LBD and which is currently used to treat prostate cancer, the chemical entities known as cyproterone acetate (6-chloro-1β,2β-dihydro-17-hydroxy-3'H-cyclopropa[1,2]pregna-4,6-diene-3,20-dione) and related compounds, which appears to be a blocker of the androgen receptor (AR) LBD and which is currently used to treat prostate cancer, the chemical entity known as docetaxel (Taxotere; 1,7β,10β-trihydroxy-9-oxo-5β,20-epoxytax-11-ene-2α,4,13α-triyl 4-acetate 2-benzoate 13-{(2R,3S)-3-

[(tert-butoxycarbonyl)amino]-2-hydroxy-3-phenylpropanoate}) and related compounds, which appears to be a cytotoxic antimicrotubule agent and is currently used in combination with prednisone to treat prostate cancer, the chemical entity known as Bevacizumab (Avastin), a monoclonal antibody that recognizes and blocks vascular endothelial growth factor A (VEGF-A) and can be used to treat prostate cancer, the chemical entity known as OSU-HDAC42 ((S)-(+)-N-hydroxy-4-(3-methyl-2-phenylbutyrylamino)-benzamide), and related compounds, which appears to act as a histone deacetylase inhibitor, and is currently being developed as a treatment for prostate cancer, the chemical entity known as VITAXN which appears to be a monoclonal antibody against the vascular integrin αvβ3 to prevent angiogenesis, and which can be used to treat prostate cancer, the chemical entity known as sunitumib (N-(2-diethylaminoethyl)-5-[(Z)-(5-fluoro-2-oxo-1H-indol-3-ylidene)methyl]-2,4-dimethyl-1H-pyrrole-3-carboxamide) and related compounds, which appears to inhibit multiple receptor tyrosine kinases (RTKs) and can be used for treatment of prostate cancer, the chemical entity known as ZD-4054 (N-(3-Methoxy-5-methylpyrazin-2-yl)-2-[4-(1,3,4-oxadiazol-2-yl)phenyl]pyridin-3-sulfonamid) and related compounds, which appears to block the edta receptor and which can be used for treatment of prostate cancer; the chemical entity known as Cabazitaxel (XRP-6258), and related compounds, which appears to be a cytotoxic microtubule inhibitor, and which is currently used to treat prostate cancer; the chemical entity known as MDX-010 (Ipilimumab), a fully human monoclonal antibody that binds to and blocks the activity of CTLA-4 which is currently in development as an immunotherapeutic agent for treatment of prostate cancer; the chemical entity known as OGX 427 which appears to target HSP27 as an antisense agent, and which is currently in development for treatment of prostate cancer; the chemical entity known as OGX 011 which appears to target clusterin as an antisense agent, and which is currently in development as a treatment for prostate cancer; the chemical entity known as finastride (Proscar, Propecia; N-(1,1-dimethylethyl)-3-oxo-(5α,17β)-4-azaandrost-1-ene-17-carboxamide), and related compounds, which appears to be a 5-alpha reductase inhibitor that reduces levels of dihydrotestosterone, and can be used to treat prostate cancer; the chemical entity known as dutasteride (Avodart; 5α,17β)-N-{2,5 bis(trifluoromethyl)phenyl}-3-oxo-4-azaandrost-1-ene-17-carboxamide) and related molecules, which appears to be a 5-alpha reductase inhibitor that reduces levels of dihydrotestosterone, and can be used in the treatment of prostate cancer; the chemical entity known as turosteride ((4aR,4bS,6aS,7S,9aS,9bS,11aR)-1,4a,6a-trimethyl-2-oxo-N-(propan-2-yl)-N-(propan-2-ylcarbamoyl)hexadecahydro-1H-indeno[5,4-f]quinoline-7-carboxamide), and related molecules, which appears to be a 5-alpha reductase inhibitor that reduces levels of dihydrotestosterone and can be used in the treatment of prostate cancer; the chemical entity known as bexlosteride (LY-191, 704; (4aS,10bR)-8-chloro-4-methyl-1,2,4a,5,6,10b-hexahydrobenzo[f]quinolin-3-one), and related compounds, which appears to be a 5-alpha reductase inhibitor that reduces levels of dihydrotestosterone and can be used in the treatment of prostate cancer; the chemical entity known as izonsteride (LY-320,236; (4aR,10bR)-8-[(4-ethyl-1,3-benzothiazol-2-yl)sulfanyl]-4,10b-dimethyl-1,4,4a,5,6,10b-hexahydrobenzo[f]quinolin-3(2H)-one) and related compounds, which appears to be a 5-alpha reductase inhibitor that reduces levels of dihydrotestosterone and can be used for the treatment of prostate cancer; the chemical entity known as FCE 28260 and related compounds, which appears to be a 5-alpha reductase inhibitor that reduces levels of dihydrotestosterone and can be used for the treatment of prostate cancer; the chemical entity known as SKF105,111, and related compounds, which appears to be a 5-alpha reductase inhibitor that reduces levels of dihydrotestosterone and can be used for treatment of prostate cancer.

Accordingly, in some embodiments, the pharmaceutical composition comprising a compound having a structure of Formula I further comprises an additional therapeutic agent selected form the group consisting of enzalutamide, Galeterone, ARN-509; abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111, ODM-201, radium 233, or related compounds thereof.

In some embodiments, compounds of Formula I which result in unstable structures and/or unsatisfied valences are not included within the scope of the invention.

In another embodiment, the present disclosure provides a pharmaceutical composition comprising any of the foregoing compounds of Formula I and a pharmaceutically acceptable carrier.

Compounds as described herein can be in the free form or in the form of a salt thereof. In some embodiments, compounds as described herein can be in the form of a pharmaceutically acceptable salt, which are known in the art (Berge et al., *J. Pharm. Sci.* 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt can be, for example, formed as a pharmaceutically acceptable salt. Compounds containing one or more basic functional groups can be capable of forming a pharmaceutically acceptable salt with, for example, a pharmaceutically acceptable organic or inorganic acid. Pharmaceutically acceptable salts can be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups can be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts can be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N-dibenzylethylenediamine or polyamine resins. In some embodiments, compounds as described herein can contain both acidic and basic groups and can be in the form of inner salts or zwitterions, for example, and without limitation, betaines. Salts as described herein can be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts can occur in situ during isolation and purification of the compounds or preparation of salts can occur by separately reacting an isolated and purified compound.

In some embodiments, compounds and all different forms thereof (e.g. free forms, salts, polymorphs, isomeric forms) as described herein can be in the solvent addition form, for example, solvates. Solvates contain either stoichiometric or non-stoichiometric amounts of a solvent in physical association the compound or salt thereof. The solvent can be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein can include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature can cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

III. Methods

The present compounds find use in any number of methods. For example, in some embodiments the compounds are useful in methods for modulating androgen receptor (AR). Accordingly, in one embodiment, the present disclosure provides the use of any one of the foregoing compounds of Formula I for modulating androgen receptor (AR) activity. For example in some embodiments, modulating androgen receptor (AR) activity is in a mammalian cell. Modulating androgen receptor (AR) can be in a subject in need thereof (e.g., a mammalian subject) and for treatment of any of the described conditions or diseases.

In other embodiments, modulating androgen receptor (AR) activity is for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, age related macular degeneration, and combinations thereof. For example in some embodiments, the indication is prostate cancer. In other embodiments, the prostate cancer is castration resistant prostate cancer (also referred to as hormone refractory, androgen-independent, androgen deprivation resistant, androgen ablation resistant, androgen depletion-independent, castration-recurrent, anti-androgen-recurrent). While in other embodiments, the prostate cancer is androgen dependent prostate cancer. In other embodiments, the spinal and bulbar muscular atrophy is Kennedy's disease.

In some embodiments, compounds as described herein can be administered to a subject. In one embodiment, the present invention is directed to a method of treating castration resistant prostate cancer comprising administering a pharmaceutical composition comprising a compound having a structure of Formula I. In some embodiments, the present invention is directed to a method of treating androgen-dependent prostate cancer comprising administering a pharmaceutical composition comprising a compound having a structure of Formula I. In other embodiments, the present invention is directed to a method of treating androgen-independent prostate cancer comprising administering a pharmaceutical composition comprising a compound having a structure of Formula I.

In other embodiments, the present disclosure provides a method of modulating androgen receptor (AR) activity, the method comprising administering any one of the foregoing compounds of Formula I, pharmaceutically acceptable salt thereof, or pharmaceutical composition of Formula I as described herein (including compositions comprising a compound of Formula I and an additional therapeutic agent), to a subject (e.g., mammal) in need thereof. In some embodiments, modulating androgen receptor (AR) activity is in a mammalian cell. In other embodiments, modulating androgen receptor (AR) activity is in a mammal. In one embodiment, modulating androgen receptor (AR) activity is in a human.

The modulating androgen receptor (AR) activity can be for inhibiting AR N-terminal domain activity. The modulating androgen receptor (AR) activity can be for inhibiting androgen receptor (AR) activity. The modulating can be in vivo. The modulating androgen receptor (AR) activity can be for treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), and age related macular degeneration. The indication can be prostate cancer. The prostate cancer can be castration-resistant prostate cancer. The prostate cancer can be androgen dependent prostate cancer.

In accordance with another embodiment, there is provided a use of the compounds of Formula I, pharmaceutically acceptable salt thereof, or pharmaceutical composition of Formula I as described herein for preparation of a medicament for modulating androgen receptor (AR).

Alternatively, in one embodiment, a method of modulating androgen receptor activity, comprising administering Formula I, pharmaceutically acceptable salt thereof, or pharmaceutical composition of Formula I as described herein, is provided. In some embodiments, the administration can be to a mammal. In other embodiments, the administering can be to a mammal in need thereof and in an effective amount for the treatment of at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy (e.g., Kennedy's disease), age related macular degeneration, and combinations thereof.

As noted above, the presently disclosed compounds can find utility in a number of medical imaging applications, including imaging of the prostate. Many currently available imaging agents tend to accumulate in the bladder, which decreases their effectiveness as imaging tools specifically for the prostate. While not wishing to be bound by theory, the present applicants believe the disclosed compounds are unexpectedly effective for imaging of the prostate due to their ability to accumulate in the prostate, rather than the bladder, allowing the prostate gland to be seen. Accordingly, the compounds can be used in methods for imaging the prostate, for example to image benign prostate diseases. In other embodiments, the compounds can be used in methods to image cancerous prostate diseases, such as tumors of the prostate.

Androgen ablation therapy causes a temporary reduction in prostate cancer tumor burden, but the malignancy will begin to grow again in the absence of testicular androgens to form castrate resistant prostate cancer (CRPC). A rising titer of serum prostate-specific antigen (PSA) after androgen ablation therapy indicates biochemical failure, the emergence of CRPC, and re-initiation of an androgen receptor (AR) transcription program. Most patients succumb to CRPC within two years of biochemical failure.

AR is a transcription factor and a validated target for prostate cancer therapy. Current therapies include androgen ablation and administration of antiandrogens. Most CRPC is suspected to be AR-dependent. AR has distinct functional domains that include the C-terminus ligand-binding domain (LBD), a DNA-binding domain (DBD), and an amino-terminal domain (NTD). AR NTD contains the activation function-1 (AF-1) that contributes most of the activity to the AR. Recently, splice variants of the AR that lack the LBD have been reported in prostate cancer cell lines (VCaP and 22Rv1), and in CRPC tissues. To date more than 20 splice variants of AR have been detected. Splice variants V7 and V567es are clinically relevant with levels of expression correlated to poor survival and CRPC. AR V567es is solely expressed in 20% of metastases. Abiraterone resistance is associated with expression of AR splice variants. Enzalutamide also increases levels of expression of these constitutively active AR splice variants. These splice variants lack LBD and thereby would not be inhibited by current therapies that target the AR LBD such as antiandrogens or androgen ablation therapy. A single patient with advanced prostate cancer can have many lesions throughout the body and skeleton and each tumor can have differing levels of expression of AR.

Biopsy of metastatic tumors in a patient to determine AR species is neither widely accessible nor feasible to sample tumors in a patient that can have multiple metastases. Thus it is essential to develop approaches to detect the expression of all AR species for the molecular classification of tumors based on the level and extent of expression of AR splice variants, or other AR species that cannot be detected using an imaging agent that interacts with the LBD, to identify patients with potentially aggressive disease and poor prognosis, or to identify patients that will not respond to hormone therapies that target the AR LBD. Accordingly, certain embodiments of the present invention provide a AR NTD-targeted molecular imaging probe (e.g., compound of formula I) which can be used to monitor response to therapy and provide insight into the role of AR in resistance mechanisms.

One current approach to image AR in prostate cancer uses positron emission tomography (PET) with 16β-[$^{18}$F]-fluoro-5a dihydrotestosterone ($^{18}$F-FDHT) that binds to AR LBD. Unfortunately this imaging agent cannot detect splice variants lacking LBD. In some embodiments, the invention employs sequential imaging with $^{18}$F-FDHT to detect full-length AR and gamma radiation emitting probes to specifically detect the AR NTD which would be the sum of both full-length AR and variant AR. In other embodiments, the invention employs sequential imaging with two different PET imaging agents to detects only full-length AR and another to specifically detect the AR NTD which would be the sum of both full-length AR and variant AR. Together these data reveal patients with tumors that express variant AR (NTD of variant plus full-length AR detected with NTD isotope minus full-length AR detected with $^{18}$F-FDHT). By using sequential imaging, a discordant distribution or discordant level of uptake between $^{18}$F-FDHT and a radiolabeled compound of this invention (i.e., compound of Formula I) indicates the presence of overexpression of splice variants lacking the LBD.

As described above, radioactive $^{18}$F labeled compounds have found use as imaging agents not only to image AR in prostate cancer but for imaging various organs and various tumors. Similarly, radioactive $^{123}$I labeled compounds have been known for the use as imaging agents. In one embodiment, the compounds of the present disclosure comprise at least one $^{18}$F and/or $^{123}$I.

In one embodiment, the present invention is directed to a method of imaging cancer by administering a compound having a structure of Formula I to a subject. In another embodiment, the present invention is directed to a method of imaging cancer by administering a pharmaceutical composition comprising a compound having a structure of Formula I to a subject.

In some embodiment, the method of imaging cancer by administering a compound having a structure of Formula I or a pharmaceutical composition comprising Formula I to a subject and detecting the presence or absence of cancer by use of SPECT or PET. In other embodiments, the method of imaging cancer by administering a compound having a structure of Formula I to a subject and the method identifies the presence or absence of a tumor. In one embodiment, the method of imaging cancer by administering a compound having a structure of Formula I to a subject and the method identifies the location of a tumor. In one embodiment, the method of imaging cancer by administering a compound having a structure of Formula I to a subject and the method identifies a presence of a prostate cancer. In other embodiments, the prostate cancer is androgen-dependent prostate cancer. In some embodiments, the subject is a mammal such as a human.

In some other embodiments, the method is useful for detecting the presence of AR splice variants or other AR species that cannot be detected by imaging agents that interact with the AR LBD (i.e., mutations, truncations). Without wishing to be bound by any particular theory, since the present compounds bind to the AR N-terminal domain (NTD), even mutants or variants which lack the AR LBD can be imaged employing the present compounds. Thus, the present methods can be useful for detecting AR species, including mutants and variants, which lack the LBD or have LBD mutations, but do comprise the AR NTD. In other embodiments the method detects the presence or overexpression of AR splice variants lacking the ligand binding domain. For example, the method can include sequential imaging with $^{18}$F-FDHT and a compound of the invention and a discordant distribution or discordant level of uptake between $^{18}$F-FDHT and the compound of the invention indicates the presence or overexpression of splice variants lacking the ligand binding domain.

In other embodiments, the compounds of the invention are used in single photon emission computed tomography methods to monitor a patient's response to therapy. In other embodiments, the methods comprise use of a compound of the invention to detect the AR NTD.

In accordance with a further embodiment, the method of imaging a cancer is by administering a compound as described anywhere herein. In one embodiment, the method of imaging a cancer is by administering a compound represented in Table 2, Table 3 or a pharmaceutically acceptable salt, tautomer, or stereoisomer thereof. In some embodiments, the imaging is in a mammalian cell. In one embodiment, the imaging is in a mammal. In other embodiments, the imaging is in a human patient.

The administering and imaging can be to a mammal in need of diagnosis of at least one indication selected from the group consisting of: prostate cancer, breast cancer, ovarian cancer, endometrial cancer, salivary gland carcinoma, benign prostatic hyperplasia, hair loss, acne, hirsutism, ovarian cysts, polycystic ovary disease, precocious puberty, spinal and bulbar muscular atrophy (e.g., Kennedy's disease), and age-related macular degeneration. The imaging can be for imaging AR splice variants, mutants or other AR species which comprise the AR NTD.

In some embodiments, the compounds as described herein or pharmaceutically acceptable salts thereof can be used for imaging and diagnosis of at least one indication selected from the group consisting of: prostate cancer, breast cancer, ovarian cancer, endometrial cancer, salivary gland carcinoma, benign prostatic hyperplasia, hair loss, acne, hirsutism, ovarian cysts, polycystic ovary disease, precocious puberty, spinal and bulbar muscular atrophy, and age-related macular degeneration. In some embodiments, the compounds as described herein or acceptable salts thereof above can be used in the preparation of a medicament or a composition for imaging the prostate, for example for imaging benign prostate conditions or for imaging prostate cancer in a subject in need of such imaging (for example for diagnosis and/or location of prostate tumors).

In some embodiments, pharmaceutical compositions useful in modulating androgen receptor (AR) activity or useful for imaging, in accordance with this invention can comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents are those known in the art for use in such modes of administration.

Suitable pharmaceutical compositions can be formulated by means known in the art and their mode of administration and dose determined by the skilled practitioner. For parenteral administration, a compound can be dissolved in sterile water or saline or a pharmaceutically acceptable vehicle used for administration of non-water soluble compounds such as those used for vitamin K. For enteral administration, the compound can be administered in a tablet, capsule or dissolved in liquid form. The tablet or capsule can be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant can be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration can, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers can be used to control the release of the compounds. Other potentially useful parenteral delivery systems for modulatory compounds include ethylene-vinyl acetate copolymer particles, osmotic pumps, implantable infusion systems, and liposomes. Formulations for inhalation can contain excipients, for example, lactose, or can be aqueous solutions containing, for example, polyoxyethylene-9-lauryl ether, glycocholate and deoxycholate, or can be oily solutions for administration in the form of nasal drops, or as a gel.

In another aspect, the present disclosure provides a pharmaceutical composition comprising a compound as described herein, and an additional therapeutic agent and/or a pharmaceutically acceptable carrier. In some embodiments, the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy or age related macular degeneration. In other embodiments, the additional therapeutic agent is enzalutamide, galeterone, ARN-509, ODN-201 abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111 ODM-201, or related compounds thereof.

Compounds described herein can also be used in assays and for research purposes. Definitions used include ligand dependent activation of the androgen receptor (AR) by androgens such as dihydrotestosterone (DHT) or the synthetic androgen (R1881) used for research purposes. Ligand-independent activation of the androgen receptor (AR) refers to transactivation of the full length androgen receptor (AR) in the absence of androgen (ligand) by, for example, stimulation of the cAMP dependent protein kinase (PKA) pathway with forskolin (FSK). Some compounds and compositions of this invention can inhibit both FSK and androgen (e.g. R1881, a synthetic androgen) induction of ARE luciferase (ARE-luc). Constitutive activity of the androgen receptor (AR) refers to splice variants lacking the androgen receptor (AR) ligand-binding domain. Such compounds can block a mechanism that is common to both ligand dependent and ligand independent activation of the androgen receptor (AR), as well as constitutively active splice variants of the androgen receptor (AR) that lack ligand-binding domain. This could involve any step in activation of the androgen receptor (AR) including dissociation of heatshock proteins, essential posttranslational modifications (e.g., acetylation, phosphorylation), nuclear translocation, protein-protein interactions, formation of the transcriptional complex, release of co repressors, and/or increased degradation. Some compounds and compositions of this invention can inhibit ligand-only activity and can interfere with a mechanism specific to ligand dependent activation (e.g., accessibility of the ligand binding domain (LBD) to androgen). Numerous disorders in addition to prostate cancer involve the androgen axis (e.g., acne, hirsutism, alopecia, benign prostatic hyperplasia) and compounds interfering with this mechanism can be used to treat such conditions. Some compounds and compositions of this invention can only inhibit FSK induction and can be specific inhibitors to ligand independent activation of the androgen receptor (AR). These compounds and compositions can interfere with the cascade of events that normally occur with FSK and/or PKA activity or any downstream effects that can play a role on the androgen receptor (AR) (e.g. FSK increases MAPK activity which has a potent effect on androgen receptor (AR) activity). Examples can include an inhibitor of cAMP and or PKA or other kinases. Some compounds and compositions of this invention can induce basal levels of activity of the AR (no androgen or stimulation of the PKA pathway). Some compounds and compositions of this invention can increase induction by R1881 or FSK. Such compounds and compositions can stimulate transcription or transactivation of the AR. Some compounds and compositions of this invention can inhibit activity of the androgen receptor. Interleukin 6 (IL 6) also causes ligand independent activation of the androgen receptor (AR) in LNCaP cells and can be used in addition to FSK.

Compounds or pharmaceutical compositions in accordance with this invention or for use in this invention can be administered by means of a medical device or appliance such as an implant, graft, prosthesis, stent, etc. Also, implants can be devised which are intended to contain and release such compounds or compositions. An example would be an implant made of a polymeric material adapted to release the compound over a period of time.

It is to be noted that dosage values can vary with the exact imaging protocol. For any particular subject, specific dosage regimens can be adjusted over time according to the individual need and the professional judgment of the person administering or supervising the administration of the compositions. Dosage ranges set forth herein are exemplary only and do not limit the dosage ranges that can be selected by medical practitioners. The amount of active compound(s) in the composition can vary according to factors such as the disease state, age, sex, and weight of the subject. Dosage regimens can be adjusted to provide the optimum imaging result. For example, a single bolus can be administered, several divided doses can be administered over time or the dose can be proportionally reduced or increased as indicated by the imaging results. It can be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances, such as in severe disease conditions, substantial excesses of the compositions can be administered for therapeutic effects. Some compounds of this invention can be toxic at some concentrations. Titration studies can be used to determine toxic and non-toxic concentrations. Toxicity can be evaluated by examining a particular compound's or composition's specificity across cell lines using PC3 or DU145 cells as possible negative controls since these cells do not express functional AR. Animal studies can be used to provide an indication if the compound has any effects on other tissues. Systemic therapy that targets the AR will not likely cause major problems to other tissues since antiandrogens and androgen insensitivity syndrome are not fatal.

Compounds for use in the present invention can be obtained from medical sources or modified using known methodologies from naturally occurring compounds. In addition, methods of preparing or synthesizing compounds of the present invention will be understood by a person of skill in the art having reference to known chemical synthesis principles. For example, Auzou et al 1974 *European Journal of Medicinal Chemistry* 9(5), 548-554 describes suitable synthetic procedures that can be considered and suitably adapted for preparing compounds of any one of the compounds of structure (I) as set out above. Other references that can be helpful include: Debasish Das, Jyh-Fu Lee and Soofin Cheng "Sulfonic acid functionalized mesoporous MCM-41 silica as a convenient catalyst for Bisphenol-A synthesis" *Chemical Communications*, (2001) 2178-2179; U.S. Pat. No. 2,571,217 Davis, Orris L.; Knight, Horace S.; Skinner, John R. (Shell Development Co.) "Halohydrin ethers of phenols." (1951); and Rokicki, G.; Pawlicki, J.; Kuran, W. "Reactions of 4-chloromethyl-1,3-dioxolan-2-one with phenols as a new route to polyols and cyclic carbonates." Journal fuer Praktische Chemie (Leipzig) (1985) 327, 718-722.

In some embodiments, compounds and all different forms thereof as described herein can be used, for example, and without limitation, in combination with other treatment methods for at least one indication selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age related macular degeneration. For example, compounds and all their different forms as described herein can be used as neoadjuvant (prior), adjunctive (during), and/or adjuvant (after) therapy with surgery, radiation (brachytherapy or external beam), or other therapies (eg. HIFU), and in combination with chemotherapies, androgen ablation, antiandrogens or any other therapeutic approach.

In an exemplary embodiment for imaging the prostate, a dose of the disclosed compounds in solution (typically 5 to 10 millicuries or 200 to 400 MBq) is typically injected rapidly into a saline drip running into a vein, in a patient. Then, the patient is placed in the SPECT for a series of one or more scans which can take from 20 minutes to as long as an hour (often, only about one quarter of the body length can be imaged at a time). Methods for SPECT scanning are well known in the art.

The compounds described herein can be used for in vivo or in vitro research uses (i.e. non-clinical) to investigate the mechanisms of orphan and nuclear receptors (including steroid receptors such as androgen receptor (AR)). Furthermore, these compounds can be used individually or as part of a kit for in vivo or in vitro research to investigate signal transduction pathways and/or the activation of orphan and nuclear receptors using recombinant proteins, cells maintained in culture, and/or animal models.

For example, exemplary compounds of the present invention can be prepared with reference to the following General Reaction Scheme I:

General Reaction Scheme I

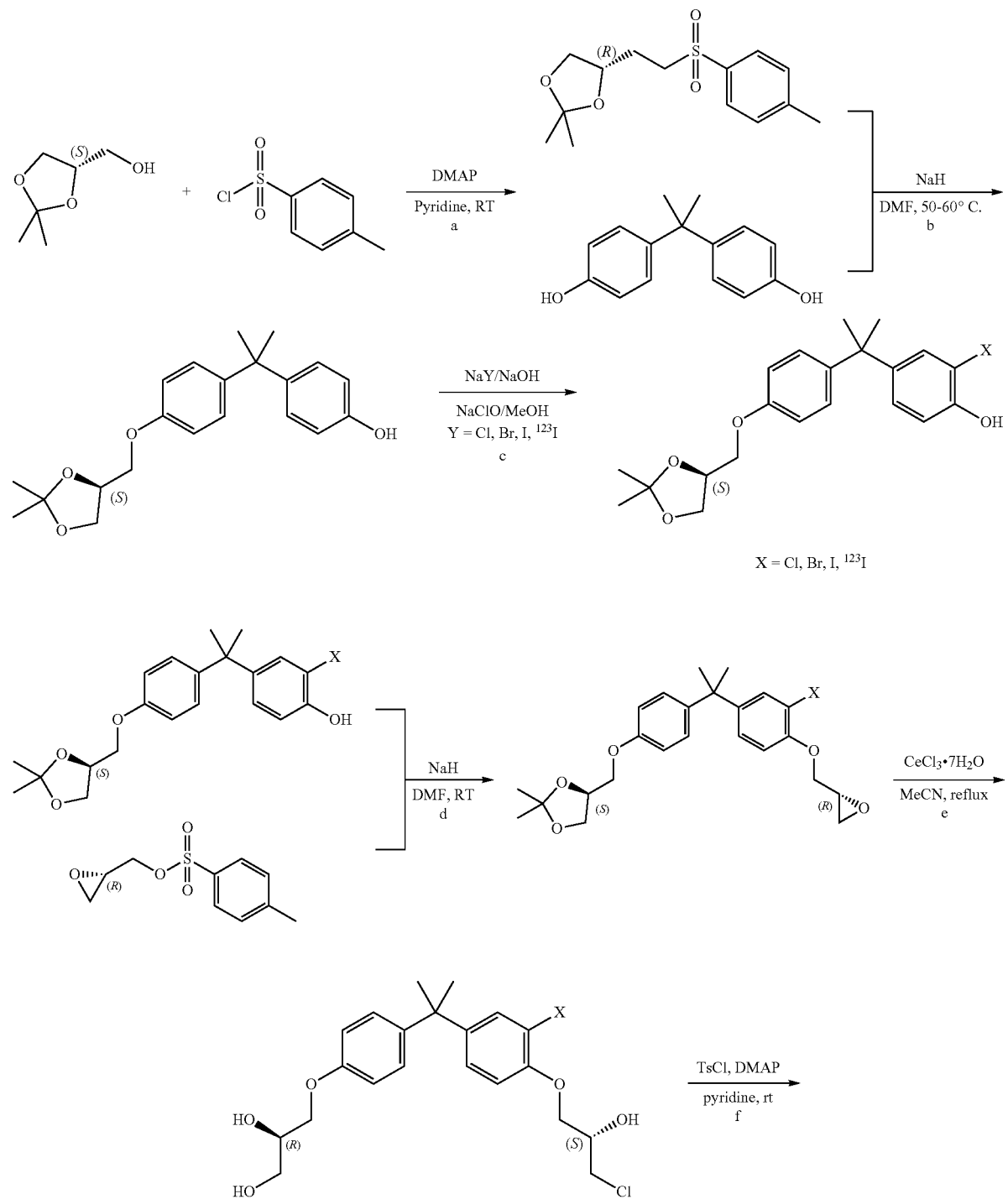

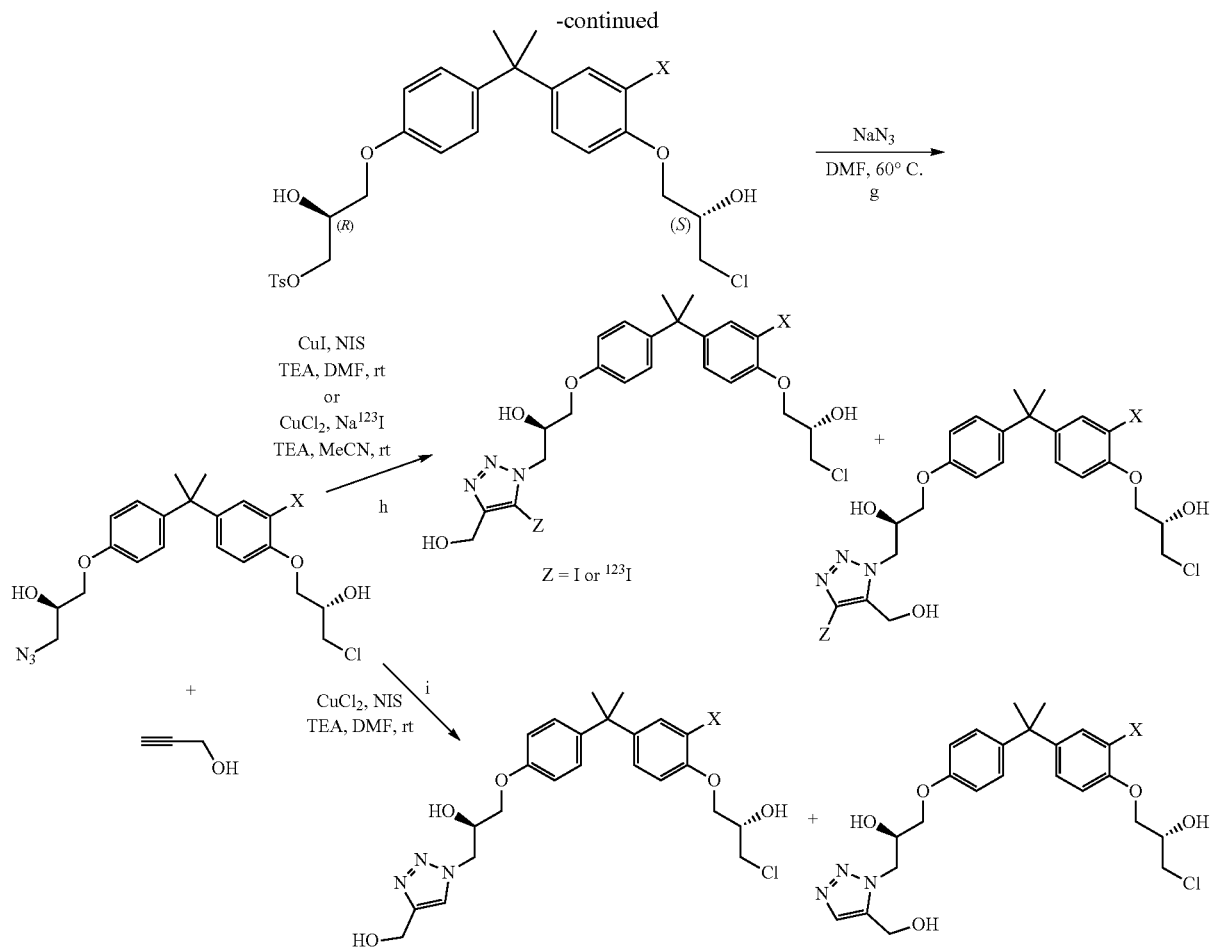

It should be noted that, although General Reaction Scheme I depicts a certain stereochemistry in the products, one skilled in the art would recognize that other stereoisomers can be synthesized by using starting materials of different stereochemistry, such as for step a and step d.

Referring to General Reaction Scheme I, (S)-(2,2-dimethyl-1,3-dioxolan-4-yl)methanol can toslyated under basic conditions as shown in step a. In step b, tosly group (p-toulenesulfonate) can be displaced with bisphenol derivatives under basic conditions. Optionally, in step c, the bisphenol derivative is halogenated on the phenyl ring. In step d, the unreacted phenol portion undergoes another elimination reaction to afford a stereospecific bisphenol derivative with an epoxide on one side and a protected diol on the other. In step e, epoxide is opened using $CeCl_3 \cdot 7H_2O$ and the diol is deprotected in situ. In step f, primary alcohol is selectively tosylated then in step g, the tosyl group is displaced with an azide using sodium azide. Lastly, Click chemistry provides triazole containing products in steps h and i. Tosyl leaving groups have been found to be particularly useful in the synthesis outlined in General Scheme I.

The radioactive iodine moiety ($^{123}I$) can be installed by step c with an appropriate iodinating reagent, for example $Na^{123}I$ and a suitable oxidant (e.g., NaClO). It should be noted that, although General Reaction Scheme I depicts iodination at only one position, other compounds of structure (I) with $^{123}I$ at different positions and/or multiple $^{123}I$ substitutions can be prepared according to analogous methods known to those of ordinary skill in the art. Further, $^{123}I$ atoms can be introduced via any number of reagents, and iodination is not limited to those methods depicted or described above. Methods for such iodination are well known in the art. Methodologies for preparation of specific exemplary compounds of structure I are described in more detail in the following examples.

One skilled in the art will recognize that variations to the order of the steps and reagents discussed in reference to the above General Synthetic Schemes I are possible. For example, epoxidation can precede dioxalone formation.

In addition, protecting group strategies can be employed for preparation of the compounds disclosed herein. Such strategies are well known to those of skill in the art. Exemplary protecting groups and related strategies are disclosed in Greene's Protective Groups in Organic Synthesis, Wiley-InterScience; 4 edition (Oct. 30, 2006), which is hereby incorporated by reference in its entirety. In certain embodiments, a protecting group is used to mask an alcohol moiety while performing other chemical transformations. After removal of the protecting group, the free hydroxyl is obtained. Such protecting groups and strategies are well known in the art.

Various alternative embodiments and examples of the invention are described herein. These embodiments and examples are illustrative and should not be construed as limiting the scope of the invention. The following examples are provided for purposes of illustration, not limitation.

EXAMPLES

All non-aqueous reactions were performed in flame-dried round bottomed flasks. The flasks were fitted with rubber septa and reactions were conducted under a positive pressure of argon unless otherwise specified. Stainless steel syringes were used to transfer air- and moisture-sensitive liquids. Flash column chromatography was performed as described by Still et al. (Still, W. C.; Kahn, M.; Mitra, A. *J. Org. Chem.* 1978, 43, 2923) using 230-400 mesh silica gel. Thin-layer chromatography was performed using aluminum plates pre-coated with 0.25 mm 230-400 mesh silica gel impregnated with a fluorescent indicator (254 nm). Thin-layer chromatography plates were visualized by exposure to ultraviolet light and a "Seebach" staining solution (700 mL water, 10.5 g Cerium (IV) sulphate tetrahydrate, 15.0 g molybdato phosphoric acid, 17.5 g sulphuric acid) followed by heating (~1 min) with a heating gun (~250° C.). Organic solutions were concentrated on Büchi R-114 rotatory evaporators at reduced pressure (15-30 torr, house vacuum) at 25-40° C.

Commercial regents and solvents were used as received. All solvents used for extraction and chromatography were HPLC grade. Normal-phase Si gel Sep Paks™ were purchased from waters, Inc. Thin-layer chromatography plates were Kieselgel 60F$_{254}$. All synthetic reagents were purchased from Sigma Aldrich and Fisher Scientific Canada.

Example 1

Synthesis of (S)-1-(4-(2-(3-bromo-4-((R)-3-chloro-2-hydroxypropoxy)phenyl)propan-2-yl)phenoxy)-3-(4-(hydroxymethyl)-5-iodo-1H-1,2,3-triazol-1-yl)propan-2-ol (1a) and (S)-1-chloro-3-(4-(2-(4-((R)-2-hydroxy-3-(5-(hydroxymethyl)-4-iodo-1H-1,2,3-triazol-1-yl)propoxy)phenyl)propan-2-yl)phenoxy)propan-2-ol (25a)

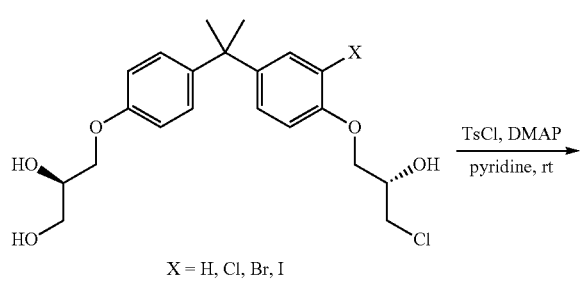

X = H, Cl, Br, I

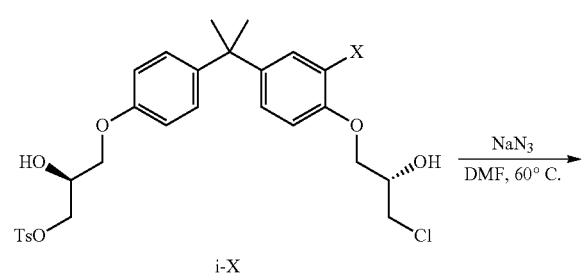

i-X

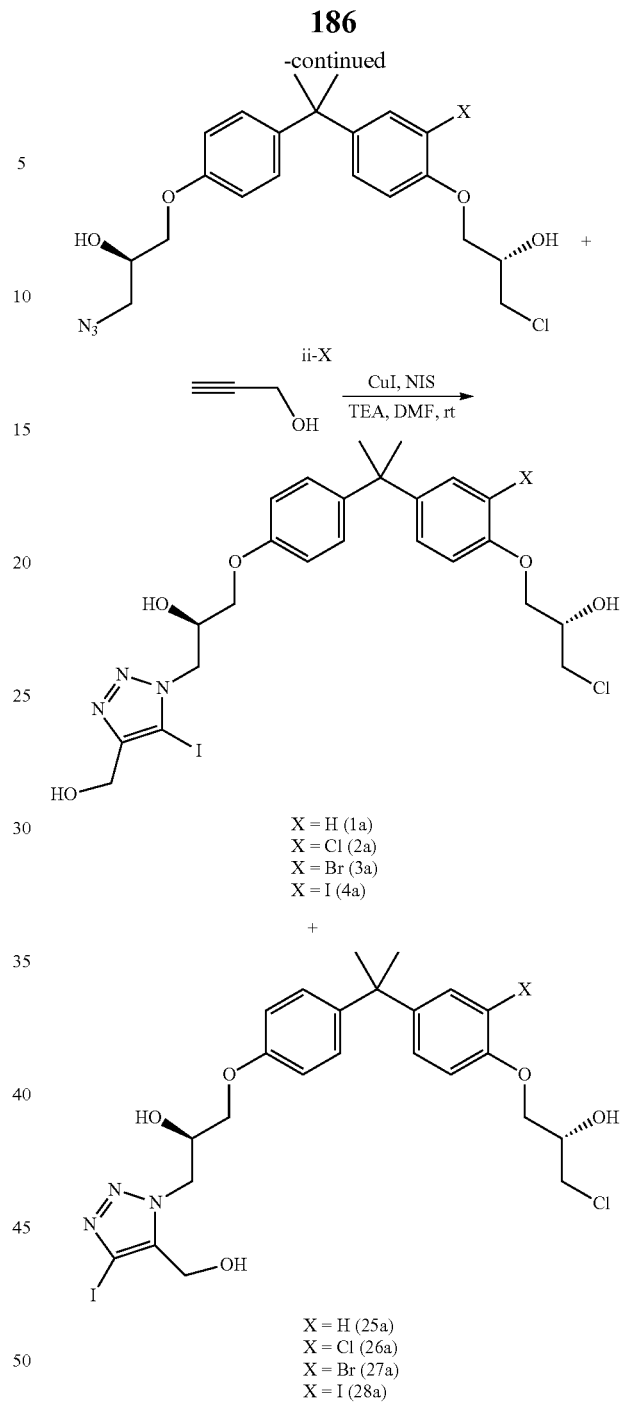

X = H (1a)
X = Cl (2a)
X = Br (3a)
X = I (4a)

+

X = H (25a)
X = Cl (26a)
X = Br (27a)
X = I (28a)

Figure 2:
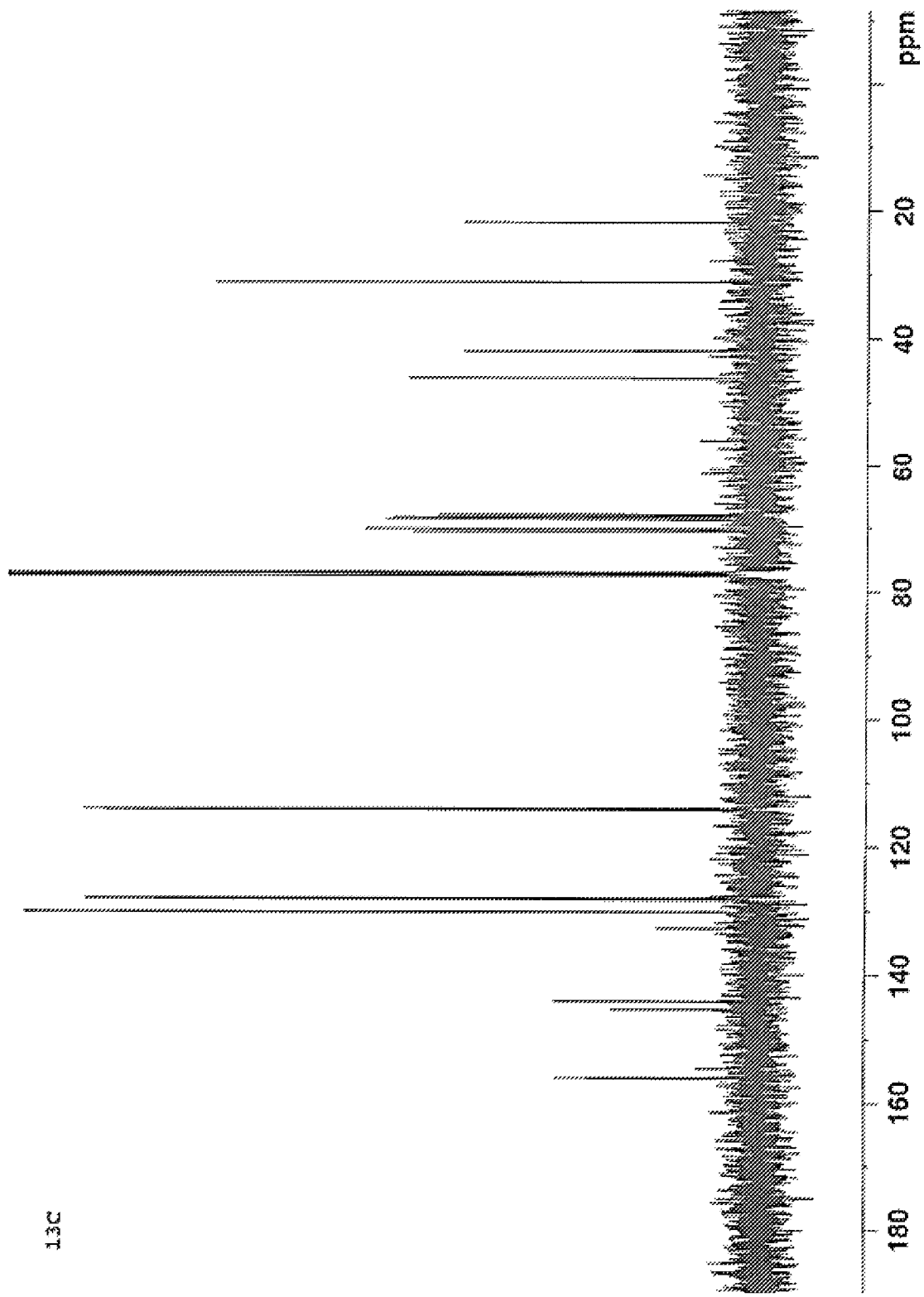
FIG. 2 is a $^{13}C$ NMR spectrum of Compound i-H.

Compound i-H (X=H)

p-Toluenesulfonyl chloride (~1.5 equiv) was added portionwise over a period of approximately 10 min to a solution of (R)-3-(4-(2-(4-((S)-3-chloro-2-hydroxypropoxy)phenyl)propan-2-yl)phenoxy)propane-1,2-diol (1 equiv) and DMAP (~0.01 equiv) in anhydrous pyridine (~1M) in a water bath. The resulting solution was stirred at room temperature. The pyridine was removed under reduced pressure, and the residue was diluted with ethyl acetate, washed subsequently with water (×2), cold aqueous 1 M HCl, saturated NaHCO$_3$ and water. The organic layer was dried over Mg$_2$SO$_4$, filtered and concentrated the crude product. The crude product was purified by column chromatography (eluent: ethyl acetate/hexane) to afford Compound i-H. $^1$H NMR and $^{13}$C NMR spectra are shown in FIGS. 1 and 2, respectively.

Compound ii-H (X=H)

Figure 3:
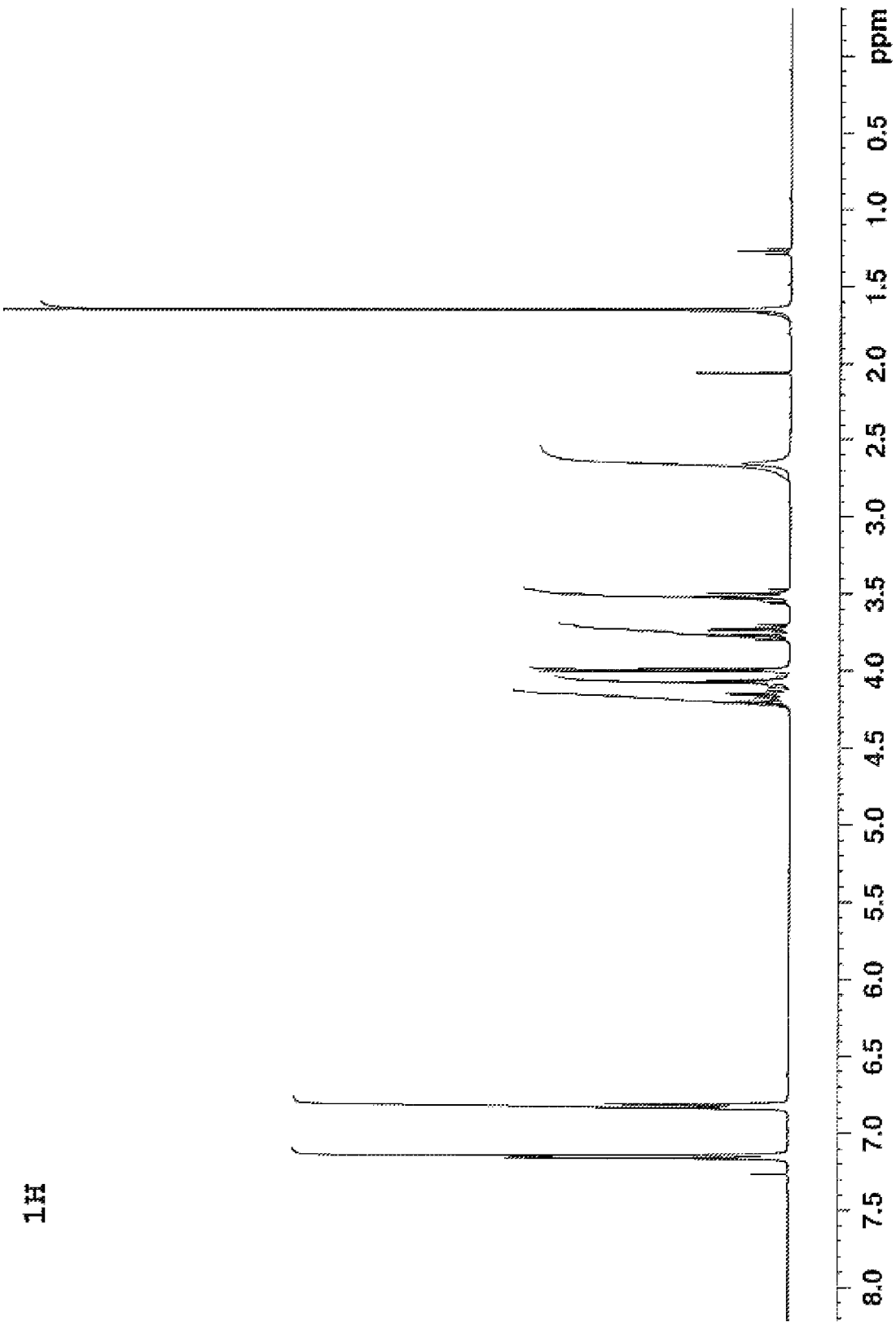
FIG. 3 is a $^1H$ NMR spectrum of Compound ii-H.
Figure 4:
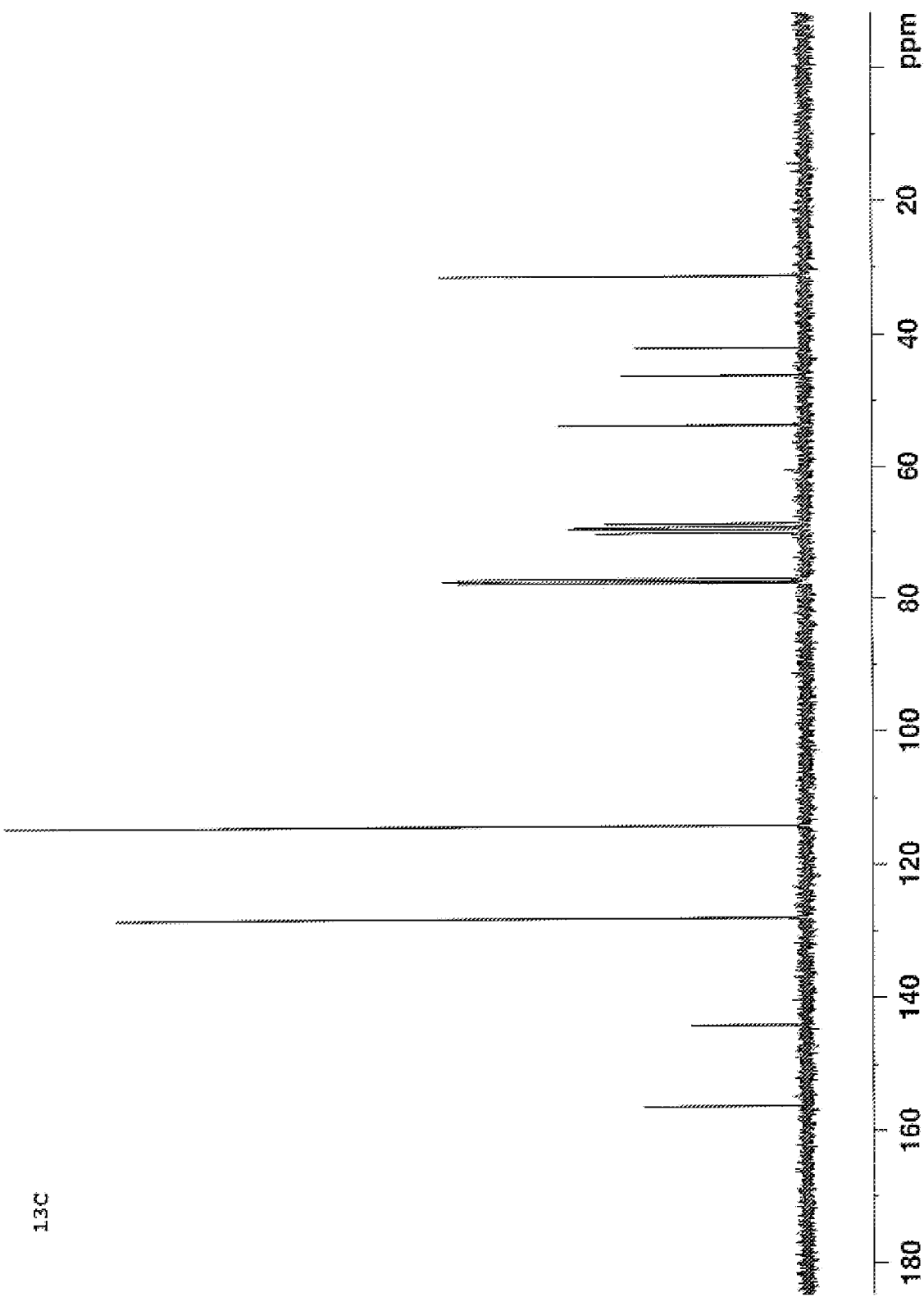
FIG. 4 is a $^{13}C$ NMR spectrum of Compound ii-H.

Sodium azide (1.5 equiv) was added to a solution of Compound i-H (1 equiv) in anhydrous dimethyl formamide, at room temperature. The reaction mixture was heated at 60° C. Once the reaction is complete, any excess sodium azide was quenched using common laboratory procedures. The product was extracted with ethyl acetate (×3). The organic layer was washed with saturated NaHCO$_3$ and water, dried over anhydrous magnesium sulfate, filtered, and then concentrated under reduced pressure. The resulting residue was purified by flash column chromatography on silica gel (eluent: ethyl acetate/hexane) to provide Compound ii-H. $^1$H NMR and $^{13}$C NMR spectra are shown in FIGS. 3 and 4, respectively.

Compounds 1a and 25a

CuI and NIS was added to a solution of Compound ii-H (1 equiv) and propargyl alcohol (~1.5 equiv) in DMF and triethylamine. The reaction mixture is stirred at room temperature. Once the reaction was complete, any excess reagents were quenched using common laboratory procedures. The product was extracted with ethyl acetate (×3). The organic layer was washed with saturated NaHCO$_3$ and water, dried over anhydrous magnesium sulfate, filtered, and then concentrated under reduced pressure. The resulting residue was purified by flash column chromatography on silica gel (eluent: ethyl acetate/hexane) to provide Compound 1a and Compound 25a.

Figure 5:
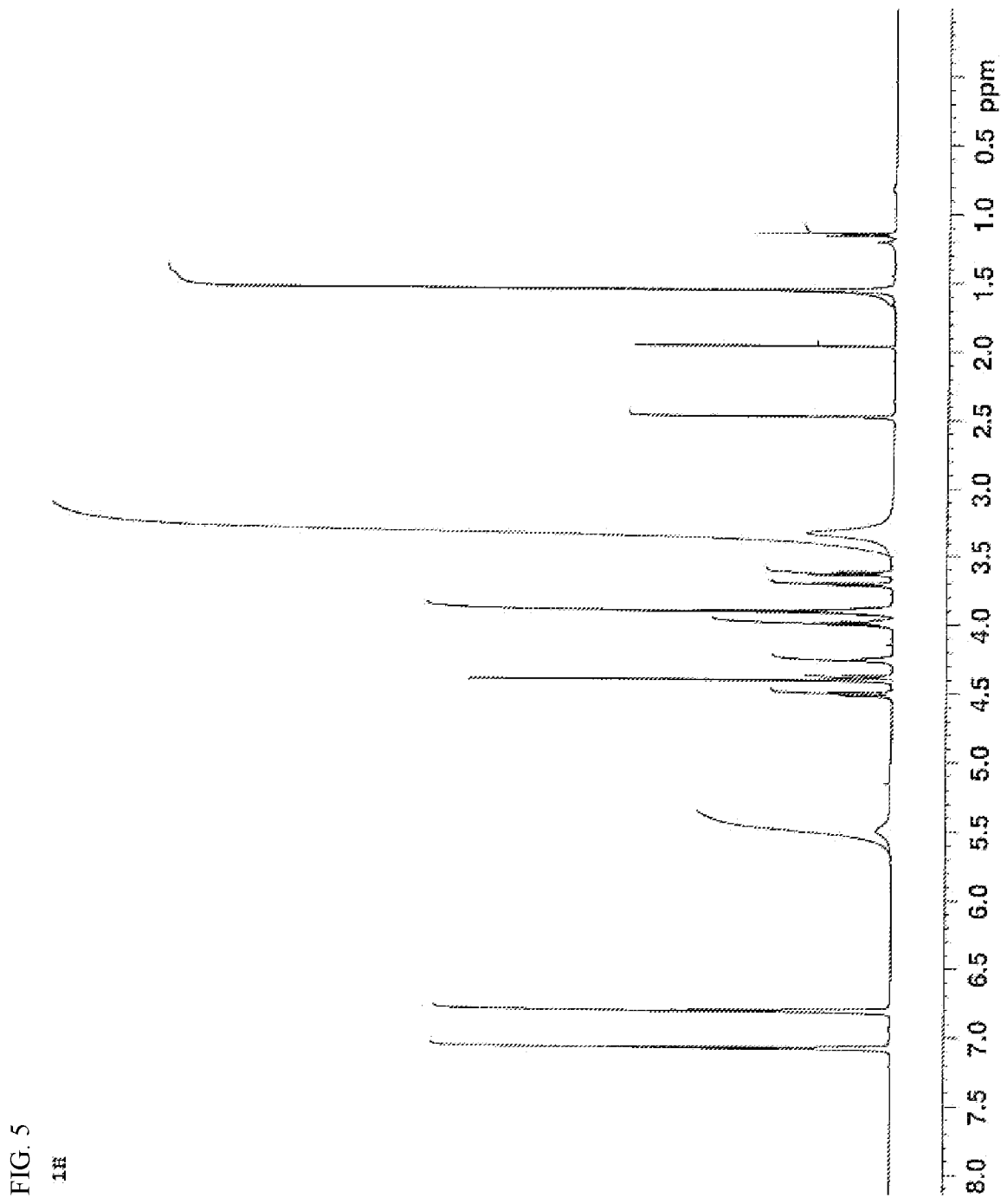
Figure 6:
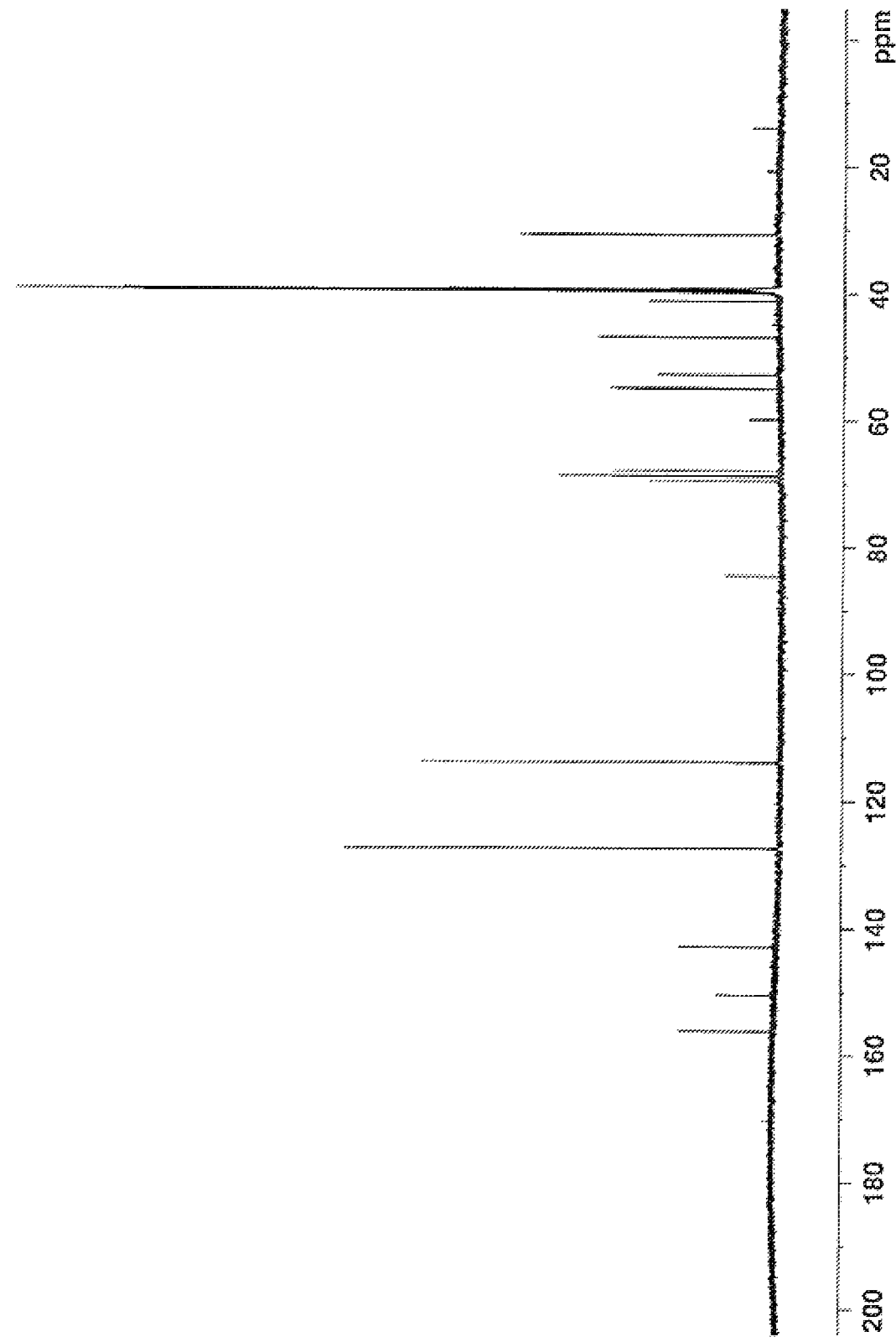

Compound 1a: $^1$H NMR and $^{13}$C NMR spectra are shown in FIGS. 5 and 6 respectively. MS (ES+): m/z 624.3 [M+Na]$^+$.

Figure 7:
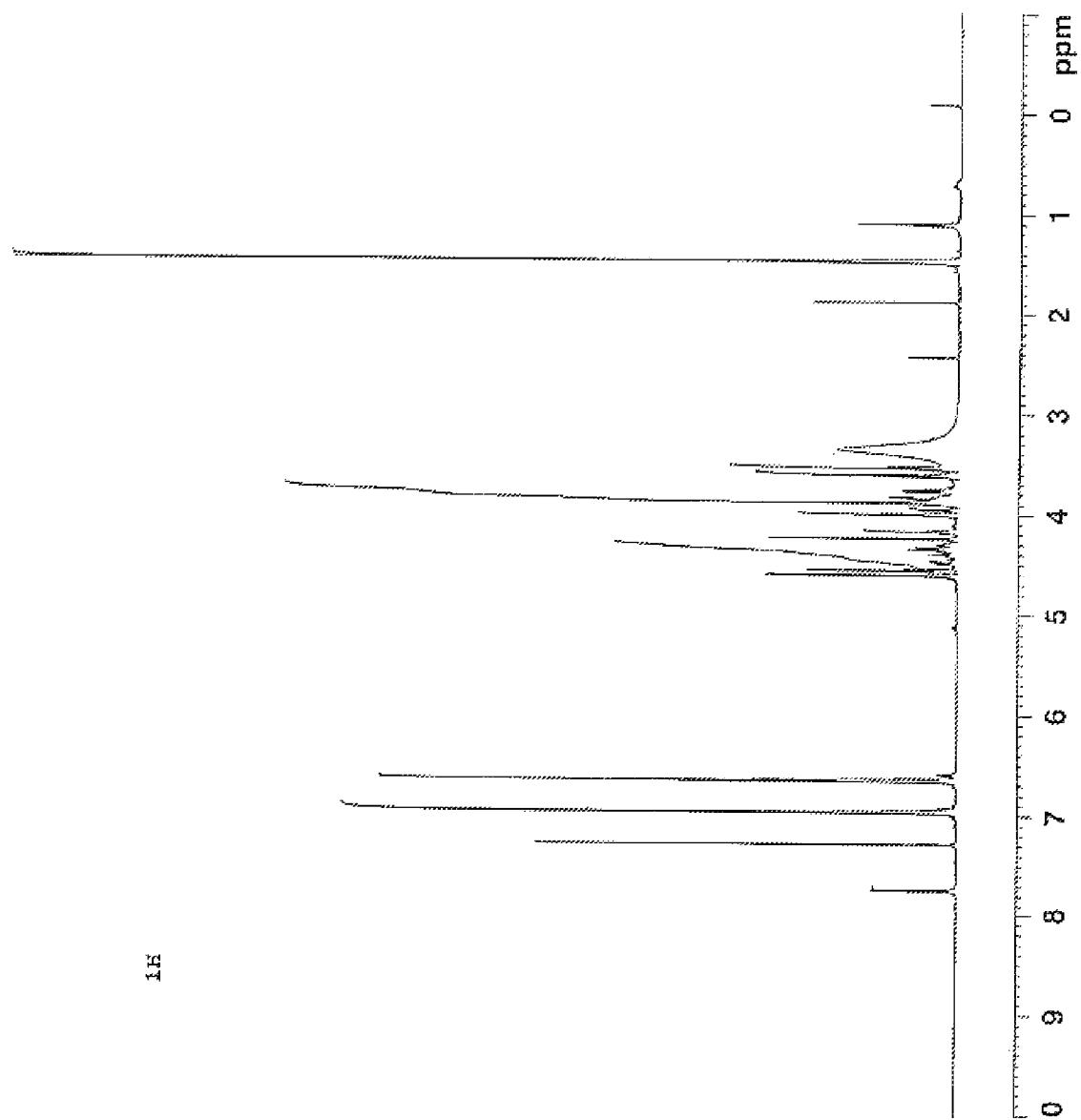
Figure 8:
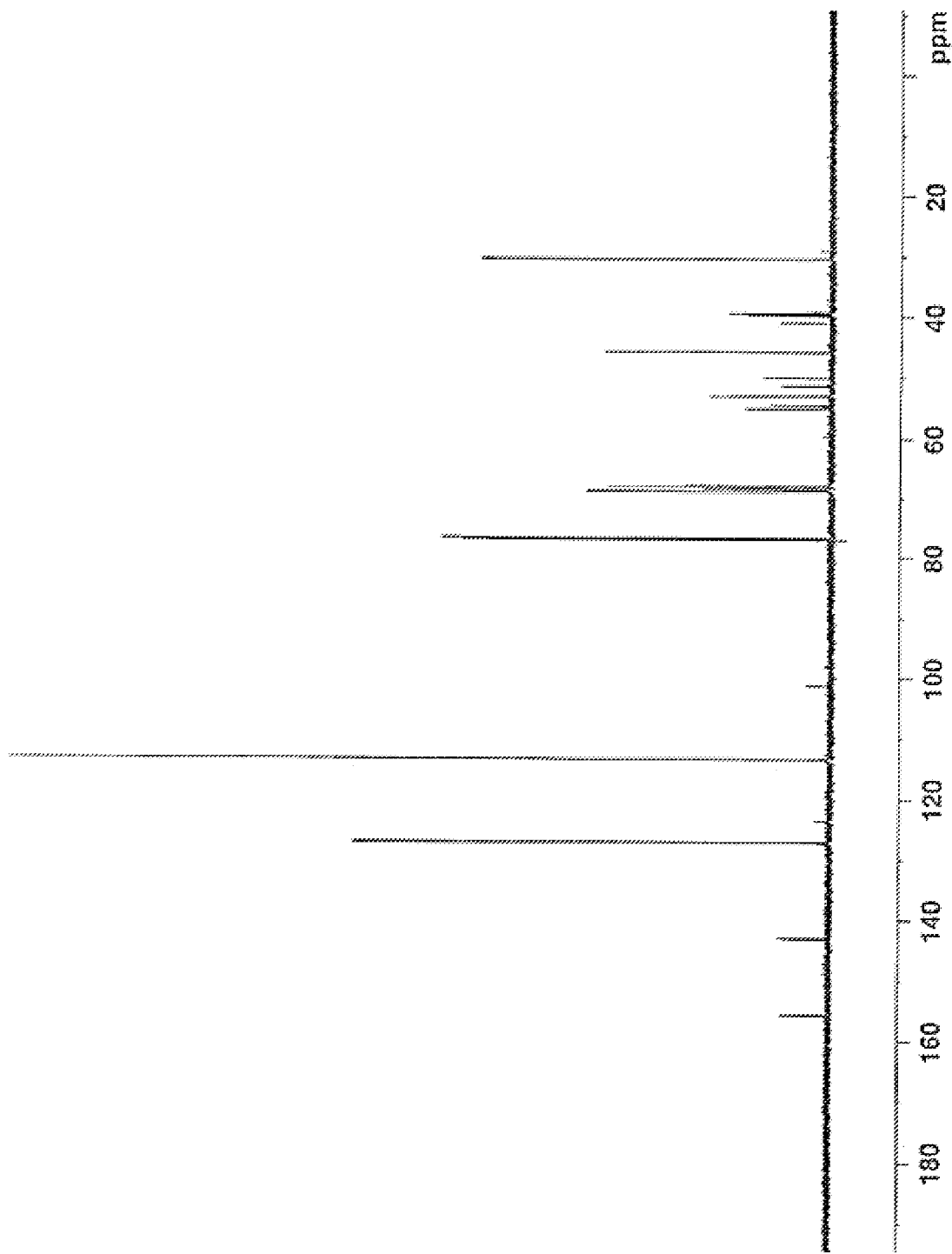

Compound 25a: $^1$H NMR and $^{13}$C NMR spectra are shown in FIGS. 7 and 8, respectively. MS (ES+): m/z 624.3 [M+Na]$^+$.

Example 2

Synthesis of (S)-1-chloro-3-(4-(2-(4-((R)-2-hydroxy-3-(4-(hydroxymethyl)-5-iodo-1H-1,2,3-triazol-1-yl)propoxy)phenyl)propan-2-yl)-2-iodophenoxy)propan-2-ol (4a) and (S)-1-chloro-3-(4-(2-(4-((R)-2-hydroxy-3-(5-(hydroxymethyl)-4-iodo-1H-1,2,3-triazol-1-yl)propoxy)phenyl)propan-2-yl)-2-iodophenoxy)propan-2-ol (28a)

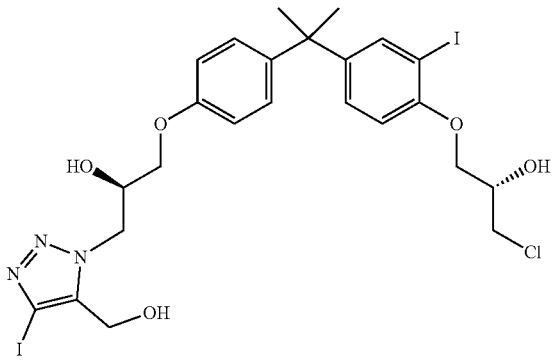

Compounds 4a and 28a

Compound 4a and Compound 28a were synthesized according to Example 1 from (R)-3-(4-(2-(4-((S)-3-chloro-2-hydroxypropoxy)-3-iodophenyl)propan-2-yl)phenoxy)propane-1,2-diol.

Figure 9:
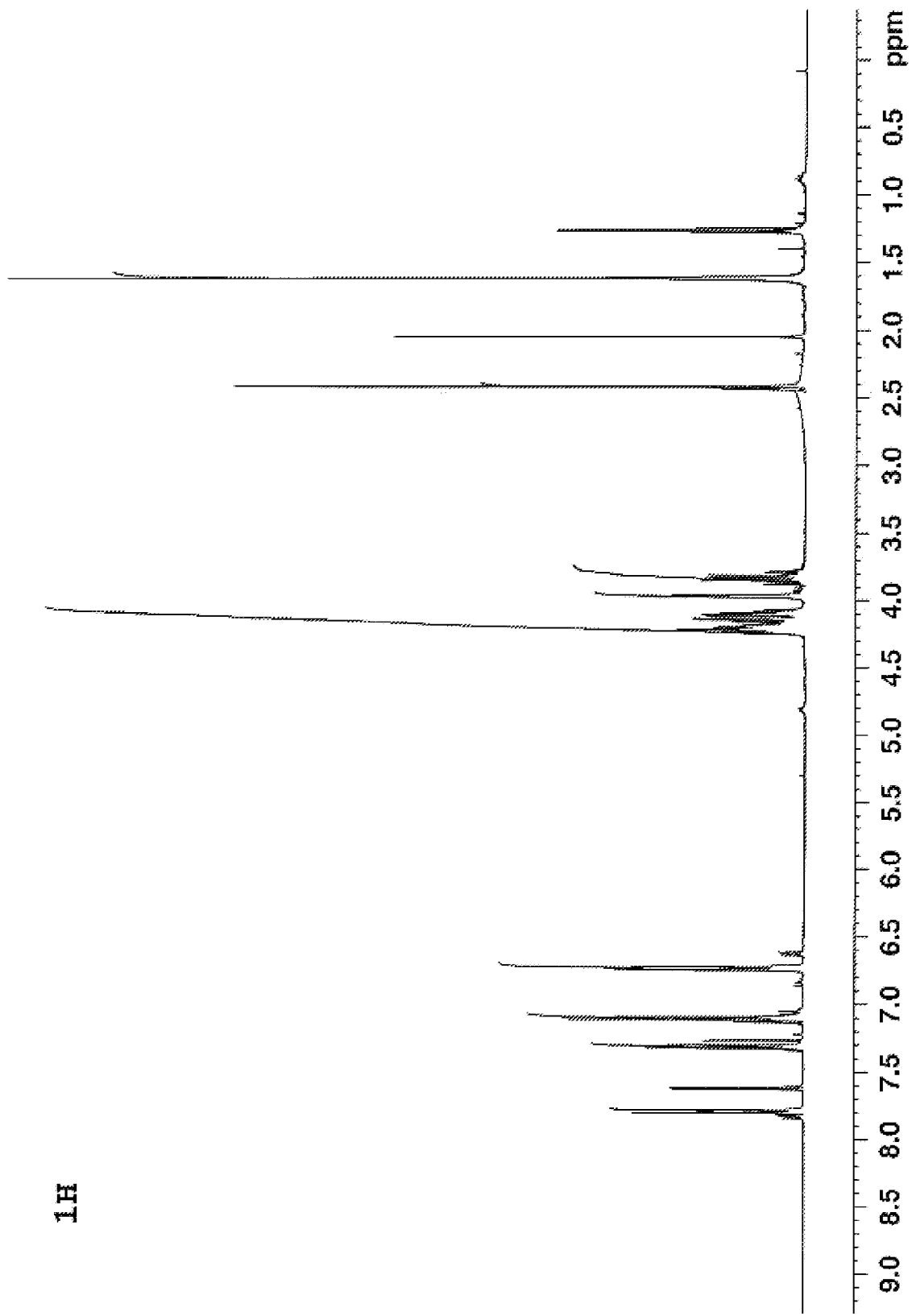
FIG. 9 is a $^1H$ NMR spectrum of Compound i-I.
Figure 10:
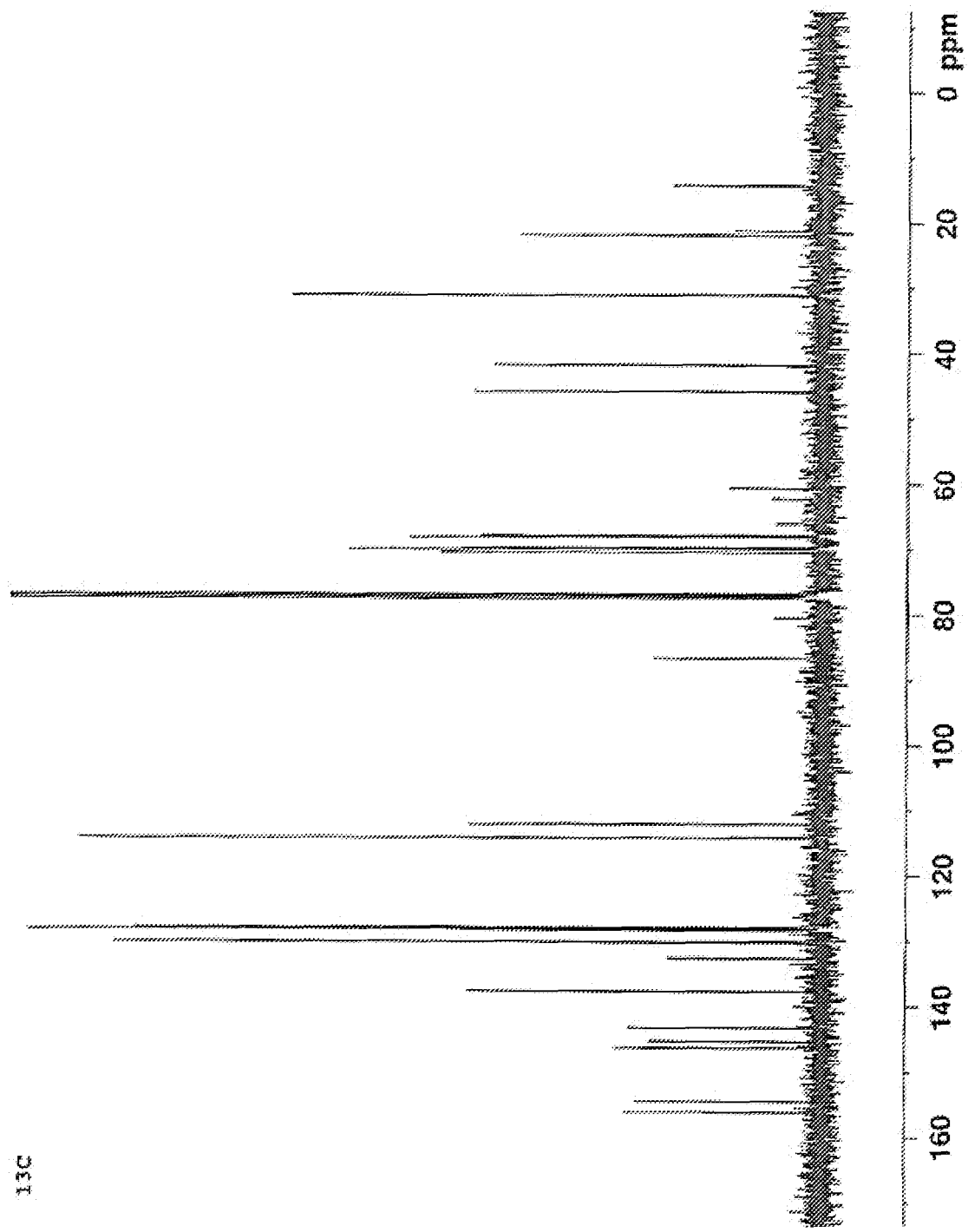
FIG. 10 is a $^{13}C$ NMR spectrum of Compound i-I.

Compound i-I (X=I): $^1$H NMR and $^{13}$C NMR spectra are shown in FIGS. 9 and 10, respectively.

Figure 11:
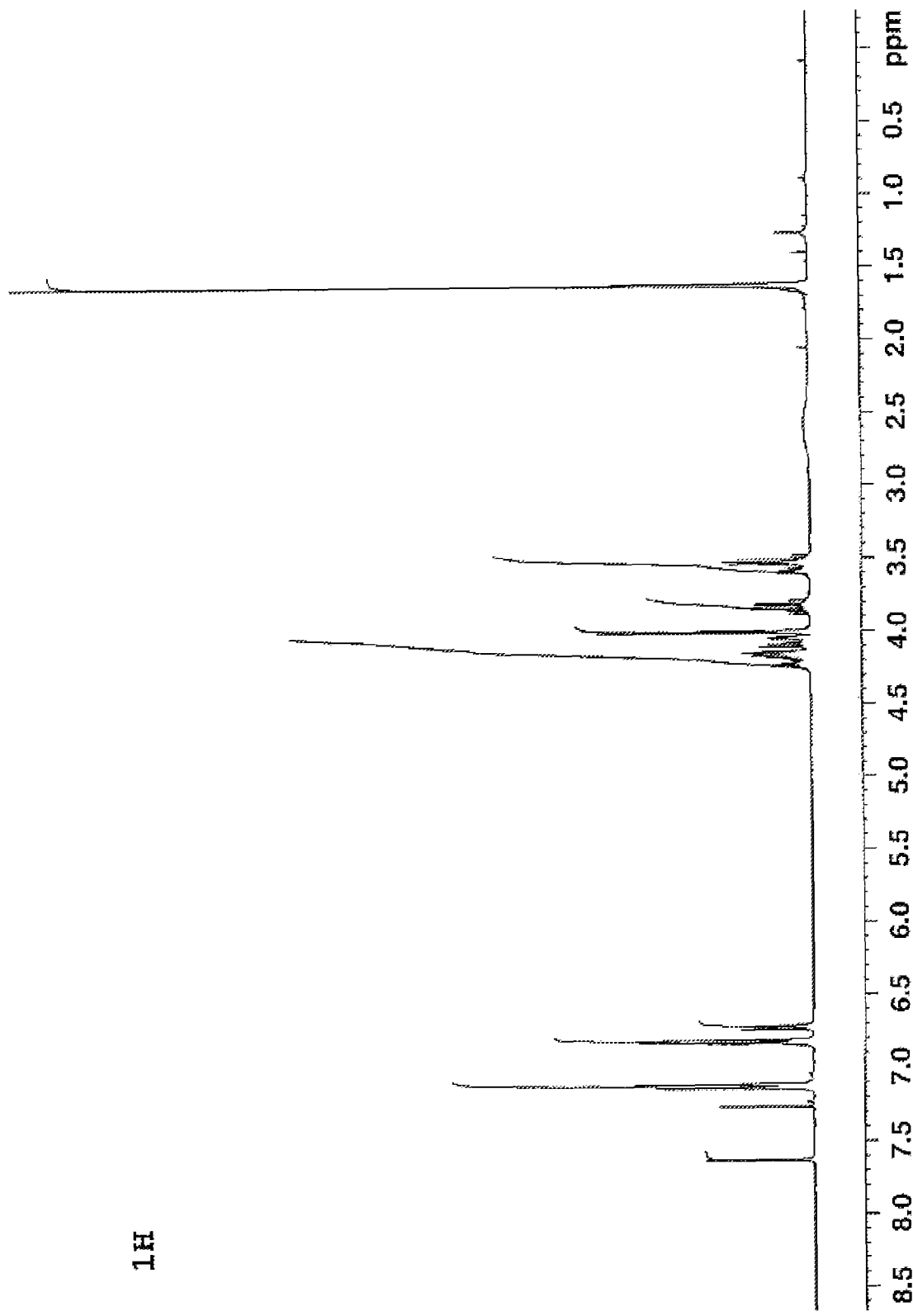
FIG. 11 is a $^1H$ NMR spectrum of Compound ii-I.
Figure 12:
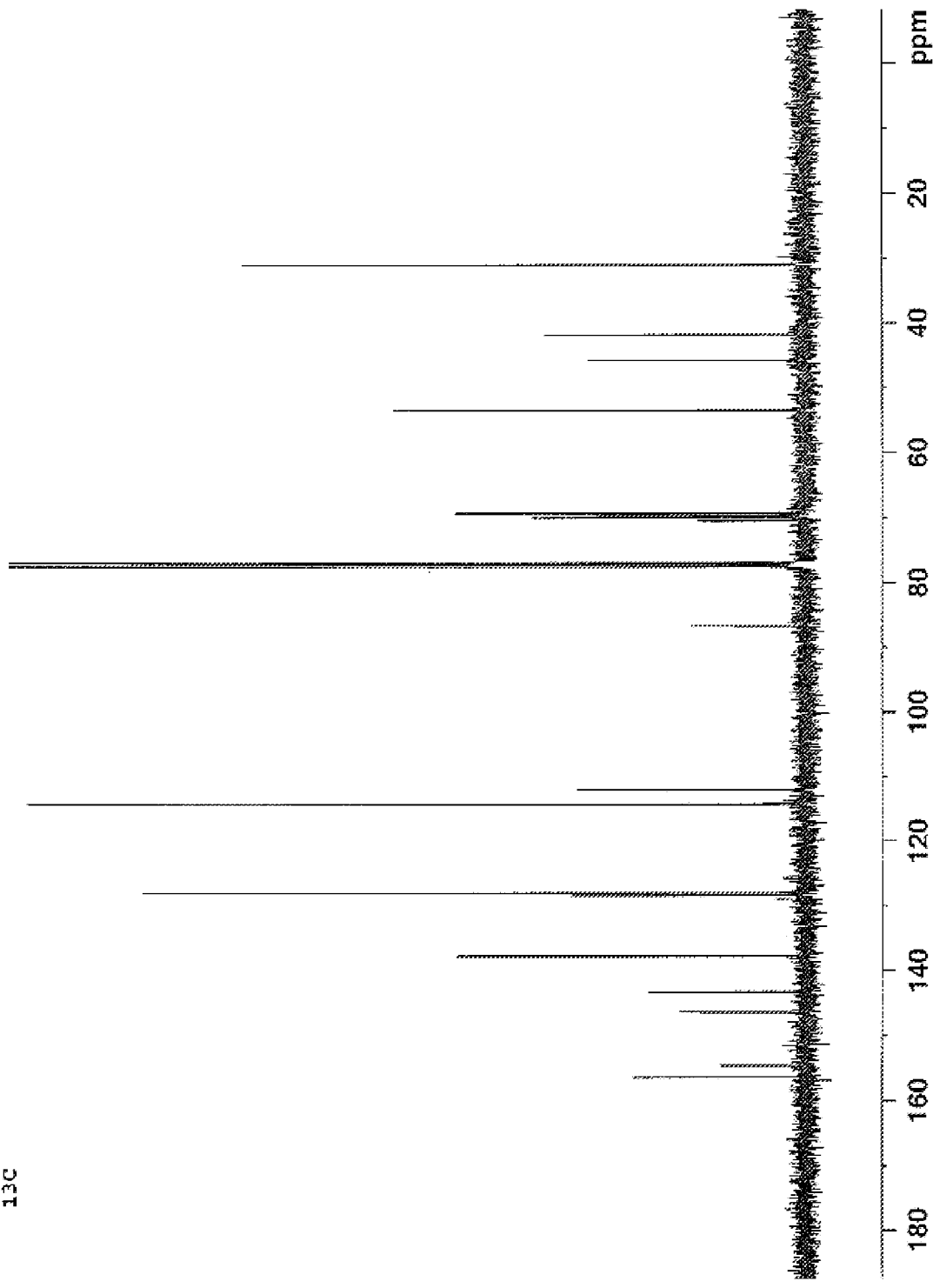
FIG. 12 is a $^{13}C$ NMR spectrum of Compound ii-I.

Compound ii-I (X=I): $^1$H NMR and $^{13}$C NMR spectra are shown in FIGS. 11 and 12, respectively.

Figure 13:
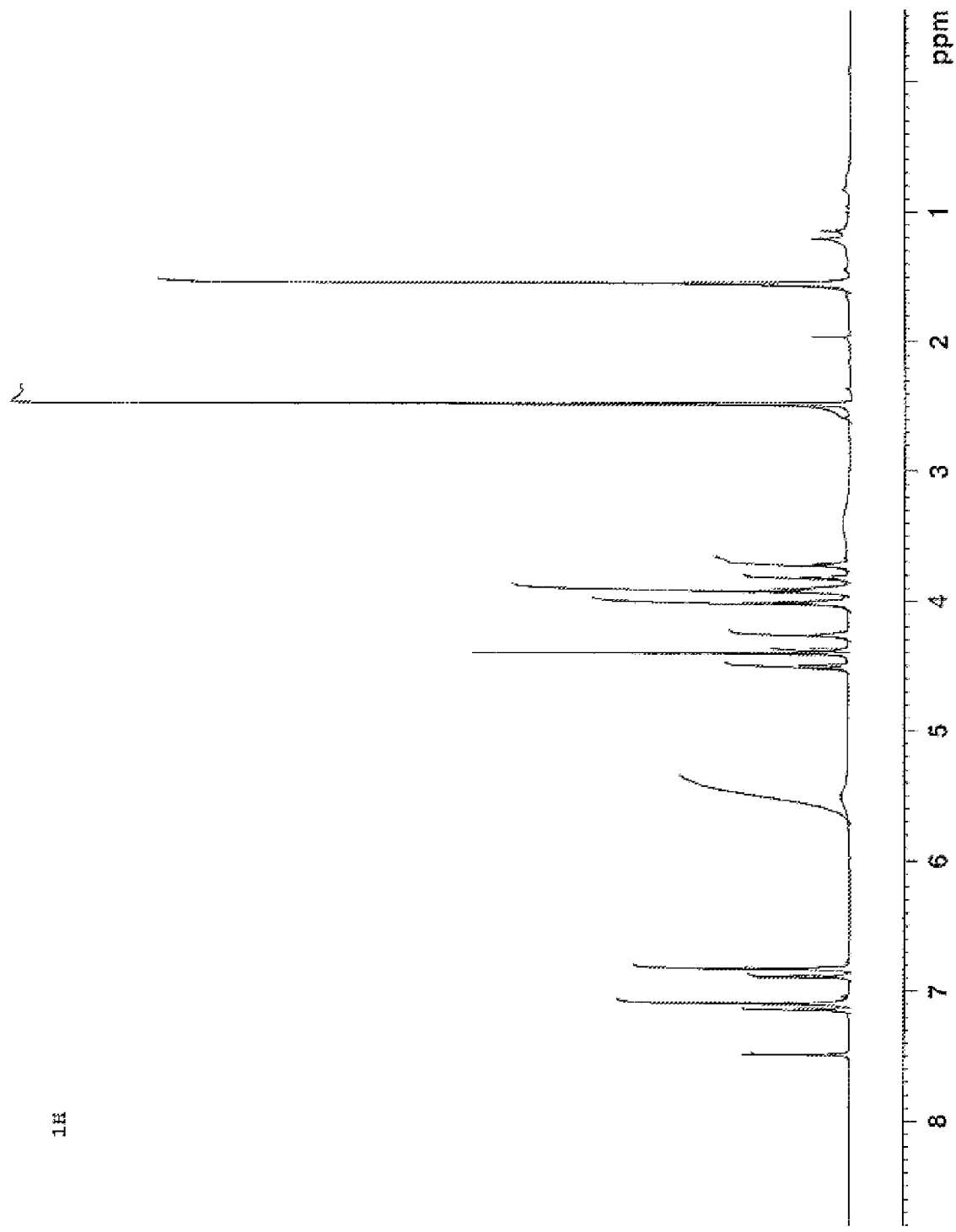
Figure 14:
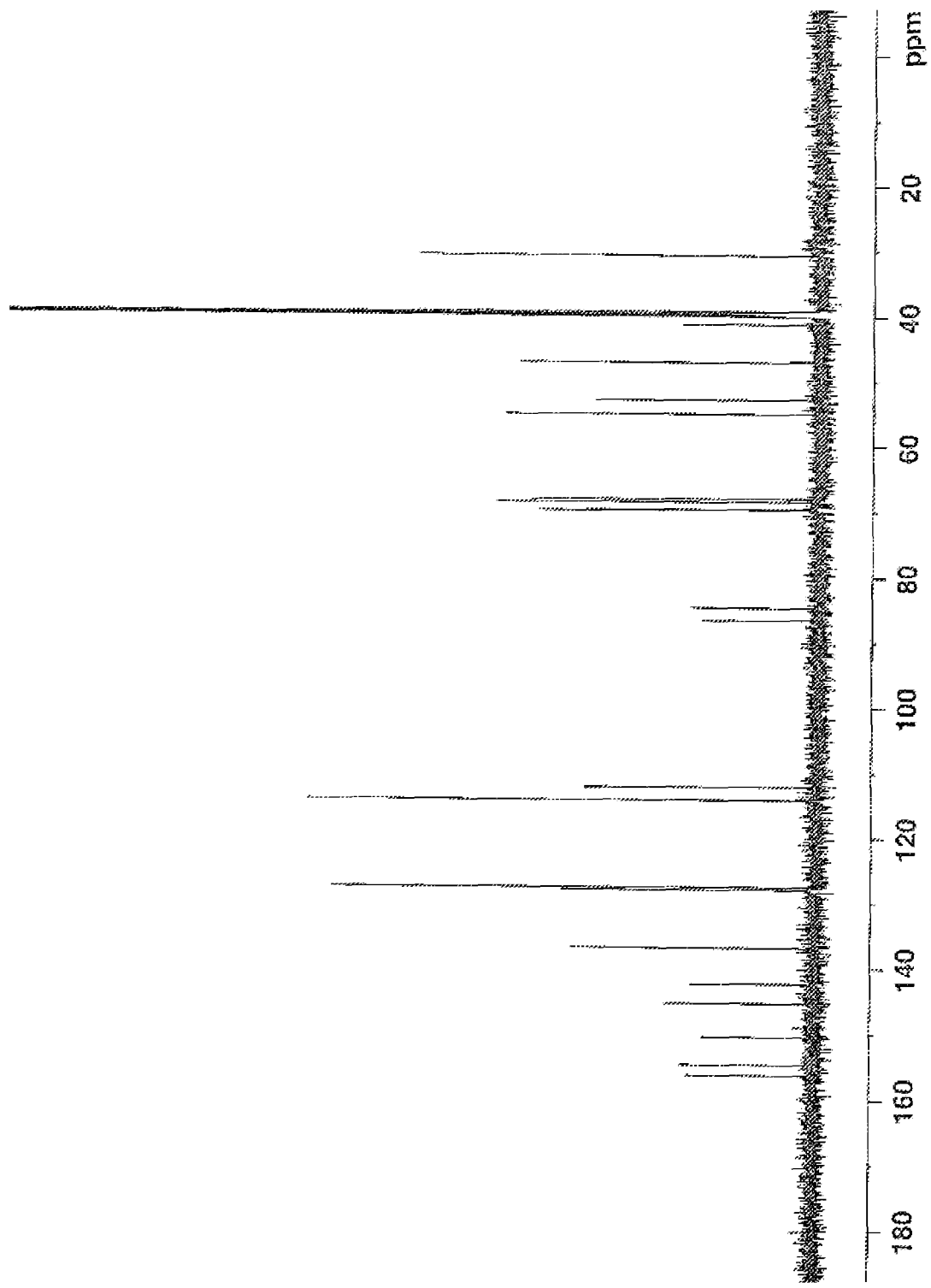

Compound 4a: $^1$H NMR and $^{13}$C NMR spectra are shown in FIGS. 13 and 14, respectively.

Figure 15:
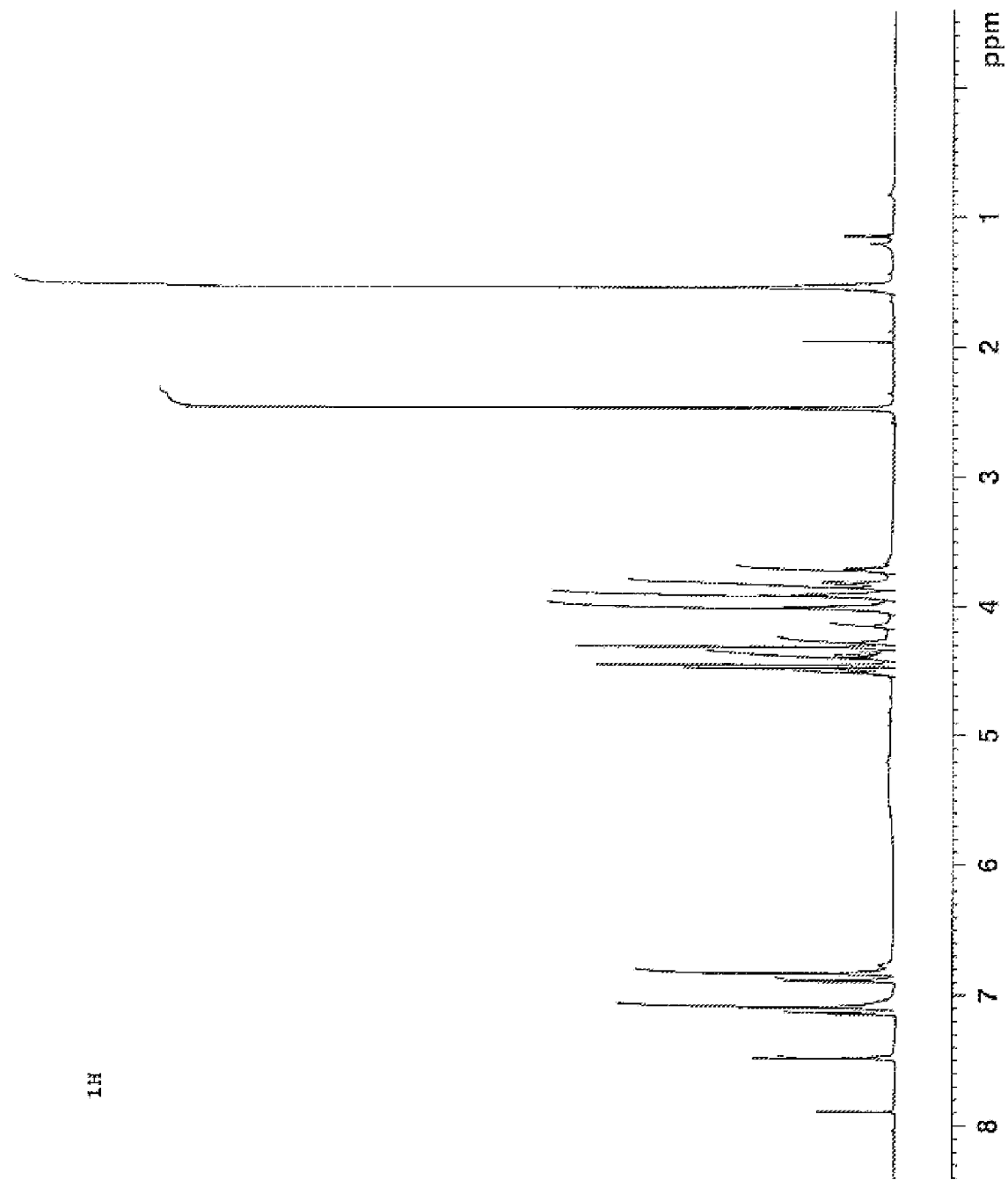
Figure 16:
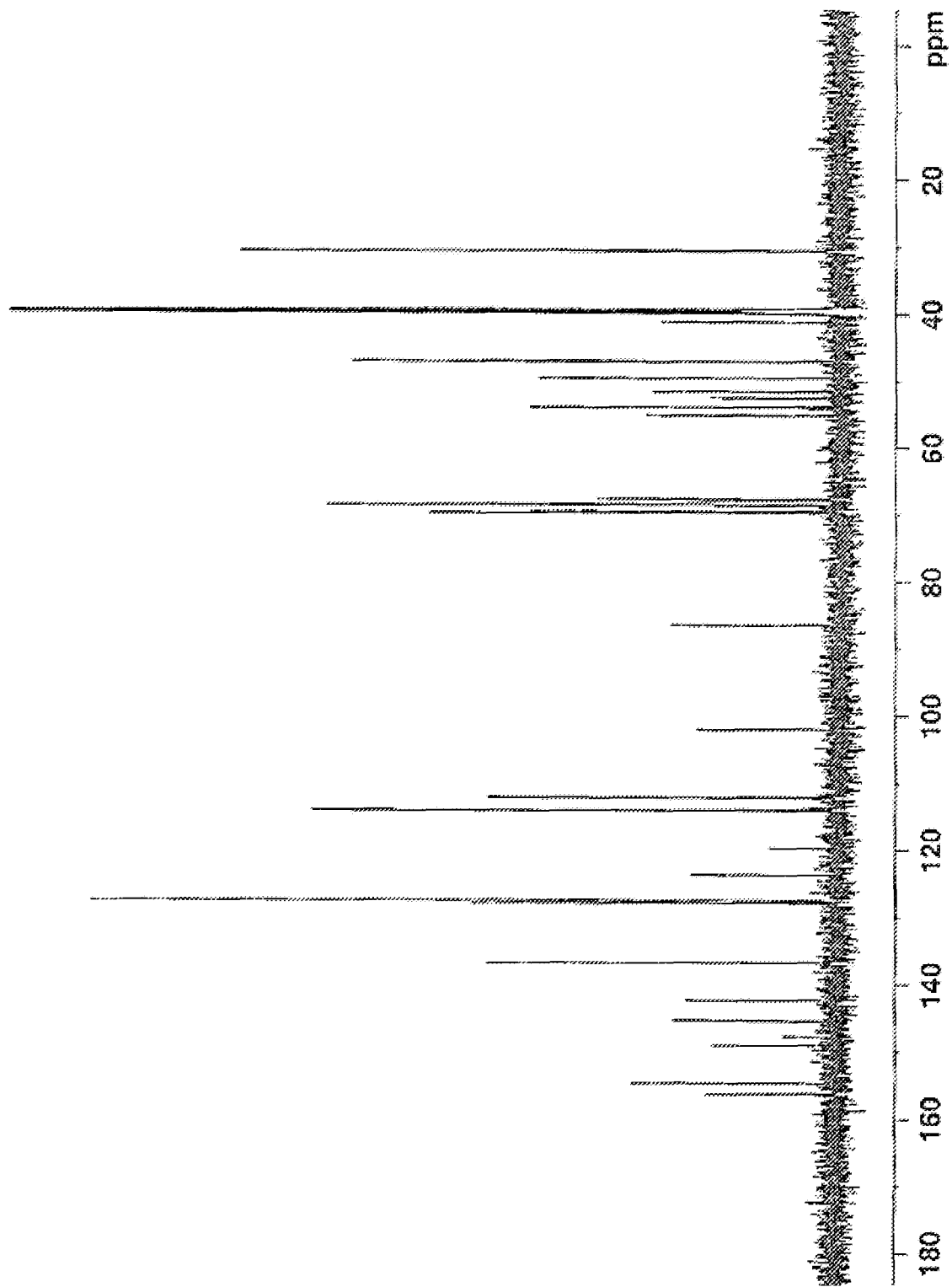

Compound 28a: $^1$H NMR and $^{13}$C NMR spectra are shown in FIGS. 15 and 16, respectively.

Example 3

Synthesis of (S)-1-chloro-3-(4-(2-(4-((R)-2-hydroxy-3-(4-(hydroxymethyl)-5-(iodo-$^{123}$I)-1H-1,2,3-triazol-1-yl)propoxy)phenyl)propan-2-yl)phenoxy)propan-2-ol (33a) and (S)-1-chloro-3-(4-(2-(4-((R)-2-hydroxy-3-(5-(hydroxymethyl)-4-(iodo-$^{123}$I)-1H-1,2,3-triazol-1-yl)propoxy)phenyl)propan-2-yl)phenoxy)propan-2-ol (41a)

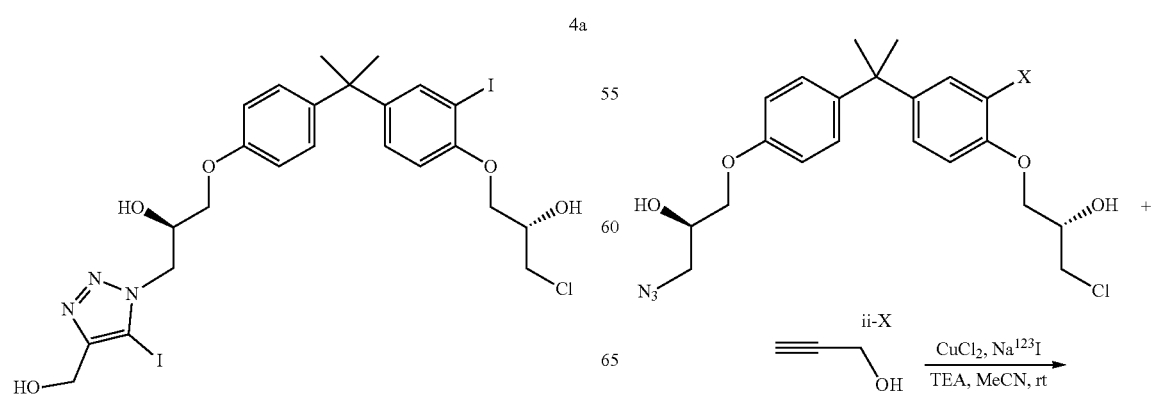

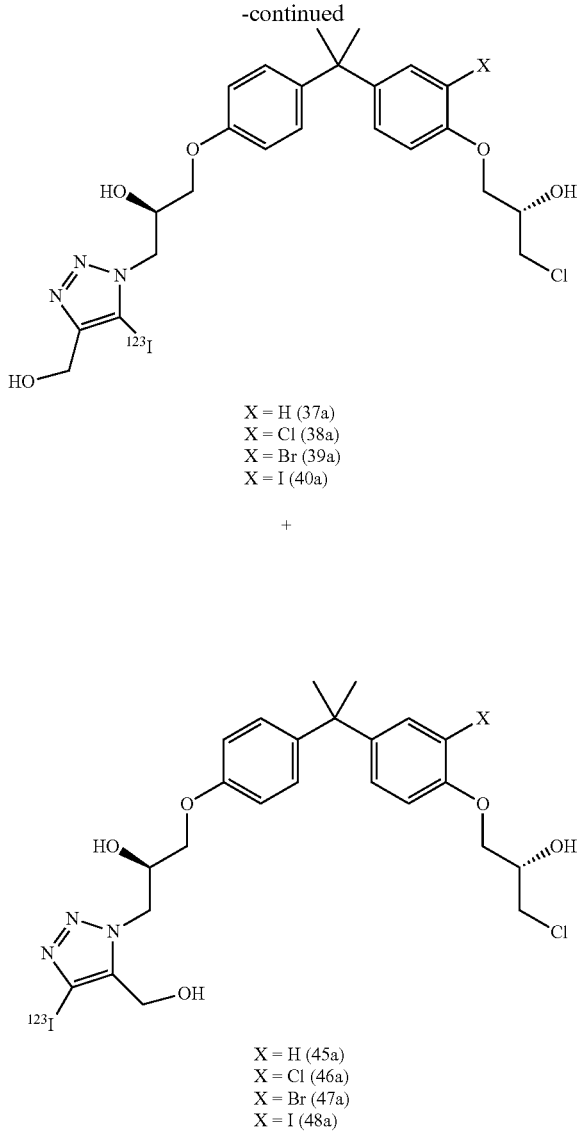

X = H (37a)
X = Cl (38a)
X = Br (39a)
X = I (40a)

+

X = H (45a)
X = Cl (46a)
X = Br (47a)
X = I (48a)

Compounds 37a and 45a

CuCl$_2$ and Na$^{123}$I are added to a solution of Compound ii-H (1 equiv) and propargyl alcohol (~1.5 equiv) in acetonitrile and triethylamine. The reaction mixture is stirred at room temperature. Once the reaction is complete, any excess reagents are quenched using common laboratory procedures. The product is extracted with ethyl acetate (×3). The organic layer is washed with saturated NaHCO$_3$ and water, dried over anhydrous magnesium sulfate, filtered, and then concentrated under reduced pressure. The resulting residue is purified by flash column chromatography on silica gel (eluent: ethyl acetate/hexane) to provide Compound 37a and Compound 45a.

Example 4

Synthesis of (S)-1-chloro-3-(4-(2-(4-((R)-2-hydroxy-3-(4-(hydroxymethyl)-1H-1,2,3-triazol-1-yl)propoxy)phenyl)propan-2-yl)phenoxy)propan-2-ol (5a) and (S)-1-chloro-3-(4-(2-(4-((R)-2-hydroxy-3-(5-(hydroxymethyl)-1H-1,2,3-triazol-1-yl)propoxy)phenyl)propan-2-yl)phenoxy)propan-2-ol (29a)

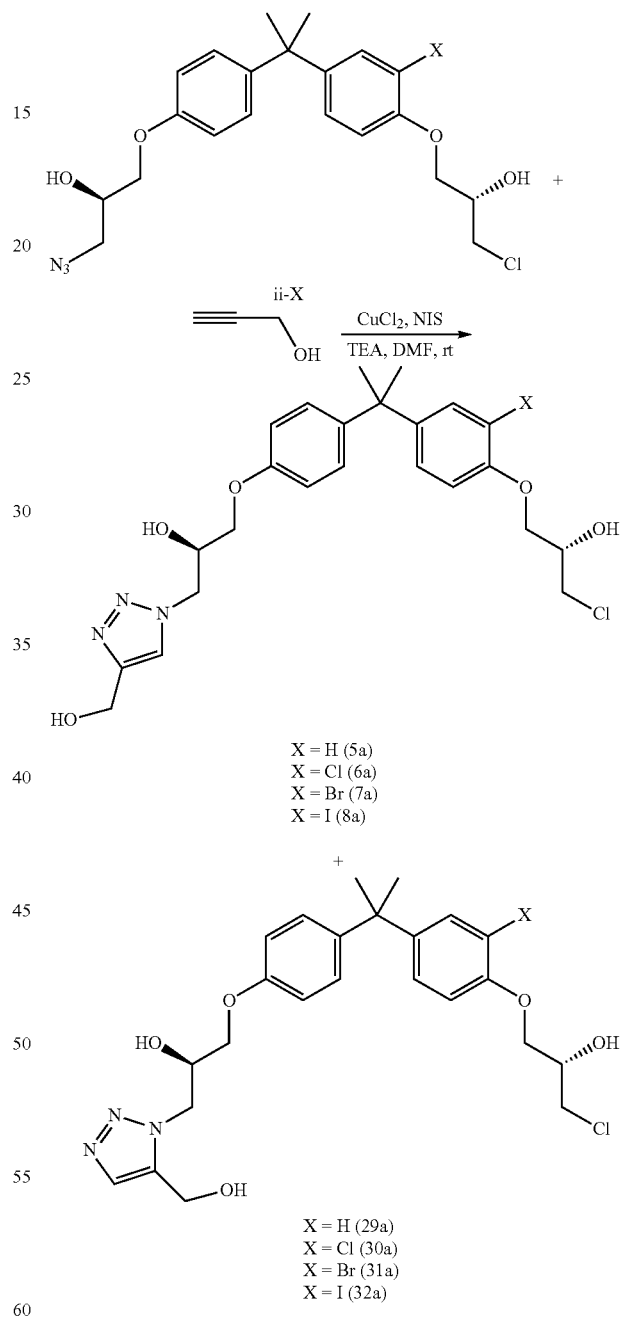

X = H (5a)
X = Cl (6a)
X = Br (7a)
X = I (8a)

+

X = H (29a)
X = Cl (30a)
X = Br (31a)
X = I (32a)

Compounds 5a and 29a

CuCl$_2$ and NIS is added to a solution of Compound ii-H (1 equiv) and propargyl alcohol (~1.5 equiv) in DMF and triethylamine. The reaction mixture is stirred at room temperature. Once the reaction is complete, any excess reagents are quenched using common laboratory procedures. The

Example 5

Synthesis of 1-chloro-3-(4-(2-(4-(2-hydroxy-3-morpholinopropoxy)phenyl)propan-2-yl)phenoxy)propan-2-ol (13)

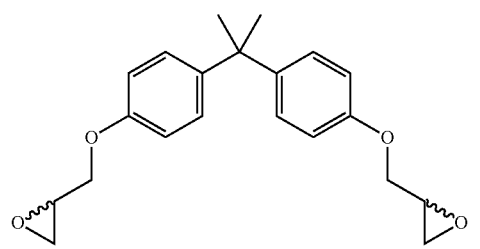

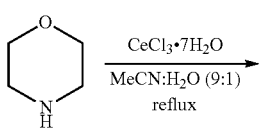

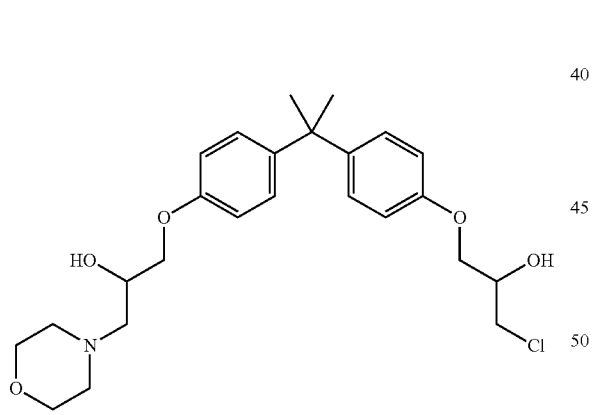

Compound 13

Figure 17:
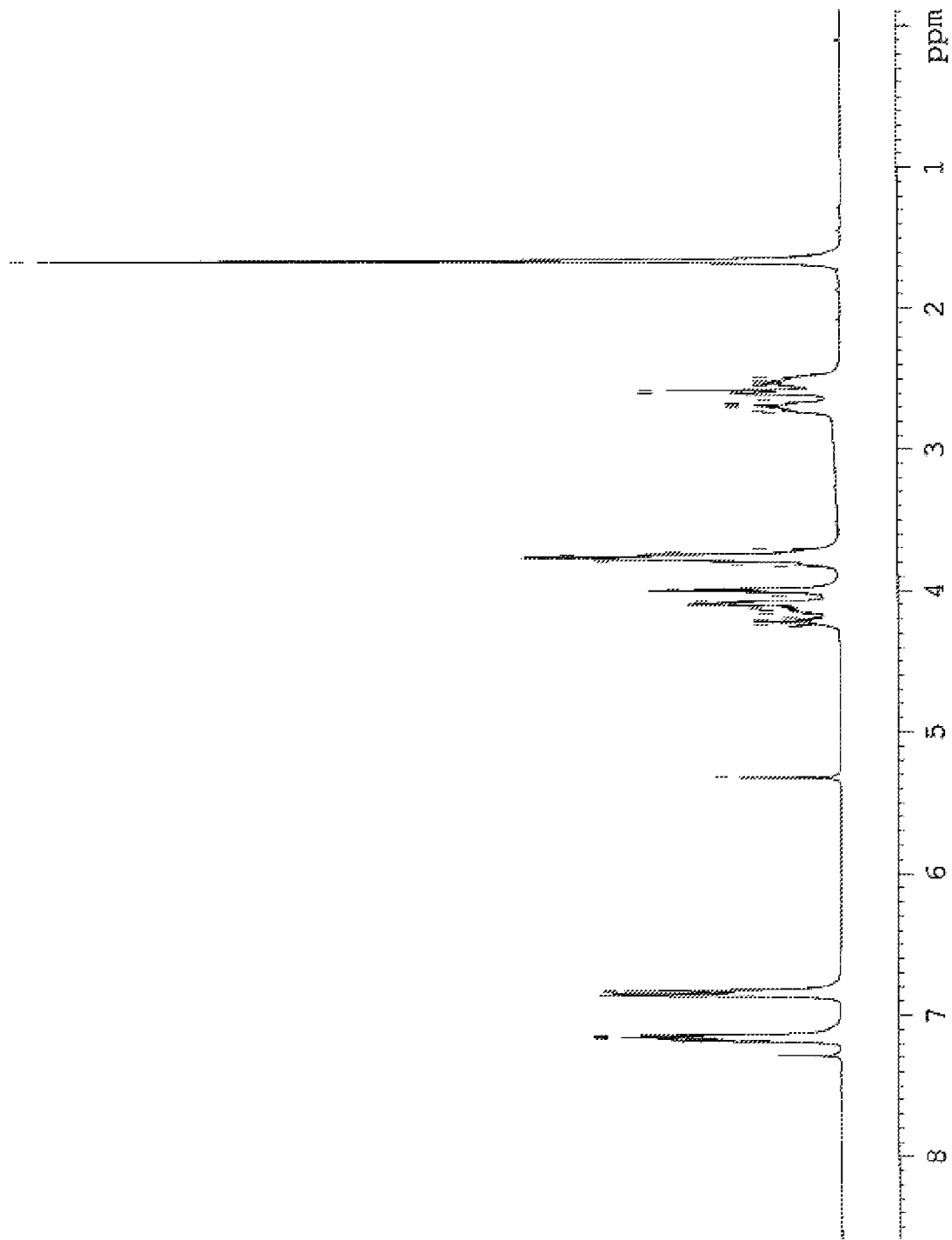
FIG. 17 is a $^1H$ NMR spectrum of Compound 13.

To a solution of 2,2'-(((propane-2,2-diylbis(4,1-phenylene))bis(oxy)))bis(methylene))bis(oxirane) (1.0 equiv) and morpholine (1 equiv) in acetonitrile/water (9:1) was added CeCl$_3$.7H$_2$O (~0.5 equiv) and the mixture was refluxed. The resulting crude mixture was filtered and washed with ethyl acetate, and the resulting suspension was concentrated under reduced pressure. The resulting residue was purified by flash column chromatography on silica gel (eluent: ethyl acetate/hexane) to provide the title Compound 13. $^1$H NMR spectrum is shown in FIG. 17. MS (ESI+): m/z 464.3 [M]$^+$.

Example 6

Synthesis of (S)-1-chloro-3-(4-(2-(4-((R)-2-hydroxy-3-morpholinopropoxy)phenyl)propan-2-yl)phenoxy)propan-2-ol (13a)

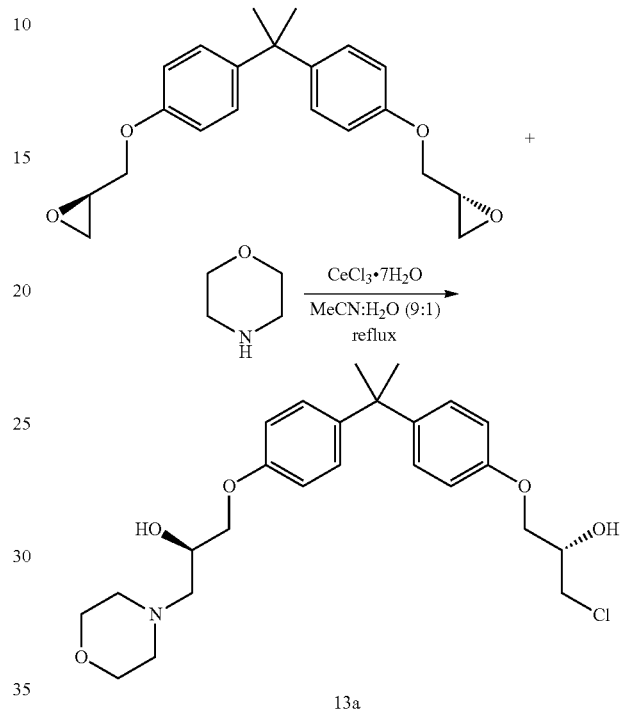

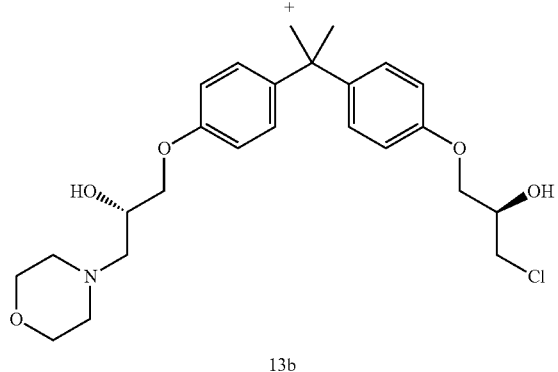

Compound 13a

To a solution of (2R,2'R)-2,2'-(((propane-2,2-diylbis(4,1-phenylene))bis(oxy)))bis(methylene))bis(oxirane) (1.0 equiv) and morpholine (~1 equiv) in acetonitrile/water (9:1) is added CeCl$_3$.7H$_2$O (~0.5 equiv) and the mixture is refluxed. The resulting crude mixture is filtered and washed with ethyl acetate, and the resulting suspension is concentrated under reduced pressure. The resulting residue is purified by flash column chromatography on silica gel (eluent: ethyl acetate/hexane) to provide Compound 13a and Compound 13b.

Example 7

Synthesis of 1-chloro-3-(4-(2-(4-(2-hydroxy-3-(1H-imidazol-1-yl)propoxy)phenyl)propan-2-yl)phenoxy)propan-2-ol (9)

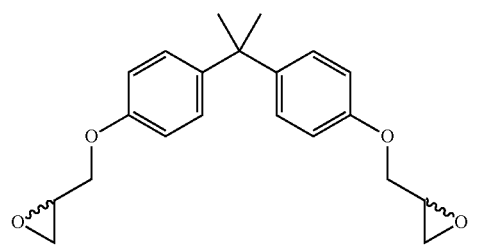
+
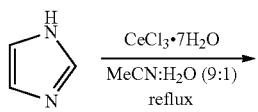
→
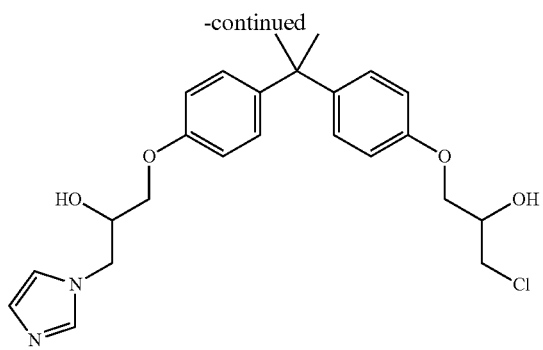

Compound 9

To a solution of 2,2'-(((propane-2,2-diylbis(4,1-phenylene))bis(oxy))bis(methylene))bis(oxirane) (1 equiv) and 1H-imidazole (~1 equiv) in acetonitrile/water (9:1) were added CeCl$_3$.7H$_2$O (~0.5 equiv) and the mixture was refluxed. The resulting crude mixture was filtered and washed with ethyl acetate, and the resulting suspension was concentrated under reduced pressure. The resulting residue was purified by flash column chromatography on silica gel (eluent: ethyl acetate/hexane) to provide Compound 9.

Example 8

Synthesis of (S)-1-chloro-3-(4-(2-(4-((R)-3-(4-((fluoro-$^{18}$F)methyl)-1H-1,2,3-triazol-1-yl)-2-hydroxypropoxy)phenyl)propan-2-yl)phenoxy)propan-2-ol (51a)

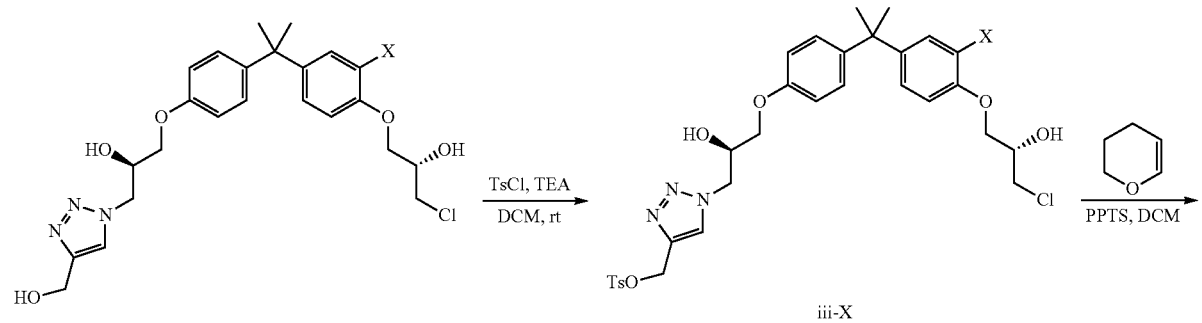

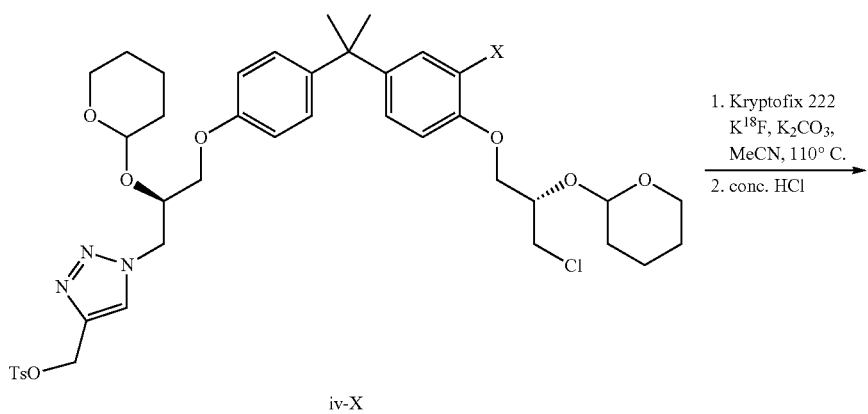

-continued

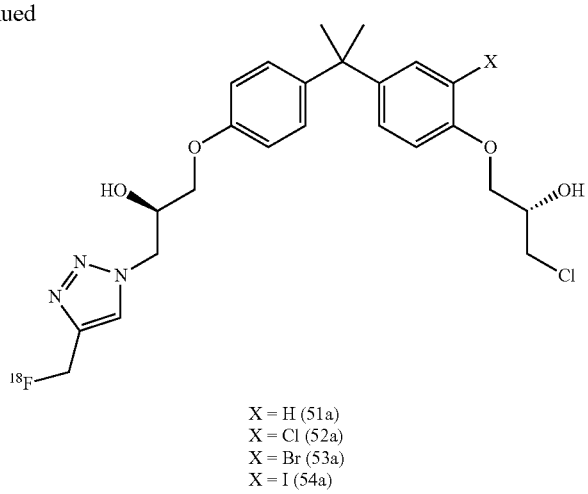

X = H (51a)
X = Cl (52a)
X = Br (53a)
X = I (54a)

Compound iii-H (X=H)

p-Toluenesulfonyl chloride (~1.5 equiv) is added portion wise over a period of approximately 10 min to a solution of Compound 5a (1 equiv) and TEA in DCM (~1M) in a water bath. The resulting solution is stirred at room temperature. The solvent is removed under reduced pressure, and the residue is diluted with ethyl acetate, washed subsequently with water (×2), cold aqueous 1 M HCl, saturated NaHCO$_3$ and water. The organic layer was dried over Mg$_2$SO$_4$, filtered and concentrated the crude product. The crude product is purified by column chromatography (eluent: ethyl acetate/hexane) to afford Compound iii-H.

Compound iv-H (X=H)

3,4-Dihydro-2H-pyran and PPTS is added to a solution of Compound iii-H (1 equiv) in DCM. The resulting solution is stirred until reaction is complete. The solvent is removed under reduced pressure, and the residue is diluted with ethyl acetate, washed subsequently with saturated NaHCO$_3$ and water. The organic layer was dried over Mg$_2$SO$_4$, filtered and concentrated the crude product. The crude product is purified by column chromatography (eluent: ethyl acetate/hexane) to afford Compound iv-H.

Compound 51a

To a solution of Compound iv-H (1 equiv) in MeCN is added K F and K$_2$CO$_3$, and the reaction mixture is heated at 110° C. Once the reaction is complete, concentrated HCl is added and stirred. The product is extracted with ethyl acetate, and the resulting suspension is concentrated under reduced pressure. The resulting residue is purified by flash column chromatography on silica gel (eluent: ethyl acetate/hexane) to provide Compound 51a.

Example 9

Compound Activity

LNCaP cells were transiently transfected with PSA (6.1 kb)-luciferase for 24 h prior to pre-treatment with compounds of the invention (e.g., compounds 1a, 9, 13) ranging in concentration from 62.5 ng/ml to 1.5 ug/ml for 1 hour before the addition of vehicle, or synthetic androgen, R1881 (1 nM) to induce luciferase production. After 24 h of incubation with R1881, the cells were harvested, and relative luciferase activities were determined. To determine the IC$_{50}$, treatments were normalized to the predicted maximal activity induction (in the absence of test compounds, vehicle only).

TABLE 4

IC$_{50}$ values for selected compounds (µM) with standard error

| Compound | Number of Trials | Average IC$_{50}$ |
|---|---|---|
| 1a | 4 | 3.23 +/− 0.37 |
| 9 | 6 | 8.45 +/− 3.14 |
| 13 | 3 | 12.84 +/− 1.95 |

Although various embodiments of the invention are disclosed herein, many adaptations and modifications can be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

What is claimed:

1. A compound having the following structure (I):

(I)

or a pharmaceutically acceptable salt, tautomer or stereoisomer thereof, wherein:

X is —O—, —S(O)$_{0-2}$—, —C(=O)—, —C(OR$^5$)$_2$—, —C(OR$^5$)(OC(=O)R$^{13}$)—, —C(R$^8$R$^9$)—, —C(=CR$^8$R$^9$)—, —N(R$^9$)—, —N(COR$^9$)—, —CHNR$^8$R$^9$—, —C(=NR$^9$)—, —C(=NOR$^5$)—, —C(=N—NHR$^5$)—;

R$^1$ and R$^2$ are each independently H, hydroxyl, —O-heterocyclyl, or —OC(=O)R$^{13}$;

R$^3$ is a 4-7 membered heterocyclyl which is optionally substituted with one or more R$^6$;

R$^5$ is each independently H, C$_1$-C$_6$ alkyl, C$_2$-C$_6$ alkenyl, or C$_2$-C$_6$ alkynyl;

R$^6$ is each independently selected from the group consisting of H, F, Cl, Br, I, $^{123}$I, hydroxyl, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;

R$^8$ is halogen, —S(O)$_{0-2}$R$^5$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^5$;

R$^9$ is H, halogen, —S(O)$_{0-2}$R$^5$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^5$; or R$^8$ and R$^9$ can join to form an unsubstituted or substituted mono-, bi-, or tri-cyclic carbocycle or heterocycle containing from 3 to 20 carbon atoms;

R$^{11a}$, R$^{11b}$, R$^{11c}$ and R$^{11d}$ are each independently H, F, Cl, Br, I, $^{123}$I, hydroxyl, C$_1$-C$_6$ alkyl, C$_2$-C$_6$ alkenyl, C$_2$-C$_6$ alkynyl, —OR$^5$, —OC(=O)R$^{13}$, C$_1$-C$_{10}$ acyl, —S(O)$_{0-2}$R$^5$, —NO$_2$, —CN, —NH$_2$, —NHR$^5$, or —N(R$^5$)$_2$;

R$^{13}$ is each independently C$_1$-C$_6$ alkyl, C$_2$-C$_6$ alkenyl, or C$_2$-C$_6$ alkynyl;

n$^1$ and n$^2$ are each independently 0, 1, or 2; and n$^3$ is 0, 1, 2, 3, 4, or 5.

2. The compound of claim 1, wherein X is —C(R$^8$R$^9$)—.

3. The compound of claim 1, wherein R$^8$ and R$^9$ are C$_1$-C$_{10}$ alkyl.

4. The compound of claim 1, wherein R$^8$ and R$^9$ are methyl.

5. The compound of claim 1, wherein R$^3$ is 5-7 membered heterocylyl, wherein said heterocyclyl comprises at least one N atom in the ring.

6. The compound of claim 1, wherein R$^3$ is selected from a group consisting of oxazine, azepine, pyrrolidine, pyrroline, imidazoline, imidazolidine, pyrazoline, pyrazolidine, piperidine, dioxane, morpholine, dithiane, thiomorpholine, piperazine, and tetrazine.

7. The compound of claim 1, wherein each R$^{13}$ is independently methyl, ethyl or propyl.

8. The compound of claim 1, wherein each R$^{13}$ is methyl.

9. The compound of claim 1, wherein at least one of R$^{11a}$, R$^{11b}$, R$^{11c}$ and R$^{11d}$ is Cl, Br, I or $^{123}$I.

10. The compound of claim 1, wherein at least one of R$^{11a}$, R$^{11b}$, R$^{11c}$, and R$^{11d}$ is I; and at least one of R$^{11a}$, R$^{11b}$, R$^{11c}$ and R$^{11d}$ is $^{123}$I.

11. The compound of claim 1, wherein n$^3$ is 0, 1, or 2.

12. The compound of claim 1, wherein the compound has one of the following structures:

199
-continued
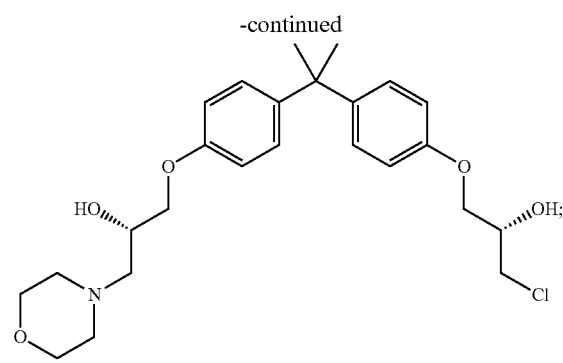
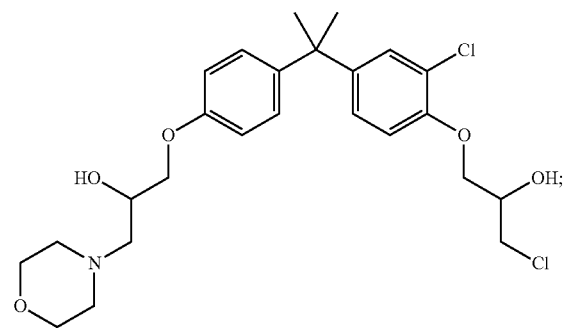
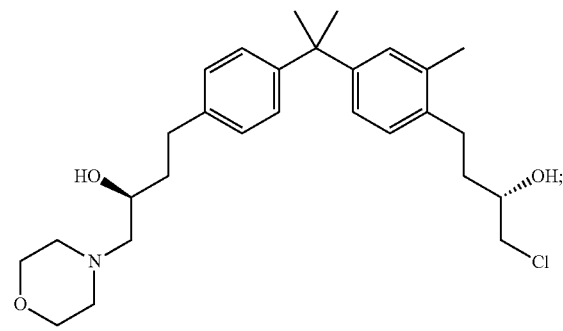
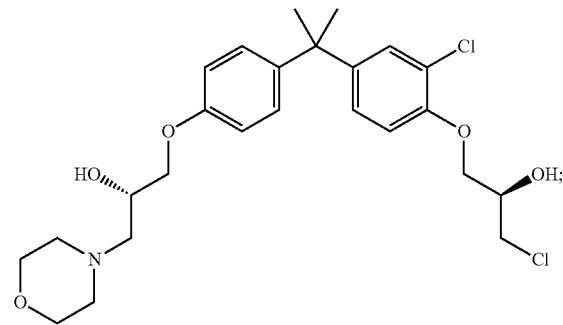
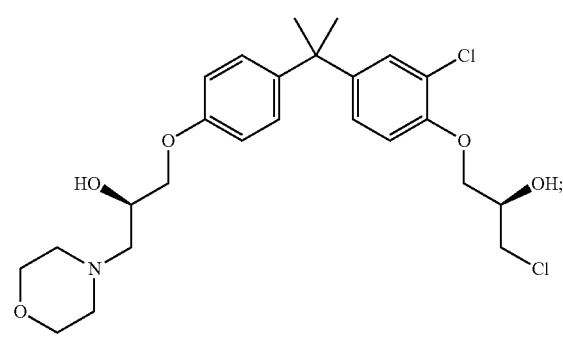
200
-continued
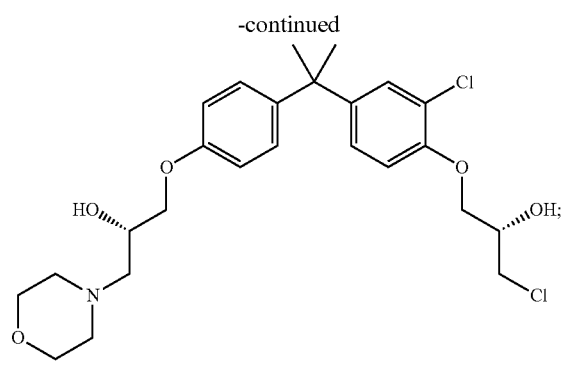
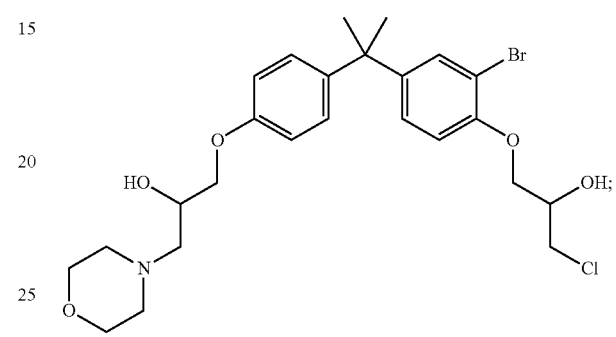
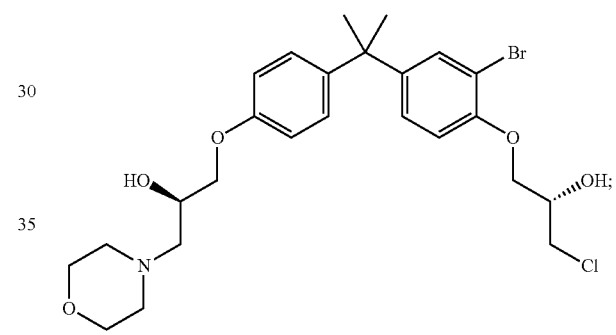
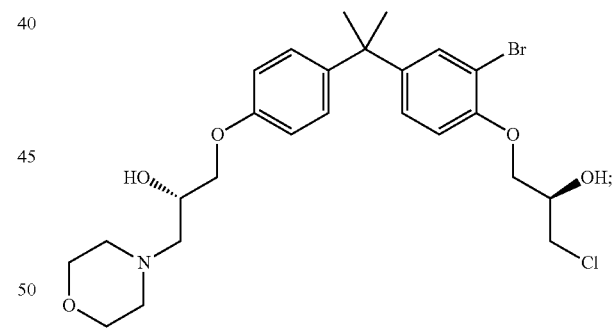
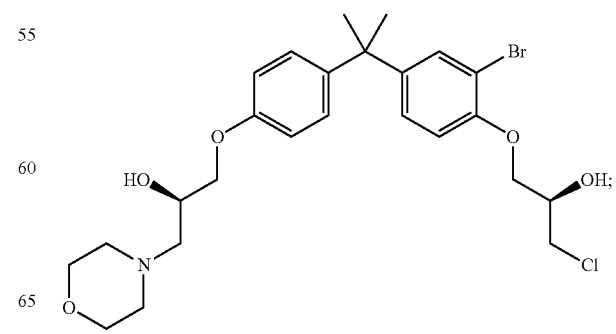

201
-continued
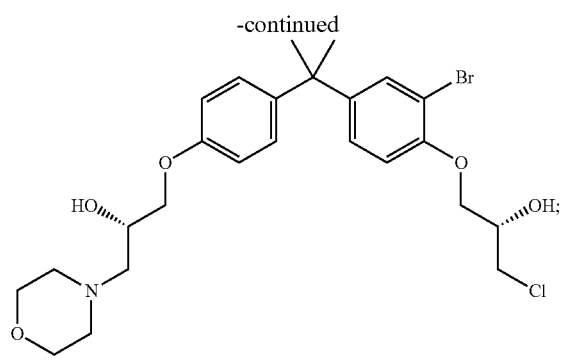
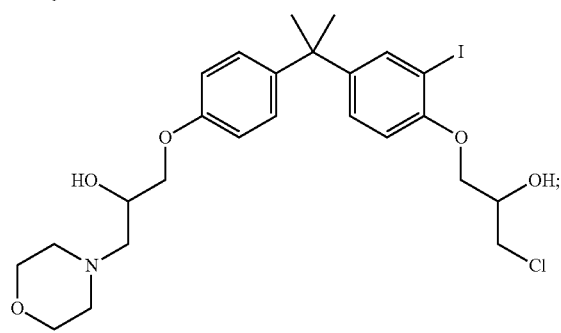
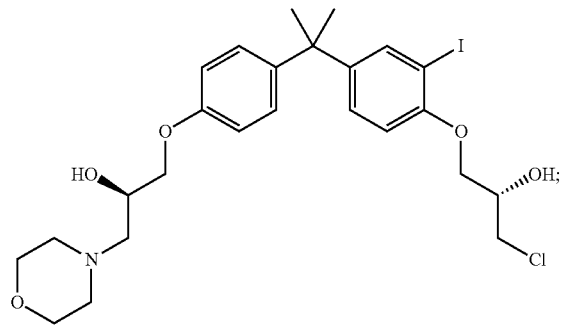
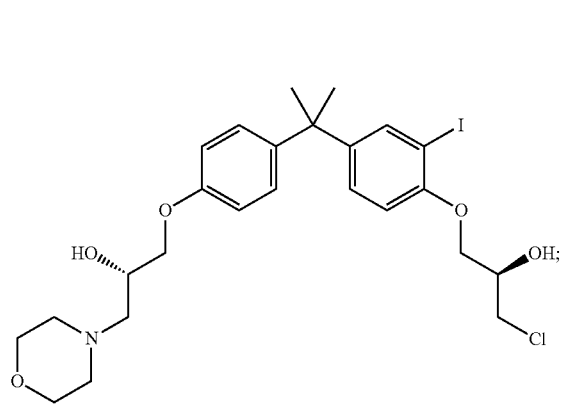
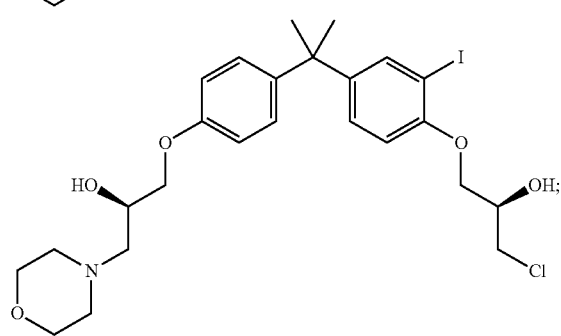
202
-continued
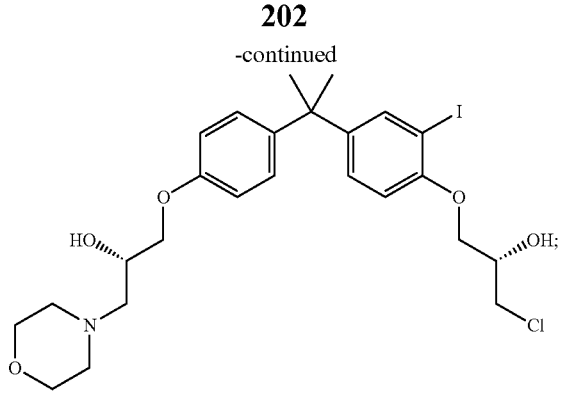
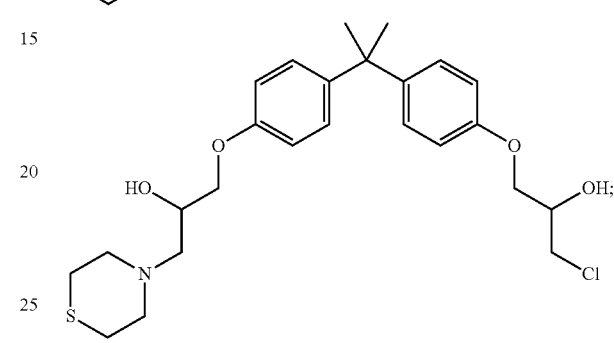
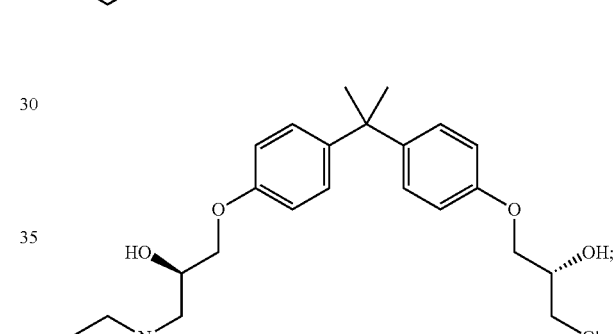
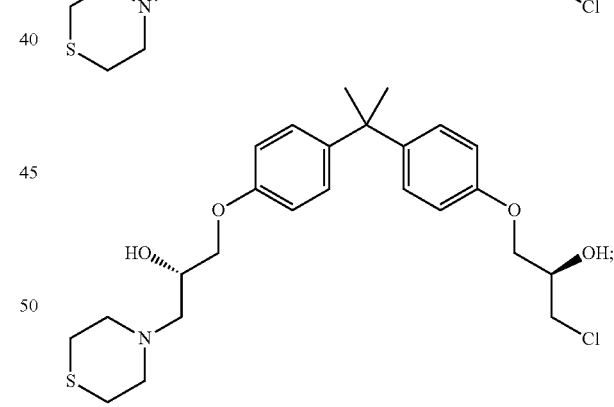
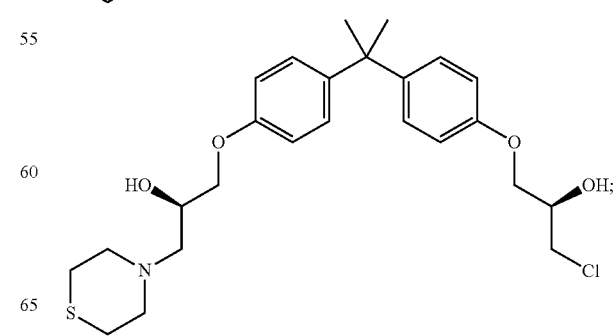

203
-continued
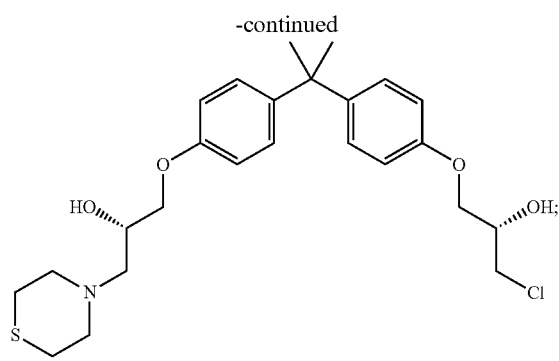
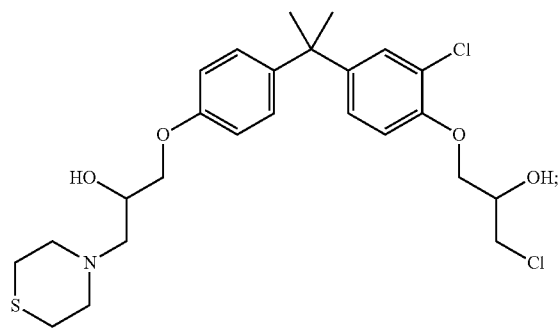
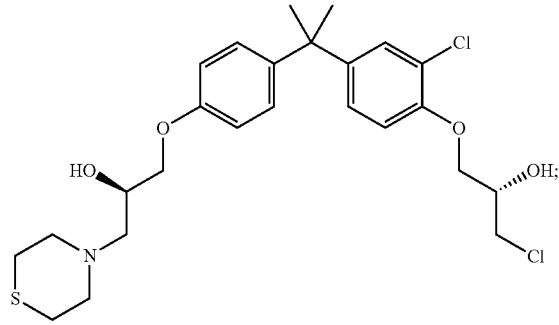
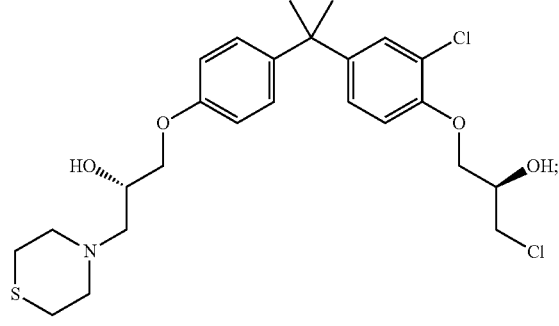
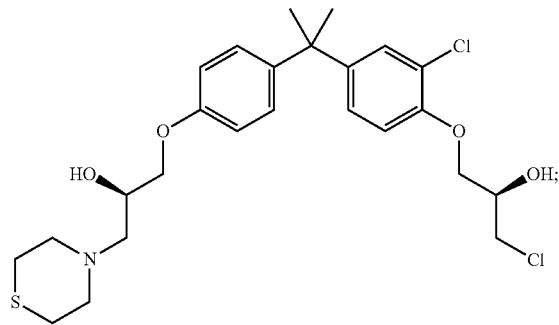
204
-continued
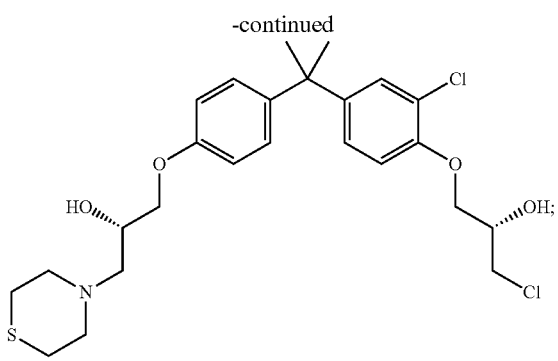
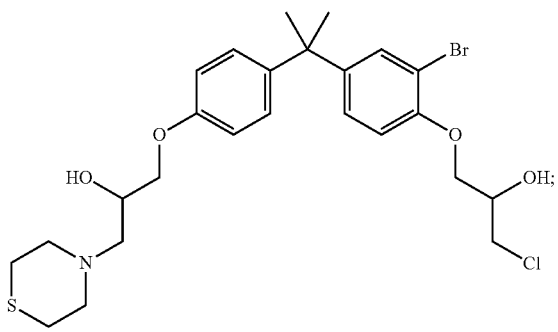
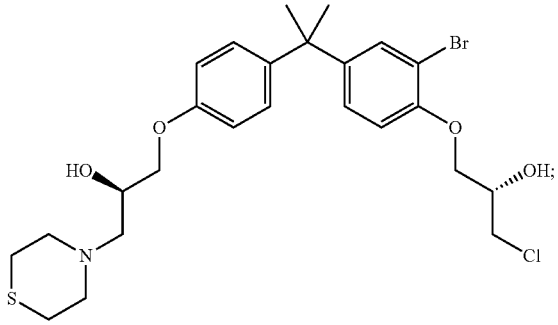
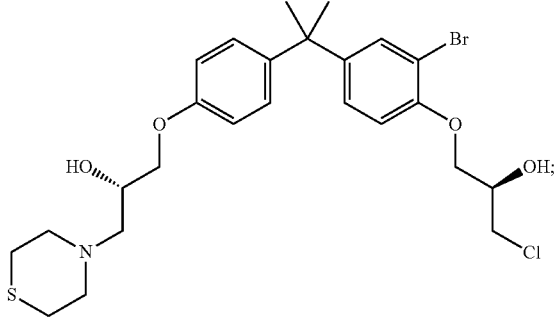
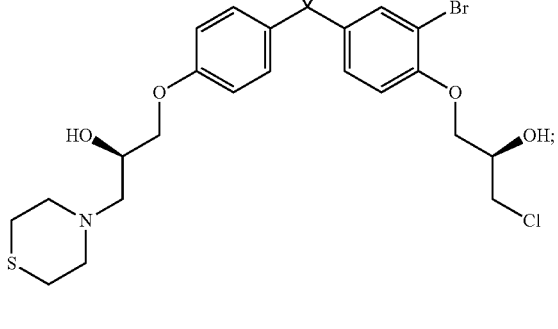

205
-continued
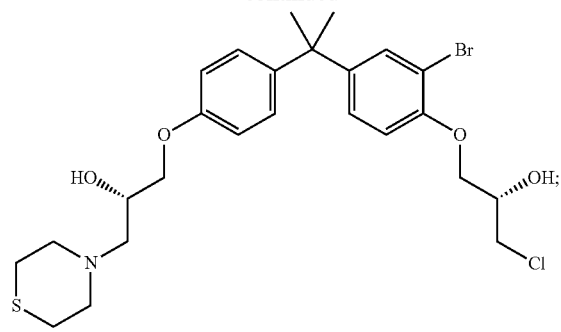
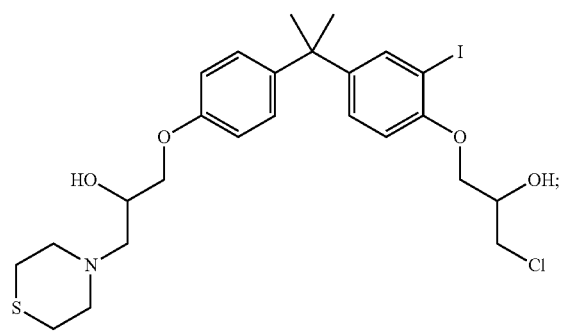
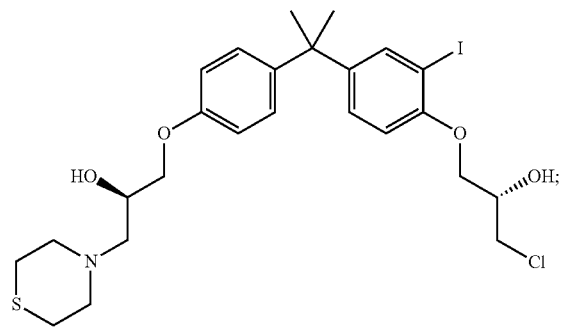
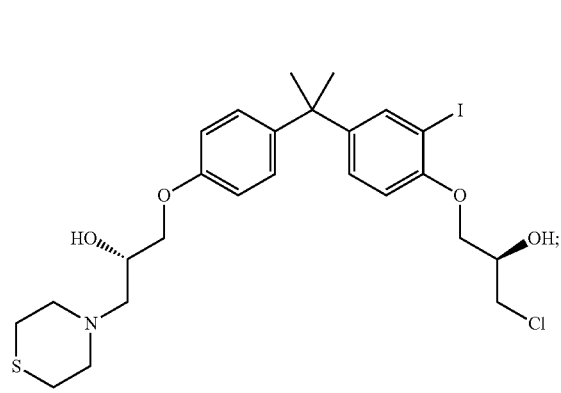
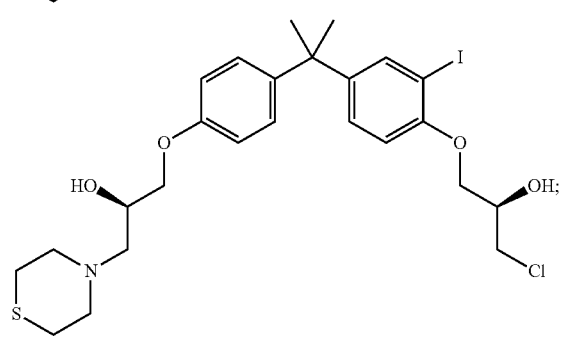
206
-continued
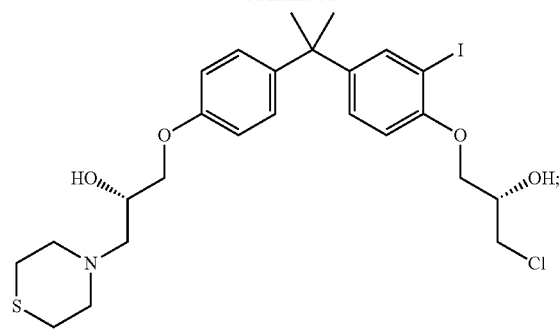
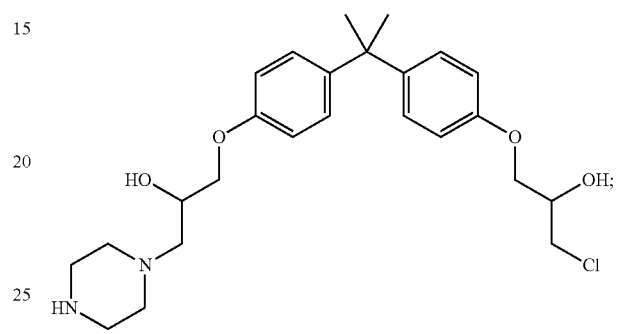
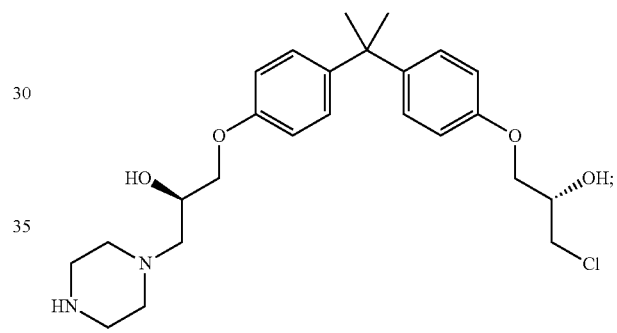
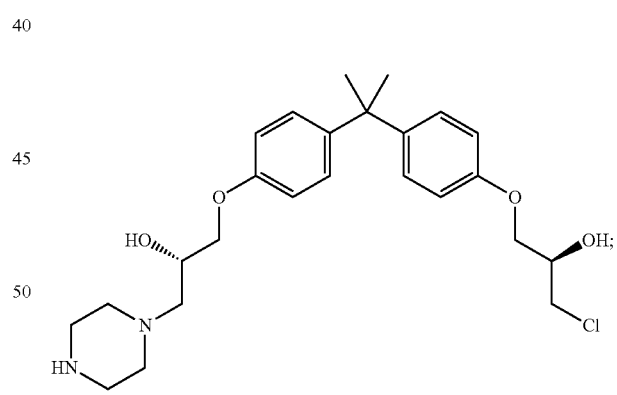
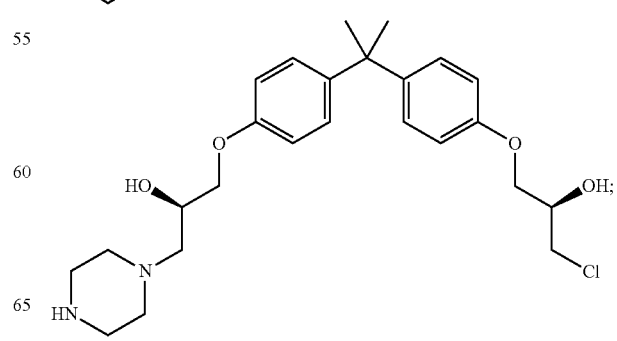

207
-continued
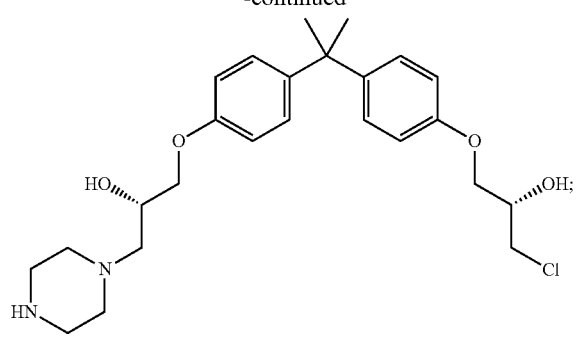
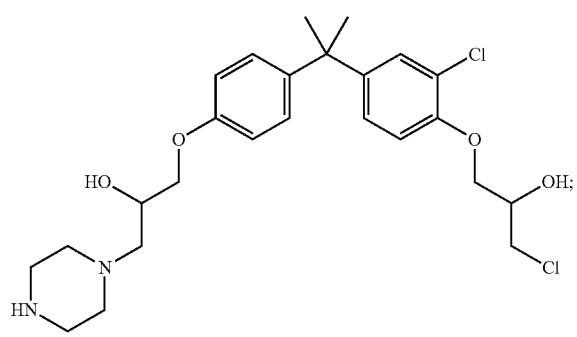
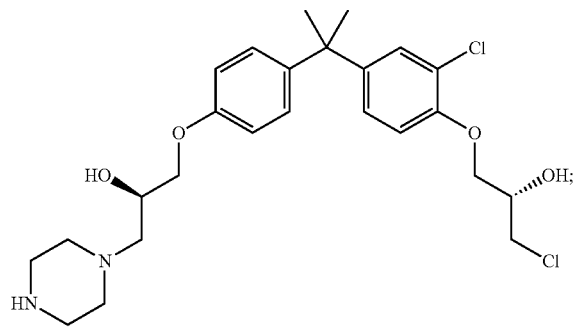
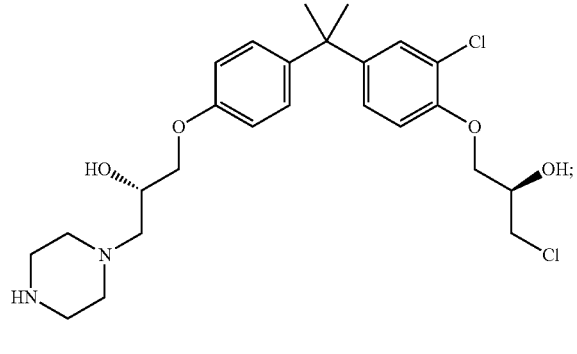
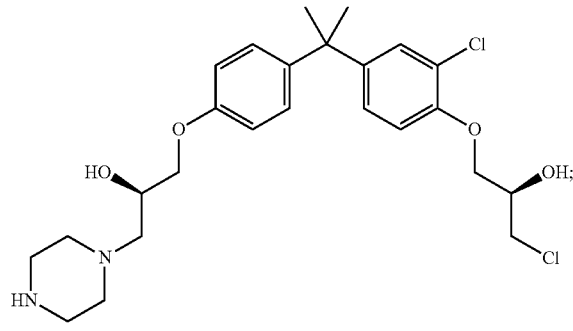
208
-continued
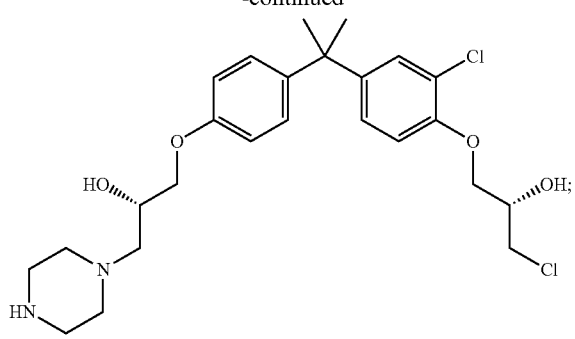
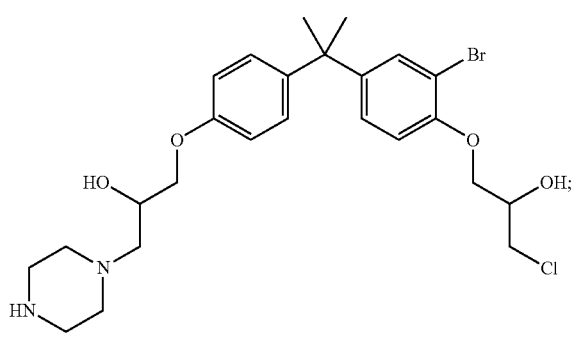
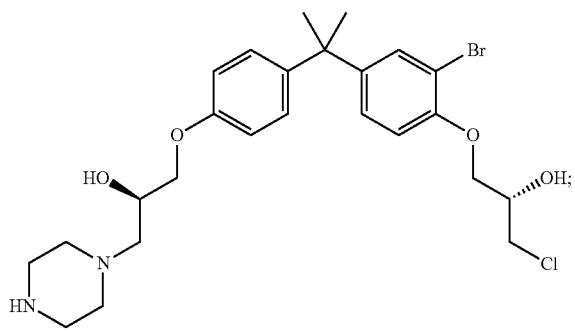
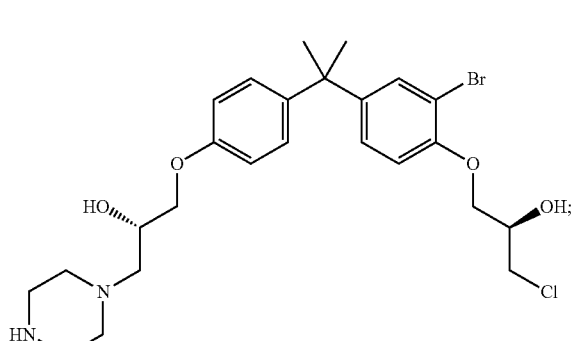
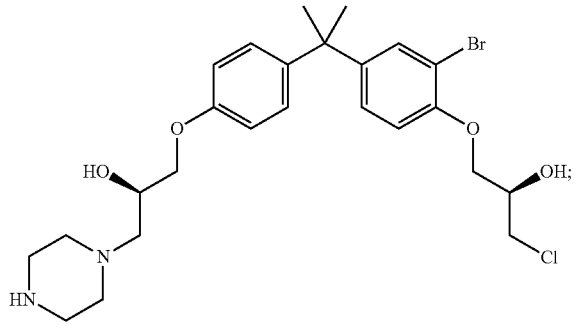

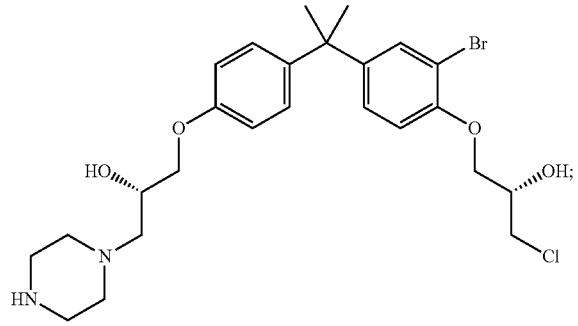
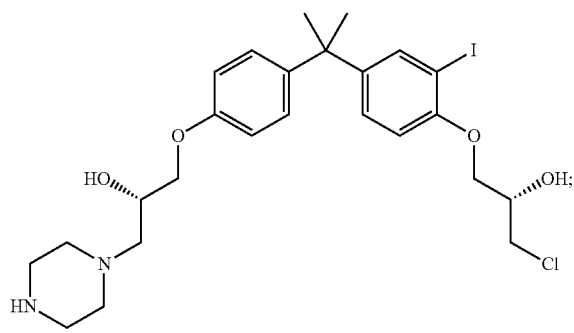
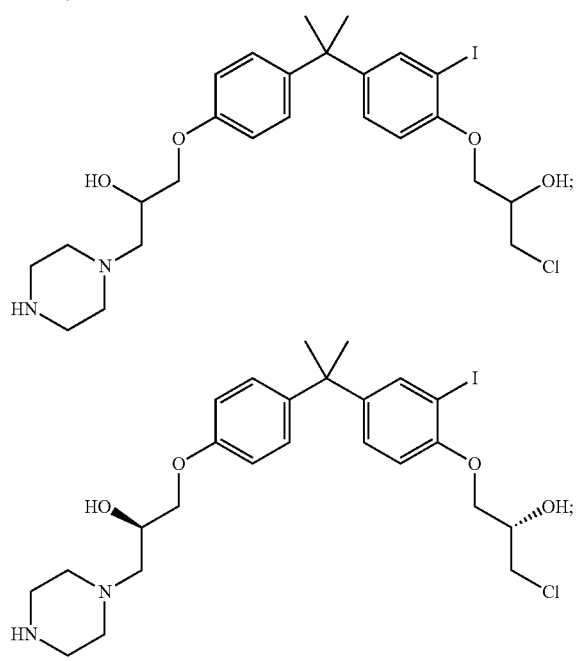
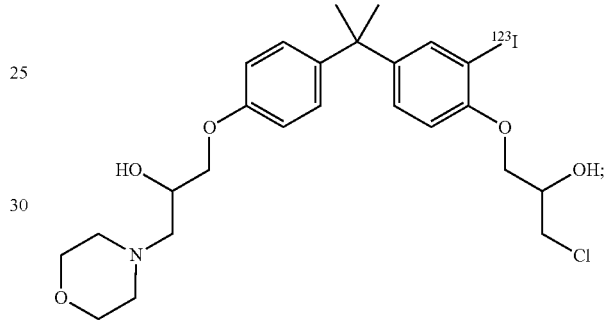
or a pharmaceutically acceptable salt, tautomer, or stereoisomer thereof.
13. The compound of claim 1, wherein the compound has one of the following structures:
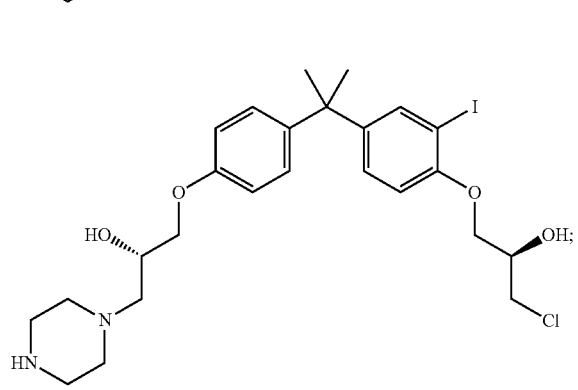
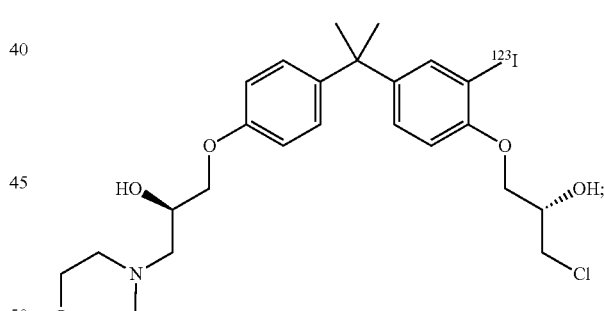
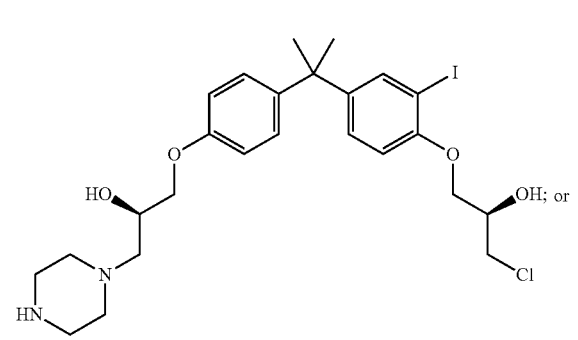
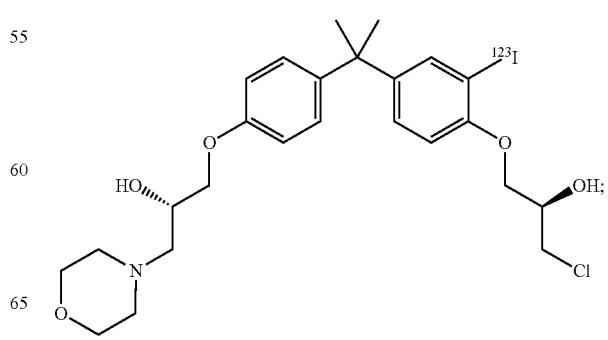

211
-continued
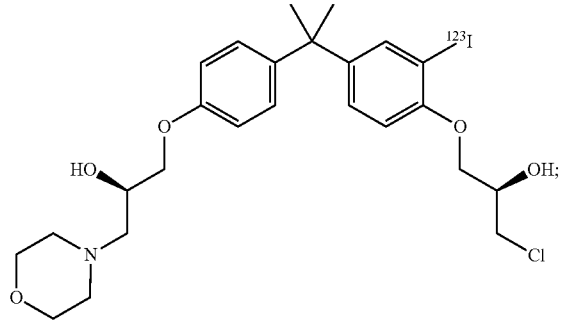
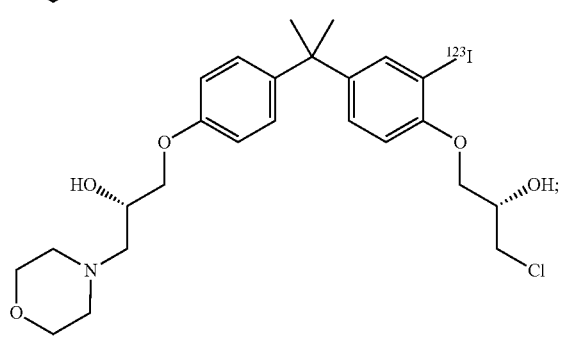
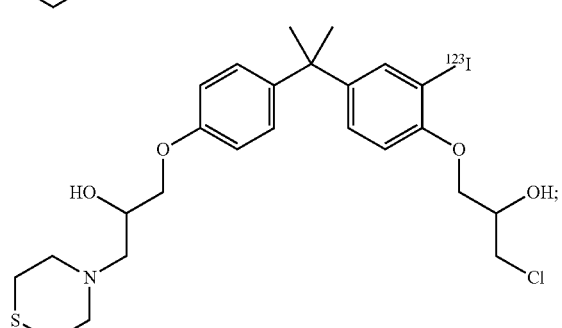
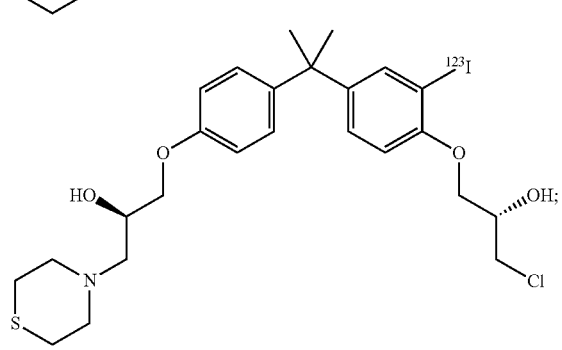
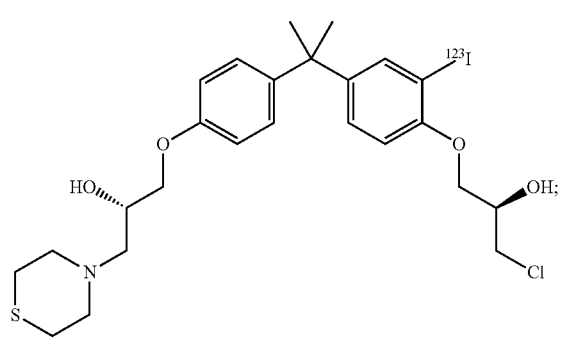
212
-continued
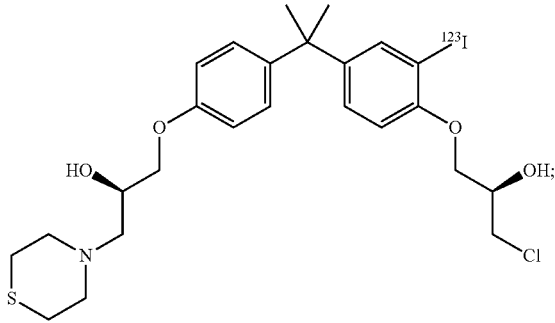
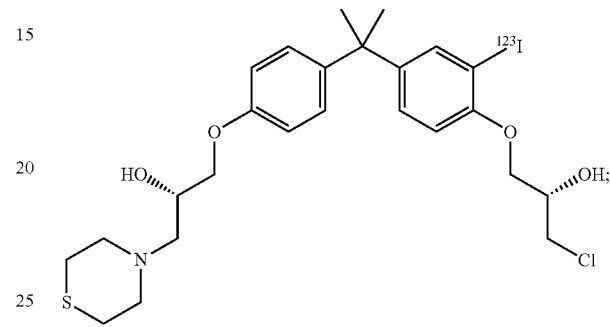
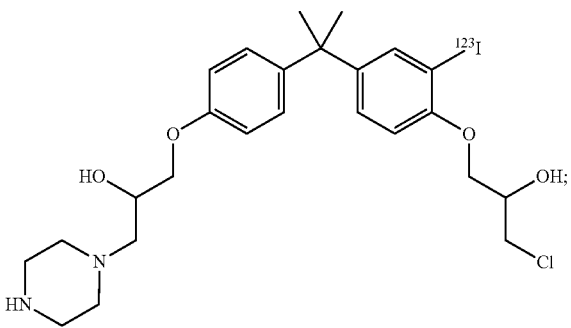
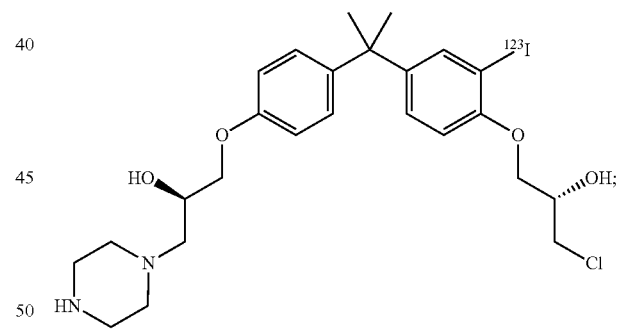
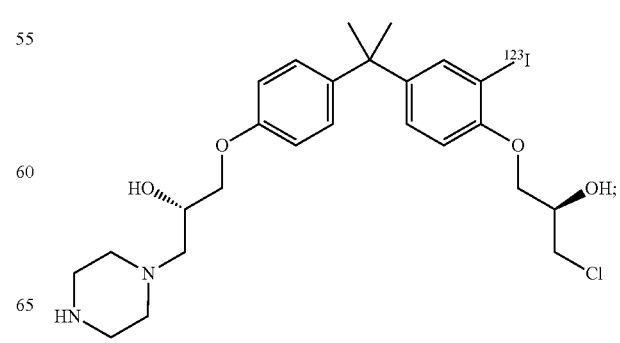

-continued

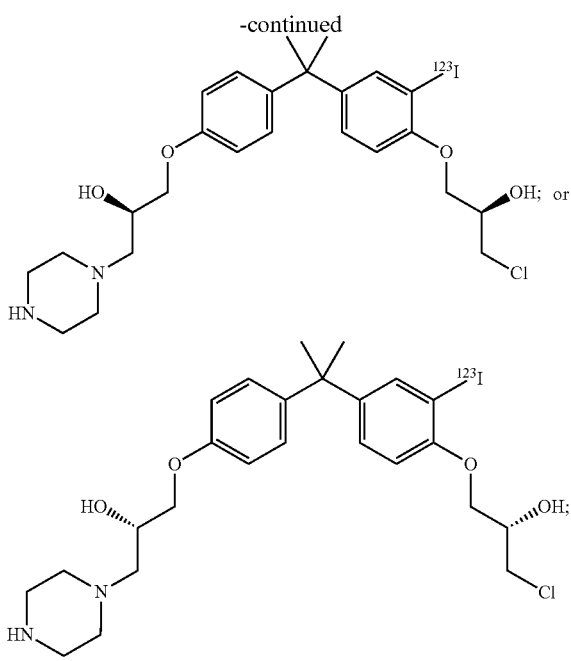

or a pharmaceutically acceptable salt, tautomer, or stereoisomer thereof.

14. A pharmaceutical composition, comprising: a pharmaceutically acceptable carrier and a compound of formula (I):

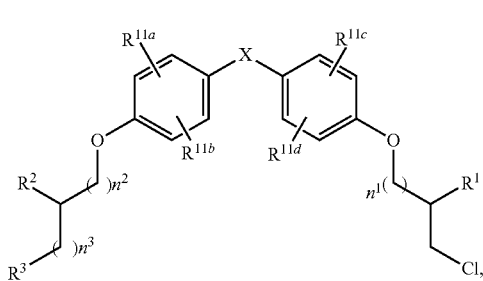

or a pharmaceutically acceptable salt, tautomer or stereoisomer thereof, wherein:

X is —O—, —S(O)$_{0-2}$—, —C(=O)—, —C(OR$^5$)$_2$—, —C(OR$^5$)(OC(=O)R$^{13}$)—, —C(R$^8$R$^9$)—, —C(=CR$^8$R$^9$)—, —N(R$^9$)—, —N(COR$^9$)—, —CHNR$^8$R$^9$—, —C(=NR$^9$)—, —C(=NOR$^5$)—, —C(=N—NHR$^5$)—;

R$^1$ and R$^2$ are each independently H, hydroxyl, —O-heterocyclyl, or —OC(=O)R$^{13}$;

R$^3$ is a 4-7 membered heterocyclyl which is optionally substituted with one or more R$^6$;

R$^5$ is each independently H, C$_1$-C$_6$ alkyl, C$_2$-C$_6$ alkenyl, or C$_2$-C$_6$ alkynyl;

R$^6$ is each independently selected from the group consisting of H, F, Cl, Br, I, $^{123}$I, hydroxyl, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;

R$^8$ is halogen, —S(O)$_{0-2}$R$^5$, C$_1$-C$_{10}$ alkyl, C$_2$-C$_{10}$ alkynyl, aryl, aralkyl, C$_1$-C$_{10}$ acyl, or —NR$^5$R$^5$;

R$^9$ is H, halogen, —S(O)$_{0-2}$R$^5$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^5$; or R$^8$ and R$^9$ can join to form an unsubstituted or substituted mono-, bi-, or tri-cyclic carbocycle or heterocycle containing from 3 to 20 carbon atoms;

R$^{11a}$, R$^{11b}$, R$^{11c}$ and R$^{11d}$ are each independently H, F, Cl, Br, I, $^{123}$I, hydroxyl, C$_1$-C$_6$ alkyl, C$_2$-C$_6$ alkenyl, C$_2$-C$_6$ alkynyl, —OR$^5$, —OC(=O)R$^{13}$, C$_1$-C$_{10}$ acyl, —S(O)$_{0-2}$R$^5$, —NO$_2$, —CN, —NH$_2$, —NHR$^5$, or —N(R$^5$)$_2$;

R$^{13}$ is each independently C$_1$-C$_6$ alkyl, C$_2$-C$_6$ alkenyl, or C$_2$-C$_6$ alkynyl;

n$^1$ and n$^2$ are each independently 0, 1, or 2; and n$^3$ is 0, 1, 2, 3, 4, or 5.

15. The pharmaceutical composition of claim 14, further comprising an additional therapeutic agent.

16. The pharmaceutical composition of claim 15, wherein the additional therapeutic agent is for treating prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

17. The pharmaceutical composition of claim 15, wherein the additional therapeutic agent is enzalutamide, Galeterone, ARN-509, abiraterone, bicalutamide, nilutamide, flutamide, cyproterone acetate, docetaxel, Bevacizumab (Avastin), OSU-HDAC42, VITAXIN, sunitumib, ZD-4054, Cabazitaxel (XRP-6258), MDX-010 (Ipilimumab), OGX 427, OGX 011, finasteride, dutasteride, turosteride, bexlosteride, izonsteride, FCE 28260, SKF105,111, ODM-201, or radium 233.

18. A method for modulating androgen receptor activity, comprising: administering a pharmaceutical composition according to claim 14 to a patient in need thereof.

19. A method for treating a condition or disease that is responsive to modulation of androgen receptor activity, comprising: administering a pharmaceutical composition according to claim 14 to a patient in need thereof, wherein said condition or disease is selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration.

20. The method of claim 19, wherein the condition or disease is prostate cancer.

21. The method of claim 19, wherein the condition or disease is castration resistant prostate cancer.

22. The method of claim 19, wherein the condition or disease is androgen-dependent prostate cancer.

23. A method for treating a condition or disease selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration, comprising:

administering to a patient in need thereof a compound having the following structure (I):

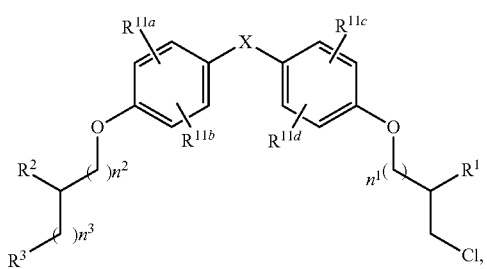

(I)

or a pharmaceutically acceptable salt, tautomer or stereoisomer thereof, wherein:
X is —O—, —S(O)$_{0-2}$—, —C(=O)—, —C(OR$^5$)$_2$—, —C(OR$^5$)(OC(=O)R$^{13}$)—, —C(R$^8$R$^9$)—, —C(=CR$^8$R$^9$)—, —N(R$^9$)—, —N(COR$^9$)—, —CHNR$^8$R$^9$—, —C(=NR$^9$)—, —C(=NOR$^5$)—, —C(=N—NHR$^5$)—;
R$^1$ and R$^2$ are each independently H, hydroxyl, —O-heterocyclyl, or —OC(=O)R$^{13}$;
R$^3$ is a 4-7 membered heterocyclyl which is optionally substituted with one or more R$^6$;
R$^5$ is each independently H, C$_1$-C$_6$ alkyl, C$_2$-C$_6$ alkenyl, or C$_2$-C$_6$ alkynyl;
R$^6$ is each independently selected from the group consisting of H, F, Cl, Br, I, $^{123}$I, hydroxyl, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;
R$^8$ is halogen, —S(O)$_{0-2}$R$^5$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^5$;
R$^9$ is H, halogen, —S(O)$_{0-2}$R$^5$, C$_1$-C$_{10}$ alkyl, C$_2$-C$_{10}$ alkenyl, C$_2$-C$_{10}$ alkynyl, aryl, aralkyl, C$_1$-C$_{10}$ acyl, or —NR$^5$R$^5$; or
R$^8$ and R$^9$ can join to form an unsubstituted or substituted mono-, bi-, or tri-cyclic carbocycle or heterocycle containing from 3 to 20 carbon atoms;
R$^{11a}$, R$^{11b}$, R$^{11c}$ and R$^{11d}$ are each independently H, F, Cl, Br, I, $^{123}$I, hydroxyl, C$_1$-C$_6$ alkyl, C$_2$-C$_6$ alkenyl, C$_2$-C$_6$ alkynyl, —OR$^5$, —OC(=O)R$^{13}$, C$_1$-C$_{10}$ acyl, —S(O)$_{0-2}$R$^5$, —NO$_2$, —CN, —NH$_2$, —NHR$^5$, or —N(R$^5$)$_2$;
R$^{13}$ is each independently C$_1$-C$_6$ alkyl, C$_2$-C$_6$ alkenyl, or C$_2$-C$_6$ alkynyl;
n$^1$ and n$^2$ are each independently 0, 1, or 2; and
n$^3$ is 0, 1, 2, 3, 4, or 5.

24. The method of claim 23, wherein the condition or disease is prostate cancer.

25. The method of claim 23, wherein the condition or disease is castration resistant prostate cancer or androgen-dependent prostate cancer.

26. A method of imaging cancer, the method comprising administering a compound of claim 1 to a subject and detecting the presence or absence of cancer by use of SPECT or PET.

27. The method of claim 26, wherein the method identifies the presence or absence of a tumor.

28. The method of claim 26, wherein the method identifies the location of a tumor.

29. The method of claim 26, wherein the cancer is prostate cancer.

30. The method of claim 26, wherein the compound of claim 1 is selected from:

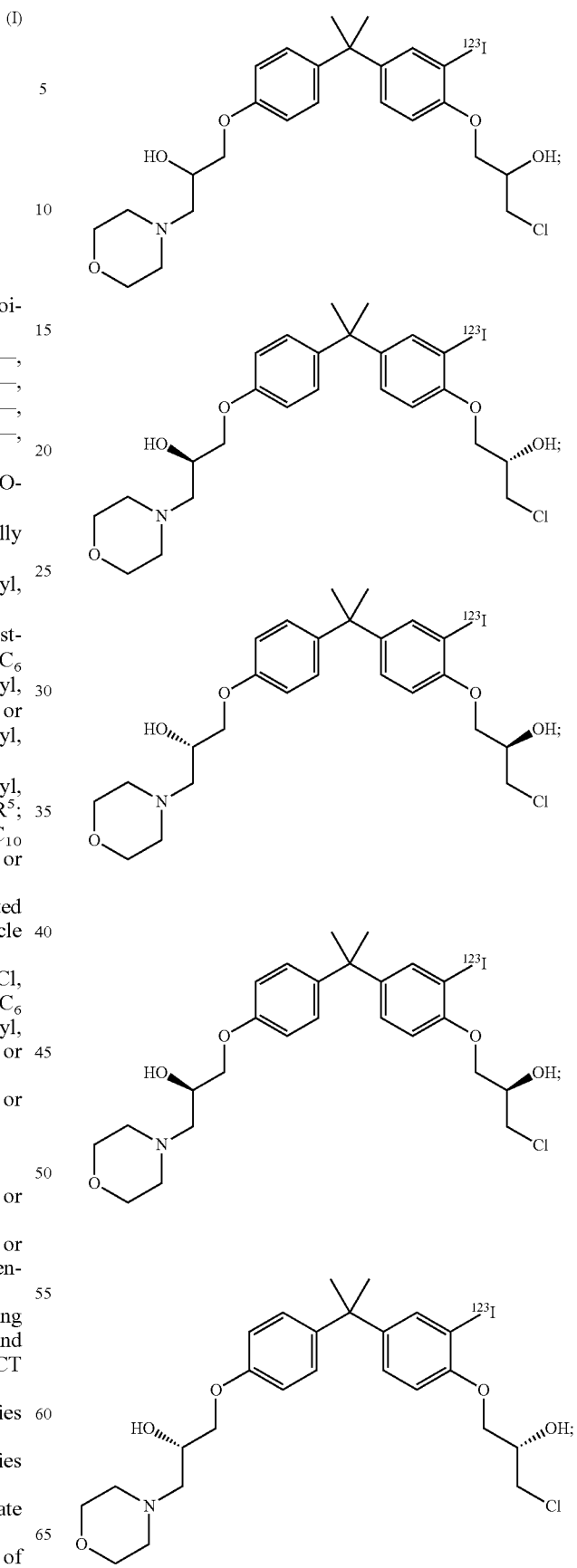

-continued
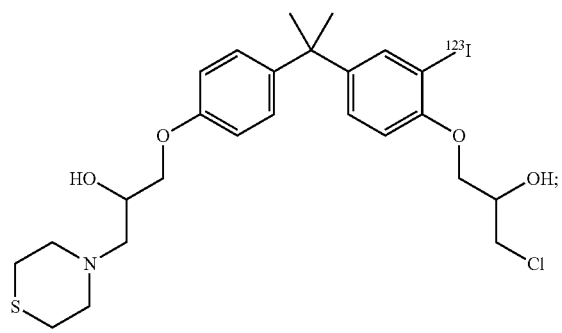
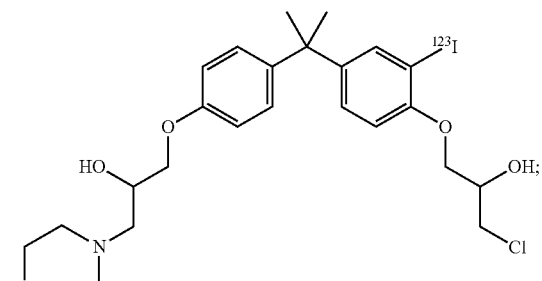
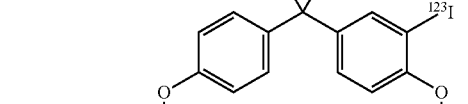
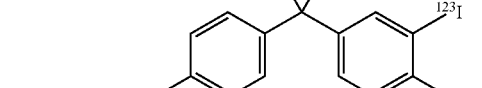
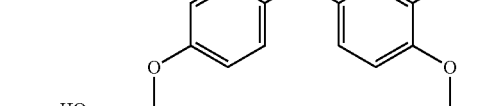
or a pharmaceutically acceptable salt, tautomer, or stereoisomer thereof.

31. A method of imaging cancer, the method comprising administering the pharmaceutical composition of claim 14 to a subject and detecting the presence or absence of cancer by use of SPECT or PET.

* * * * *

UNITED STATES PATENT AND TRADEMARK OFFICE
CERTIFICATE OF CORRECTION

| | | |
|---|---|---|
| PATENT NO. | : 11,345,670 B2 | Page 1 of 1 |
| APPLICATION NO. | : 16/864479 | |
| DATED | : May 31, 2022 | |
| INVENTOR(S) | : Raymond John Andersen et al. | |

It is certified that error appears in the above-identified patent and that said Letters Patent is hereby corrected as shown below:

In the Claims

Claim 12, Column 199, Lines 27-39 (third structure from the top):

Please replace " 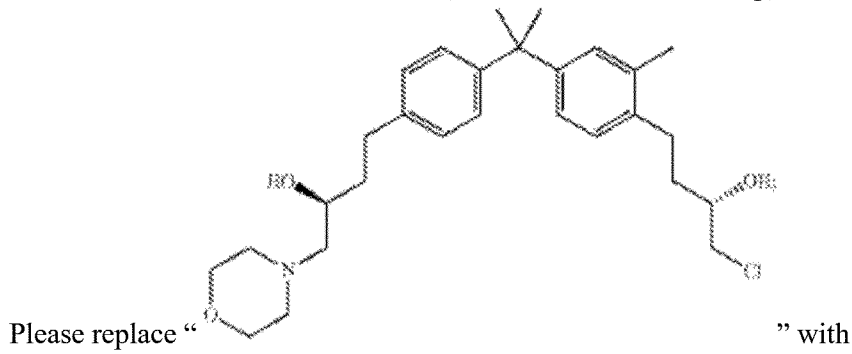 " with

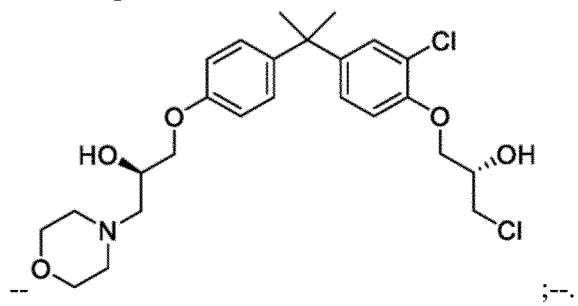 ;--.

Signed and Sealed this
Eleventh Day of October, 2022

Katherine Kelly Vidal
*Director of the United States Patent and Trademark Office*